US010766930B2

(12) United States Patent
Hourioux et al.

(10) Patent No.: US 10,766,930 B2
(45) Date of Patent: Sep. 8, 2020

(54) FUSION PROTEINS AND USE THEREOF FOR PREPARING VACCINES

(71) Applicants: UNIVERSITE DE TOURS, Tours (FR); CENTRE HOSPITALIER REGIONAL UNIVERSITAIRE DE TOURS, Tours (FR); INSTITUT NATIONAL DE LA SANTE ET DE LA RECHERCHE MEDICALE-INSERM, Paris (FR)

(72) Inventors: Christophe Hourioux, Druye (FR); Romuald Patient, Joue-les-Tours (FR); Elodie Beaumont, Ballan-Mire (FR); Philippe Roingeard, Savonnieres (FR)

(73) Assignees: UNIVERSITE DE TOURS, Tours (FR); CENTRE HOSPITALIER REGIONAL UNIVERSITAIRE DE TOURS, Tours (FR); INSTITUT NATIONAL DE LA SANTE ET DE LA RECHERCHE MEDICALE—INSERM, Paris (FR)

( * ) Notice: Subject to any disclaimer, the term of this patent is extended or adjusted under 35 U.S.C. 154(b) by 0 days.

(21) Appl. No.: 16/310,666

(22) PCT Filed: Jun. 16, 2017

(86) PCT No.: PCT/FR2017/051591
§ 371 (c)(1),
(2) Date: Dec. 17, 2018

(87) PCT Pub. No.: WO2017/216505
PCT Pub. Date: Dec. 21, 2017

(65) Prior Publication Data

US 2019/0389912 A1 Dec. 26, 2019

(30) Foreign Application Priority Data

Jun. 17, 2016 (FR) ..................................... 16 55677

(51) Int. Cl.

| | |
|---|---|
| ***C07K 14/02*** | (2006.01) |
| ***A61K 39/29*** | (2006.01) |
| ***A61K 39/12*** | (2006.01) |
| ***C12N 7/00*** | (2006.01) |
| ***C07K 14/005*** | (2006.01) |
| ***A61P 31/20*** | (2006.01) |
| ***A61P 31/14*** | (2006.01) |
| ***C12P 21/02*** | (2006.01) |
| *A61K 39/00* | (2006.01) |

(52) U.S. Cl.
CPC ............ *C07K 14/005* (2013.01); *A61K 39/12* (2013.01); *A61K 39/292* (2013.01); *A61P 31/14* (2018.01); *A61P 31/20* (2018.01); *C12N 7/00* (2013.01); *C12P 21/02* (2013.01); *A61K 2039/70* (2013.01); *C07K 2319/03* (2013.01); *C07K 2319/33* (2013.01); *C12N 2730/10134* (2013.01); *C12N 2770/24134* (2013.01)

(58) Field of Classification Search
None
See application file for complete search history.

(56) References Cited

U.S. PATENT DOCUMENTS 8,765,143 B2 7/2014 Roingeard et al.
2011/0150921 A1 * 6/2011 Roingeard ............. A61K 39/29
424/192.1

FOREIGN PATENT DOCUMENTS

WO 2009/153518 A2 12/2009

OTHER PUBLICATIONS

Cox et al. Predicting Zika virus structural biology: Challenges and opportunities for intervention. Antiviral Chemistry and Chemotherapy 2015, vol. 24(3-4) 118-126.*
B. D. Cox et al: “Predicting Zika virus structural biology: Challenges and opportunities for intervention”, Antiviral Chemistry & Chemotherapy., vol. 24, No. 3-4, Aug. 1, 2015 (Aug. 1, 2015), GB, pp. 118-126, XP055328128, ISSN: 0956-3202, DOI: 10.1177/2040206616653873.
International Search Report, dated Sep. 27, 2017, from corresponding PCT/FR2017/051591 application.
FR Search Report, dated Dec. 22, 2016, from corresponding FR 1655677 application.

* cited by examiner

*Primary Examiner* — Nianxiang Zou
(74) *Attorney, Agent, or Firm* — Nixon & Vanderhye

(57) ABSTRACT

An immunogenic fusion protein includes at least the following two peptides a) —on the C-terminal side, a first peptide constituted of: —the amino acid sequence of the protein S or the protein M of a human hepatitis B virus (HBV) isolate, which protein S or protein M is optionally deleted at the N-terminal end thereof, and b) —on the N-terminal side, a second peptide constituted of: —the sequence of amino acids of at least one transmembrane domain and the ectodomain of at least one protein of a Zika virus isolate selected from the envelope protein E or a fusion peptide including the envelope protein E and the protein prM.

13 Claims, 17 Drawing Sheets

Figure 1:
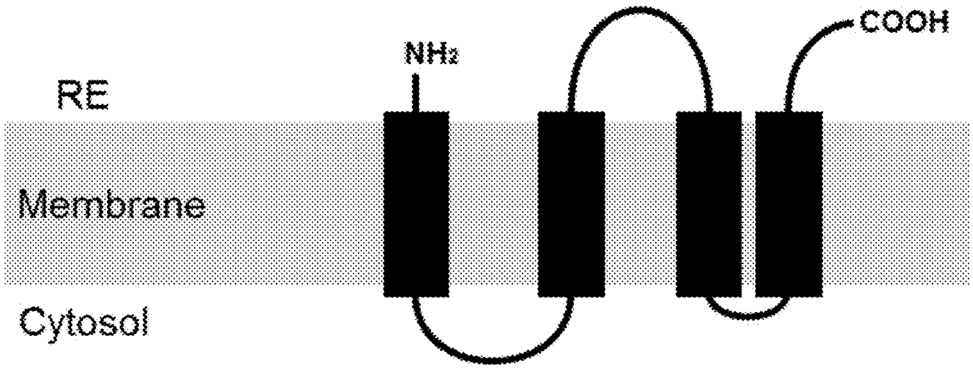

Specification includes a Sequence Listing.

FUSION PROTEINS AND USE THEREOF FOR PREPARING VACCINES

The present invention is applicable to new fusion proteins and use thereof for preparing vaccines.

The Zika virus (ZIKV) was first detected in a monkey in Uganda in 1947. The first human cases were identified in the 1970s in Africa (Uganda, Tanzania, Egypt, Central African Republic, Sierra Leone, Gabon and Senegal), then in certain Asian countries (India, Malaysia, Philippines, Thailand, Vietnam and Indonesia).

Many cases have been confirmed today, e.g. 55,000 cases of Zika virus infections were identified in French Polynesia between 2013 and 2014. The Zika virus was also detected for the first time in Brazil in May 2015, and to date, between 440,000 and 1,500,000 suspected cases have been reported. Zika virus epidemics have thus intensified over the last few years, and the World Health Organization notably indicated in February 2016 that the Zika virus constituted a public health emergency of international concern.

The majority of people infected by the Zika virus do not develop any symptoms (approximately 70 to 80% of cases). In the rest of the population, the symptoms caused by the Zika virus resemble flu symptoms: fatigue, fever, headaches and muscle and joint pain. Rashes, conjunctivitis, pain behind the eyes, digestive disorders or even hand or foot edema may also occur, as well as serious post-infection neurological complications like Guillain-Barrè syndrome or fetal malformations in pregnant women.

At this time, there is no vaccine preventing the Zika virus infections, nor specific medication to treat said infections.

There is thus a real need to provide a means of preventing and/or treating Zika virus infections.

There is notably a real need to provide a vaccine against the Zika virus.

One of the objects of the invention is thus to provide a means of preventing and/or treating Zika virus infections.

One of the objects of the invention is thus to provide a vaccine against the Zika virus.

The present invention is based on the unexpected results of the Inventors, according to which Zika-HBV fusion proteins are capable of forming subviral, non-infectious and immunogenic particles that are well structured and efficaciously secreted and that can be used to prevent and/or treat Zika virus infections.

The interest in such fusion proteins lies in preventing and/or treating Zika virus infections and/or hepatitis B virus infections, i.e. inducing double immunization against the Zika virus and the hepatitis B virus.

An additional interest of the invention can be found in the fact that it can be easily adapted to existing industrial manufacturing chains for currently commercialized vaccines against hepatitis B.

This is why one of the objects of the invention is an immunogenic Zika-HBV fusion protein.

Another object of the invention is a nucleic acid molecule coding an immunogenic Zika-HBV fusion protein.

Another object of the invention is a vector comprising a nucleic acid molecule coding an immunogenic Zika-HBV fusion protein.

Another object of the invention is a subviral, non-infectious and immunogenic particle comprising at least one immunogenic Zika-HBV fusion protein.

Another object of the invention is an immunogenic Zika-HBV fusion protein for use as a medication.

Another object of the invention is an immunogenic Zika-HBV fusion protein for use in the prevention and/or treatment of hepatitis B and/or Zika virus infections.

Another object of the invention is a cellular line that expresses subviral, non-infectious and immunogenic particles comprising at least one immunogenic Zika-HBV fusion protein.

Finally, another object of the invention is a method for producing subviral, non-infectious and immunogenic particles comprising at least one immunogenic Zika-HBV fusion protein.

In a first embodiment, the invention thus relates to an immunogenic fusion protein comprising at least the two following peptides:

a) —on the C-terminal side, a first peptide constituted of:

the amino acid sequence of the protein S or the protein M of a human hepatitis B virus (HBV) isolate, which protein S or protein M is optionally deleted at the N-terminal end thereof, or an amino acid sequence with a percent identity of at least 91%, notably at least 93%, particularly at least 95% and more particularly at least 97%, with said amino acid sequence of the protein S or the protein M optionally deleted at the N-terminal end thereof, provided that said amino acid sequence maintains the ability to form subviral, non-infectious particles and/or immunogenic properties against the HBV virus, or, the amino acid sequence of a natural variant from another isolate of the HBV, or of a synthetic variant derived from said amino acid sequence of the protein S or the protein M optionally deleted at the N-terminal end thereof, provided that said amino acid sequence maintains the ability to form subviral, non-infectious particles and/or immunogenic properties against the HBV virus, and b) —on the N-terminal side, a second peptide constituted of:

the sequence of amino acids of at least one transmembrane domain and the ectodomain of at least one protein of a Zika virus isolate selected from the envelope protein, an amino acid sequence with a percent identity of at least 90%, notably at least 95%, with said amino acid sequence of at least one transmembrane domain and the ectodomain of at least one protein of a Zika virus isolate, provided that said amino acid sequence maintains the ability to form subviral, non-infectious particles and/or immunogenic properties against the Zika virus, or the amino acid sequence of a natural variant from another isolate of the Zika virus, or of a synthetic variant derived from said amino acid sequence of at least one transmembrane domain and the ectodomain of at least one protein of a Zika virus isolate, provided that said amino acid sequence maintains the ability to form subviral, non-infectious particles and/or immunogenic properties against the Zika virus, said protein of a Zika virus isolate being chosen from among the envelope protein E or a fusion peptide comprising the envelope protein E and the protein prM.

The expression "fusion protein" refers to any artificial/chimeric protein comprising at least the protein S or the protein M of the HBV, optionally deleted at the N-terminal end thereof, and at least one transmembrane domain and the ectodomain of at least one envelope protein E of a Zika virus isolate. Examples of such fusion proteins are represented in FIGS. 8, 10, 12, 14, 16, 18, 20 and 22.

The term "protein S" or "wild-type protein S" or "S" or "HBs-S(HBV)" refers to:

the envelope protein of an HBV isolate notably comprising 226 amino acids and comprising four transmembrane domains (FIG. 1), and notably the envelope protein of the HBVadw isolate, or any amino acid sequence with a percent identity of at least 91% with the amino acid sequence of the protein S of an HBV isolate, or the natural variant(s) of the protein S of all the HBV isolates, or the synthetic variant(s) of said protein S.

The wild-type protein S contains four transmembrane domains, but does not contain an ectodomain. It possesses an antigenic loop that corresponds to the amino acids situated between the transmembrane domains 2 and 3. The wild-type protein S is represented, for example, by SEQ ID NO. 2.

The term "protein M" or "wild-type protein M" or "M" or "HBs-M(HBV)" refers to:

the envelope protein of an HBV isolate notably comprising 281 amino acids and comprising four transmembrane domains (FIGS. 2A and 2B), and notably the envelope protein of the HBVadw isolate, or any amino acid sequence with a percent identity of at least 91% with the amino acid sequence of the protein M of an HBV isolate, or the natural variant(s) of the protein M of all the HBV isolates, or the synthetic variant(s) of said protein M.

The protein M sequence differs from that of the protein S through the presence of the N-terminal end of 55 additional amino acids. These 55 amino acids correspond to the preS2 domain.

The wild-type protein M contains four transmembrane domains and a preS2 domain. The wild-type protein M is represented, for example, by SEQ ID NO. 4.

The expression "optionally deleted at the N-terminal end thereof" means that all (or nearly all) or part of the protein S or the protein M is used in the invention's fusion proteins. More precisely:

if the protein S is not deleted at the N-terminal end thereof, all (or nearly all) of the protein S sequence, as defined above, is used in the invention's fusion proteins;

if the protein S is deleted at the N-terminal end thereof, said protein S is deleted from its transmembrane domain located at the N-terminal end thereof and is named delete S in such a case. In such a case, said protein S is thus essentially constituted of its three transmembrane domains located at the C-terminal end thereof. Thus, this is also understood, in the protein S defined above, to be the deletion of the region from the amino acid in position 1 to that in position 23 of the protein S of an HBV isolate;

if the protein M is not deleted at the N-terminal end thereof, all (or nearly all) of the protein M sequence, as defined above, is used in the invention's fusion proteins. In this particular embodiment, said protein M is thus not deleted in its preS2 domain;

if the protein M is deleted at the N-terminal end thereof, said protein M is deleted from its preS2 domain (i.e. the domain constituted of the amino acids located position 1 to position 55 of the N-terminal end) and is named delete M in such a case. Thus, said protein M is deleted from a sequence of 1 to 54 amino acids located at the N-terminal end thereof. A deletion of a sequence of 1 to 54 amino acids is understood to be a deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 and 54 amino acids. In a particular embodiment of the invention, said protein M is deleted from a sequence of 54 amino acids located at the N-terminal end thereof. In such a case, said protein M thus remains essentially constituted of its four transmembrane domains, despite the deletion. The protein M fully deleted from its preS2 domain corresponds to the non-deleted protein S.

A protein S deleted at the N-terminal end thereof is represented, for example, by SEQ ID NO. 1.

A protein M deleted at the N-terminal end thereof is represented, for example, by SEQ ID NO. 3.

In a particular embodiment of the invention, the deleted amino acids are contiguous.

The expression "nearly all" means that the proteins S or M may be deleted from some amino acids at the N or C-terminal ends thereof when they are present in the fusion proteins according to the invention. For example, the methionine (M) in position 1 of SEQ ID NO. 2 and SEQ ID NO. 4 may not be present in the fusion protein sequences according to the invention.

The expression "N-terminal end" is understood to be the "N-terminal side" or the "N-terminal."

The expression "C-terminal end" is understood to be the "C-terminal side" or the "C-terminal."

In the fusion proteins according to the invention, when said protein S is deleted at the N-terminal end thereof, the transmembrane domain of the protein of a Zika virus isolate, notably the envelope protein E, replaces the one deleted at the N-terminal of the HBV protein S.

Alternatively, in the fusion proteins according to the invention, when said protein S is not deleted at the N-terminal end thereof, the C-terminal end of the protein of a Zika virus isolate, and more particularly the second transmembrane domain of the envelope protein E of the Zika virus, is fused to the first amino acids at the N-terminal end of the HBV protein S.

Alternatively, in the fusion proteins according to the invention, when said protein M is deleted at the N-terminal end thereof, the transmembrane domain of the protein of a Zika virus isolate replaces the sequence deleted from 1 to 54 amino acids in the N-terminal of the HBV protein M.

Alternatively, in the fusion proteins according to the invention, when said protein M is not deleted at the N-terminal end thereof, the transmembrane domain of the protein of a Zika virus isolate is fused to the preS2 domain at the N-terminal end of the HBV protein M.

The expression "isolate of the human hepatitis B virus" or "isolate of the human HBV" means any isolate belonging to the family Hepadnaviridae and the genus *Orthohepadnavirus*, or any isolate classified by the International Committee for the Taxonomy of Viruses (ICTV) as being related to the HBV [Schaefer S. Hepatitis B virus taxonomy and hepatitis B virus genotypes. World J Gastroenterol. 2007 Jan. 7: 13(1):14-21].

In a particular embodiment, the human HBV isolate in the fusion protein mentioned above is the HBVadw isolate.

The term "Zika virus isolate" means any isolate belonging to the family Flaviviridae and the genus *Flavivirus*, or any isolate classified by the International Committee for the Taxonomy of Viruses (ICTV) as being related to the Zika virus.

In a particular embodiment, the Zika virus isolate in the fusion protein mentioned above is the isolate described under GenBank accession number KU312312.1 (Enfissi et al., Lancet. 2016 Jan. 16:387(10015):227-8. Doi: 10.1016/S0140-6736(16)00003). In a particular embodiment, said Zika virus isolate is represented by SEQ ID NO. 29.

In a particular embodiment, the Zika virus isolate in the fusion protein mentioned above is the isolate described under GenBank accession number KU321639 (First Complete Genome Sequence of Zika Virus (Flaviviridae, Flavivirus) from an Autochtonous Transmission in Brazil. Cunha M S, Esposito D L, Rocco I M, Maeda A Y, Vasami F G, Nogueira J S, de Souza R P, Suzuki A, Addas-Carvalho M, Barjas-Castro Mde L, Resende M R, Stucchi R S, Boin Ide F, Katz G, Angerami R N, da Fonseca B A. Genome Announc. 2016 Mar. 3:4(2). Pii: e00032-16. Doi: 0.1128/genomeA.00032-16). In a particular embodiment, said Zika virus isolate is represented by SEQ ID NO. 52. It is SEQ ID NO. 52 that was used to determine the cartography of Zika in the present invention.

In a particular embodiment of the invention, the Zika virus is the human Zika virus.

The expression "percent identity" means the percentage determined by the direct comparison of two sequences (nucleic or protein) by determining the number of nucleic acids or amino acid residues common to both sequences, then dividing this by the number of nucleic acids or amino acid residues in the longer of the two sequences and multiplying the result by 100.

The expression "at least 91%" means 91%, 92%, 93%, 94%, 95%, 96%, 97%, 98%, 99% and 100%.

The expression "at least 90%" means 90%, 91%, 92%, 93%, 94%, 95%, 96%, 97%, 98%, 99% and 100%.

The expression "maintains the ability to form subviral, non-infectious particles" refers to the ability of any protein, notably the protein S of the human HBV virus, particularly of the protein S deleted from its transmembrane domain at the N-terminal end thereof, and more particularly of a fusion protein of the invention comprising, for example, the protein S deleted at the N-terminal, to assemble in the presence of the wild-type protein S. This also refers to the ability of the wild-type proteins S to assemble themselves into filamentous or spherical subviral particles.

The protein M of the human HBV virus, optionally deleted from a sequence of 1 to 54 amino acids located at the N-terminal end thereof, also possesses the ability to assemble in the presence of the wild-type protein S.

The protein E of the Zika virus, optionally deleted from a transmembrane domain at the N-terminal end thereof, also possesses the ability to assemble in the presence of the wild-type protein S.

The protein prM of the Zika virus also possesses the ability to assemble in the presence of the wild-type protein S.

Said ability to form subviral particles may also be demonstrated through observation, notably through an electron microscope analysis, and notably through the test mentioned in examples 1 and 2.

The term "assemble" or "assembly" refers to the ability of a protein to form subviral particles by combining with the wild-type protein S. The term "self-assembly" is to be understood as the ability of a protein to form subviral particles by itself.

The term "immunogenic/immunogenic properties" means that the fusion proteins according to the invention are provided with antigenic properties and are capable of inducing a reaction or an immune response.

In particular, a protein is considered immunogenic to HBV if, after immunization, it induces an anti-S and/or anti-M humoral response, as detected, for example:

according to a protocol described by Huzly et al., 2008 [Huzly D, Schenk T, Jilg W, Neumann-Haefelin D. Comparison of nine commercially available assays for quantification of antibody response to hepatitis B virus surface antigen. *J Clin Microbiol.* 2008 April, 46(4): 1298-306], or by performing immunoblots associated with a revelation by an anti-HBs antibody (e.g. the R247 antibody, as mentioned by Jenna, S., and C. Sureau. Mutations in the carboxyl-terminal domain of the small hepatitis B virus envelope protein impair the assembly of hepatitis delta virus particles. J. Virol. 1999. 73: 3351-3358). Such an antibody may demonstrate a greater size of the fusion protein according to the invention. Such tests allow it to be determined, for example, whether the amino acid sequences or the fusion proteins according to the invention maintain the immunogenic properties against the human HBV.

A protein is considered immunogenic to Zika if, after immunization, it induces an anti-E and/or anti-prM humoral response, as detected, for example:

by a sandwich ELISA test involving the 4G2 antibody (clone D1-4G2-4-15, commercialized by Millipore under the reference number MAB10216). This antibody is directed against *Flavivirus* antigens, and it thus allows the immunocapture of particles comprising such antigens and their detection using immunoenzymatic techniques; or by performing immunoblots associated with a revelation by an anti-Zika antibody commercialized by Biofront Technologies under the reference number BF-1176-56 (clone 0302156). Such tests allow it to be determined, for example, whether the amino acid sequences or the fusion proteins according to the invention maintain the immunogenic properties against the Zika virus.

The expression "natural variant" refers to all variability, all polymorphism, all diversity of a DNA sequence, of an allele, of a protein sequence, or more generally, of any protein or nucleic sequence, between the isolates of a single species or a single population. The percent of natural variability is determined through a direct comparison of two molecules (polypeptides or polynucleotides), derived from a wild-type reference molecule with biological properties of interest, such as immunogenic properties and/or the ability to form subviral particles. This is quantified by determining the exact number of amino acid or nucleic acid residues, identical between the two sequences, then dividing them by the number of amino acid or nucleic acid residues of the shorter of the two sequences and multiplying the result by 100.

The expression "synthetic variant" refers to any polypeptide molecule (amino acid sequence) or polynucleotide molecule (nucleic acid sequence), according to the invention, derived by recombining a wild-type reference molecule through addition, deletion or substitution of one or more nucleic acids or amino acids in said wild-type reference molecule, provided that it maintains the biological properties of interest, such as immunogenic properties and/or the ability to form subviral particles. The percent of synthetic variability is determined through a direct comparison of said molecule derived from said wild-type reference molecule, by determining the exact number of amino acid or nucleic acid residues, identical between the two sequences, with regard to their position and nature, then dividing them by the number of amino acid or nucleic acid residues of the shorter of the two sequences and multiplying the result by 100.

The term "envelope protein E" or "wild-type envelope protein E" or E(Zika) refers to the structural protein of a Zika virus isolate, and notably:

- the protein of a Zika virus isolate notably comprising 504 amino acids and consisting of two transmembrane domains (FIG. 3), and notably the protein of the Zika isolate with SEQ ID NO. 29 or SEQ ID NO. 52, or
- any amino acid sequence presenting a percent identity of at least 90% with the amino acid sequence of the envelope protein E of a Zika virus isolate, or
- the natural variant(s) of the envelope protein E of all the Zika virus isolates, or the synthetic variant(s) of the envelope protein E.

The wild-type protein E comprises 2 transmembrane domains and an ectodomain. The wild-type protein E is represented, for example, by SEQ ID NO. 15.

In one embodiment of the invention, in the above-mentioned fusion proteins, said envelope protein E comprises its two transmembrane domains.

In another embodiment of the invention, in the above-mentioned fusion proteins, said envelope protein E comprises only one of its two transmembrane domains. In such a case, it is always the second transmembrane domain of E (i.e. the one located at the C-terminal end thereof, from position 485 to position 504) that is deleted. In such a case, said envelope protein E is named deleted E. The first transmembrane domain of the envelope protein E is never involved in a deletion.

In one embodiment of the invention, the ectodomain of the envelope protein E is understood to be the amino acids in position 1 to the amino acids in position 455.

In one embodiment of the invention, the first transmembrane domain of the envelope protein E is understood to be the amino acids in position 456 to the amino acids in position 484. The last seven amino acids in the C-terminal position (i.e. the amino acids in positions 478 to 484) correspond to an extramembrane loop that binds the first and the second transmembrane domains.

In one embodiment of the invention, the second transmembrane domain of the envelope protein E is understood to be the amino acids in position 485 to the amino acids in position 504.

According to a particularly advantageous embodiment of the invention, the transmembrane domains of the envelope protein E are deleted from at least one of the last three amino acids, and notably from the last three amino acids, located in the C-terminal position. Said deletion of at least one of the three amino acids, and notably of the last three amino acids, in the C-terminal position presents the advantage of deactivating the peptidase cleavage site, which is necessary for the maturation of the Zika polyprotein, but which is not necessary in the scope of chimeric constructions of the present invention.

The term "protein prM" or "wild-type protein prM" refers to the structural protein of a Zika virus isolate, and notably:

- the protein of a Zika virus isolate notably comprising 164 amino acids and containing two transmembrane domains (FIG. 4), and notably the protein of the Zika virus isolate from SEQ ID NO. 29 or SEQ ID NO. 52, or
- any amino acid sequence presenting a percent identity of at least 90% with the amino acid sequence of the protein prM of a Zika virus isolate, or
- the natural variant(s) of the protein prM of all the Zika virus isolates, or the synthetic variant(s) of the protein prM.

The protein prM is in its native form in the polyprotein comprising the fusion proteins according to the invention: the sequence of the protein prM is complete/whole in the polyprotein comprising the fusion proteins according to the invention. In other words, the protein prM is never deleted from one or both transmembrane domains in the fusion proteins according to the invention.

The wild-type protein prM comprises 2 transmembrane domains and an ectodomain. The protein prM is constituted of a pro-peptide portion and an M portion (prM=pro-peptide (pr)+M). The protein pr/M undergoes two cleavages, one located at the junction between the pro-peptide and M, the second at the junction between M and E; these cleavages take place before assembly of the particle in the cell by two cellular proteases. In the present invention, the production of the protein prM in the context of the polyprotein containing the fusion protein is sought to allow the correct three-dimensional folding of the Zika envelope protein E included in the chimeric proteins. This three-dimensional folding is necessary to minimize the non-specific aggregation of the Zika protein E included in the chimeric protein, an incident capable of inducing the premature degradation of the chimeric protein by the proteasome. Likewise, the three-dimensional folding of the protein E under the dependence of prM allows an optimal presentation of the protein E included in the chimeric protein to the immune system in the scope of its use as an anti-Zika immunogen. The integral protein prM is considered a chaperone protein of the Zika protein E, as this function is described in the literature on flaviviruses (Roby J A, Setoh Y X, Hall R A, Khromykh A A, J Gen Virol. 2015 July: 96(Pt 7):1551-69. Doi: 10.1099/vir.0.000097).

In one embodiment of the invention, the ectodomain of the uncleaved protein prM is understood to be the amino acids in position 1 to the amino acids in position 123.

In one embodiment of the invention, the ectodomain of the cleaved protein prM is understood to be the amino acids in position 90 to the amino acids in position 123.

In one embodiment of the invention, the first transmembrane domain of the protein prM is understood to be the amino acids in position 124 to the amino acids in position 143 or from position 124 to 149 if the first transmembrane domain also comprises the amino acids in position 144 to 149 corresponding to the extramembrane loop that binds the first and second transmembrane domains.

In one embodiment of the invention, the second transmembrane domain of the protein prM is understood to be the amino acids in position 150 to the amino acids in position 164.

In one embodiment of the invention, the pro-peptide portion of the protein prM is understood to be the amino acids in position 1 to the amino acids in position 89. The pro-peptide portion is thus part of the ectodomain.

In one embodiment of the invention, the M portion of the protein prM is understood to be the amino acids in position 90 to the amino acids in position 164.

The wild-type protein prM is represented, for example, by SEQ ID NO. 50.

The interest in using the protein prM could, for example, be the improvement of the addressing and/or immunogenicity of the fusion proteins according to the invention.

The invention also relates to a fusion protein having an amino acid sequence presenting a percent identity of at least 83%, notably of at least 85%, particularly of at least 90%, and more particularly of at least 95% with the amino acid sequence of an above-mentioned fusion protein.

In a particular embodiment, in said above-mentioned fusion protein, the first peptide located on the C-terminal side is constituted of:

- the amino acid sequence of the protein S of a human HBV isolate, which protein S is deleted from its transmembrane domain located at the N-terminal end thereof, or
- an amino acid sequence presenting a percent identity of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or the immunogenic properties against the human HBV, or,
- the amino acid sequence of a natural variant from another variant of the human HBV isolate, or of a synthetic variant derived from said amino acid sequence of the protein S deleted from its transmembrane domain located at the N-terminal end thereof, provided that said amino acid sequence maintains the ability to form subviral, non-infectious particles and/or the immunogenic properties against the human HBV.

In another particular embodiment, in said above-mentioned fusion protein, the first peptide located on the C-terminal side is constituted of:

- the amino acid sequence of the protein S of a human HBV isolate, which protein S is not deleted from its transmembrane domain located at the N-terminal end thereof, or
- an amino acid sequence presenting a percent identity of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or the immunogenic properties against the human HBV, or,
- the amino acid sequence of a natural variant from another variant of the human HBV isolate, or of a synthetic variant derived from said amino acid sequence of the protein S not deleted from its transmembrane domain located at the N-terminal end thereof, provided that said amino acid sequence maintains the ability to form subviral, non-infectious particles and/or the immunogenic properties against the human HBV.

In another particular embodiment, in said above-mentioned fusion protein, the first peptide located on the C-terminal side is constituted of:

- the amino acid sequence of the protein M of a human HBV isolate, which protein M is deleted from a sequence of 1 to 54 amino acids located at the N-terminal end thereof, or
- an amino acid sequence presenting a percent identity of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV, or,
- the amino acid sequence of a natural variant from another variant of the human HBV isolate, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV.

In another particular embodiment, in said above-mentioned fusion protein, the first peptide located on the C-terminal side is constituted of:

- the amino acid sequence of the protein M of a human HBV isolate, which protein M is not deleted from a sequence of 1 to 54 amino acids located at the N-terminal end thereof, or
- an amino acid sequence presenting a percent identity of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV, or,
- the amino acid sequence of a natural variant from another variant of the human HBV isolate, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV.

In another particular embodiment, in said above-mentioned fusion protein, the second peptide located on the N-terminal side is constituted of:

- the amino acid sequence of at least one transmembrane domain and the ectodomain of the envelope protein E of a Zika virus isolate, or
- an amino acid sequence presenting an identity percent of at least 90%, notably of at least 95%, with said amino acid sequence of at least one transmembrane domain and the ectodomain of the envelope protein E of a Zika virus isolate, provided that said amino acid sequence maintains the ability to form subviral, non-infectious particles and/or the immunogenic properties against the Zika virus, or
- the amino acid sequence of a natural variant from another Zika virus isolate, or of a synthetic variant derived from said amino acid sequence of at least one transmembrane domain and the ectodomain of the envelope protein E of a Zika virus isolate, provided that said amino acid sequence maintains the ability to form subviral, non-infectious particles and/or the immunogenic properties against the Zika virus.

In another particular embodiment, in said above-mentioned fusion protein, the second peptide located on the N-terminal side is constituted of:

- the amino acid sequence comprising only one of the two transmembrane domains and the ectodomain of the envelope protein E of a Zika virus isolate, or
- an amino acid sequence presenting an identity percent of at least 90%, notably of at least 95%, with said amino acid sequence comprising only one of the two transmembrane domains and the ectodomain of the envelope protein E of a Zika virus isolate, provided that said amino acid sequence maintains the ability to form subviral, non-infectious particles and/or the immunogenic properties against the Zika virus, or
- the amino acid sequence of a natural variant from another Zika virus isolate, or of a synthetic variant derived from said amino acid sequence comprising only one of the two transmembrane domains and the ectodomain of the envelope protein E of a Zika virus isolate, provided that said amino acid sequence maintains the ability to form subviral, non-infectious particles and/or the immunogenic properties against the Zika virus.

In another particular embodiment, in said above-mentioned fusion protein, the second peptide located on the N-terminal side is constituted of:

the amino acid sequence comprising both transmembrane domains and the ectodomain of the envelope protein E of a Zika virus isolate, or an amino acid sequence presenting an identity percent of at least 90%, notably of at least 95%, with said amino acid sequence comprising both transmembrane domains and the ectodomain of the envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising both transmembrane domains and the ectodomain of the envelope protein E of a Zika virus isolate, provided that said amino acid sequence maintains the ability to form subviral, non-infectious particles and/or the immunogenic properties against the Zika virus.

In another particular embodiment, in said above-mentioned fusion protein, the second peptide located on the N-terminal side is constituted of:

the amino acid sequence of a fusion peptide comprising at least one transmembrane domain and the ectodomain of the envelope protein E of a Zika virus isolate and the protein prM of a Zika virus isolate, or an amino acid sequence presenting an identity percent of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the Zika virus.

In another particular embodiment, in said above-mentioned fusion protein, the second peptide located on the N-terminal side is constituted of:

the amino acid sequence of a fusion peptide comprising both transmembrane domains and the ectodomain of the envelope protein E of a Zika virus isolate and the protein prM of a Zika virus isolate, or an amino acid sequence presenting an identity percent of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the Zika virus.

In another particular embodiment, in said above-mentioned fusion protein, the second peptide located on the N-terminal side is constituted of:

the amino acid sequence of a fusion peptide comprising only one of the two transmembrane domains and the ectodomain of the envelope protein E of a Zika virus isolate and the protein prM of a Zika virus isolate, or an amino acid sequence presenting an identity percent of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the Zika virus.

In a particular embodiment, the present invention relates to an immunogenic fusion protein comprising at least the two following peptides:

a) —on the C-terminal side, a first peptide constituted of:

the amino acid sequence of the protein S of a human HBV isolate, which protein S is deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising only one of the two transmembrane domains and the ectodomain of an envelope protein E of a Zika virus isolate, or an amino acid sequence presenting an identity percentage of at least 90%, notably of at least 95%, with said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising both transmembrane domains and the ectodomain of an envelope protein E of a Zika virus isolate, or an amino acid sequence presenting an identity percentage of at least 90%, notably of at least 95%, with said amino acid sequence comprising both transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising both transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising both transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is not deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S not deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate, or an amino acid sequence presenting an identity percentage of at least 90%, notably of at least 95%, with said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is not deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S not deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is not deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S not deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising both transmembrane domains and the ectodomain of an envelope protein E of a Zika virus isolate, or an amino acid sequence presenting an identity percentage of at least 90%, notably of at least 95%, with said amino acid sequence comprising both transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising both transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein S of a human HBV isolate, which protein S is not deleted from its transmembrane domain located at the N-terminal end thereof, or an amino acid sequence presenting an identity percentage of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein S not deleted from its transmembrane domain located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising both transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising only one of the two transmembrane domains and the ectodomain of an envelope protein E of a Zika virus isolate, or an amino acid sequence presenting an identity percentage of at least 90%, notably of at least 95%, with said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising both transmembrane domains and the ectodomain of an envelope protein E of a Zika virus isolate, or an amino acid sequence presenting an identity percentage of at least 90%, notably of at least 95%, with said amino acid sequence comprising both transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising both transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is not deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising only one of the two transmembrane domains and the ectodomain of an envelope protein E of a Zika virus isolate, or an amino acid sequence presenting an identity percentage of at least 90%, notably of at least 95%, with said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising only one of the two transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is not deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising only one of the two transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is not deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence comprising both transmembrane domains and the ectodomain of an envelope protein E of a Zika virus isolate, or an amino acid sequence presenting an identity percentage of at least 90%, notably of at least 95%, with said amino acid sequence comprising both transmembrane domains and the ectodomain of an envelope protein E of a Zika virus isolate, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence comprising both transmembrane domains and the ectodomain of an envelope protein E of a Zika virus isolate, provided that said amino acid sequence maintains the ability to form subviral, non-infectious particles and/or the immunogenic properties against the human Zika virus.

In another particular embodiment, the present invention relates to an immunogenic fusion protein comprising at least the two following peptides:

a) —on the C-terminal side, a first peptide constituted of:

the amino acid sequence of the protein M of a human HBV isolate, which protein M is not deleted from a sequence of 1 to 54 amino acids located at the N-terminal end thereof, or an amino acid sequence presenting an identity percentage of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, or the amino acid sequence of a natural variant from another human HBV virus isolate, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV virus, and b) —on the N-terminal side, a second peptide constituted of:

the amino acid sequence of a fusion peptide comprising both transmembrane domains and the ectodomain of an envelope protein E of a Zika virus isolate and the protein prM of a Zika virus isolate, or an amino acid sequence presenting an identity percentage of at least 90%, notably of at least 95%, with said amino acid sequence of said fusion peptide, provided that said amino acid sequence maintains the ability to form subviral, non-infectious particles and/or the immunogenic properties against the Zika virus, or the amino acid sequence of a natural variant from another Zika virus isolate, or of a synthetic variant derived from said amino acid sequence of said fusion peptide, provided that said amino acid sequence maintains the ability to form subviral, non-infectious particles and/or the immunogenic properties against the human Zika virus.

In a particular embodiment, the present invention relates to an above-mentioned fusion protein, said protein also comprising another peptide at the N-terminal end thereof (i.e. at the N-terminal end of the second peptide) constituted of:

- the amino acid sequence of a transfer initiation peptide of a Zika virus isolate, or
- an amino acid sequence presenting an identity percent of at least 83%, notably of at least 85%, particularly of at least 90%, and more particularly of at least 95%, with said amino acid sequence of the transfer initiation peptide of a Zika virus isolate, provided that said amino acid sequence maintains the properties of a transfer initiation peptide,
- the amino acid sequence of a natural variant from another Zika virus isolate, or of a synthetic variant derived from said amino acid sequence of said transfer initiation peptide, provided that said amino acid sequence maintains the properties of a transfer initiation peptide.

In a particular embodiment of the invention, the transfer initiation peptide sequence corresponds to the 19 C-terminal amino acids of the sequence coding the capsid (core) protein of the Zika virus, and is notably represented by SEQ ID NO. 25. The synthesis of this transfer initiation peptide (and consequently the fusion protein) is initiated by an initiation codon internal to the sequence coding the capsid protein (notably represented by SEQ ID NO. 27), located 17 codons before the first codon coding this transfer initiation peptide. Advantageously, a transfer initiation peptide of the art is used in the fusion proteins whose Zika virus isolate protein comprises a fusion peptide comprising the envelope protein E and the protein prM.

In another embodiment of the invention, the transfer initiation peptide sequence corresponds to the second transmembrane domain of prM, i.e. to the 15 amino acids located at the C-terminal end of prM, and is notably represented by SEQ ID NO. 26. The synthesis of this transfer initiation peptide is initiated by introduction through directed mutagenesis of an initiation codon (notably represented by SEQ ID NO. 28), located 9 codons before the first codon coding this transfer initiation peptide. Advantageously, a transfer initiation peptide of the art is used in the fusion proteins whose Zika virus isolate protein comprises only the envelope protein E.

The insertion of a transfer initiation peptide at the N-terminal end of the above-mentioned fusion protein is particularly advantageous in that it adds the properties of a transfer initiation peptide to the fusion peptide according to the invention. In particular, this allows co-translational address of the invention to the endoplasmic reticulum, such that it is correctly glycolyzed and that its three-dimensional conformation and/or that its antigenic qualities do not present substantial alterations with regards to the wild-type proteins.

In a particular embodiment, the present invention relates to the above-mentioned fusion protein in which the first and second peptides are contiguous and the C-terminal end of the second peptide is covalently bonded to the N-terminal end of the first peptide.

In a particular embodiment, the above-mentioned fusion protein is capable of forming spherical and/or filamentous subviral, non-infectious and immunogenic particles.

In a particular embodiment of the invention, a binding peptide binds the first and second peptides constituting the above-mentioned fusion protein, said binding peptide being constituted of 1 amino acid, or of 2 amino acids, or of 3 amino acids, or of 4 amino acids, or of 5 amino acids, provided that said fusion protein maintains the ability to form subviral, non-infectious particles and/or immunogenic properties against the human HBV and/or the Zika virus.

In another particular embodiment, the present invention relates to an above-mentioned fusion protein, in which the first peptide in the C-terminal position is constituted of:

- an amino acid sequence defined by the contiguous amino acids located from position 24 to position 226 of the protein S of a human HBV isolate, notably the amino acid sequence represented by SEQ ID NO. 1, or
- an amino acid sequence presenting an identity percent of at least 91%, notably of at least 93%, particularly of at least 95%, and more particularly of at least 97%, with said amino acid sequence of the protein S deleted from its transmembrane domain located at the N-terminal end thereof, provided that said amino acid sequence maintains the ability to form subviral, non-infectious particles and/or immunogenic properties against the HBV virus, or,
- the amino acid sequence of a natural variant from another isolate of the HBV, or of a synthetic variant derived from said amino acid sequence of the protein S deleted from its transmembrane domain at the N-terminal end thereof, provided that said amino acid sequence maintains the ability to form subviral, non-infectious particles and/or immunogenic properties against the HBV virus.

The term "position 24" refers to the amino acid 24 of the sequence of the protein S of the human HBV, the amino acid 1 being the first amino acid from the N-terminal side, and the amino acid 226 being the first amino acid from the C-terminal side.

In another particular embodiment, the present invention relates to an above-mentioned fusion protein, in which the first peptide in the C-terminal position is constituted of:

- an amino acid sequence defined by the contiguous amino acids located from position 1 to position 226 of the protein S of a human HBV isolate, notably the amino acid sequence represented by SEQ ID NO. 2, or
- an amino acid sequence presenting an identity percent of at least 91%, notably of at least 93%, particularly of at least 95%, and more particularly of at least 97%, with said amino acid sequence of the protein S not deleted from its transmembrane domain located at the N-terminal end thereof, provided that said amino acid sequence maintains the ability to form subviral, non-infectious particles and/or immunogenic properties against the HBV virus, or,
- the amino acid sequence of a natural variant from another isolate of the HBV, or of a synthetic variant derived from said amino acid sequence of the protein S not deleted from its transmembrane domain at the N-terminal end thereof, provided that said amino acid sequence maintains the ability to form subviral, non-infectious particles and/or immunogenic properties against the HBV virus.

The sequence of the protein S not deleted at the N-terminal end thereof, SEQ ID NO. 2, corresponds to the complete sequence of the protein S, notably the protein S of the human HBVadw isolate.

In another particular embodiment, the present invention relates to an above-mentioned fusion protein, in which the first peptide in the C-terminal position is constituted of:

- an amino acid sequence defined by the contiguous amino acids located from position 55 to position 281 of the protein M of a human HBV isolate, notably the amino acid sequence represented by SEQ ID NO. 3, or an amino acid sequence presenting an identity percent of at least 91%, notably of at least 93%, particularly of at least 95%, and more particularly of at least 97%, with said amino acid sequence of the protein M deleted from a sequence of 1 to 54 amino acids located at the N-terminal end thereof, provided that said amino acid sequence maintains the ability to form subviral, non-infectious particles and/or immunogenic properties against the HBV virus, or, the amino acid sequence of a natural variant from another isolate of the HBV, or of a synthetic variant derived from said amino acid sequence of the protein M deleted from a sequence of 1 to 54 amino acids located at the N-terminal end thereof, provided that said amino acid sequence maintains the ability to form subviral, non-infectious particles and/or immunogenic properties against the HBV virus.

In another particular embodiment, the present invention relates to an above-mentioned fusion protein, in which the first peptide in the C-terminal position is constituted of:

an amino acid sequence defined by the contiguous amino acids located from position 1 to position 281 of the protein M of a human HBV isolate, notably the amino acid sequence represented by SEQ ID NO. 4, or an amino acid sequence presenting an identity percent of at least 91%, notably of at least 93%, particularly of at least 95%, and more particularly of at least 97%, with said amino acid sequence of the protein M not deleted from a sequence of 1 to 54 amino acids located at the N-terminal end thereof, provided that said amino acid sequence maintains the ability to form subviral, non-infectious particles and/or immunogenic properties against the HBV virus, or, the amino acid sequence of a natural variant from another isolate of the HBV, or of a synthetic variant derived from said amino acid sequence of the protein M not deleted from a sequence of 1 to 54 amino acids located at the N-terminal end thereof, provided that said amino acid sequence maintains the ability to form subviral, non-infectious particles and/or immunogenic properties against the HBV virus.

The sequence of the protein M not deleted from a sequence of 1 to 54 amino acids at the N-terminal end thereof, SEQ ID NO. 4, corresponds to the complete sequence of the protein M, notably the protein M of the human HBVadw isolate.

In another particular embodiment, the present invention relates to an above-mentioned fusion protein, in which the second peptide in the N-terminal position is constituted of:

an amino acid sequence defined by the contiguous amino acids located from position 1 to position 484 of the envelope protein E of a Zika virus isolate, notably the amino acid sequence represented by SEQ ID NO. 5, or an amino acid sequence presenting an identity percent of at least 90%, notably of at least 95%, with said amino acid sequence of the envelope protein E of a Zika virus isolate, provided that said amino acid sequence maintains the ability to form subviral, non-infectious particles and/or immunogenic properties against the Zika virus, or, the amino acid sequence of a natural variant from another isolate of the Zika virus, or of a synthetic variant derived from said amino acid sequence of the envelope protein E of a Zika virus, provided that said amino acid sequence maintains the ability to form subviral, non-infectious particles and/or immunogenic properties against the Zika virus.

In another particular embodiment, the present invention relates to an above-mentioned fusion protein, in which the second peptide in the N-terminal position is constituted of:

an amino acid sequence defined by the contiguous amino acids located from position 1 to position 504 of the envelope protein E of a Zika virus isolate, notably the amino acid sequence represented by SEQ ID NO. 15, or an amino acid sequence presenting an identity percent of at least 90%, notably of at least 95%, with said amino acid sequence of the envelope protein E of a Zika virus isolate, provided that said amino acid sequence maintains the ability to form subviral, non-infectious particles and/or immunogenic properties against the Zika virus, or, the amino acid sequence of a natural variant from another isolate of the Zika virus, or of a synthetic variant derived from said amino acid sequence of the envelope protein E of a Zika virus, provided that said amino acid sequence maintains the ability to form subviral, non-infectious particles and/or immunogenic properties against the Zika virus.

In another particular embodiment, the present invention relates to an above-mentioned fusion protein, in which the second peptide in the N-terminal position is constituted of:

an amino acid sequence of a fusion peptide comprising the contiguous amino acids located from position 1 to position 484 of the envelope protein E of a Zika virus isolate and the contiguous amino acids located from position 1 to position 164 of the protein prM of a Zika virus isolate, notably the amino acid sequence represented by SEQ ID NO. 6, or an amino acid sequence presenting an identity percent of at least 90%, notably of at least 95%, with said amino acid sequence of said fusion peptide, provided that said amino acid sequence maintains the ability to form subviral, non-infectious particles and/or immunogenic properties against the Zika virus, or, the amino acid sequence of a natural variant from another isolate of the Zika virus, or of a synthetic variant derived from said amino acid sequence of said fusion peptide, provided that said amino acid sequence maintains the ability to form subviral, non-infectious particles and/or immunogenic properties against the Zika virus.

In another particular embodiment, the present invention relates to an above-mentioned fusion protein, in which the second peptide in the N-terminal position is constituted of:

an amino acid sequence of a fusion peptide comprising the contiguous amino acids located from position 1 to position 504 of the envelope protein E of a Zika virus isolate and the contiguous amino acids located from position 1 to position 164 of the protein prM of a Zika virus isolate, notably the amino acid sequence represented by SEQ ID NO. 16, or an amino acid sequence presenting an identity percent of at least 90%, notably of at least 95%, with said amino acid sequence of said fusion peptide, provided that said amino acid sequence maintains the ability to form subviral, non-infectious particles and/or immunogenic properties against the Zika virus, or, the amino acid sequence of a natural variant from another isolate of the Zika virus, or of a synthetic variant derived from said amino acid sequence of said fusion peptide, provided that said amino acid sequence maintains the ability to form subviral, non-infectious particles and/or immunogenic properties against the Zika virus.

In a particular embodiment, a fusion protein such as those mentioned above comprises or is constituted of:

the amino acid sequence represented by SEQ ID NO. 7, or an amino acid sequence presenting an identity percent of at least 88%, notably of at least 89%, particularly of at least 92%, and more particularly of at least 95%, with said SEQ ID NO. 7, provided that said amino acid sequence maintains the ability to form subviral, non-infectious particles and/or immunogenic properties against the human HBV and/or the Zika virus, or the amino acid sequence of a synthetic variant derived from said SEQ ID NO. 7, provided that said amino acid sequence maintains the ability to form subviral, non-infectious particles and/or immunogenic properties against the human HBV and/or the Zika virus.

As indicated in Table 1 of the present patent application, SEQ ID NO. 7 corresponds to the fusion protein sequence "deleted E+deleted S." SEQ ID NO. 7 thus corresponds to the fusion of SEQ ID NO. 5 and SEQ ID NO. 1. However, it should be noted that in SEQ ID NO. 7, the last amino acid in the C-terminal (D, aspartic acid) of SEQ ID NO. 5 is not present. This presents the advantage of deactivating a peptidase cleavage site. This reasoning applies mutatis mutandis to the other fusion protein sequences according to the invention.

In a particular embodiment, the fusion protein of the above-mentioned SEQ ID NO. 7 also comprises a transfer initiation peptide located on the N-terminal side and comprises or is constituted of:

the amino acid sequence represented by SEQ ID NO. 17, or an amino acid sequence presenting an identity percent of at least 83%, notably at least 85%, particularly of at least 90%, and more particularly of at least 95%, with said SEQ ID NO. 17, provided that said amino acid sequence maintains the ability to form subviral, non-infectious particles and/or immunogenic properties against the human HBV and/or the Zika virus, or the amino acid sequence of a synthetic variant derived from said SEQ ID NO. 17, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 8, or an amino acid sequence presenting an identity percent of at least 88%, notably at least 89%, particularly of at least 92%, and more particularly of at least 95%, with said SEQ ID NO. 8, provided that said amino acid sequence maintains the ability to form subviral, non-infectious particles and/or immunogenic properties against the human HBV and/or the Zika virus, or the amino acid sequence of a synthetic variant derived from said SEQ ID NO. 8, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 8 also comprises a transfer initiation peptide located on the N-terminal side and comprises or is constituted of:

the amino acid sequence represented by SEQ ID NO. 18, or an amino acid sequence presenting an identity percent of at least 83%, notably at least 85%, particularly of at least 90%, and more particularly of at least 95%, with said SEQ ID NO. 18, provided that said amino acid sequence maintains the ability to form subviral, non-infectious particles and/or immunogenic properties against the human HBV and/or the Zika virus, or the amino acid sequence of a synthetic variant derived from said SEQ ID NO. 18, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 9, or an amino acid sequence presenting an identity percent of at least 88%, notably at least 89%, particularly of at least 92%, and more particularly of at least 95%, with said SEQ ID NO. 9, provided that said amino acid sequence maintains the ability to form subviral, non-infectious particles and/or immunogenic properties against the human HBV and/or the Zika virus, or the amino acid sequence of a synthetic variant derived from said SEQ ID NO. 9, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 9 also comprises a transfer initiation peptide located on the N-terminal side and comprises or is constituted of:

the amino acid sequence represented by SEQ ID NO. 19, or an amino acid sequence presenting an identity percent of at least 83%, notably at least 85%, particularly of at least 90%, and more particularly of at least 95%, with said SEQ ID NO. 19, provided that said amino acid sequence maintains the ability to form subviral, non-infectious particles and/or immunogenic properties against the human HBV and/or the Zika virus, or the amino acid sequence of a synthetic variant derived from said SEQ ID NO. 19, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 10, or an amino acid sequence presenting an identity percent of at least 88%, notably at least 89%, particularly of at least 92%, and more particularly of at least 95%, with said SEQ ID NO. 10, provided that said amino acid sequence maintains the ability to form subviral, non-infectious particles and/or immunogenic properties against the human HBV and/or the Zika virus, or the amino acid sequence of a synthetic variant derived from said SEQ ID NO. 10, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 10 also comprises a transfer initiation peptide located on the N-terminal side and comprises or is constituted of:

the amino acid sequence represented by SEQ ID NO. 20, or an amino acid sequence presenting an identity percent of at least 83%, notably at least 85%, particularly of at least 90%, and more particularly of at least 95%, with said SEQ ID NO. 20, provided that said amino acid sequence maintains the ability to form subviral, non-infectious particles and/or immunogenic properties against the human HBV and/or the Zika virus, or the amino acid sequence of a synthetic variant derived from said SEQ ID NO. 20, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 11, or an amino acid sequence presenting an identity percent of at least 88%, notably at least 89%, particularly of at least 92%, and more particularly of at least 95%, with said SEQ ID NO. 11, provided that said amino acid sequence maintains the ability to form subviral, non-infectious particles and/or immunogenic properties against the human HBV and/or the Zika virus, or the amino acid sequence of a synthetic variant derived from said SEQ ID NO. 11, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 11 also comprises a transfer initiation peptide located on the N-terminal side and comprises or is constituted of:

the amino acid sequence represented by SEQ ID NO. 21, or an amino acid sequence presenting an identity percent of at least 83%, notably at least 85%, particularly of at least 90%, and more particularly of at least 95%, with said SEQ ID NO. 21, provided that said amino acid sequence maintains the ability to form subviral, non-infectious particles and/or immunogenic properties against the human HBV and/or the Zika virus, or the amino acid sequence of a synthetic variant derived from said SEQ ID NO. 21, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 12, or an amino acid sequence presenting an identity percent of at least 88%, notably at least 89%, particularly of at least 92%, and more particularly of at least 95%, with said SEQ ID NO. 12, provided that said amino acid sequence maintains the ability to form subviral, non-infectious particles and/or immunogenic properties against the human HBV and/or the Zika virus, or the amino acid sequence of a synthetic variant derived from said SEQ ID NO. 12, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 12 also comprises a transfer initiation peptide located on the N-terminal side and comprises or is constituted of:

the amino acid sequence represented by SEQ ID NO. 22, or an amino acid sequence presenting an identity percent of at least 83%, notably at least 85%, particularly of at least 90%, and more particularly of at least 95%, with said SEQ ID NO. 22, provided that said amino acid sequence maintains the ability to form subviral, non-infectious particles and/or immunogenic properties against the human HBV and/or the Zika virus, or the amino acid sequence of a synthetic variant derived from said SEQ ID NO. 22, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 13, or an amino acid sequence presenting an identity percent of at least 88%, notably at least 89%, particularly of at least 92%, and more particularly of at least 95%, with said SEQ ID NO. 13, provided that said amino acid sequence maintains the ability to form subviral, non-infectious particles and/or immunogenic properties against the human HBV and/or the Zika virus, or the amino acid sequence of a synthetic variant derived from said SEQ ID NO. 13, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 13 also comprises a transfer initiation peptide located on the N-terminal side and comprises or is constituted of:

the amino acid sequence represented by SEQ ID NO. 23, or an amino acid sequence presenting an identity percent of at least 83%, notably at least 85%, particularly of at least 90%, and more particularly of at least 95%, with said SEQ ID NO. 23, provided that said amino acid sequence maintains the ability to form subviral, non-infectious particles and/or immunogenic properties against the human HBV and/or the Zika virus, or the amino acid sequence of a synthetic variant derived from said SEQ ID NO. 23, provided that said amino acid sequence maintains the ability to form subviral, non-infectious particles and/or immunogenic properties against the human HBV and/or the Zika virus.

In a particular embodiment, a fusion protein such as those mentioned above comprises or is constituted of:

the amino acid sequence represented by SEQ ID NO. 14, or an amino acid sequence presenting an identity percent of at least 88%, notably at least 89%, particularly of at least 92%, and more particularly of at least 95%, with said SEQ ID NO. 14, provided that said amino acid sequence maintains the ability to form subviral, non-infectious particles and/or immunogenic properties against the human HBV and/or the Zika virus, or the amino acid sequence of a synthetic variant derived from said SEQ ID NO. 14, provided that said amino acid sequence maintains the ability to form subviral, non-infectious particles and/or immunogenic properties against the human HBV and/or the Zika virus.

In a particular embodiment, the fusion protein of the above-mentioned SEQ ID NO. 14 also comprises a transfer initiation peptide located on the N-terminal side and comprises or is constituted of:

the amino acid sequence represented by SEQ ID NO. 24, or an amino acid sequence presenting an identity percent of at least 83%, notably at least 85%, particularly of at least 90%, and more particularly of at least 95%, with said SEQ ID NO. 24, provided that said amino acid sequence maintains the ability to form subviral, non-infectious particles and/or immunogenic properties against the human HBV and/or the Zika virus, or the amino acid sequence of a synthetic variant derived from said SEQ ID NO. 24, provided that said amino acid sequence maintains the ability to form subviral, non-infectious particles and/or immunogenic properties against the human HBV and/or the Zika virus.

Said SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24 also comprise, at the N-terminal ends thereof, the amino acid sequence allowing the synthesis of said transfer initiation peptide (and notably the initiation sequence of SEQ ID NO. 27 or SEQ ID NO. 28).

The initiating SEQ ID NO. 27 is more particularly used when the fusion protein according to the invention comprises the protein prM.

The initiating SEQ ID NO. 28 is more particularly used when the fusion protein according to the invention does not comprise the protein prM.

In a second embodiment, the present invention also relates to a nucleic acid molecule coding an above-mentioned fusion protein.

The expression “nucleic acid molecule” refers to a nucleic acid molecule comprising at least one sequence coding the protein S or the protein M of a human HBV isolate deleted at the N-terminal end thereof, and at least one sequence coding at least the transmembrane domain and the ectodomain of at least one envelope protein E of a Zika virus isolate, or any molecule from a molecule defined above and modified following the natural degeneration of its genetic code.

In an embodiment of the invention, this nucleic acid molecule is a hybrid. In a particular embodiment, the nucleic acid molecule mentioned above, coding an above-mentioned fusion protein, comprises at least the following two nucleic acid sequences:

a) —on side 3', a first constituted nucleic acid sequence coding the protein S or the protein M of a human hepatitis B virus (HBV) isolate, which protein S or protein M is optionally deleted at the N-terminal end thereof, or a nucleic acid sequence presenting an identity percent of at least 91%, notably of at least 93%, particularly of at least 95%, and more particularly of at least 97%, with said amino acid sequence of the protein S or the protein M optionally deleted at the N-terminal end thereof, provided that said protein coded by said nucleic acid sequence maintains the ability to form subviral, non-infectious particles and/or immunogenic properties against the human HBV, or the nucleic acid sequence of a natural variant from another human HBV isolate, or of a synthetic variant derived from said nucleic acid sequence of the protein S or the protein M optionally deleted at the N-terminal end thereof, provided that said protein coded by said nucleic acid sequence maintains the ability to form subviral, non-infectious particles and/or immunogenic properties against the human HBV, and b) —on side 5' of the first sequence, a second nucleic acid sequence coding at least one transmembrane domain and the ectodomain of at least one protein of a Zika virus isolate, or a nucleic acid sequence presenting an identity percent of at least 90%, notably of at least 95%, with said nucleic acid sequence coding at least one transmembrane domain and the ectodomain of at least one protein of a Zika virus isolate, provided that said at least one transmembrane domain and ectodomain coded by said nucleic acid sequence maintain the ability to form subviral, non-infectious particles and/or immunogenic properties against the Zika virus, or the nucleic acid sequence of a natural variant from another Zika isolate, or of a synthetic variant derived from said nucleic acid sequence of at least one transmembrane domain and the ectodomain of at least one protein of a Zika virus isolate, provided that said at least one transmembrane domain and ectodomain coded by said nucleic acid sequence maintain the ability to form subviral, non-infectious particles and/or immunogenic properties against the Zika virus, said protein of a Zika virus isolate being chosen from among the envelope protein E or a fusion peptide comprising the envelope protein E and the protein prM.

The nucleic acid molecule can also comprise, on the side 5' of the second sequence, a nucleic acid sequence coding a transfer initiation peptide.

In another particular embodiment, the present invention relates to an above-mentioned nucleic acid molecule also comprising, at its end 5' (i.e. at the end 5' of the second peptide), another peptide constituted of:

the nucleic acid sequence coding a transfer initiation peptide of a Zika virus isolate, or a nucleic acid sequence presenting an identity percentage of at least 83%, notably of at least 85%, particularly of at least 90%, and more particularly of at least 95%, with said nucleic acid sequence coding a transfer initiation peptide of a Zika virus isolate, the nucleic acid sequence of a natural variant from another Zika isolate, or of a synthetic variant derived from said nucleic acid sequence coding a transfer initiation peptide, provided that said nucleic acid sequence maintains the properties of a transfer initiation peptide.

In a particular embodiment of the invention, the nucleic acid sequence coding a transfer initiation peptide corresponds to the 57 C-terminal nucleic acids of the sequence coding the capsid (core) protein of the Zika virus, and is notably represented by SEQ ID NO. 30. The synthesis of this transfer initiation peptide (and consequently of the fusion protein) is initiated by an initiation codon internal to the sequence coding the capsid protein (notably represented by SEQ ID NO. 32), located 17 codons before the first codon coding this transfer initiation peptide. Advantageously, a transfer initiation peptide of the art is used in the nucleic acid molecules coding the fusion protein whose protein of a Zika virus isolate comprises a fusion peptide comprising the envelope protein E and the protein prM.

In another embodiment of the invention, the transfer initiation peptide sequence corresponds to the second transmembrane domain of prM, i.e. to the 45 nucleic acids located at the C-terminal end of prM, and is notably represented by SEQ ID NO. 31. The synthesis of this transfer initiation peptide is initiated by introduction through directed mutagenesis of an initiation codon (notably represented by SEQ ID NO. 33), located 9 codons before the first codon coding this transfer initiation peptide. Advantageously, a transfer initiation peptide of the art is used in the nucleic acid molecules coding the fusion proteins whose Zika virus isolate protein comprises only the envelope protein E.

In one embodiment of the invention, the nucleic acid sequences coding the transmembrane domains, notably the nucleic acid sequences coding the transmembrane domains of the envelope protein E are deleted from one, two or three codons in position 3' to delete one, two or three amino acids in the C-terminal position, which presents the advantage of deactivating the peptidase cleavage site, which is necessary for the maturation of the Zika polyprotein, but which is not necessary in the scope of chimeric constructions of the present invention.

In another embodiment of the invention, the first and second nucleic acid sequences of the above-mentioned nucleic acid molecule coding the above-mentioned immunogenic fusion protein are contiguous, and the end 5' of the first nucleic acid sequence is covalently bonded to end 3' of the second nucleic acid sequence.

The term "end 5'" is understood to be the position 5' or the side 5' of a nucleic acid sequence.

The term "end 3'" is understood to be the position 3' or the side 3' of a nucleic acid sequence.

In a particular embodiment, said nucleic acid molecule coding an above-mentioned fusion protein comprises or is constituted of:

the nucleic acid sequence represented by SEQ ID NO. 34, or a nucleic acid sequence presenting an identity percent of at least 80%, notably at least 85%, particularly of at least 90%, and more particularly of at least 95%, with said SEQ ID NO. 34, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 34, provided that said fusion protein coded by said nucleic acid sequence maintains the ability to form subviral, non-infectious particles and/or immunogenic properties against the human HBV and/or the Zika virus.

The expression "at least 80%" means 80%, 81%, 82%, 83%, 84%, 85%, 86%, 87%, 88%, 89%, 90%, 91%, 92%, 93%, 94%, 95%, 96%, 97%, 98%, 99% and 100%.

In a particular embodiment, the nucleic acid molecule of the above-mentioned SEQ ID NO. 34 also comprises, on side 5', a nucleic acid sequence coding a transfer initiation peptide, said nucleic acid molecule comprising or being thus constituted of:

the nucleic acid sequence represented by SEQ ID NO. 42, or a nucleic acid sequence presenting an identity percent of at least 78%, notably at least 80%, particularly of at least 85%, and more particularly of at least 90%, with said SEQ ID NO. 42, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 42, provided that said fusion protein coded by said nucleic acid sequence maintains the ability to form subviral, non-infectious particles and/or immunogenic properties against the human HBV and/or the Zika virus.

The expression "at least 78%" means 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In a particular embodiment, said nucleic acid molecule coding an above-mentioned fusion protein comprises or is constituted of:

the nucleic acid sequence represented by SEQ ID NO. 35, or a nucleic acid sequence presenting an identity percent of at least 80%, notably at least 85%, particularly of at least 90%, and more particularly of at least 95%, with said SEQ ID NO. 35, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 35, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 35 also comprises, on side 5', a nucleic acid sequence coding a transfer initiation peptide, said nucleic acid molecule comprising or being thus constituted of:

the nucleic acid sequence represented by SEQ ID NO. 43, or a nucleic acid sequence presenting an identity percent of at least 78%, notably at least 80%, particularly of at least 85%, and more particularly of at least 90%, with said SEQ ID NO. 43, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 43, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 36, or a nucleic acid sequence presenting an identity percent of at least 80%, notably at least 85%, particularly of at least 90%, and more particularly of at least 95%, with said SEQ ID NO. 36, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 36, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 36 also comprises, on side 5', a nucleic acid sequence coding a transfer initiation peptide, said nucleic acid molecule comprising or being thus constituted of:

the nucleic acid sequence represented by SEQ ID NO. 44, or a nucleic acid sequence presenting an identity percent of at least 78%, notably at least 80%, particularly of at least 85%, and more particularly of at least 90%, with said SEQ ID NO. 44, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 44, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 37, or a nucleic acid sequence presenting an identity percent of at least 80%, notably at least 85%, particularly of at least 90%, and more particularly of at least 95%, with said SEQ ID NO. 37, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 37, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 37 also comprises, on side 5', a nucleic acid sequence coding a transfer initiation peptide, said nucleic acid molecule comprising or being thus constituted of:

the nucleic acid sequence represented by SEQ ID NO. 45, or a nucleic acid sequence presenting an identity percent of at least 78%, notably at least 80%, particularly of at least 85%, and more particularly of at least 90%, with said SEQ ID NO. 45, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 45, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 38, or a nucleic acid sequence presenting an identity percent of at least 80%, notably at least 85%, particularly of at least 90%, and more particularly of at least 95%, with said SEQ ID NO. 38, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 38, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 38 also comprises, on side 5', a nucleic acid sequence coding a transfer initiation peptide, said nucleic acid molecule comprising or being thus constituted of:

the nucleic acid sequence represented by SEQ ID NO. 46, or a nucleic acid sequence presenting an identity percent of at least 78%, notably at least 80%, particularly of at least 85%, and more particularly of at least 90%, with said SEQ ID NO. 46, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 46, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 39, or a nucleic acid sequence presenting an identity percent of at least 80%, notably at least 85%, particularly of at least 90%, and more particularly of at least 95%, with said SEQ ID NO. 39, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 39, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 39 also comprises, on side 5', a nucleic acid sequence coding a transfer initiation peptide, said nucleic acid molecule comprising or being thus constituted of:

the nucleic acid sequence represented by SEQ ID NO. 47, or a nucleic acid sequence presenting an identity percent of at least 78%, notably at least 80%, particularly of at least 85%, and more particularly of at least 90%, with said SEQ ID NO. 47, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 47, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 40, or a nucleic acid sequence presenting an identity percent of at least 80%, notably at least 85%, particularly of at least 90%, and more particularly of at least 95%, with said SEQ ID NO. 40, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 40, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 40 also comprises, on side 5', a nucleic acid sequence coding a transfer initiation peptide, said nucleic acid molecule comprising or being thus constituted of:

the nucleic acid sequence represented by SEQ ID NO. 48, or a nucleic acid sequence presenting an identity percent of at least 78%, notably at least 80%, particularly of at least 85%, and more particularly of at least 90%, with said SEQ ID NO. 48, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 48, provided that said fusion protein coded by said nucleic acid sequence maintains the ability to form subviral, non-infectious particles and/or immunogenic properties against the human HBV and/or the Zika virus.

In a particular embodiment, said nucleic acid molecule coding an above-mentioned fusion protein comprises or is constituted of:

the nucleic acid sequence represented by SEQ ID NO. 41, or a nucleic acid sequence presenting an identity percent of at least 80%, notably at least 85%, particularly of at least 90%, and more particularly of at least 95%, with said SEQ ID NO. 41, provided that the fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 41, provided that said fusion protein coded by said nucleic acid sequence maintains the ability to form subviral, non-infectious particles and/or immunogenic properties against the human HBV and/or the Zika virus.

In a particular embodiment, the nucleic acid molecule of the above-mentioned SEQ ID NO. 41 also comprises, on side 5', a nucleic acid sequence coding a transfer initiation peptide, said nucleic acid molecule comprising or being thus constituted of:

the nucleic acid sequence represented by SEQ ID NO. 49, or a nucleic acid sequence presenting an identity percent of at least 78%, notably at least 80%, particularly of at least 85%, and more particularly of at least 90%, with said SEQ ID NO. 49, provided that said fusion protein coded by said nucleic acid sequence maintains the ability to form subviral, non-infectious particles and/or immunogenic properties against the human HBV and/or the Zika virus, or the nucleic acid sequence of a synthetic variant derived from said SEQ ID NO. 49, provided that said fusion protein coded by said nucleic acid sequence maintains the ability to form subviral, non-infectious particles and/or immunogenic properties against the human HBV and/or the Zika virus.

Said SEQ ID NO. 42, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49 also comprises, at their end 5', a nucleic acid sequence coding said transfer initiation peptide (and notably the initiation sequence of SEQ ID NO. 32 or SEQ ID NO. 33).

The initiation sequence of SEQ ID NO. 32 is used in nucleic acid molecules comprising the nucleic acid sequence coding the protein prM.

The initiation sequence of SEQ ID NO. 33 is used in the nucleic acid molecules not comprising the nucleic acid sequence coding the protein prM.

In a third embodiment, the present invention also relates to a vector comprising an above-mentioned nucleic acid molecule, coding an above-mentioned fusion protein, as well as the means necessary for its expression. Said means necessary for its expression are operationally bonded to said nucleic acid molecule.

In one embodiment of the invention, said molecule of nucleic acids comprised in an above-mentioned sector comprises SEQ ID NO. 34; SEQ ID NO. 35; SEQ ID NO. 36; SEQ ID NO. 37; SEQ ID NO. 38; SEQ ID NO. 39; SEQ ID NO. 40; SEQ ID NO. 41; SEQ ID NO. 42; SEQ ID NO. 43; SEQ ID NO. 44; SEQ ID NO. 45; SEQ ID NO. 46; SEQ ID NO. 47; SEQ ID NO. 48 and/or SEQ ID NO. 49.

The expression "means necessary for the expression" of a protein (the term protein being used for any amino acid molecule, such as a protein, fusion protein, protein fragment, peptide, polyprotein, polypeptide, etc.) is understood to be any means that allows the protein to be obtained, notably a promoter, a transcription terminator, a replication origin and preferably a selection marker. The means necessary for the expression of a peptide are operationally bonded to the nucleic acid sequence coding said peptide (of interest).

The means necessary for the expression of a peptide may be homologous means, i.e. included in the genome of the vector used, or heterologous. In the latter case, said means are cloned with the peptide of interest to be expressed.

The expression "operationally bonded" refers to a juxtaposition of said elements necessary for expression and of the gene coding said peptide (of interest), which are in a relationship such that it allows them to function in an expected way. For example, there may be additional bases between the promoter and the gene of interest so long as their functional relationship is maintained.

In a particular embodiment, said vector is chosen from among the plasmids, the lentiviral vectors, the Semliki vector, an adenovirus, a poxvirus, the virus of the vaccine, a baculovirus, *Salmonella* bacterial vectors and BCG.

In a particularly preferred embodiment, said vector is a lentiviral vector, notably the pLenti vector. This was previously described (Naldini, L., Blomer, U., Gallay, P., Ory, D., Mulligan, R., Gage, F. H., Verma, I. M., and Trono, D. (1996). In vivo gene delivery and stable transduction of nondividing cells by a lentiviral vector. *Science* 272(5259), 263-7).

In a particularly preferred embodiment, said vector is the Semliki vector.

In a particularly preferred embodiment, said vector is a defective viral vector derived from the genome of the Semliki Forest virus, notably the pSFV1 vector.

These viruses were previously described by Schlesinger, S., and T. M. Dubensky, Jr. 1999. Alphavirus vectors for gene expression and vaccines. *Curr. Opin. Biotechnol.* 10:434-439.

In a particular embodiment, the above-mentioned vector also comprises a promoter, notably a heterologous promoter, chosen from among:

(i) viral promoters such as the SV40 promoter (simian virus 40), the promoter of the thymidine-kinase gene of the herpes simplex virus (TK-HSV-1), the LTR of Rous sarcoma virus (RSV), the promoter of the cytomegalovirus (CMV) and the adenovirus major late promoter (MLP);

(ii) any cellular promoter that controls the transcription of genes coding four peptides in superior eukaryotes, such as the constitutive promoter of the phosphoglycerate-kinase (PGK) gene ((Adra et al., 1987, *Gene,* 60: 65-74)), the promoter of genes specific to the alpha-1 antitrypsine liver and FIX and the SM22 promoter specific to smooth muscle tissues (Moessler et al., 1996, Development, 122: 2415-2425).

In a preferred embodiment, the promoter is that of the cytomegalovirus (CMV).

In a fourth embodiment, the present invention also relates to a subviral, non-infectious and immunogenic particle comprising the following proteins:

the protein constituted of the wild-type domain S of the surface antigen of a hepatitis B virus isolate, and at least one above-mentioned fusion protein.

In one embodiment, the invention also relates to a subviral, non-infectious and immunogenic particle comprising the following proteins:

the protein constituted of the wild-type domain S of the surface antigen of a hepatitis B virus isolate, and at least one fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24.

The particles according to the invention are thus well structured and efficaciously secreted and are capable of inducing a quality antigenic response.

The expression "subviral, non-infectious particle" refers to a filamentous or spherical particle, resulting from the assembly of the wild-type protein S of the HBV and/or the protein S deleted from its N-terminal transmembrane domain, said particle being devoid of viral genome, and notably synthesized and secreted in very great excess, and which can be analyzed by any protocol allowing demonstration of the absence of nucleotide fragments specific to HBV or Zika, such as the amplification by PCR or RT-PCR previously described:

concerning Zika, by [Faye O1, Faye O, Dupressoir A, Weidmann M, Ndiaye M, Alpha Sall A. One-step RT-PCR for detection of Zika virus. J Clin Virol. 2008 September; 43 (1): 96-101];

concerning HBV, by [Thibault V, Pichoud C, Mullen C, Rhoads J, Smith J B, Bitbol A, Thamm S, Zoulim F. Characterization of a new sensitive PCR assay for quantification of viral DNA isolated from patients with hepatitis B virus infections. J. Clin. Microbiol. 2007 December 45(12):2948-53];

and whose result is negative.

In a fifth embodiment, the invention also relates to an above-mentioned fusion protein for its use as a medication.

The invention also relates to an above-mentioned subviral particle for its use as a medication.

In a preferred embodiment, said medication is a vaccine.

In one embodiment, the invention also relates to a fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24 for its use as a medication.

In another embodiment, the invention also relates to a subviral, non-infectious and immunogenic particle comprising the following proteins:

the protein constituted of the wild-type domain S of the surface antigen of a hepatitis B virus isolate, and at least one fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24 for its use as a medication.

In a particular embodiment, the invention also relates to a composition comprising an above-mentioned fusion protein as an active substance.

The invention also relates to a composition comprising an above-mentioned subviral particle as an active substance.

In a preferred embodiment, said composition is a vaccine composition.

In one embodiment, the invention also relates to a composition comprising a fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24 as an active substance.

In another embodiment, the invention also relates to a composition comprising, as an active substance, a subviral, non-infectious and immunogenic particle comprising the following proteins:

the protein constituted of the wild-type domain S of the surface antigen of a hepatitis B virus isolate, and at least one fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO.

17, SEQ ID NO. 18, SEQ ID NO. 19, SEQ ID NO. 20, SEQ ID NO. 21, SEQ ID NO. 22, SEQ ID NO. 23 or SEQ ID NO. 24.

In a sixth embodiment, the invention also relates to an above-mentioned fusion protein for its use in preventing and/or treating hepatitis B and/or Zika virus infections.

The invention also relates to an above-mentioned subviral particle for its use in preventing and/or treating hepatitis B and/or Zika virus infections.

The expression "Zika virus infections" is understood to be infections by the Zika virus or infections linked to Zika virus.

In one embodiment, the invention also relates to a fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24 for its use in preventing and/or treating hepatitis B and/or Zika virus infections.

In another embodiment, the invention also relates to a subviral, non-infectious and immunogenic particle comprising the following proteins:

- the protein constituted of the wild-type domain S of the surface antigen of a hepatitis B virus isolate, and
- at least one fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24 for its use in preventing and/or treating hepatitis B and/or Zika virus infections.

In a seventh embodiment, the invention also relates to a cellular line that expresses above-mentioned subviral, non-infectious and immunogenic particles.

In one embodiment, the invention also relates to a cellular line that expresses a subviral, non-infectious and immunogenic particle comprising the following proteins:

- the protein constituted of the wild-type domain S of the surface antigen of a hepatitis B virus isolate, and
- at least one fusion protein represented by SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23 or SEQ ID NO. 24.

In a particular embodiment, said cellular line is chosen from among:

- yeasts, such as those from the following families: *Saccharomyces, Schizosaccharomyces, Kluveromyces, Pichia, Hanseluna, Yarowia, Schwaniomyces, Zygosaccharomyces, Saccharomyces cerevisiae, Saccharomyces carlsbergensis* and *Kluveromyces lactis;*
- bacteria, such as *E. coli* and those from the following families: *Lactobillicus, Lactococcus, Salmonella, Streptococcus, Bacillus* and *Streptomyces.*

In a particular embodiment, said cellular line is chosen from among the eukaryotic cells, notably the cells from animals like mammals, reptiles, insects and the equivalent, and more particularly:

- cells from Chinese hamsters (CHO cells);
- cells from monkeys (COS and Vero cells);
- cells from the dwarf hamster kidneys (BHK cells);
- cells from the pig kidneys (PK 15 cells);
- cells from rabbit kidneys (RK13 cells);
- the human cellular lines of osteosarcoma (143 B cells);
- HeLa human cellular cells;
- the human cellular lines of hepatoma (Hep G2 cells);
- insect cellular lines (e.g. from *Spodoptera frugiperda*).

In a particularly preferred embodiment, said cellular line is the ovary line of Chinese hamsters, called CHO. For more on this, see, for example, Michael ML, Pontisso P, Sobczak E, Malpièce Y, Streeck R E, Tiollais P. Synthesis in animal cells of hepatitis B surface antigen particles carrying a receptor for polymerized human serum albumin. *Proc Natl Acad Sci USA.* 1984 December; 81(24)7708-12.

In a particularly preferred embodiment, said cellular line is a yeast, notably *Saccharomyces cerevisae.*

In a particularly preferred embodiment, said cellular line is a cellular line from a newborn hamster kidney (BHK) and is particularly the cellular line from a newborn hamster kidney (BHK-21). For more on this, see, for example, Goldman R D, Follet E A. Birefringent filamentous organelle in BHK-21 cells and its possible role in cell spreading and motility. *Science.* 1970 Jul. 17; 169(942):286-8.

In an eighth embodiment, the present invention also relates to a method of producing the above-mentioned particles from an above-mentioned cellular line, comprising the following steps:

1—a step of TRANSDUCING the cells of the cellular line with a lentiviral vector comprising a nucleic acid sequence coding the wild-type protein S of a hepatitis B virus isolate, 2—a step of CULTIVATING said cells to produce a cellular line capable of expressing the subviral particles of wild-type envelope of the hepatitis B virus, 3—a step of SELECTING a clone presenting an optimal secretion of subviral particles of wild-type envelope of the hepatitis B virus, 4—a step of SUPERTRANSDUCING said clone with an above-mentioned vector, 5—a step of CULTIVATING said cells to produce a cellular line capable of expressing the above-mentioned subviral, non-infectious and immunogenic particles, 6—a step of SELECTING said cells capable of optimally secreting the above-mentioned subviral, non-infectious and immunogenic particles, 7—a step of CULTIVATING said cells to produce a the above-mentioned subviral, non-infectious and immunogenic particles, and 8—a step of PURIFYING the subviral particles from the collected culture environment (centrifugation, gradient ultracentrifugation, positive fraction collection for the chimeric subviral particles, dialysis).

Table 1 indicates the correspondence between the nucleic acid sequences and the amino acid sequences described in the present invention, as well as the genes/proteins associated with these sequences.

| Nucleic sequence | Protein sequence | Gene/protein associated with these sequences |
|---|---|---|
| / | SEQ ID NO. 1 | deleted S |
| / | SEQ ID NO. 2 | S |
| / | SEQ ID NO. 3 | deleted M |
| / | SEQ ID NO. 4 | M |
| / | SEQ ID NO. 5 | deleted E |
| / | SEQ ID NO. 6 | prM + deleted E |
| SEQ ID NO. 34 | SEQ ID NO. 7 (= SEQ ID NO. 5 + SEQ ID NO. 1) | deleted E + deleted S |

-continued

Figure 6:

| Nucleic sequence | Protein sequence | Gene/protein associated with these sequences |
|---|---|---|
| SEQ ID NO. 35 | SEQ ID NO. 8 | prM + deleted E + deleted S |
| SEQ ID NO. 36 | SEQ ID NO. 9 | E + S |
| SEQ ID NO. 37 | SEQ ID NO. 10 | prM + E + S |
| SEQ ID NO. 38 | SEQ ID NO. 11 | deleted E + M |
| SEQ ID NO. 39 | SEQ ID NO. 12 | prM + deleted E + M |
| SEQ ID NO. 40 | SEQ ID NO. 13 | E + M |
| SEQ ID NO. 41 | SEQ ID NO. 14 | prM + E + M |
| | SEQ ID NO. 15 | E |
| | SEQ ID NO. 16 | prM + E |
| SEQ ID NO. 42 | SEQ ID NO. 17 | TIP + deleted E + deleted S |
| SEQ ID NO. 43 | SEQ ID NO. 18 | TIP + prM + deleted E + deleted S |
| SEQ ID NO. 44 | SEQ ID NO. 19 | TIP + E + S |
| SEQ ID NO. 45 | SEQ ID NO. 20 | TIP + prM + E + S |
| SEQ ID NO. 46 | SEQ ID NO. 21 | TIP + deleted E + M |
| SEQ ID NO. 47 | SEQ ID NO. 22 | TIP + prM + deleted E + M |
| SEQ ID NO. 48 | SEQ ID NO. 23 | TIP + E + M |
| SEQ ID NO. 49 | SEQ ID NO. 24 | TIP + prM + E + M |
| SEQ ID NO. 30 | SEQ ID NO. 25 | Transfer initiation peptide |
| SEQ ID NO. 31 | SEQ ID NO. 26 | Transfer initiation peptide |
| SEQ ID NO. 32 | SEQ ID NO. 27 | Initiation sequence |
| SEQ ID NO. 33 | SEQ ID NO. 28 | Initiation sequence |
| SEQ ID NO. 29 | / | Zika virus, accession number KU312312.1 |
| / | SEQ ID NO. 50 | prM |
| SEQ ID NO. 51 | | Synthesis gene (as represented in FIG. 6) allowing the fusion peptide prM + E to be obtained, or allowing all the structural peptides of Zika to be obtained (the capsid protein C, the protein prM and the envelope protein E). |
| SEQ ID NO. 52 | / | Zika virus, accession number KU32169 |
| SEQ ID NO. 53 | / | pSFV1-prM + E + S |
| SEQ ID NO. 54 | / | pSFV1-prM + deleted E + deleted S" |
| SEQ ID NO. 55 | / | pSFV1-prM + E + S |
| SEQ ID NO. 56 | / | pSFV1$^{puro}$-HBV-prM + E + S |
| SEQ ID NO. 57 | / | pSFV1$^{puro}$-HBV-prM + deleted E + deleted S |
| SEQ ID NO. 58 | / | pSFV1$^{puro}$-HBV-prM + E + M |
| SEQ ID NO. 59 | / | Zika virus Polynesian strain |

The term “TIP” means that:

the initiation sequence (allowing the synthesis of the transfer initiation peptide) and the sequence of said transfer initiation peptide are present in the fusion protein sequences according to the invention, or the sequence coding the initiation sequence and the sequence coding said transfer initiation peptide are present in the sequences coding the fusion proteins according to the invention.

SEQ ID NO. 34; SEQ ID NO. 35; SEQ ID NO. 36; SEQ ID NO. 37; SEQ ID NO. 38; SEQ ID NO. 39; SEQ ID NO. 40; SEQ ID NO. 41; SEQ ID NO. 42; SEQ ID NO. 43; SEQ ID NO. 44; SEQ ID NO. 45; SEQ ID NO. 46; SEQ ID NO. 47; SEQ ID NO. 48 and SEQ ID NO. 49 possess a “taa” stop codon at their end 3'.

TABLE 2

| lists the sequences of the present invention: | |
|---|---|
| SEQ ID NO: 1 | Riltipqsldswwtslnflggspvclgqnsqsptsnhsptscppicpgyrwmclrrfiiflfillllcliflllvlldyqgmlpvcplipgstttstgpcktcttpaqgnsmfpsccctkptdgnctcipi psswafakylwcwasvrfswlsllvpfvqwfvqlsptvwlsaiwmmwywgpslysivspfipllpiffclwvyi |
| SEQ ID NO: 2 | Menitsgflgpllvlqagffllltriltipqsldswwtslnflggspvclgqnsqsptsnhsptscppicpgyrwmclrrfiiflfillllcliflllvlldyqgmlpvcplipgstttstgpcktcttpaqgns mfpsccctkptdgnctcipipsswafakylwewasvrfswlsllvpfvqwfvglsptvwlsaiwmmwywgpslysivspfipllpiffclwvyi |
| SEQ ID NO: 3 | nmenitsgflgpllvlqagffllltriltipqsldswwtslnflggspvclgqnsqsptsnhspfscppicpgyrwmclrrfiiflfillllcliflllvlldyqgmlpvcplipgstttstgpcktcttpaqgn smfpsccctkptdgnctcipipsswafakylwewasvrfswlsllvpfvqwfvglsptvwlsaiwmmwywgpslysivspfipllpiffclwvyi |
| SEQ ID NO: 4 | Mqwnstafhqtlqdprvrglylpaggsssgtvnpapniashissisartgdpvtnmenitsgflgpllvlqagffllltriltipqsldswwtslnflggspvclgqnsqsptsnhsptscppicpgy rwmclrrfiiflfillllcliflllvlldyqgmlpvcplipgstttstgpcktcttpaqgnsmfpsccctkptdgnctcipipsswafakylwewasvrfswlsllvpfvqwfvglsptvwlsaiwmm wywgpslysivspfipllpiffclwvyi |
| SEQ ID NO: 5 | ircigvsnrdfvegmsggtwvdvvlchggcvtvmaqdkptvdielvtttvsnmaevrsycyeasisdmasdsrcptqgeayldkqsdtqyvckrtlvdrgwgngcglfgkgslvtcakfa cskkmtgksiqpenleyrimlsvhgsqhsgmivndtghetdenrakveitpnspraeatlggfgslgldceprtgldfsdlyyltmnnkhwlvhkewfhdiplpwhagadtgtphwnnke alvefkdahakrqtvvvlgsqegavhtalagaleaemdgakgrlssghlkcrlkmdklrlkgvsyslctaaftftkipaetlhgtvtvevqyagtdgpckvpaqmavdmqtltpvgrlitanp vitestenskmmleldppfgdsyivigvgekkithhwhrsgstigkafeatvrgakmavlgdtawdfgsvggalnslgkgihqifgaafkslfggmswfsqiligtllmnwlglnakngsd |
| SEQ ID NO: 6 | rrgsayymyldrndageaisfpttlgmnkcyiqimdlghtcdatmsyecpmldegvepddvdcwcnttstwvvygtchhkkgearrsrravtlpshstrklqtrsqtwlesreytkhlirve nwifrnpgfalaaaaiawllgsstsqkviylvmilliapaysircigvsnrdfvegmsggtwvdvvlehggcvtvmaqdkptvdielvtttvsnmaevrsycyeasisdmasdsrcptqgea yldkqsdtqyvckrtlvdrgwgngcglfgkgslvtcakfacskkmtgksiqpenleyrimlsvhgsqhsgmivndtghetdenrakveitpnspraeatlggfgslgldceprtgldfsdlyyl tmnnkhwlvhkcwfhdiplpwhagadtgtphwnnkealvefkdahakrqtvvvlgsqegavhtalagaleaemdgakgrlssghlkcrlkmdklrlkgvsyslctaaftftkipaetlhgt vtvevqyagtdgpckvpaqmavdmqtltpvgrlitanpvitestenskmmleldppfgdsyivigvgekkithhwhrsgstigkafeatvrgakrmavlgdtawdfgsvggalnslgkgi hqifgaafkslfggmswfsqiligtllmwlglnakngsd |
| SEQ ID NO: 7 | ircigvsnrdfvcgmsggtwvdvvlehggcvtvmaqdkptvdielvtttvsnmaevrsycyeasisdmasdsrcptqgeayldkqsdtqyvckrtlvdrgwgngcglfgkgslvtcakfa cskkmtgksiqpenleyrimlsvhgsqhsgmivndtghetdenrakveitpnspraeatlggfgslgldceprtgldfsdlyyltmnnkhwlvhkcwfhdiplpwhagadtgtphwnnke alvefkdahakrqtvvvlgsqegavhtalagaleaemdgakgrlssghlkcrlkmdklrlkgvsyslctaaftftkipaetlhgtvtvevqyagtdgpckvpaqmavdmqtltpvgrlitanp vitestenskmmleldppfgdsyivigvgekkithhwhrsgstigkafeatvrgakrmavlgdtawdfgsvggalnslgkgihqifgaafkslfggmswfsqiligtllmwlglnakngsrilt ipqsldswwtslnflggspvclgqnsqsptsnhsptscppicpgyrwmclrrfiiflfillllcliflllvlldyqgmlpvcplipgstttstgpcktcttpaqgnsmfpsccctkptdgnctcipipss wafakylwewasvrfswlsllvpfvqwfvglsptvwlsaiwmmvywgpslysivspfipllpiffclwvyi |
| SEQ ID NO: 8 | rrgsayymyldrndageaisfpttlgmnkcyiqimdlghtcdatmsyecpmldegvepddvdcwcnttstwvvygtchhkkgearrsrravtlpshstrklqtrsqtwlesreytkhlirve nwifrnpgfalaaaaiawllgsstsqkviylvmilliapaysircigvsnrdfvegmsggtwvdvvlehggcvtvmaqdkptvdielvtttvsnmaevrsycyeasisdmasdsrcptqgea yldkqsdtqyvckrtlvdrgwgngcglfgkgslvtcakfacskkmtgksiqpenleyrimlsvhgsqhsgmivndtghetdenrakveitpnspraeatlggfgslgldceprtgldfsdlyyl tmnnkhwlvhkewfhdiplpwhagadtgtphwnnkealvefkdahakrqtvvvlgsqegavhtalagaleaemdgakgrlssghlkcrlkmdklrlkgvsyslctaaftftkipaetlhgt vtvevqyagtdgpckvpaqmavdmqtltpvgrlitanpvitestenskmmleldppfgdsyivigvgekkithhwhrsgstigkafeatvrgakrmavlgdtawdfgsvggalnslgkgi hqifgaafkslfggmswfsqiligtllmwlglnakngsriltipqsldswwtslnflggspvclgqnsqsptsnhsptscppicpgyrwmclrrfiiflfillllcliflllvlldyqgmlpvcplipgst ttstgpcktcttpaqgasmfpsccctkptdgnctcipipsswafakylwewasvrfswlsllvpfvqwfvglsptvwlsaiwmmwywgpslysivspfipllpiffclwvyi |

TABLE 2-continued

| | lists the sequences of the present invention: |
|---|---|
| SEQ ID NO: 9 | ircigvsnrdvegmsggtwvdvvlehggcvtvmaqdkptvdielvtttvsnmaevrsycyeasisdmasdsrcptqgeayldkqsdtqyvckrtlvdrgwgngcglfgkgslvtcakfa<br>cskkmtgksiqpenleyrimlsvhgsqhsgmivndtghetdenrakveitpnspraeatlggfgslgldceprtgldfsdlyyltmmnkhwlvhkewfhdiplpwhagadtglphwnnke<br>alvefkdahakrqtvvvlgsqegavhtalagaleaemdgakgrlssghlkcrlkmdklrlkgvsyslctaaftftkipaetlhgtvtvevqyagtdgpckvpaqmavdmqtltpvgrlitanp<br>vitestenskmmleldppfgdsyivigvgekkithhwhrsgstigkafeatvrgakrmavlgdtawdfgsvggalnslgkgihqifgaafkslfggmswfsqiligtllmwlglnakngsisl<br>mclalggvliflstavsaenitsgflgpllvlqagffllltriltipqsldswwtslnflggspvclgqnsqsptsnhsptscppicpgyrwmclrrfiiflfillllcliflllvlldyqgmlpvcplipgs<br>tttstgpcktcttpaqgnsmfpsccctkptdgnctcipipsswafakylwewasvrfswlsllvpfvqwfvglsptvwlsaiwmmwywgpslysivspfipllpiffclwvyi |
| SEQ ID NO: 10 | rrgsayymyldrndageaisfpttlgmnkcyiqimdlghtcdatmsyecpmldcgvepddvdcwcnttstwvygtchhkkgearrsrravtlpshstrklqtrsqtwlesreytkhlirve<br>nwifrnpgfalaaaaiawllgsstsqkviylvmilliapaysircigvsnrdfvegmsggtwvdvvlehggcvtvmaqdkptvdielvtttvsnmaevrsycyeasisdmasdsrcptqgea<br>yldkqsdtqyvckrtlvdrgwgngcglfgkgslvtcakfacskkmtgksiqpenleyrimlsvhgsqhsgmivndtghetdenrakveitpnspraeatlggfgslgldceprtgldfsdlyyl<br>tmnnkhwlvhkewfhdiplpwhagadtgtphwnnkealvefkdahakrqtvvvlgsqegavhtalagaleaeindgakgrlssghlkcrlkindklrlkgvsyslctaaftftkipaetlhgt<br>vtvevqyagtdgpckvpaqmavdmqtltpvgrlitanpvitestenskmmleldppfgdsyivigvgekkitlihwhrsgstigkafeatvrgakrmavlgdtawdfgsvggalnslgkgi<br>hqifgaafkslfggmswfsqiligtllmwlglnakngsislmclalggvliflstavsaenitsgflgpllvlqagffllltriltipqsldswwtslnflggspvclgqnsqsptsnhsptscppicpg<br>yrwmclrrfiiflfillllcliflllvlldyqgmlpvcplipgstttstgpcktcttpaqgmmfpsccctkptdgnctcipipsswafakylwcwasvrfswlsllvpfvqwfvglsptvwlsaiwm<br>mwywgpslysivspfipllpiffclwvyi |
| SEQ ID NO: 11 | ircigvsnrdfvegmsggtwvdvvlehggcvtvmaqdkptvdielvtttvsnmaevrsycyeasisdmasdsrcptqgeayldkqsdtqyvckrtlvdrgwgngcglfgkgslvtcakfa<br>cskkmtgksiqpenleyrimlsvhgsqhsgmivndtghetdenrakveitpnspracatlggfgslgldccprtgldfsdlyyltmnnkhwlvhkewfhdiplpwhagadtgtphwnnkc<br>alvefkdahakrqtvwlgsqegavhtalagaleaemdgakgrlssghlkcrlkmdklrlkgvsyslctaaftftkipactlhgtvtvevqyagtdgpckvpaqmavdmqtltpvgrlitanp<br>vitestenskmmleldppfgdsyivigvgekkithhwhrsgstigkafeatvrgakrmavlgdtawdfgsvggalnslgkgihqifgaafkslfggmswfsqiligtllmwlglnalcngsq<br>wnstafhqtlqdprvrglylpaggsssgtvnpapniaslussisartgdpvtnmenitsgflgpllvlqagfnitriltipqsldswwtslnflggspvclgqnsqsptsnhsptscppicpgyrw<br>mclrrfiiflfillllcliflllvlldyqgmlpvcplipgstttstgpcktcttpaqgnsmfpsccctkptdgnctcipipsswafakylwewasvrfswlsllvpfvqwfvglsptvwlsaiwminw<br>ywgpslysivspfipllpiffclwvyi |
| SEQ ID NO: 12 | rrgsayymyldrndageaisfpttlgmnkcyiqimdlghtcdatmsyecpmldegvepddvdcwcnttstwvvygtchhkkgearrsrravtlpshstrklqtrsqtwlesreytkhlirve<br>nwifrnpgfalaaaaiawllgsstsqkviylvmilliapaysircigvsnrdfvegmsggtwvdvvlehggcvtvmaqdkptvdielvtttvsnmaevrsycyeasisdmasdsrcptqgea<br>yldkqsdtqyvckrtlvdrgwgngcglfgkgslvtcakfacskkmtgksiqpenleyrimlsvhgsqhsgmivndtghetdenrdkveitpnspraeatlggfgslgldceprtgldfsdlyyl<br>tmnnkhwlvhkewfhdiplpwhagadtgtphwnnkealvefkdahakrqtvvvlgsqegavhtalagaleaemdgakgrlssghlkcrlkmdklrlkgvsyslctaaftftkipaetlhgt<br>vtvevqyagtdgpckvpaqmavdmqtltpvgrlitanpvitestenskmmleldppfgdsyivigvgckkithhwhrsgstigkafcatvrgakrmavlgdtawdfgsvggalnslgkgi<br>hqifgaafkslfggmswfsqiligtllmwlglnakngsqwnstafhqtlqdprvrglylpaggsssgtvnpapniashissisartgdpvtnmenitsgflgpllvlqagffllltriltipqsldsw<br>wtslnflggspvclgqnsqsptsnhsptscppicpgyrwmclrrfiiflfillllcliflllvlldyqgmlpvcplipgstttstgpcktcttpaqgnsmfpsccctkptdgnctcipipsswafakylw<br>ewasvrfswlsllvpfvqwfvglsptvwlsaiwmmwywgpslysivspfipllpiffclwvyi |
| SEQ ID NO: 13 | ircigvsnrdfvegmsggtwvdvvlehggcvtvmaqdkptvdielvtttvsnmaevrsycyeasisdmasdsrcptqgeayldkqsdtqyvckrtlvdrgwgngcglfgkgslvtcakfa<br>cskkmtgksiqpenleyrimlsvhgsqhsgmivndtghctdenrakveitpnspraeatlggfgslgldceprtgldfsdlyyltmnnkhwlvhkcwfhdiplpwhagadtgtphwnnke<br>alvefkdahakrqtvvvlgsqegavhtalagaleaemdgakgrlssghlkcrlkmdklrlkgvsyslctaaftftkipaetlhgtvtvevqyagtdgpckvpaqmavdmqtltpvgrlitanp<br>vitestenskmmleldppfgdsyivigvgekkithliwhrsgstigkafeatvrgaknnavlgdtawdfgsvggalnslgkgihqifgaafkslfggmswfsqiligtllmwlglnakngsisl<br>mclalggvliflstavsaqwnstafliqtlqdprvrglylpaggsssgtvnpapmashissisartgdpvtnmenitsgflgpllvlqagllfllltriltipqsldswwtslnflggspvclgqnsqspt<br>snhsptscppicpgyrwmclrrfiiflfillllcliflllvlldyqgmlpvcplipgstttstgpcktcttpaqgnsmfpsccctkptdgnctcipipsswafakylwewasvrfswlsllvpfvqwfv<br>glsptvwlsaiwmmwywgpslysivspflpllpiffclwvyi |
| SEQ ID NO: 14 | rrgsayymyldrndageaisfpttlgmnkcyiqimdlghtcdatmsyecpmldegvepddvdcwcnttstwvvygtchhkkgcarrsrravtlpshstrklqtrsqtwlesreytkhlirve<br>nwifmpgfalaaaaiawllgsstsqkviylvmilliapaysircigvsnrdfvegmsggtwvdvvlehggcvtvniaqdkptvdielvtttvsnmaevrsycyeasisdmasdsrcptqgea<br>yldkqsdtqyvckrtlvdrgwgngcglfgkgslvtcakfacskkmtgksiqpenleyrimlsvhgsqhsgmivndtghetdenrakveitpnspraeatlggfgslgldceprtgldfsdlyyl<br>tmrmkhwlvhkewfhdiplpwhagadtgtphwnnkealvefkdahakrqtvvvlgsqcgavhtalagaleaemdgakgrlssghlkcrlkmdklrlkgvsyslctaaftftkipaetlhgt<br>vtvevqyagtdgpckvpaqmavdmqtltpvgrlitanpvitestenskmmleldppfgdsyivigvgekkithhwhrsgstigkafeatvrgakrmavlgdtawdfgsvggalnslgkgi<br>liqifgaafkslfggmswfsqiligtllmwlglnakngsislmclalggvliflstavsaqwnstafhqtlqdprvrglylpaggsssgtvnpapniashissisartgdpvtnmenitsgflgpllv<br>lqagffllltriltipqsldswwtslnflggspvclgqnsqsptsnhsptscppicpgyrwmclrrfiiflfillllcliflllvlldyqgmlpvcplipgstttstgpcktcttpaqgnsmfpsccctkptdg<br>nctcipipsswafakylwcwasvrfswlsllvpfvqwfvglsptvwlsaiwmmwywgpslysivspfipllpiffclwvyi |

TABLE 2-continued

| lists the sequences of the present invention: | |
|---|---|
| SEQ ID NO: 15 | ircigvsnrdfvegmsggtwvdvvldiggcvtvmaqdkptvdielvtttvsnmaevrsycyeasisdmasdsrcptqgeayldkqsdtqyvckrtlvdrgwgngcglfgkgslvteakfa<br>cskkmtgksiqpenleyrimlsvhgsqhsgmradtghetdenrakveitpnspraeatlggfgslgldceprtgldfsdlyyltnmnkhwlvhkewfhdiplpwhagadtgtphwnnke<br>alvcfkdahakrqtvvvlgsqegavhtalagaleaemdgakgrlssghlkcrlkmdklrlkgvsyslctaaftftkipaetlhgtvtvevqyagtdgpckvpaqmavdmqtltpvgrlitanp<br>vitestenskmmleldppfgdsyivigvgekkithhwhrsgstigkafeatvrgakrmavlgdtawdfgsvggalnslgkgihqifgaafkslfggmswfsqiligtllmwlglnakngsisl<br>mclalggvliflstavsa |
| SEQ ID NO: 16 | rrgsayymyldrndageaisfpttlgmnkcyiqimdlghtcdatmsyccpmldcgvepddvdcwcnttstwvvygtchhkkgearrsrravtlpshstrklqtrsqtwlesreytkhlirve<br>nwifrnpgfaiaaaaiawllgsstsqkviylvmilliapaysircigvsnrdivegmsggtwvdvvlehggcvtvmaqdkptvdielvttlvsnmaevrsycyeasisdmasdsrcptqgea<br>yldkqsdtqyvckrtlvdrgwgngcglfgkgslvtcakfacskkrntgksiqpenleyrimlsvhgsqhsgmivndtghetdenrakveitpnspraeatlggfgslgldceprtgldfsdlyyl<br>tmnnkhwlvhkewfhdiplpwhagadtgtphwnnkealvefkdahakrqtvwlgsqegavhtalagaleaemdgakgrlssghlkcrlkmdklrlkgvsyslctaaftftkipaetlhgt<br>vtvevqyagtdgpckvpaqmavdmqtltpvgrlitanpvitestenskmmleldppfgdsyivigvgekkithhwhrsgstigkafealvrgakrmavlgdtawdfgsvggalnslgkgi<br>liqifgaafkslfggmswfsqiligtllmwlglnakngsislmclalggvliflstavsa |
| SEQ ID NO: 17 | mlgsstsqkviylvmilliapaysircigvsnrdfvegmsggtwvdvvlehggcvtvrnaqdkptvdielvtttvsnmaevrsycyeasisdniasdsrcptqgeayldkqsdtqyvckrtlv<br>drgwgngcglfgkgslvtcakfacskkmtgksiqpcnleyrimlsvhgsqhsgmivndtghetdenrakveitpnspraeatlggfgslgldceprtgldfsdlyyltmnnkhwlvhkewf<br>hdiplpwhagadtgtphwmikealvefkdahakrqtvvvlgsqegavhtalagaleaemdgakgrlssghlkcrlkmdklrlkgvsyslctaaftftkipactlhgtvtvcvqyagtdgpck<br>vpaqmavdmqtltpvgrlitanpvitestenskninileldppfgdsyivigvgekkithhwhrsgstigkafcatvrgakrmavlgdtawdfgsvggalnslgkgihqifgaafkslfggms<br>wfsqiligtllmwlglnakngsriltipqsldswwtslnflggspvclgqnsqsptsnhsptscppicpgyrwmclrrfiiflfillllcliflllvlldyqgmlpvcplipgstttstgpcktcttpaqgn<br>smfpsccctkptdgnctcipipsswafakylwewasvrfswlsllvpfvqwfvglsptvwlsaiwmmwywgpslysivspfipllpiffclwvyi |
| SEQ ID NO: 18 | mlriinarkekkrrgadtsvgivglllttamaaevtrrgsayymyldmdageaisfpttlgnmkcyiqimdlghtcdatmsyecpmldegvepddvdcwcnttstwvvygtchhkkgear<br>rsrravtlpshstrklqtrsqtwlesreytkhlirvenwifrnpgfalaaaaiawllgsstsqkviylvmilliapaysircigvsnrdfvcgmsggtwvdvvlehggcvtvmaqdkptvdielvtt<br>tvsnmaevrsycyeasisdmasdsrcptqgeayldkqsdtqyvckrtlvdrgwgngcglfgkgslvtcakfacskkmtgksiqpenleyrimlsvhgsqhsgmnivndtghetdenrakve<br>itpnspraeatlggfgslgldceprtgldfsdlyyltmnnkhwlvhkewfhdiplpwhagadtgtphwnnkealvefkdahakrqtvwlgsqegavhtalagaleaemdgakgrlssghl<br>kcrlkmdklrlkgvsyslctaaftftkipaetlhgtvtvevqyagtdgpckvpaqmavdinqtltpvgrlitanpvitestenskmmleldppfgdsyivigvgekkithliwhrsgstigkafea<br>tvrgaknnavlgdtawdfgsvggalnslgkgihqifgaafkslfggmswfsqiligtllmwlglnakngsriltipqsldswwtslnflggspvclgqnsqsptsnhsptscppicpgyrwmc<br>lrrfnflfilllcliflllvlldyqgmlpvcplipgstttstgpcktcttpaqgnsmfpsccctkptdgnctcipipsswafakylwewasvrfswlsllvpfvqwfvglsptvwIsaiwmmwyw<br>gpslysivspfipllpiffclwvyi |
| SEQ ID NO: 19 | migsstsqkviylvmilliapaysircigvsnrdfvegmsggtwvdvvlehggcvtvmaqdkptvdielvtttvsnmaevrsycyeasisdmasdsrcptqgeayldkqsdtqyvckrtlv<br>drgwgngcglfgkgslvtcakfacskkmtgksiqpenleyrimlsvhgsqhsgmivndtgheldenrakveitpnspraeatlggfgslgldceprtgldfsdlyyltmnnkhwlvhkcwf<br>hdiplpwhagadtgtphwnnkealvefkdahakrqtvvvlgsqegavhtalagaleaemdgakgrlssghlkcrlkmdklrlkgvsyslctaaftftkipaetlhgtvtvevqyagtdgpck<br>vpaqmavdmqtltpvgrlitanpvitestenskmmleldppfgdsyivigvgekkithhwhrsgstigkafeatvrgakrmavlgdtawdfgsvggalnslgkgihqifgaafkslfggms<br>wfsqiligtllmwlglnakngsislmclalggvliflstavsaenitsgflgpllvlqagffIltriltipqsldswwtslnflggspvclgqnsqsptsnhsptscppicpgyrwmclrrfiiflfillllcl<br>ifllvlldyqgmlpvcplipgstttstgpcktcttpaqgnsmfpsccctkptdgnctcipipsswafakylwewasvrfswlsllvpfvqwfvglsptvwlsaiwmmwywgpslysivspfi<br>pllpiffclwvyi |
| SEQ ID NO: 20 | mlriinarkekkrrgadtsvgivglllttamaacvlrrgsayymyldrndageaisfpttlgmnkcyiqimdlghtcdatmsyecpmldegvcpddvdcwcnttstwvvygtdihkkgear<br>rsrravtlpshstrklqtrsqtwlcsrcytkhlirvenwifrnpgfalaaaaiawllgsstsqkviylvmilliapaysircigvsnrdfvegmsggtwvdwlehggcvtvmaqdkptvdielvtt<br>tvsnmaevrsycyeasisdmasdsrcptqgeayldkqsdtqyvckrtlvdrgwgngcglfgkgslvtcakfacskkmtgksiqpenleyrimlsvhgsqhsgmivndtghetdenrakve<br>itpnspraeatlggfgslgldceprtgldfsdlyyltmnnkhwlvhkewfhdiplpwhagadtgtphwnnkealvefkdahakrqtvvvlgsqegavhtalagaleaemdgakgrlssghl<br>kcrlkmdklrlkgvsyslctaaftftkipaetlhgtvtvevqyagtdgpckvpaqmavdmqtltpvgrlitanpvitestenskmmleldppfgdsyivigvgekkithhwhrsgstigkafea<br>tvrgakrmavlgdtawdfgsvggalnslgkgihqifgaafkslfggmswfsqiligtllmwlglnakngsislmclalggvliflstavsaenitsgflgpllvlqagfflltriltipqsldswwtsl<br>nflggspvclgqnsqsptsnhsptscppicpgyrwmclrrfiiflfillllcliflllvlldyqgmlpvcplipgstttstgpcktcttpaqgiismfpsccctkptdgiictcipipsswafakylwewa<br>svrfswlsllvpfVqwfVglsptvwlsaiwmmwywgpslysivspfipllpiffclwvyi |
| SEQ ID NO: 21 | mlgsstsqkviylvmilliapaysircigvsnrdfvegmsggtwvdvvlehggcvtvmaqdkptvdielvtttvsnmaevrsycyeasisdmasdsrcptqgcayldkqsdtqyvckrtlv<br>drgwgngcglfgkgslvtcakfacskkmtgksiqpcnlcyrimlsvhgsqhsgmivndtghctdcnrakveitpnspracatlggfgslgldccprtgldfsdlyyltmnnkhwlvhkewf<br>hdiplpwhagadtgtphwnnkealvefkdahakiqtvwlgsqegavhtalagalcaemdgakgrlssghlkcrlkmdklrlkgvsyslctaaflftkipaetlhgtvtvevqyagtdgpck<br>vpaqmavdmqtltpvgrlitanpvitestenskmmleldppfgdsyivigvgekkithhwhrsgstigkafeatvrgakrmavlgdtawdfgsvggalnslgkgihqifgaafkslfggms<br>wfsqiligtllmwlglnakngsqwnstafliqtlqdprvrglylpaggsssgtvnpapniashissisarfgdpvtnmenitsgflgpllvlqagfflltriltipqsldswwtslnflggspvclgqn |

TABLE 2-continued

| lists the sequences of the present invention: | |
|---|---|
| | sqsptsnhsptscppicpgyrwmclrrfiiflfilllcliflllvlldyqgmlpvcplipgstttstgpcktcttpaqgnsmfpsccctkptdgnctcipipsswafakylwewasvrfswlsllvpfv qwfvglsptvwlsaiwmmwywgpslysivspfipllpiffclwvyi |
| SEQ ID NO: 22 | mlriinarkekkngadtsvgivglllttamaaevtrrgsayymyldrndageaisfpttlginnkcyiqimdlghtcdatmsyecpmldegvepddvdcwcnttstwvvygtchhkkgear rsrravtlpshstrklqtreqtwlesreytkhlirvenwifmpgfalaaaaiawllgsstsqkviylvmilliapaysircigvsnrdfvegmsggtwvdvvlehggcvtvmaqdkptvdielvtt tvsnmaevrsycyeasisdmasdsrcptqgeayldkqsdtqyvckrtlvdrgwgngcglfgkgslvtcakfkcskkmtgksiqpenleyrimlsvhgsqhsgmivndtghetdcnrakvc itpnspraeatlggfgslgldceprtgldfsdlyyltmnnkhwlvhkewfhdiplpwhagadtgtphwnnkealvefkdahakrqmvlgsqcgavhtalagalcacmdgakgrlssghl kcrlkmdklrlkgvsyslctaaftftkipaetlhgtvtvevqyagtdgpckvpaqmavdmqtltpvgrlitanpvitestenskmmleldppfgdsyivigvgekkithhwhrsgstigkafea tvrgakrmavlgdtawdfgsvggalnslgkgihqifgaafkslfggmswfsqiligtllmwlglnakngsqwnstafhqtlqdprvrglylpaggsssgtvnpapniashissisartgdpvtn memtsgflgpllvlqagffllltriltipqsldswwtslnflggspvclgqnsqsptsnhsptscppicpgyrwniclrrfiiflfilllcliflllvlldyqgmlpvcplipgstttstgpcktcttpaqgns mfpsccctkptdgnctcipipsswafakylwewasvrfswlsllvpfvqwfvglsptvwlsaiwmmwywgpslysivspfipllpiffclwvyi |
| SEQ ID NO: 23 | mlgsstsqkviylvmilliapaysircigvsnrdfvegmsggtwvdvvlehggcvtvmaqclkptvdielvtttvsnmaevrsycyeasisdmasdsrcptqgeayldkqsdtqyvckrtlv drgwgngcglfgkgslvtcakfacskkmtgksiqpenleyrimlsvhgsqhsgmivndtghetdenrakveitpnspraeatlggfgslgldceprtgldfsdlyyltmimkhwlvhkewf hdiplpwhagadtgtphwnnkealvefkdahakrqtvwlgsqegavhtalagaleaemdgakgrlssghlkcrlkmdklrlkgvsyslctaaftftkipaetlhgtvtvevqyagtdgpck vpaqinavdmqtltpvgrlitanpvitestenskmmleldppfgdsyivigvgekkithhwhisgstigkafeatvrgaknnavlgdtawdfgsvggalnslgkgihqifgaafkslfggins wfsqiligtllmwlglnakngsislmclalggvliflstovsaqwnstafliqtlqdpmglylpaggsssgtvnpapniashissisartgdpvtnmenitsgflgpllvlqagffllltriltipqslds wwtslnflggspvclgqnsqsptsnhsptscppicpgyrwniclrrfiiflfilllcliflllvlldyqginlpvcplipgsttlstgpcktcttpaqgnsmfpsccctkptdgnctcipipsswafakyl wewasvrfswlsllvpfvqwfvglsptvwlsaiwmmwywgpslysivspfipllpiffclwvyi |
| SEQ ID NO: 24 | mlriinarkekkrrgadtsvgivglllttamaaevtrrgsayymyldrndageaisfpttlgmnkcyiqimdlghtcdatmsyccpmldegvepddvdcwcnttstwwygtchhkkgcar rsrravtlpslistrklqtrsqtwlesrcytkhlirvenwifrnpgfalaaaaiawllgsstsqkviylvmilliapaysircigvsnrdfvcgmsggtwvdwlchggcvtvmaqdkptvdielvtt tvsnmaevrsycyeasisdmasdsrcptqgeayldkqsdtqyvckillvdrgwgngcglfgkgslvtcakfacskkmtgksiqpenleyrinilsvhgsqhsgmivndtghetdenrakve itpnspraeatlggfgslgldccprtgldfsdlyyltmnnkhwlvhkewfhdiplpwhagadtgtphwnnkealvefkdahakrqtvvvlgsqegavhtalagaleaemdgakgrlssghl kcrllamdklrlkgvsyslctaaflftkipaetlhgtvtvevqyagtdgpckvpaqmavdmqtltpvgrlitanpvitestenskmmleldppfgdsyivigvgekkithhwhrsgstigkafea tvrgaknnavlgdtawdfgsvggalnslgkgihqifgaafkslfggmswfsqiligtllmwlglnakngsislmclalggvliflstavsaqwnstafhqtlqdprvrglylpaggsssgtvnpa pniashissisartgdpvtnnienitsgflgpllvlqagffllltriltipqsldswwtslnflggspvclgqnsqsptsnhsptscppicpgyrwmclrrfiiflfilllcliflllvlldyqgmlpvcplipg stttstgpcktcttpaqgnsmfpsccctkptdgnctcipipsswafakylwcwasvrfswlsllvpfVqwfvglsptvwlsaiwminwywgpslysivspfipllpiffclwvyi |
| SEQ ID NO: 25 | Tsvgivglllttamaaevt |
| SEQ ID NO: 26 | viylvmilliapays |
| SEQ ID NO: 27 | Mlriinarkekkrrgad |
| SEQ ID NO: 28 | mlgsstsqk |

TABLE 2-continued

| lists the sequences of the present invention: | |
|---|---|
| SEQ ID NO: 29 | acaggtttta ttttggattt ggaaacgaga gtttctggtc atgaaaaacc caaaaaagaa atccggagga ttccggattg tcaatatgct aaaacgcgga gtagcccgtg tgagcccctt<br>tgggggcttg aagaggctgc cagccggact tctgctgggt catgggccca tcaggatggt cttggcgatt ctagcctttt tgagattcac ggcaatcaag ccatcactgg gtctcatcaa<br>tagatggggt tcagtgggga aaaaagaggc tatggaaata ataaagaagt tcaagaaaga tctggctgcc atgctgagaa taatcaatgc taggaaggag aagaagagac<br>gaggcgcaga tactagtgtc ggaattgttg gcctcctgct gaccacagct atggcagcgg aggtcactag acgtgggagt gcatactata tgtacttgga cagaaacgat<br>gctggggagg ccatatcttt tccaaccaca ttggggatga ataagtgtta tatacagatc atggatcttg gacacacgtg tgatgccacc atgagctatg aatgccctat gctggatgag<br>ggggtggaac cagatgacgt cgattgttgg tgcaacacga cgtcaacttg ggttgtgtac ggaacctgcc atcacaaaaa aggtgaagca cggagatcta gaagagctgt<br>gacgctcccc tcccattcca ctaggaagct gcaaacgcgg tcgcaaacct ggttggaatc aagagaatac acaaagcact tgattagagt cgaaaattgg atattcagga accctggctt<br>cgcgttagca gcagctgcca tcgcttggct tttgggaagc tcaacgagcc aaaaagtcat atacttggtc atgatactgc tgattgcccc ggcatacagc atcaggtgca taggagtcag<br>caatagggac tttgtggaag gtatgtcagg tgggacttgg gttgatgttg tcttggaaca tggaggttgt gtcactgtaa tggcacagga caaaccgact gtcgacatag agctggttac<br>aacaacagtc agcaacatgg cggaggtaag atcctactgc tatgaggcat caatatcaga catggcttcg gacagccgct gcccaacaca aggtgaagcc taccttgaca<br>agcaatcaga cactcaatat gtctgcaaaa gaacgttagt ggacagaggc tggggaaatg gatgtggact ttttggcaaa gggagcctgg tgacatgcgc taagtttgca tgctccaaga<br>aaatgaccgg gaagagcatc cagccagaga atctggagta ccggataatg ctgtcagttc atggctccca gcacagtggg atgatcgtta atgacacagg acatgaaact<br>gatgagaata gagcgaaagt tgagataacg cccaattcac caagagccga agccaccctg ggggggtttg gaagcctagg acttgattgt gaaccgagga caggccttga<br>cttttcagat ttgtattact tgactatgaa taacaagcac tggctggttc acaaggagtg gttccacgac attccattac cttggcacgc tggggcagac accggaactc cacactggaa<br>caacaaagaa gcactggtag agttcaagga cgcacatgcc aaaaggcaaa ctgtcgtggt tctagggagt caagaaggag cagttcacac ggcccttgct ggagctctgg<br>aggctgagat ggatggtgca aagggaaggc tgtcctctgg ccacttgaaa tgtcgcctga aaatggataa acttagattg aagggcgtgt catactcctt gtgtactgca gcgttcacat<br>tcaccaagat cccggctgaa acactgcacg ggacagtcac agtggaggta cagtacgcag ggacagatgg accttgcaag gttccagctc agatggcggt ggacatgcaa<br>actctgaccc cagttgggag gttgataacc gctaaccccg taatcactga aagcactgag aactctaaga tgatgctgga acttgatcca ccatttgggg actcttacat tgtcatagga<br>gtcggggaga agaagatcac ccaccactgg cacaggagtg gcagcaccat tggaaaagca tttgaagcca ctgtgagagg tgccaagaga atggcagtct tgggagacac<br>agcctgggac tttggatcag ttggaggcgc tctcaactca ttgggcaagg gcatccatca aatctttgga gcagctttca aatcattgtt tggaggaatg tcctggttct cacaaattct<br>cattggaacg ttgctgatgt ggttgggtct gaacgcaaag aatggatcta tttcccttat gtgcttggcc ttagggggag tgttgatctt cttatccaca gccgtctctg ctgatgtggg<br>gtgctcggtg gacttctcaa agaaggagac gagatgcggt acaggggtgt tcgtctataa cgacgttgaa gcctggaggg acaggtacaa gtaccatcct gactcccccc<br>gtagattggc agcagcagtc aagcaagcct gggaagatgg tatctgcggg atctcctctg tttcaagaat ggaaaacatc atgtggagat cagtagaagg ggagctcaac<br>gcaatcctgg aagagaatgg agttcaactg acggtcgttg tgggatctgt aaaaaacccc atgtggagag gtccacagag attgcccgtg cctgtgaacg agctgcccca<br>cggctggaag gcttggggga aatcgtactt cgtcagagca gcaaagacaa ataacagctt tgtcgtggat ggtgacacac tgaaggaatg cccactcaaa catagagcat<br>ggaacagctt tcttgtggag gatcatgggt tcggggtatt tcacactagt gtctggctca aggttagaga agattattca ttagagtgtg atccagccgt tattggaaca gctgttaagg<br>gaaaggaggc tgtacacagt gatctaggct actggattga gagtgagaag aatgacacat ggaggctgaa gagggcccat ctgatcgaga tgaaaacatg tgaatggcca<br>aagtcccaca cattgtggac agatggaata gaagagagtg atctgatcat acccaagtct ttagctgggc cactcagcca tcacaatacc agagagggct acaggaccca<br>aatgaaaggg ccatggcaca gtgaagagct tgaaattcgg tttgaggaat gcccaggcac taaggtccac gtggaggaaa catgtggaac gagaggacca tctctgagat<br>caaccactgc aagcggaagg gtgatcgagg aatggtgctg cagggagtgc acaatgcccc cactgtcgtt ccgggctaaa gatggctgtt ggtatggaat ggagataagg<br>cccaggaaag aaccagaaag caacttagta aggtcaatgg tgactgcagg atcaactgat cacatggacc acttctccct tggagtgctt gtgattctgc tcatggtgca ggaagggttg<br>aagaagagaa tgaccacaaa gatcatcata agcacatcaa tggcagtgct ggtagctatg atcctgggag gattttcaat gagtgacctg gctaagcttg caattttgat gggtgccacc<br>ttcgcggaaa tgaacactgg aggagatgta gctcatctgg cgctgatagc ggcattcaaa gtcagaccag cgttgctggt atctttcatc ttcagagcta attggacacc ccgtgaaagc<br>atgctgctgg ccttggcctc gtgtcttttg caaactgcga tctccgcctt ggaaggcgac ctgatggttc tcatcaatgg ttttgctttg gcctggttgg caatacgagc gatggttgtt<br>ccacgcactg ataacatcac cttggcaatc ctggctgctc tgacaccact ggcccggggc acactgcttg tggcgtggag agcaggcctt gctacttgcg gggggtttat gctcctctct<br>ctgaagggaa aaggcagtgt gaagaagaac ttaccatttg tcatggccct gggactaacc gctgtgaggc tggtcgaccc catcaacgtg gtgggactgc tgttgctcac<br>aaggagtggg aagcggagct ggccccctag cgaagtactc acagctgttg gcctgatatg cgcattggct ggagggttcg ccaaggcaga tatagagatg gctgggccca<br>tggccgcggt cggtctgcta attgtcagtt acgtggtctc aggaaagagt gtggacatgt acattgaaag agcaggtgac atcacatggg aaaaagatgc ggaagtcact<br>ggaaacagtc cccggctcga tgtggcgcta gatgagagtg gtgatttctc cctggtggag gatgacggtc cccccatgag agagatcata ctcaaggtgg tcctgatgac catctgtggc<br>atgaacccaa tagccatacc ctttgcagct ggagcgtggt acgtatacgt gaagactgga aaaaggagtg gtgctctatg ggatgtgcct gctcccaagg aagtaaaaaa<br>gggggagacc acagatggag tgtacagagt aatgactcgt agactgctag gttcaacaca agttggagtg ggagttatgc aagaggggt ctttcacact atgtggcacg<br>tcacaaaagg atccgcgctg agaagcggtg aagggagact tgatccatac tggggagatg tcaagcagga tctggtgtca tactgtggtc catggaagct agatgccgcc<br>tgggacgggc acagcgaggt gcagctcttg gccgtgcccc ccggagagag agcgaggaac atccagactc tgcccggaat atttaagaca aaggatgggg acattggagc<br>ggttgcgctg gattacccag caggaacttc aggatctcct atcctagaca agtgtgggag agtgatagga ctttatggca atggggtcgt gatcaaaaat gggagttatg ttagtgccat<br>cacccaaggg aggagggagg aagagactcc tgttgagtgc ttcgagcctt cgatgctgaa gaagaagcag ctaactgtct tagacttgca tcctggagct gggaaaacca<br>ggagagttct tcctgaaata gtccgtgaag ccataaaaac aagactccgt actgtgatct tagctccaac cagggttgtc gctgctgaaa tggaggaggc ccttagaggg cttccagtgc<br>gttatatgac aacagcagtc aatgtcaccc actctggaac agaaatcgtc gacttaatgt gccatgccac cttcacttcg cgtctactac agccaatcag agtccccaac tataatctgt<br>atattatgga tgaggcccac ttcacagatc cctcaagtat agcagcaaga ggatacattt caacaagggt tgagatgggc gaggcggccg ccatcttcat gaccgccacg<br>ccaccaggaa cccgtgacgc atttccggac tccaactcac caattatgga caccgaagtg gaagtcccag agagagcctg gagctcaggc tttgattggg tgacggatca<br>ttctggaaaa acagtttggt ttgttccaag cgtgaggaac ggcaatgaga tcgcagcttg tctgacaaag gctggaaaac gggtcataca gctcagcaga aagacttttg agacagagtt<br>ccagaaaaca aaacatcaag agtgggactt tgtcgtgaca actgacattt cagagatggg cgccaacttt aaagctgacc gtgtcataga ttccaggaga tgcctaaagc cggtcatact |

TABLE 2-continued

| lists the sequences of the present invention: | |
|---|---|
| | tgatggcgag agagtcattc tggctggacc catgcctgtc acacatgcca gcgctgccca gaggaggggg cgcataggca ggaatcccaa caaacctgga gatgagtatc<br>tgtatggagg tgggtgcgca gagactgacg aagaccatgc acactggctt gaagcaagaa tgctccttga caatatttac ctccaagatg gcctcatagc ctcgctctat cgacctgagg<br>ccgacaaagt agcagccatt gagggagagt tcaagcttag gacggagcaa aggaagacct ttgtggaact catgaaaaga ggagatcttc ctgtttggct ggcctatcag gttgcatctg<br>ccggaataac ctacacagat agaagatggt gctttgatgg cacgaccaac aacaccataa tggaagacag tgtgccggca gaagtgtgga ccagacacgg agagaaaaga<br>gtgctcaaac cgaggtggat ggacgccaga gtttgttcag atcatgcggc cctgaagtca ttcaaggagt ttgccgctgg gaaaagagga gcggcttttg gagtgatgga<br>agccctggga acactgccag gacacatgac agagagattc caggaagcca ttgacaacct cgctgtgctc atgcgggcag agactggaag caggccttac aaagccgcgg<br>cggcccaatt gccggagacc ctagagacca ttatgctttt ggggttgctg ggaacagtct cgctgggaat cttcttcgtc ttgatgagga acaagggcat agggaagatg ggctttggaa<br>tggtgactct tggggccagc gcatggctca tgtggctctc ggaaattgag ccagccagaa ttgcatgtgt cctcattgtt gtgttcctat tgctggtggt gctcatacct gagccagaaa<br>agcaaagatc tccccaggac aaccaaatgg caatcatcat catggtagca gtaggtcttc tgggcttgat taccgccaat gaactcggat ggttggagag aacaaagagt gacctaagcc<br>atctaatggg aaggagagag gagggggcaa ccataggatt ctcaatggac attgacctgc ggccagcctc agcttgggcc atctatgctg ccttgacaac tttcattacc ccagccgtcc<br>aacatgcagt gaccacctca tacaacaact actccttaat ggcgatggcc acgcaagctg gagtgttgtt tggtatgggc aaagggatgc cattctacgc atgggacttt ggagtcccgc<br>tgctaatgat aggttgctac tcacaattaa cacccctgac cctaatagtg gccatcattt tgctcgtggc gcactacatg tacttgatcc cagggctgca ggcagcagct gcgcgtgctg<br>cccagaagag aacggcagct ggcatcatga agaaccctgt tgtggatgga atagtggtga ctgacattga cacaatgaca attgaccccc aagtggagaa aaagatggga<br>caggtgctac tcatagcagt agccgtctcc agcgccatac tgtcgcggac cgcctggggg tggggggagg ctggggccct gatcacagcc gcaacttcca ctttgtggga<br>aggctctccg aacaagtact ggaactcctc tacagccact tcactgtgta acatttttag gggaagttac ttggctggag cttctctaat ctacacagta acaagaaacg ctggcttggt<br>caagagacgt gggggtggaa caggagagac cctgggagag aaatggaagg cccgcttgaa ccagatgtcg gccctggagt tctactccta caaaaagtca ggcatcaccg<br>aggtgtgcag agaagaggcc cgccgcgccc tcaaggacgg tgtggcaacg ggaggccatg ctgtgtcccg aggaagtgca aagctgagat ggttggtgga gcggggatac<br>ctgcagccct atggaaaggt cattgatctt ggatgtggca gagggggctg gagttactac gccgccacca tccgcaaagt tcaagaagtg aaaggataca caaaaggagg<br>ccctggtcat gaagaacccg tgttggtgca aagctatggg tggaacatag tccgtcttaa gagtggggtg gacgtctttc atatggcggc tgagccgtgt gacacgttgc tgtgtgacat<br>aggtgagtca tcatctagtc ctgaagtgga agaagcacgg acgctcagag tcctctccat ggtgggggat tggcttgaaa aaagaccagg agccttttgt ataaaagtgt tgtgcccata<br>caccagcact atgatggaaa ccctcgagcg actgcagcgt aggtatgggg gaggactggt cagagtgcca ctctcccgca actctacaca tgagatgtac tgggtctctg<br>gagcgaaaag caacaccata aaaagtgtgt ccaccacgag ccagctcctc ttggggcgca tggacgggcc taggaggcca gtgaaatatg aggaggatgt gaatctcggc<br>tctggcacgc gggctgtggt aagctgcgct gaagctccca acatgaagat cattggtaac cgcattgaaa ggatccgcag tgagcacgcg gaaacgtggt tctttgacga<br>gaaccaccca tataggacat gggcttacca tggaagctat gaggccccca cacaagggtc agcgtcctct ctaataaacg gggttgtcag gctcctgtca aaaccctggg<br>atgtggtgac tggagtcaca ggaatagcca tgaccgacac cacaccgtat ggtcagcaaa gagttttcaa ggaaaaagtg gacactaggg tgccagaccc ccaagaaggc<br>actcgtcagg ttatgagcat ggtctcttcc tggttgtgga aagagctagg caaacacaaa cggccacgag tctgtaccaa agaagagttc atcaacaagg ttcgtagcaa tgcagcatta<br>ggggcaatat ttgaagagga aaaagagtgg aagactgcag tggaagctgt gaacgatcca aggttctggg ctctagtgga caaggaaaga gagcaccacc tgagaggaga<br>gtgccagagt tgtgtgtaca acatgatggg aaaaagagaa aagaaacaag gggaatttgg aaaggccaag ggcagccgcg ccatctggta tatgtggcta ggggctagat<br>ttctagagtt cgaagccctt ggattcttga acgaggatca ctggatgggg agagagaact caggaggtgg tgttgaaggg ctgggattac aaagactcgg atatgtccta gaagagatga<br>gtcgtatacc aggaggaagg atgtatgcag atgacactgc tggctgggac acccgcatta gcaggtttga tctggagaat gaagctctaa tcaccaacca aatggagaaa<br>gggcacaggg ccttggcatt ggccataatc aagtacacat accaaaacaa agtggtaaag gtccttagac cagctgaaaa agggaaaaca gttatggaca ttatttcgag<br>acaagaccaa agggggagcg gacaagttgt cacttacgct cttaacacat ttaccaacct agtggtgcaa ctcattcgga atatggaggc tgaggaagtt ctagagatgc aagacttgtg<br>gctgctgcgg aggtcagaga aagtgactaa ctggttgcag agcaacggat gggataggct caaacgaatg gcagtcagtg gagatgattg cgttgtgaag ccaattgatg<br>ataggtttgc acatgccctc aggttcttga atgatatggg aaaagttagg aaggacacac aagagtggaa accctcaact ggatgggaca actgggaaga agttccgttt tgctcccacc<br>acttcaacaa gctccatctc aaggacggga ggtccattgt ggttccctgc cgccaccaag atgaactgat tggccgggcc cgcgtctctc caggggcggg atggagcatc<br>cgggagactg cttgcctagc aaaatcatat gcgcaaatgt ggcagctcct ttatttccac agaagggacc tccgactgat ggccaatgcc atttgttcat ctgtgccagt tgactgggtt<br>ccaactggga gaactacctg gtcaatccat ggaaagggag aatggatgac cactgaagac atgcttgtgg tgtggaacag agtgtggatt gaggagaacg accacatgga<br>agacaagacc ccagttacga aatggacaga cattccctat ttgggaaaaa gggaagactt gtggtgtgga tctctcatag ggcacagacc gcgcaccacc tgggctgaga<br>acattaaaaa cacagtcaac atggtgcgca ggatcatagg tgatgaagaa aagtacatgg actacctatc cacccaagtt cgctacttgg gtgaagaagg gtctacacct ggagtgctgt<br>aagcaccaat cttaatgttg tcaggcctgc tagtcagcca cagcttgggg aaagctgtgc agcc |
| SEQ ID NO: 30 | acaagtgtcggaattgttggcctcctgctgaccacagctatggcagcggaggtcact |
| SEQ ID NO: 31 | Gtcatatacttggtcatgatactgctgattgccccggcatacagc |

TABLE 2-continued

| lists the sequences of the present invention: | |
|---|---|
| SEQ ID NO: 32 | atgctgagaataatcaatgctaggaaggagaagaagagacgaggcgcagat |
| SEQ ID NO: 33 | Atgttgggaagctcaacgagccaaaaa |
| SEQ ID NO: 34 | atcaggtgcataggagtcagcaatagggactttgtggaaggtatgtcaggtgggacttgggttgatgttgtcttggaacatggaggttgtgtcactgtaatggcacaggacaaaccgactgtcgacat<br>agagctggttacaacaacagtcagcaacatggcggaggtaagatcctactgctatgaggcatcaatatcagacatggcttcggacagccgctgcccaacacaaggtgaagcctaccttgacaagc<br>aatcagacactcaatatgtctgcaaaagaacgttagtggacagaggctggggaaatggatgtggactttttggcaaagggagcctggtgacatgcgctaagtttgcatgctccaagaaaatgaccg<br>ggaagagcatccagccagagaatctggagtaccggataatgctgtcagttcatggctcccagcacagtgggatgatcgttaatgacacaggacatgaaactgatgagaatagagcgaaagttgag<br>ataacgcccaattcaccaagagccgaagccaccctggggggtttggaagcctaggacttgattgtgaaccgaggacaggccttgacttttcagatttgtattacttgactatgaataacaagcactg<br>gctggttcacaaggagtggttccacgacattccattaccttggcacgctggggcagacaccggaactccacactggaacaacaaagaagcactggtagagttcaaggacgcacatgccaaaagg<br>caaactgtcgtggttctagggagtcaagaaggagcagttcacacggcccttgctggagctctggaggctgagatggatggtgcaaagggaaggctgtcctctggccacttgaaatgtcgcctgaa<br>aatggataaacttagattgaagggcgtgtcatactccttgtgtactgcagcgttcacattcaccaagatcccggctgaaacactgcacgggacagtcacagtggaggtacagtacgcagggacaga<br>tggaccttgcaaggttccagctcagatggcggtggacatgcaaactctgaccccagttgggaggttgataaccgctaaccccgtaatcactgaaagcactgagaactctaagatgatgctggaactt<br>gatccaccatttggggactcttacattgtcataggagtcggggagaagaagatcacccaccactggcacaggagtggcagcaccattggaaaagcatttgaagccactgtgagaggtgocaagag<br>aatggcagtcttgggagacacagcctgggactttggatcagttggaggcgctctcaactcattgggcaagggcatccatcaaatctttggagcagctttcaaatcattgtttggaggaatgtcctggtt<br>ctcacaaattctcattggaacgttgctgatgtggttgggtctgaacgcaaagaatggatctagaatcctcacaataccgcagagtctagactcgtggtggacttctctcaattttctaggggatctccc<br>gtgtgtcttggccaaaaucgcagtccccaacctccaatcactcaccaacctcctgtcctccaatttgtcctggttatcgctggatgtgtctgcggcgttttatcatattcctcttcatcctgctgctatgcctc<br>atcttcttattggttcttctggattatcaaggtatgttgcccgtttgtcctctaattccaggatcaacaacaaccagtacgggaccatgcaaaacctgcacgactcctgctcaaggcaactctatgtttccct<br>catgttgctgtacaaaacctacggatggaaattgcacctgtattcccatcccatcgtcctgggctttcgcaaaatacctatgggagtgggcctcagtccgtttctcttggctcagtttactagtgccatttgt<br>tcagtggttcgtagggctttcccccactgtttggctttcagctatatggatgatgtggtattgggggccaagtctgtacagcatcgtgagtccctttataccgctgttaccaattttcttttgtctctgggtat<br>acatttaa |
| SEQ ID NO: 35 | agacgtgggagtgcatactatatgtacttggacagaaacgatgctggggaggccatatcttttccaaccacattggggatgaataagtgttatatacagatcatggatcttggacacacgtgtgatgcc<br>accatgagctatgaatgccctatgctggatgagggggtggaaccagatgacgtcgattgttggtgcaacacgacgtcaacttgggttgtgtacggaacctgccatcacaaaaaaggtgaagcacg<br>gagatctagaagagctgtgacgctcccctcccattccactaggaagctgcaaacgcggtcgcaaacctggttggaatcaagagaatacacaaagcacttgattagagtcgaaaattggatattcag<br>gaaccctggcttcgcgttagcagcagctgccatcgcttggcttttgggaagctcaacgagccaaaaagtcatatacttggtcatgatactgctgattgccccggcatacagcatcaggtgcataggag<br>tcagcaatagggactttgtggaaggtatgtcaggtgggacttgggttgatgttgtcttggaacatggaggttgtgtcactgtaatggcacaggacaaaccgactgtcgacatagagctggttacaaca<br>acagtcagcaacatggcggaggtaagatcctactgctatgaggcatcaatatcagacatggcttcggacagccgctgcccaacacaaggtgaagcctaccttgacaagcaatcagacactcaatat<br>gtctgcaaaagaacgttagtggacagaggctggggaaatggatgtggactttttggcaaagggagcctggtgacatgcgctaagtttgcatgctccaagaaaatgaccgggaagagcatccagcc<br>agagaatctggagtaccggataatgctgtcagttcatggctcccagcacagtgggatgatcgttaatgacacaggacatgaaactgatgagaatagagcgaaagttgagataacgcccaattcacc<br>aagagccgaagccaccctggggggtttggaagcctaggacttgattgtgaaccgaggacaggccttgacttttcagatttgtattacttgactatgaataacaagcactggctggttcacaaggagt<br>ggttccacgacattccattaccttggcacgctggggcagacaccggaactccacactggaacaacaaagaagcactggtagagttcaaggacgcacatgccaaaaggcaaactgtcgtggttcta<br>gggagtcaagaaggagcagttcacacggcccttgctggagctctggaggctgagatggatggtgcaaagggaaggctgtcctctggccacttgaaatgtcgcctgaaaatggataaacttagatt<br>gaagggcgtgtcatactccttgtgtactgcagcgttcacattcaccaagatcccggctgaaacactgcacgggacagtcacagtggaggtacagtacgcagsgacagatggaccttgcaaggttc<br>cagctcagatggcggtggacatgcaaactctgaaccagttgggaggttgataaccgctaaccccgtaatcactgaaagcactgagaactctaagatgatgctggaacttgatccaccatttgggga<br>ctcttacattgtcataggagtcggggagaagaagatcacccaccactggcacaggagtggcagcaccattggaaaagcatttgaagccactgtgagaggtgccaagagaatggcagtcttggga<br>gacacagcctgggactttggatcagttggaggcgctctcaactcattgggcaagggcatccatcaaatctttggagcagctttcaaatcattgtttggaggaatgtcctggttctcacaaattctcattgg<br>aacgttgctgatgtggttgggtctgaacgcaaagaatggatctagaatcctcctcaataccgcagagtctagactcgtggtggacttctctcaattttctaggggatctcccgtgtgtcttggccaaaatt<br>cgcagtccccaacctccaatcactcaccaacctcctgtcctccaatttgtcctggttatcgctggatgtgtctgcggcgttttatcatattcctcttcatcctgctgctatgcctcatcttcttattggttct<br>tctggattatcaaggtatgttgcccgtttgtcctctaattccaggatcaacaacaaccagtacgggaccatgcaaaacctgcacgactcctgctcaaggcaactctatgtttccctcatgttgctgtacaaaac<br>ctacggatggaaattgcacctgtattcccatcccatcgtcctgggctttcgcaaaatacctatgggagtgggcctcagtccgtttctcttggctcagtttactagtgccatttgttcagtggttcgtagggct<br>ttcccccactgtttggctttcagctatatggatgatgtggtattgggggccaagtctgtacagcatcgtgagtccctttataccgctgttaccaattttcttttgtctctgggtatacatttaa |

TABLE 2-continued

| lists the sequences of the present invention: | |
|---|---|
| SEQ ID NO: 36 | atcaggtgcataggagtcagcaatagggactttgtggaaggtatgtcaggtgggacttgggttgatgttgtcttggaacatggaggttgtgtcactgtaatggcacaggacaaaccgactgtcgacat<br>agagctggttacaacaacagtcagcaacatggcggaggtaagatcctactgctatgaggcatcaatatcagacatggcttcggacagccgctgcccaacacaaggtgaagcctaccttgacaagc<br>aatcagacactcaatatgtctgcaaaagaacgttagtggacagaggctggggaaatggatgtggactttttggcaaagggagcctggtgacatgcgctaagtttgcatgctccaagaaaatgaccg<br>ggaagagcatccagccagagaatctggagtaccggataatgctgtcagttcatggctcccagcacagtgggatgatcgttaatgacacaggacatgaaactgatgagaatagagcgaaagttgag<br>ataacgcccaattcaccaagagccgaagccaccctggggggggtttggaagcctaggacttgattgtgaaccgaggacaggccttgacttttcagatttgtattacttgactatgaataacaagcactg<br>gctggttcacaaggagtggttccacgacattccattaccttggcacgctggggcagacaccggaactccacactggaacaacaaagaagcactggtagagttcaaggacgcacatgccaaaagg<br>caaactgtcgtggttctagggagtcaagaaggagcagttcacacggcccttgctggagctctggaggctgagatggatggtgcaaagggaaggctgtcctctggccacttgaaatgtcgcctgaa<br>aatggataaacttagattgaagggcgtgtcatactccttgtgtactgcagcgttcacattcaccaagatcccggctgaaacactgcacgggacagtcacagtggaggtacagtacgcagggacaga<br>tggaccttgcaaggttccagctcagatggcggtggacatgcaaactctgaccccagttgggaggttgataaccgctaaccccgtaatcactgaaagcactgagaactctaagatgatgctggaactt<br>gatccaccatttggggactcttacattgtcataggagtcggggagaagaagatcacccaccactggcacaggagtggcagcaccattggaaaagcatttgaagccactgtgagaggtgccaagag<br>aatggcagtcttgggagacacagcctgggactttggatcagttggaggcgctctcaactcattgggcaagggcatccatcaaatctttggagcagctttcaaatcattgtttggaggaatgtcctggtt<br>ctcacaaattctcattggaacgttgctgatgtggttgggtctgaacgcaaagaatggatctatttcccttatgtgcttggccttagggggagtgttgatcttcttatccacagccgtctctgctgagaacatc<br>acatcaggattcctaggacccctgctcgtgttacaggcggggtttttcttgttgacaagaatcctcacaataccgcagagtctagactcgtggtggacttctctcaattttctaggggggatctcccgtgtg<br>tcttggccaaaattcgcagtccccaacctccaatcactcaccaacctcctgtcctccaatttgtcctggttatcgctggatgtgtctgcggcgttttatcatattcctcttcatcctgctgctatgcctcatct<br>tcttattggttcttctggattatcaaggtatgttgcccgtttgtcctctaattccaggatcaacaacaaccagtacgggaccatgcaaaacctgcacgactcctgctcaaggcaactctatgtttccctcatgt<br>tgctgtacaaaacctacggatggaaattgcacctgtattcccatcccatcgtcctgggctttcgcaaaatacctatgggagtgggcctcagtccgtttctcttggctcagtttactagtgccatttgttcagt<br>ggttcgtagggctttcccccactgtttggctttcagctatatggatgatgtggtattgggggccaagtctgtacagcatcgtgagtccctttataccgctgttaccaattttcttttgtctctgggtatacat<br>ttaa |
| SEQ ID NO: 37 | agacgtgggagtgcatactatatgtacttggacagaaacgatgctggggaggccatatcttttccaaccacattggggatgaataagtgttatatacagatcatggatcttggacacacgtgtgatgcc<br>accatgagctatgaatgccctatgctggatgaggggggtggaaccagatgacgtcgattgttggtgcaacacgacgtcaacttgggttgtgtacggaacctgccatcacaaaaaaggtgaagcacg<br>gagatctagaagagctgtgacgctcccctcccattccactaggaagctgcaaacgcggtcgcaaacctggttggaatcaagagaatacacaaagcacttgattagagtcgaaaattggatattcag<br>gaaccctggcttcgcgttagcagcagctgccatcgcttggcttttgggaagctcaacgagccaaaaagtcatatacttggtcatgatactgctgattgccccggcatacagcatcaggtgcataggag<br>tcagcaatagggactttgtggaaggtatgtcaggtgggacttgggttgatgttgtcttggaacatggaggttgtgtcactgtaatggcacaggacaaaccgactgtcgacatagagctggttacaaca<br>acagtcagcaacatggcggaggtaagatcctactgctatgaggcatcaatatcagacatggcttcggacagccgctgcccaacacaaggtgaagcctaccttgacaagcaatcagacactcaatat<br>gtctgcaaaagaacgttagtggacagaggctggggaaatggatgtggactttttggcaaagggagcctggtgacatgcgctaagtttgcatgctccaagaaaatgaccgggaagagcatccagcc<br>agagaatctggagtaccggataatgctgtcagttcatggctcccagcacagtgggatgatcgttaatgacacaggacatgaaactgatgagaatagagcgaaagttgagataacgcccaattcacc<br>aagagccgaagccaccctggggggggtttggaagcctaggacttgattgtgaaccgaggacaggccttgacttttcagatttgtattacttgactatgaataacaagcactggctggttcacaaggagt<br>ggttccacgacattccattaccttggcacgctggggcagacaccggaactccacactggaacaacaaagaagcactggtagagttcaaggacgcacatgccaaaaggcaaactgtcgtggttcta<br>gggagtcaagaaggagcagttcacacggcccttgctggagctctggaggctgagatggatggtgcaaagggaaggctgtcctctggccacttgaaatgtcgcctgaaaatggataaacttagatt<br>gaagggcgtgtcatactccttgtgtactgcagcgttcacattcaccaagatcccggctgaaacactgcacgggacagtcacagtggaggtacagtacgcagggacagatggaccttgcaaggttc<br>cagctcagatggcggtggacatgcaaactctgaccccagttgggaggttgataaccgctaaccccgtaatcactgaaagcactgagaactctaagatgatgctggaacttgatccaccatttgggga<br>ctcttacattgtcataggagtcggggagaagaagatcacccaccactggcacaggagtggcagcaccattggaaaagcatttgaagccactgtgagaggtgccaagagaatggcagtcttggga<br>gacacagcctgggactttggatcagttggaggcgctctcaactcattgggcaagggcatccatcaaatctttggagcagctttcaaatcattgtttggaggaatgtcctggttctcacaaattctcattgg<br>aacgttgctgatgtggttgggtctgaacgcaaagaatggatctatttcccttatgtgcttggccttagggggagtgttgatcttcttatccacagccgtctctgctgagaacatcacatcaggattcctagg<br>acccctgctcgtgttacaggcggggtttttcttgttgacaagaatcctcacaataccgcagagtctagactcgtggtggacttctctcaattttctaggggggatctcccgtgtgtcttggccaaaattcgca<br>gtccccaacctccaatcactcaccaacctcctgtcctccaatttgtcctggttatcgctggatgtgtctgcggcgttttatcatattcctcttcatcctgctgctatgcctcatcttcttattggttcttctg<br>gattatcaaggtatgttgcccgtttgtcctctaattccaggatcaacaacaaccagtacgggaccatgcaaaacctgcacgactcctgctcaaggcaactctatgtttccctcatgttgctgtacaaaacctac<br>ggatggaaattgcacctgtattcccatcccatcgtcctgggctttcgcaaaatacctatgggagtgggcctcagtccgtttctcttggctcagtttactagtgccatttgttcagtggttcgtagggctttcc<br>cccactgtttggctttcagctatatggatgatgtggtattgggggccaagtctgtacagcatcgtgagtccctttataccgctgttaccaattttcttttgtctctgggtatacatttaa |
| SEQ ID NO: 38 | atcaggtgcataggagtcagcaatagggactttgtggaaggtatgtcaggtgggacttgggttgatgttgtcttggaacatggaggttgtgtcactgtaatggcacaggacaaaccgactgtcgacat<br>agagctggttacaacaacagtcagcaacatggcggaggtaagatcctactgctatgaggcatcaatatcagacatggcttcggacagccgctgcccaacacaaggtgaagcctaccttgacaagc<br>aatcagacactcaatatgtctgcaaaagaacgttagtggacagaggctggggaaatggatgtggactttttggcaaagggagcctggtgacatgcgctaagtttgcatgctccaagaaaatgaccg<br>ggaagagcatccagccagagaatctggagtaccggataatgctgtcagttcatggctcccagcacagtgggatgatcgttaatgacacaggacatgaaactgatgagaatagagcgaaagttgag<br>ataacgcccaattcaccaagagccgaagccaccctggggggggtttggaagcctaggacttgattgtgaaccgaggacaggccttgacttttcagatttgtattacttgactatgaataacaagcactg<br>gctggttcacaaggagtggttccacgacattccattaccttggcacgctggggcagacaccggaactccacactggaacaacaaagaagcactggtagagttcaaggacgcacatgccaaaagg<br>caaactgtcgtggttctagggagtcaagaaggagcagttcacacggcccttgctggagctctggaggctgagatggatggtgcaaagggaaggctgtcctctggccacttgaaatgtcgcctgaa<br>aatggataaacttagattgaagggcgtgtcatactccttgtgtactgcagcgncacattcaccaagatcccggctgaaacactgcacgggacagtcacagtggaggtacagtacgcagggacaga<br>tggaccttgcaaggttccagctcagatggcggtggacatgcaaactctgaccccagttgggaggttgataaccgctaaccccgtaatcactgaaagcactgagaactctaagatgatgctggaactt<br>gatccaccatttggggactcttacattgtcataggagtcggggagaagaagatcacccaccactggcacaggagtggcagcaccattggaaaagcatttgaagccactgtgagaggtgccaagag |

TABLE 2-continued

| lists the sequences of the present invention: | |
|---|---|
| | aatggcagtcttgggagacacagcctgggactttggatcagttggaggcgctctcaactcattgggcaagggcatccatcaaatctttggagcagctttcaaatcattgtttggaggaatgtcctggtt<br>ctcacaaattctcattggaacgttgctgatgtggttgggtctgaacgcaaagaatggatctcagtggaattccactgccttccaccaaactctgcaggatcccagagtcaggggtctgtatcttcctgct<br>ggtggctccagttcaggaacagtaaaccctgctccgaatattgcctctcacatctcgtcaatctccgcgaggactggggaccctgtgacgaacatggagaacatcacatcaggattcctaggacccc<br>tgctcgtgttacaggcggggtttttcttgttgacaagaatcctcacaataccgcagagtctagactcgtggtggacttctctcaattttctagggggatctcccgtgtgtcttggccaaaattcgcagtccc<br>caacctccaatcactcaccaacctcctgtcctccaatttgtcctggttatcgctggatgtgtctgcggcgttttatcatattcctcttcatcctgctgctatgcctcatcttcttattggttcttctggatta<br>tcaaggtatgttgcccgtttgtcctctaattccaggatcaacaacaaccagtacgggaccatgcaaaacctgcacgactcctgctcaaggcaactctatgtttccctcatgttgctgtacaaaacctacggatg<br>gaaattgcacctgtattcccatcccatcgtcctgggctttcgcaaaatacctatgggagtgggcctcagtccgtttctcttggctcagtttactagtgccatttgttcagtggttcgtagggctttcccccac<br>tgtttggctttcagctatatggatgatgtggtattgggggccaagtctgtacagcatcgtgagtccctttatctaccgctgttaccaattttcttttgtctctgggtatacatttaa |
| SEQ ID NO: 39 | agacgtgggagtgcatactatatgtacttggacagaaacgatgctggggaggccatatcttttccaaccacattggggatgaataagtgttatatacagatcatggatcttggacacacgtgtgatgcc<br>accatgagctatgaatgccctatgctggatgagggggtggaaccagatgacgtcgattgttggtgcaacacgacgtcaacttgggttgtgtacggaacctgccatcacaaaaaaggtgaagcacg<br>gagatctagaagagctgtgacgctcccctcccattccactaggaagctgcaaacgcggtcgcaaacctggttggaatcaagagaatacacaaagcacttgattagagtcgaaaattggatattcag<br>gaaccctggcttcgcgttagcagcagctgccatcgcttggcttttgggaagctcaacgagccaaaaagtcatatacttggtcatgatactgctgattgccccggcatacagcatcaggtgcataggag<br>tcagcaatagggactttgtggaaggtatgtcaggtgggacttgggttgatgttgtcttggaacatggaggttgtgtcactgtaatggcacaagacaaaccgactgtcgacatagagctggttacaaca<br>acagtcagcaacatggcggaggtaagatcctactgctatgaggcatcaatatcagacatggcttcggacagccgctgcccaacacaaggtgaagcctaccttgacaagcaatcagacactcaatat<br>gtctgcaaaagaacgttagtggacagaggctggggaaatggatgtggactttttggcaaagggagcctggtgacatgcgctaagtttgcatgctccaagaaaatgaccgggaagagcatccagcc<br>agagaatctggagtaccggataatgctgtcagttcatggctcccagcacagtgggatgatcgttaatgacacaggacatgaaactgatgagaatagagcgaaagttgagataacgcccaattcacc<br>aagagccgaagccaccctgggggggtttggaagcctaggacttgattgtgaaccgaggacaggccttgacttttcagatttgtattacttgactatgaataacaagcactggctggttcacaaggagt<br>ggttccacgacattccattaccttggcacgctggggcagacaccggaactccacactggaacaacaaagaagcactggtagagttcaaggacgcacatgccaaaaggcaaactgtcgtggttcta<br>gggagtcaagaaggagcagttcacacggcccttgctggagctctggaggctgagatggatggtgcaaagggaaggctgtcctctggccacttgaaatgtcgcctgaaaatggataaacttagatt<br>gaagggcgtgtcatactccttgtgtactgcagcgttcacattcaccaagatcccggctgaaacactgcacgggacagtcacagtggaggtacagtacgcagggacagatggaccttgcaaggttc<br>cagctcagatggcggtggacatgcaaactctgaccccagttgggaggttgataactgctaaccccgtaatcactgaaagcactgagaactctaagatgatgctggaacttgataaccatttgggga<br>ctcttacattgtcataggagtcggggagaagaagatcacccaccactggcacaggagtggcagcaccattggaaaagcatttgaagccactgtgagaggtgccaagagaatggcagtcttggga<br>gacacagcctgggactttggatcagttggaggcgctctcaactcattgggcaagggcatccatcaaatctttggagcagctttcaaatcattgtttggaggaatgtcctggttctcacaaattctcattgg<br>aacgttgctgatgtggttgggtctgaacgcaaagaatggatctcagtggaattccactgccttccaccaaactctgcaggatcccagagtcaggggtctgtatcttcctgctggtggctccagttcagg<br>aacagtaaaccctgctccgaatattgcctctcacatctcgtcaatctccgcgaggactggggaccctgtgacgaacatggagaacatcacatcaggattcctaggacccctgctcgtgttacaggcg<br>gggtttttcttgttgacaagaatcctcacaataccgcagagtctagactcgtggtggacttctctcaattttctagggggatctcccgtgtgtcttggccaaaattcgcagtccccaacctccaatcactca<br>ccaacctcctgtcctccaatttgtcctggttatcgctggatgtgtctgcggcgttttatcatattcctcttcatcctgctgctatgcctcatcttcttattggttcttctggattatcaaggtatgttgcccg<br>tttgtcctctaattccaggatcaacaacaaccagtacgggaccatgcaaaacctgcacgactcctgctcaaggcaactctatgtttccctcatgttgctgtacaaaacctacggatggaaattgcacctgtatt<br>cccatcccatcgtcctgggctttcgcaaaatacctatgggagtgggcctcagtccgtttctcttggctcagtttactagtgccatttgttcagtggttcgtagggctttcccccactgtttggctttcagctat<br>atggatgatgtggtattgggggccaagtctgtacagcatcgtgagtccctttataccgctgttaccaattttcttttgtctctgggtatacatttaa |
| SEQ ID NO: 40 | atcaggtgcataggagtcagcaatagggactttgtggaaggtatgtcaggtgggacttgggttgatgttgtcttggaacatggaggttgtgtcactgtaatggcacaggacaaaccgactgtcgacat<br>agagctggttacaacaacagtcagcaacatggcggaggtaagatcctactgctatgaggcatcaatatcagacatggcttcggacagccgctgcccaacacaaggtgaagcctaccttgacaagc<br>aatcagacactcaatatgtctgcaaaagaacgttagtggacagaggctggggaaatggatgtggactttttggcaaagggagcctggtgacatgcgctaagtttgcatgctccaagaaaatgaccg<br>ggaagagcatccagccagagaatctggagtaccggataatgctgtcagttcatggctcccagcacagtgggatgatcgttaatgacacaggacatgaaactgatgagaatagagcgaaagttgag<br>ataacgcccaattcaccaagagccgaagccaccctgggggggtttggaagcctaggacttgattgtgaaccgaggacaggccttgacttttcagatttgtattacttgactatgaataacaagcactg<br>gctggttcacaaggagtggttccacgacattccattaccttggcacgctggggcagacaccggaactccacactggaacaacaaagaagcactggtagagttcaaggacgcacatgccaaaagg<br>caaactgtcgtggttctagggagtcaagaaggagcagttcacacggcccttgctggagctctggaggctgagatggatggtgcaaagggaaggctgtcctctggccacttgaaatgtcgcctgaa<br>aatggataaacttagattgaagggcgtgtcatactccttgtgtactgcagcgttcacattcaccaagatcccggctgaaacactgcacgggacagtcacagtggaggtacagtacgcagggacaga<br>tggaccttgcaaggttccagctcagatggcggtggacatgcaaactctgaccccagttgggaggttgataaccgctaaccccgtaatcactgaaagcactgagaactctaagatgatgctggaactt<br>gatccaccatttggggactcttacattgtcataggagtcggggagaagaagatcacccaccactggcacaggagtggcagcaccattggaaaagcatttgaagccactgtgagaggtgccaagag<br>aatggcagtcttgggagacacagcctgggactttggatcagttggaggcgctctcaactcattgggcaagggcatccatcaaatctttggagcagctttcaaatcattgtttggaggaatgtcctggtt<br>ctcacaaattctcattggaacgttgctgatgtggttgggtctgaacgcaaagaatggatctatttcccttatgtgcttggccttagggggagtgttgatcttcttatccacagccgtctctgctcagtggaat<br>tccactgccttccaocaaactctgcaggatcccagagtcaggggtctgtatcttcctgctggtggctccagttcaggaacagtaaaccctgctccgaatattgcctctcacatctcgtcaatctccgcga<br>ggactggggaccctgtgacgaacatggagaacatcacatcaggattcctaggacccctgctcgtgttacaggcggggtttttcttgttgacaagaatcctcacaataccgcagagtctagactcgtg<br>gtggacttctctcaattttctagggggatctcccgtgtgtcttggccaaaattcgcagtccccaacctccaatcactcaccaacctcctgtcctccaatttgtcctggttatcgctggatgtgtctgcggcg<br>ttttatcatattcctcttcatcctgctgctatgcctcatcttcttattggttcttctggattatcaaggtatgttgcccgtttgtcctctaattccaggatcaacaacaaccagtacgggaccatgcaaaacc<br>tgcacgactcctgctcaaggcaactctatgtttccctcatgttgctgtacaaaacctacggatggaaattgcacctgtattcccatcccatcgtcctgggctttcgcaaaatacctatgggagtgggcctcagt<br>ccgtttctcttggctcagtttactagtgccatttgttcagtggttcgtagggctttcccccactgtttggctttcagctatatggatgatgtggtattgggggccaagtctgtacagcatcgtgagtccctttta<br>taccgctgttaccaattttcttttgtctctgggtatacatttaa |

TABLE 2-continued

| lists the sequences of the present invention: | |
|---|---|
| SEQ ID NO: 41 | agacgtgggagtgcatactatatgtacttggacagaaacgatgctggggaggccatatcttttccaaccacattggggatgaataagtgttatatacagatcatggatcttggacacacgtgtgatgcc<br>accatgagctatgaatgccctatgctggatgagggggtggaaccagatgacgtcgattgttggtgcaacacgacgtcaacttgggttgtgtacggaacctgccatcacaaaaaaggtgaagcacg<br>gagatctagaagagctgtgacgctcccctcccattccactaggaagctgcaaacgcggtcgcaaacctggttggaatcaagagaatacacaaagcacttgattagagtcgaaaattggatattcag<br>gaaccctggcttcgcgttagcagcagctgccatcgcttggcttttgggaagctcaacgagccaaaaagtcatatacttggtcatgatactgctgattgccccggcatacagcatcaggtgcataggag<br>tcagcaatagggactttgtggaaggtatgtcaggtgggacttgggttgatgttgtcttggaacatggaggttgtgtcactgtaatggcacaggacaaaccgactgtcgacatagagctggttacaaca<br>acagtcagcaacatggcggaggtaagatcctactgctatgaggcatcaatatcagacatggcttcggacagccgctgcccaacacaaggtgaagcctaccttgacaagcaatcagacactcaatat<br>gtctgcaaaagaacgttagtggacagaggctggggaaatggatgtggactttttggcaaagggagcctggtgacatgcgctaagtttgcatgctccaagaaaatgaccgggaagagcatccagcc<br>agagaatctggagtaccggataatgctgtcagttcatggctcccagcacagtgggatgatcgttaatgacacaggacatgaaactgatgagaatagagcgaaagttgagataacgcccaattcacc<br>aagagccgaagccaccctgggggggtttggaagcctaggacttgattgtgaaccgaggacaggccttgacttttcagatttgtattacttgactatgaataacaagcactggctggttcacaaggagt<br>ggttccacgacattccattaccttggcacgctggggcagacaccggaactccacactggaacaacaaagaagcactggtagagttcaaggacgcacatgccaaaaggcaaactgtcgtggttcta<br>gggagtcaagaaggagcagttcacacggcccttgctggagctctggaggctgagatggatggtgcaaagggaaggctgtcctctggccacttgaaatgtcgcctgaaaatggataaacttagatt<br>gaagggcgtgtcatactccttgtgtactgcagcgttcacattcaccaagatcccggctgaaacactgcacgggacagtcacagtggaggtacagtacgcagggacagatggaccttgcaaggttc<br>cagctcagatggcggtggacatgcaaactctgaccccagttgggaggttgataaccgctaaccccgtaatcactgaaagcactgagaactctaagatgatgctggaacttgatccaccatttgggga<br>ctcttacattgtcataggagtcggggagaagaagatcacccaccactggcacaggagtggcagcaccattggaaaagcatttgaagccactgtgagaggtgccaagagaatggcagtcttggga<br>gacacagcctgggactttggatcagttggaggcgctctcaactcattgggcaagggcatccatcaaatctttggagcagctttcaaatcattgtttggaggaatgtcctggttctcacaaattctcattgg<br>aacgttgctgatgtggttgggtctgaacgcaaagaatggatctatttcccttatgtgcttggccttagggggagtgttgatcttcttatccacagccgtctctgctcagtggaattccactgccttccacca<br>aactctgcaggatcccagagtcaggggtctgtatcttcctgctggtggctccagttcaggaacagtaaaccctgctccgaatattgcctctcacatctcgtcaatctccgcgaggactggggaccctgt<br>gacgaacatggagaacatcacatcaggattcctaggacccctgctcgtgttacaggcggggtttttcttgttgacaagaatcctcacaataccgcagagtctagactcgtggtggacttctctcaatttt<br>ctagggggatctcccgtgtgtcttggccaaaattcgcagtccccaacctccaatcactcaccaacctcctgtcctccaatttgtcctggttatcgctggatgtgtctgcggcgttttatcatattcctcttcat<br>cctgctgctatgcctcatcttcttattggttcttctggattatcaaggtatgttgcccgtttgtcctctaattccaggatcaacaacaaccagtacgggaccatgcaaaacctgcacgactcctgctcaagg<br>caactctatgtttccctcatgttgctgtacaaaacctacggatggaaattgcacctgtattcccatcccatcgtcctgggctttcgcaaaatacctatgggagtgggcctcagtccgtttctcttggctcagt<br>ttactagtgccatttgttcagtggttcgtagggctttcccccactgtttggctttcagctatatggatgatgtggtattgggggccaagtctgtacagcatcgtgagtccctttataccgctgttaccaatttt<br>cttttgtctctgggtatacatttaa |
| SEQ ID NO: 42 | atgttgggaagctcaacgagccaaaaagtcatatacttggtcatgatactgctgattgccccggcatacagcatcaggtgcataggagtcagcaatagggactttgtggaaggtatgtcaggtggga<br>cttgggttgatgttgtcttggaacatggaggttgtgtcactgtaatggcacaggacaaaccgactgtcgacatagagctggttacaacaacagtcagcaacatggcggaggtaagatcctactgctat<br>gaggcatcaatatcagacatggcttcggacagccgctgcccaacacaaggtgaagcctaccttgacaagcaatcagacactcaatatgtctgcaaaagaacgttagtggacagaggctggggaa<br>atggatgtggactttttggcaaagggagcctggtgacatgcgctaagtttgcatgctccaagaaaatgaccgggaagagcatccagccagagaatctggagtaccggataatgctgtcagttcatgg<br>ctcccagcacagtgggatgatcgttaatgacacaggacatgaaactgatgagaatagagcgaaagttgagataacgcccaattcaccaagagccgaagccaccctgggggggtttggaagccta<br>ggacttgattgtgaaccgaggacaggccttgacttttcagatttgtattacttgactatgaataacaagcactggctggttcacaaggagtggttccacgacattccattaccttggcacgctggggcag<br>acaccggaactccacactggaacaacaaagaagcactggtagagttcaaggacgcacatgccaaaaggcaaactgtcgtggttctagggagtcaagaaggagcagttcacacggcccttgctg<br>gagctctggaggctgagatggatggtgcaaagggaaggctgtcctctggccacttgaaatgtcgcctgaaaatggataaacttagattgaagggcgtgtcatactccttgtgtactgcagcgttcaca<br>ttcaccaagatcccggctgaaacactgcacgggacagtcacagtggaggtacagtacgcagggacagatggaccttgcaaggttccagctcagatggcggtggacatgcaaactctgaccccag<br>ttgggaggttgataaccgctaaccccgtaatcactgaaagcactgagaactctaagatgatgctggaacttgatccaccatttggggactcttacattgtcataggagtcggggagaagaagatcacc<br>caccactggcacaggagtggcagcaccattggaaaagcatttgaagccactgtgagaggtgccaagagaatggcagtcttgggagacacagcctgggactttggatcagttggaggcgctctca<br>actcattgggcaagggcatccatcaaatctttggagcagctttcaaatcattgtttggaggaatgtcctggttctcacaaattctcattggaacgttgctgatgtggttgggtctgaacgcaaagaatgga<br>tctagaatcctcacaataccgcagagtctagactcgtggtggacttctctcaattttctagggggatctcccgtgtgtcttggccaaaattcgcagtccccaacctccaatcactcaccaacctcctgtcc<br>tccaatttgtcctggttatcgctggatgtgtctgcggcgttttatcatattcctcttcatcctgctgctajgcctcatcttcttattggttcttctggattatcaaggtatgttgcccgtttgtcctctaatt<br>ccaggatcaacaacaaccagtacgggaccatgcaaaacctgcacgactcctgctcaaggcaactctatgtttccctcatgttgctgtacaaaacctacggatggaaattgcacctgtattcccatcccatcgt<br>cctgggctttcgcaaaatacctatgggagtgggcctcagtccgtttctcttggctcagtttactagfgccatttgttcagtggttcgtagggctttcccccactgtttggctttcagctatatggatgatgtg<br>gtattgggggccaagtctgtacagcatcgtgagtccctttataccgctgttaccaattttcttttgtctctgggtatacatttaa |
| SEQ ID NO: 43 | atgctgagaataatcaatgctaggaaggagaagaagagacgaggcgcagatacaagtgtcggaattgttggcctcctgctgaccacagctatggcagcggaggtcactagacgtgggagtgcat<br>actatatgtacttggacagaaacgatgctggggaggccatatcttttccaaccacattggggatgaataagtgttatatacagatcatggatcttggacacacgtgtgatgccaccatgagctatgaatg<br>ccctatgctggatgagggggtggaaccagatgacgtcgattgttggtgcaacacgacgtcaacttgggttgtgtacggaacctgccatcacaaaaaaggtgaagcacggagatctagaagagctg<br>tgacgctcccctcccattccactaggaagctgcaaacgcggtcgcaaacctggttggaatcaagagaatacacaaagcacttgattagagtcgaaaattggatattcaggaaccctggcttcgcgtt<br>agcagcagctgccatcgcttggcttttgggaagctcaacgagccaaaaagtcatatacttggtcatgatactgctgattgccccggcatacagcatcaggtgcataggagtcagcaatagggactttg<br>tggaaggtatgtcaggtgggacttgggttgatgttgtcttggaacatggaggttgtgtcactgtaatggcacaggacaaaccgactgtcgacatagagctggttacaacaacagtcagcaacatggc<br>ggaggtaagatcctactgctatgaggcatcaatatcagacatggcttcggacagccgctgcccaacacaaggtgaagcctaccttgacaagcaatcagacactcaatatgtctgcaaaagaacgtt<br>agtggacagaggctggggaaatggatgtggactttttggcaaagggagcctggtgacatgcgctaagtttgcatgctccaagaaaatgaccgggaagagcatccagccagagaatctggagtac |

TABLE 2-continued

| lists the sequences of the present invention: | |
|---|---|
| | cggataatgctgtcagttcatggctcccagcacagtgggatgatcgttaatgacacaggacatgaaactgatgagaatagagcgaaagttgagataacgcccaattcaccaagagccgaagccac<br>cctgggggggtttggaagcctaggacttgattgtgaaccgaggacaggccttgacttttcagatttgtattacttgactatgaataacaagcactggctggttcacaaggagtggttccacgacattcca<br>ttaccttggcacgctggggcagacaccggaactccacactggaacaacaaagaagcactggtagagttcaaggacgcacatgccaaaaggcaaactgtcgtggttctagggagtcaagaagga<br>gcagttcacacggcccttgctggagctctggaggctgagatggatggtgcaaagggaaggctgtcctctggccacttgaaatgtcgcctgaaaatggataaacttagattgaagggcgtgtcatact<br>ccttgtgtactgcagcgttcacattcaccaagatcccggctgaaacactgcacgggacagtcacagtggaggtacagtacgcagggacagatggaccttgcaaggttccagctcagatggcggtg<br>gacatgcaaactctgaccccagttgggaggttgataaccgctaaccccgtaatcactgaaagcactgagaactctaagatgatgctggaacttgatccaccatttggggactcttacattgtcatagga<br>gtcggggagaagaagatcacccaccactggcacaggagtggcagcaccattggaaaagcatttgaagccactgtgagaggtgccaagagaatggcagtcttgggagacacagcctgggacttt<br>ggatcagttggaggcgctctcaactcattgggcaagggcatccatcaaatctttggagcagctttcaaatcattgtttggaggaatgtcctggttctcacaaattctcattggaacgttgctgatgtggttg<br>ggtctgaacgcaaagaatggatctagaatcctcacaataccgcagagtctagactcgtggtggacttctctcaattttctaggggggatctcccgtgtgtcttggccaaaattcgcagtccccaacctcc<br>aatcactcaccaacctcctgtcctccaatttgtcctggttatcgctggatgtgtctgcggcgttttatcatattcctcttcatcctgctgctatgcctcatcttcttattggttcttctggattatcaaggta<br>tgttgcccgtttgtcctctaattccaggatcaacaacaaccagtacgggaccatgcaaaacctgcacgactcctgctcaaggcaactctatgtttccctcatgttgctgtacaaaacctacggatggaaattgc<br>acctgtattcccatcccatcgtcctgggctttcgcaaaatacctatgggagtgggcctcagtccgtttctcttggctcagtttactagtgccatttgttcagtggttcgtagggctttcccccactgtttggct<br>ttcagctatatggatgatgtggtattgggggccaagtctgtacagcatcgtgagtccctttataccgctgttaccaattttcttttgtctctgggtatacatttaa |
| SEQ ID NO: 44 | atgttgggaagctcaacgagccaaaaagtcatatacttggtcatgatactgctgattgccccggcatacagcatcaggtgcataggagtcagcaatagggactttgtggaaggtatgtcaggtggga<br>cttgggttgatgttgtcttggaacatggaggttgtgtcactgtaatggcacaggacaaaccgactgtcgacatagagctggttacaacaacagtcagcaacatggcggaggtaagatcctactgctat<br>gaggcatcaatatcagacatggcttcggacagccgctgcccaacacaaggtgaagcctaccttgacaagcaatcagacactcaatatgtctgcaaaagaacgttagtggacagaggctggggaa<br>atggatgtggactttttggcaaagggagcctggtgacatgcgctaagtttgcatgctccaagaaaatgaccgggaagagcatccagwagagaatctggagtaccggataatgctgtcagttcatgg<br>ctcccagcacagtgggatgatcgttaatgacacaggacatgaaactgatgagaatagagcgaaagttgagataacgcccaattcaccaagagccgaagccaccctgggggggtttggaagccta<br>ggacttgattgtgaaccgaggacaggccttgacttttcagatttgtattacttgactatgaataacaagcactggctggttcacaaggagtggttccacgacattccattaccttggcacgctggggcag<br>acaccggaactccacactggaacaacaaagaagcactggtagagttcaaggacgcacatgccaaaaggcaaactgtcgtggttctagggagtcaagaaggagcagttcacacggcccttgctg<br>gagctctggaggctgagatggatttgtgcaaagggaaggctgtcctctggccacttgaaatgtcgcctgaaaatggataaacttagattgaagggcgtgtcatactccttgtgtactgcagcgttcaca<br>ttcaccaagatcccggctgaaacactgcacgggacagtcacagtggaggtacagtacgcagggacagatggaccttgcaaggttccagctcagatggcggtggacatgcaaactctgaccccag<br>ttgggaggttgataaccgctaaccccgtaatcactgaaagcactgagaactctaagatgatgctggaacttgatccaccatttggggactcttacattgtcataggagtcggggagaagaagatcacc<br>caccactggcacaggagtggcagcaccattggaaaagcatttgaagccactgtgagaggtgccaagagaatggcagtcttgggagacacagcctgggactttggatcagttggaggcgctctca<br>actcattgggcaagggcatccatcaaatctttggagcagctttcaaatcattgtttggaggaatgtcctggttctcacaaattctcattggaacgttgctgatgtggttgggtctgaacgcaaagaatgga<br>tctatttcccttatgtgcttggccttaggggggagtgttgatcttcttatccacagccgtctctgctgagaacatcacatcaggattcctaggacccctgctcgtgttacaggcggggtttttcttgttgacaa<br>gaatcctcacaataccgcagagtctagactcgtggtggacttctctcaattttctaggggggatctcccgtgtgtcttggccaaaattcgcagtccccaacctccaatcactcaccaacctcctgtcctcc<br>aatttgtcctggttatcgctggatgtgtctgcggcgttttatcatattcctcttcatcctgctgctatgcctcatcttcttattggttcttctggattatcaaggtatgttgcccgtttgtcctctaattcca<br>ggatcaacaacaaccagtacgggaccatgcaaaacctgcacgactcctgctcaaggcaactctatgtttccctcatgttgctgtacaaaacctacggatggaaattgcacctgtattcccatcccatcgtcctg<br>ggctttcgcaaaatacctatgggagtgggcctcagtccgtttctcttggctcagtttactagtgccatttgttcagtggttcgtagggctttcccccactgtttggctttcagctatatggatgatgtggtatt<br>gggggccaagtctgtacagcatcgtgagtccctttataccgctgttaccaattttcttttgtctctgggtatacatttaa |
| SEQ ID NO: 45 | atgctgagaataatcaatgctaggaaggagaagaagagacgaggcgcagatacaagtgtcggaattgttggcctcctgctgaccacagctatggcagcggaggtcactagacgtgggagtgcat<br>actatatgtacttggacagaaacgatgctggggaggccatatctttttccaaccacattggggatgaataagtgttatatacagatcatggatcttggacacacgtgtgatgccaccatgagctatgaatg<br>ccctatgctggatgaggggggtggaaccagatgacgtcgattgttggtgcaacacgacgtcaacttgggttgtgtacggaacctgccatcacaaaaaaggtgaagcacggagatctagaagagctg<br>tgacgctcccctcccattccactaggaagctgcaaacgcggtcgcaaacctggttggaattaagagaatacacaaagcacttgattagagtcgaaaattggatattcaggaaccctggcttcgcgtt<br>agcagcagctgccatcgcttggcttttgggaagctcaacgagccaaaaagtcatatacttggtcatgatactgctgattgccccggcatacagcatcaggtgcataggagtcagcaatagggactttg<br>tggaaggtatgtcaggtgggacttgggttgatgttgtcttggaacatggaggttgtgtcactgtaatggcacaggacaaaccgactgtcgacatagagctggttacaacaacagtcagcaacatggc<br>ggaggtaagatcctactgctatgaggcatcaatatcagacatggcttcggacagccgctgcccaacacaaggtgaagcctaccttgacaagcaatcagacactcaatatgtctgcaaaagaacgtt<br>agtggacagaggctggggaaatggatgtggactttttggcaaagggagcctggtgacatgcgctaagtttgcatgctccaagaaaatgaccgggaagagcatccagccagagaatctggagtac<br>cggataatgctgtcagttcatggctcccagcacagtgggatgatcgttaatgacacaggacatgaaactgatgagaatagagcgaaagttgagataacgcccaattcaccaagagccgaagccac<br>cctgggggggtttggaagcctaggacttgattgtgaaccgaggacaggccttgacttttcagatttgtattacttgactatgaataacaagcactggctggttcacaaggagtggttccacgacattcca<br>ttaccttggcacgctggggcagacaccggaactccacactggaacaacaaagaagcactggtagagttcaaggacgcacatgccaaaaggcaaactgtcgtggttctagggagtcaagaagga<br>gcagttcacacggcccttgctggagctctggaggctgagatggatggtgcaaagggaaggctgtcctctggccacttgaaatgtcgcctgaaaatggataaacttagattgaagggcgtgtcatact<br>ccttgtgtactgcagcgttcacattcaccaagatcccggctgaaacactgcacgggacagtcacagtggaggtacagtacgcagggacagatggaccttgcaaggttccagctcagatggcggtg<br>gacatgcaaactctgaccccagttgggaggttgataaccgctaaccccgtaatcactgaaagcactgagaactctaagatgatgctggaacttgatccaccatttggggactcttacattgtcatagga<br>gtcggggagaagaagatcacccaccactggcacaggagtggcagcaccattggaaaagcatttgaagccactgtgagaggtgccaagagaatggcagtcttgggagacacagcctgggacttt<br>ggatcagttggaggcgctctcaactcattgggcaagggcatccatcaaatctttggagcagctttcaaatcattgtttggaggaatgtcctggttctcacaaattctcattggaacgttgctgatgtggttg<br>ggtctgaacgcaaagaatggatctatttcccttatgtgcttggccttaggggggagtgttgatcttcttatccacagccgtctctgctgagaacatcacatcaggattcctaggacccctgctcgtgttaca<br>ggcggggtttttcttgttgacaagaatcctcacaataccgcagagtctagactcgtggtggacttctctcaattttctaggggggatctcccgtgtgtcttggccaaaattcgcagtccccaacctccaatc |

TABLE 2-continued

| | lists the sequences of the present invention: |
|---|---|
| | actcaccaacctcctgtcctccaatttgtcctggttatcgctggatgtgtctgcggcgttttatcatattcctcttcatcctgctgctatgcctcatcttcttattggttcttctggattatcaaggtatgttg<br>cccgtttgtcctctaattccaggatcaacaacaaccagtacgggaccatgcaaaacctgcacgactcctgctcaaggcaactctatgtttccctcatgttgctgtacaaaacctacggatggaaattgcacctg<br>tattcccatcccatcgtcctgggctttcgcaaaatacctatgggagtgggcctcagtccgtttctcttggctcagtttactagtgccatttgttcagtggttcgtagggctttcccccactgtttggctttcag<br>ctatatggatgatgtggtattggcggccaagtctgtacastcatcgtgagtccctttataccgctgttaccaattttcttttgtctctgggtatacatttaa |
| SEQ ID NO: 46 | atgttgggaagctcaacgagccaaaaagtcatatacttggtcatgatactgctgattgccccggcatacagcatcaggtgcataggagtcagcaatagggactttgtggaaggtatgtcaggtggga<br>cttgggttgatgttgtcttggaacatggaggttgtgtcactgtaatggcacaggacaaaccgactgtcgacatagagctggttacaacaacagtcagcaacatggcggaggtaagatcctactgctat<br>gaggcatcaatatcagacatggcttcggacagccgctgcccaacacaaggtgaagcctaccttgacaagcaatcagacactcaatattttctgcaaaagaacgttagtggacasaggctggggaa<br>atggatgtggacttttttggcaaagggagcctggtgacatgcgctaagtttgcatgctccaagaaaatgaccgggaagagcatccagccagagaatctggagtaccggataatgctgtcagttcatgg<br>ctcccagcacagtgggatgatcgttaatgacacaggacatgaaactgatgagaatagagcgaaagttgagataacgcccaattcaccaagagccgaagccaccctgggggggtttggaagccta<br>ggacttgattgtgaaccgaggacaggccttgacttttcagatttgtattacttgactatgaataacaagcactggctggttcacaaggagtggttccacgacattccattaccttggcacgctggggcag<br>acaccggaactccacactggaacaacaaagaagcactggtagagttcaaggacgcacatgccaaaaggcaaactgtcgtggttctagggagtcaagaaggagcagttcacacggcccttgctg<br>gagctctggaggctgagatggatggtgcaaagggaaggctgtcctctggccacttgaaatgtcgcctgaaaatggataaacttagattgaagggcgtgtcatactccttgtgtactgcagcgttcaca<br>ttcaccaagatcccggctgaaacactgcacgggacagtcacagtggaggtacagtacgcagggacagatggaccttgcaaggttccagctcagatggcggtggacatgcaaactctgaccccag<br>ttgggaggttgataaccgctaaccccgtaatcactgaaagcactgagaactctaagatgatgctggaacttgatccaccatttggggactcttacattgtcataggagtcggggagaagaagatcacc<br>caccactggcacaggagtggcagcaccattggaaaagcatttgaagccactgtgagaggtgccaagagaatggcagtcttgggagacacagcctgggactttggatcagttggaggcgctctca<br>actcattgggcaagggcatccatcaaatctttggagcagctttcaaatcattgtttggaggaatgtcctggttctcacaaattctcattggaacgttgctgatgtggttgggtctgaacgcaaagaatgga<br>tctcagtggaattccactgccttccaccaaactctgcaggatcccagagtcaggggtctgtatcttcctgctggtggctccagttcaggaacagtaaaccctgctccgaatattgcctctcacatctcgt<br>caatctccgcgaggactggggaccctgtgacgaacatggagaacatcacatcaggattcctaggacccctgctcgtgttacaggcggggtttttcttgttgacaagaatcctcacaataccgcagag<br>tctagactcgtggtggacttctctcaattttctagggggatctcccgtgtgtcttggccaaaattcgcagtccccaacctccaatcactcaccaacctcctgtcctccaatttgtcctggttatcgctggatg<br>tgtctgcggcgttttatcatattcctcttcatcctgctgctatgcctcatcttcttattggttcttctggattatcaaggtatgttgcccgtttgtcctctaattccaggatcaacaacaaccagtacgggacc<br>atgcaaaacctgcacgactcctgctcaaggcaactctatgtttccctcatgttgctgtacaaaacctacggatggaaattgcacctgtattcccatcocatcgtcctgggctttcgcaaaatacctatggga<br>gtgggcctcagtccgtttctcttggctcagtttactagtgccatttgttcagtggttcgtagggctttcccccactgtttggctttcagctatatggatgatgtggtattgggggccaagtctgtacagcatc<br>gtgagtccctttataccgctgttaccaattttcttttgtctctgggtatacatttaa |
| SEQ ID NO: 47 | atgctgagaataatcaatgctaggaaggagaagaagagacgaggcgcagatacaagtgtcggaattgttggcctcctgctgaccacagctatggcagcggaggtcactagacgtgggagtgcat<br>actatatgtacttggacagaaacgatgctggggaggccatatcttttccaaccacattggggatgaataagtgttatatacagatcatggatcttggacacacgtgtgatgccaccatgagctatgaatg<br>ccctatgctggatgaggggggtggaaccagatgacgtcgattgttggtgcaacacgacgtcaacttgggttgtgtacggaacctgccatcacaaaaaaggtgaagcacggagatctagaagagctg<br>tgacgctcccctcccattccactaggaagctgcaaacgcggtcgcaaacctggttggaatcaagagaatacacaaagcacttgattagagtcgaaaattggatattcaggaaccctggcttcgcgtt<br>agcagcagctgccatcgcttggcttttgggaagctcaacgagccaaaaagtcatatacttggtcatgatactgctgattgccccggcatacagcatcaggtgcataggagtcagcaatagggactttg<br>tggaaggtatgtcaggtgggacttgggttgatgttgtcttggaacatggaggttgtgtcactgtaatggcacaggacaaaccgactgtcgacatagagctggttacaacaacagtcagcaacatggc<br>ggaggtaagatcctactgctatgaggcatcaatatcagacatggcttcggacagccgctgcccaacacaaggtgaagcctaccttgacaagcaatcagacactcaatatgtctgcaaaagaacgtt<br>agtggacagaggctggggaaatggatgtggactttttggcaaagggagcctggtgacatgcgctaagtttgcatgctccaagaaaatgaccgggaagagcatccagccagagaatctggagtac<br>cggataatgctgtcagttcatggctcccagcacagtgggatgatcgttaatgacacaggacatgaaactgatgagaatagagcgaaagttgagataacgcccaattcaccaagagccgaagccac<br>cctgggggggtttggaagcctaggacttgattgtgaaccgaggacaggccttgacttttcagatttgtattacttgactatgaataacaagcactggctggttcacaaggagtggttccacgacattcca<br>ttaccttggcacgctggggcagacaccggaactccacactggaacaacaaagaagcactggtagagttcaaggacgcacatgccaaaaggcaaactgtcgtggttctagggagtcaagaagga<br>gcagttcacacggcccttgctggagctctggaggctgagatggatggtgcaaagggaaggctgtcctctggccacttgaaatgtcgcctgaaaatggataaacttagattgaagggcgtgtcatact<br>ccttgtgtactgcagcgttcacattcaccaagatcccggctgaaacactgcacgggacagtcacagtggaggtacagtacgcagggacagatggaccttgcaaggttccagctcagatggcggtg<br>gacatgcaaactctgaccccagttgggaggttgataaccgctaaccccgtaatcactgaaagcactgagaactctaagatgatgctggaacttgatcgaccatttggggactcttacattgtcatagga<br>gtcggggagaagaagatcacccaccactggcacaggagtggcagcaccattggaaaagcatttgaagccactgtgagaggtgccaagagaatggcagtcttgggagacacagcctgggacttt<br>ggatcagttggaggcgctctcaactcattgggcaagggcatccatcaaatctttggagcagctttcaaatcattgtttggaggaatgtcctggttctcacaaattctcattggaacgttgctgatgtggttg<br>ggtctgaacgcaaagaatggatctcagtggaattccactgccttccaccaaactctgcaggatcccagagtcaggggtctgtatcttcctgctggtggctccagttcaggaacagtaaaccctgctcc<br>gaatattgcctctcacatctcgtcaatctccgcgaggactggggaccctgtgacgaacatggagaacatcacatcaggattcctaggacccctgctcgtgttacaggcggggtttttcttgttgacaag<br>aatcctcacaaraccgcagagtctagactcgtggtggacttctctcaattttctagggggatctcccgtgtgtcttggccaaaattcgcagtccccaacctccaatcactcaccaacctcctgtcctccaa<br>tttgtcctggttatcgctggatgtgtctgcggcgttttatcatattcctcttcatcctgctgctatgcctcatcttcttattggttcttctggattatcaaggtatgttgcccgtttgtcctctaattccagg<br>atcaacaacaaccagtacgggaccatgcaaaacctgcacgactcctgctcaaggcaactctatgtttccctcatgttgctgtacaaaacctacggatggaaattgcacctgtattcccatcccatcgtcctggg<br>ctttcgcaaaatacctatgggagtgggcctcagtccgtttctcttggctcagtttactagtgccatttgttcagtggttcgtagggctttcccccactgtttggctttcagctatatggatgatgtggtattgg<br>gggccaagtctatacagcatcgtgagtccctttataccgctgttaccaattttcttttgtctctaggtatacatttaa |

TABLE 2-continued lists the sequences of the present invention:

| | |
|---|---|
| SEQ ID NO: 48 | atgttgggaagctcaacgagccaaaaagtcatatacttggtcatgatactgctgattgccccggcatatagcatcaggtgcataggagtcagcaatagggactttgtggaaggtatgtcaggtggga<br>cttgggttgatgttgtcttggaacatggaggttgtgtcactgtaatggcacaggacaaaccgactgtcgacatagagctggttacaacaacagtcagcaacatggcggaggtaagatcctactgctat<br>gaggcatcaatatcagacatggcttcggacagccgctgcccaacacaaggtgaagcctaccttgacaagcaatcagacactcaatatgtctgcaaaagaacgttagtggacagaggctggggaa<br>atggatgtggacttttggcaaagggagcctggtgacatgcgctaagtttgcatgctccaagaaaatgaccgggaagagcatccagccagagaatctggagtaccggataatgctgtcagttcatgg<br>ctcccagcacagtgggatgatcgttaatgacacaggacatgaaactgatgagaatagagcgaaagttgagataacgcccaattcaccaagagccgaagccaccctggggggtttggaagccta<br>ggacttgattgtgaaccgaggacaggccttgacttttcagatttgtattacttgactatgaataacaagcactggctggttcacaaggagtggttccacgacattccattaccttggcacgctggggcag<br>acaccggaactccacactggaacaacaaagaagcactggtagagttcaaggacgcacatgccaaaaggcaaactgtcgtggttctagggagtcaagaaggagcagttcacacggcccttgctg<br>gagctctggaggctgagatggatggtgcaaagggaaggctgtcctctggccacttgaaatgtcgcctgaaaatggataaacttagattgaagggcgtgtcatactccttgtgtactgcagcgttcaca<br>ttcaccaagatcccggctgaaacactgcacgggacagtcacagtggaggtacagtacgcagggacagatggaccttgcaaggttccagctcagatggcggtggacatgcaaactctgaccccag<br>ttgggaggttgataaccgctaaccccgtaatcactgaaagcactgagaactctaagatgatgctggaacttgatccaccatttggggactcttacattgtcataggagtcggggagaagaagatcacc<br>caaactggcacaggagtggcagcaccattggaaaagcatttgaagccactgtgagaggtgccaagagaatggcagtcttgggagacacagcctgggactttggatcagttggaggcgctctca<br>actcattgggcaagggcatccatcaaatctttggagcagctttcaaatcattgtttggaggaatgtcctggttctcacaaattctcattggaacgttgctgatgtggttgggtctgaacgcaaagaatgga<br>tctatttcccttatgtgcttggccttaggggagtgttgatcttcttatccacagccgtctctgctcagtggaattccactgccttccaccaaactctgcaggatcccagagtcaggggtctgtatcttcctg<br>ctggtggctccagttcaggaacagtaaaccctgctccgaatattgcctctcacatctcgtcaatctccgcgaggactggggaccctgtgacgaacatggagaacatcacatcaggattcctaggacc<br>cctgctcgtgttacaggcggggtttttcttgttgacaagaatcctcacaataccgcagagtctagactcgtggtggacttctctcaattttctagggggatctcccgtgtgtcttggccaaaattcgcagtc<br>cccaacctccaatcactcaccaacctcctgtcctccaatttgtcctggttatcgctggatgtgtctgcggcgttttatcatattcctcttcatcctgctgctatgcctcatcttcttattggttcttctggat<br>tatcaaggtatgttgcccgtttgtcctctaattccaggatcaacaacaaccagtacgggaccatgcaaaacctgcacgactcctgctcaaggcaactctatgtttccctcatgttgctgtacaaaacctacgga<br>tggaaattgcacctgtattcccatcccatcgtcctgggctttcgcaaaatacctatgggagtgggcctcagtccgtttctcttggctcagtttactagtgccatttgttcagtggttcgtagggctttcccccca<br>ctgtttggctttcagctatatggatgatgtggtattgggggccaagtctgtacagcatcgtgagtccctttataccgctgttaccaattttcttttgtctctgggtatacatttaa |
| SEQ ID NO: 49 | atgctgagaataatcaatgctaggaaggagaagaagagacgaggcgcagatacaagtgtcggaattgttggcctcctgctgaccacagctatggcagcggaggtcactagacgtgggagtgcat<br>actatatgtacttggacagaaacgatgctggggaggccatatcttttccaaccacattggggatgaataagtgttatatacagatcatggatcttggacacacgtgtgatgccaccatgagctatgaatg<br>ccctatgctggatgaggggggtggaaccagatgacgtcgattgttggtgcaacacgacgtcaacttgggttgtgtacggaacctgccatcacaaaaaaggtgaagcacggagatctagaagagctg<br>tgacgctcccctcccattccactaggaagctgcaaacgcggtcgcaaacctggttggaatcaagagaatacacaaagcacttgattagagtcgaaaattggatattcaggaaccctggcttcgcgtt<br>agcagcagctgccatcgcttggcttttgggaagctcaacgagccaaaaagtcatatacttggtcatgatactgctgattgccccggcatacagcatcaggtgcataggagtcagcaatagggactttg<br>tggaaggtatgtcaggtgggacttgggttgatgttgtcttggaacatggaggttgtgtcactgtaatggcacaggacaaaccgactgtcgacatagagctggttacaacaacagtcagcaacatggc<br>ggaggtaagatcctactgctatgaggcatcaatatcagacatggcttcggacagccgctgcccaacacaaggtgaagcctaccttgacaagcaatcagaGactcaatatgtctgcaaaagaacgtt<br>agtggacagaggctggggaaatggatgtggacttttggcaaagggagcctggtgacatgcgctaagtttgcatgctccaagaaaatgaccgggaagagcatccagccagagaatctggagtac<br>cggataatgctgtcagttcatggctcccagcacagtgggatgatcgttaatgacacaggacatgaaactgatgagaatagagcgaaagttgagataacgcccaattcaccaagagccgaagccac<br>cctggggggtttggaagcctaggacttgattgtgaaccgaggacaggccttgacttttcagatttgtattacttgactatgaataacaagcactggctggttcacaaggagtggttccacgacattcca<br>ttaccttggcacgctggggcagacaccggaactccacactggaacaacaaagaagcactggtagagttcaaggacgcacatgccaaaaggcaaactgtcgtggttctagggagtcaagaagga<br>gcagttcacacggcccttttctggagctctggaggctgagatggatggtgcaaagggaaggctgtcctctggccacttgaaatgtcgcctgaaaatggataaacttagattgaattggcgtgtcatact<br>ccttgtgtactgcagcgttcacattcaccaagatcccggctgaaacactgcacgggacagtcacagtggaggtacagtacgcagggacagatggaccttgcaaggttccagctcagatggcggtg<br>gacatgcaaactctgaccccagttgggaggttgataaccgctaaccccgtaatcactgaaagcactgagaactctaagatgatgctggaacttgatccaccatttggggactcttacattgtcatagga<br>gtcggggagaagaagatcacccaccactggcacaggagtggcagcaccattggaaaagcatttgaagccactgtgagaggtgccaagagaatggcagtcttgggagacacagcctgggacttt<br>ggatcagttggaggcgctctcaactcattgggcaagggcatccatcaaatctttggagcagctttcaaatcattgtttggaggaatgtcctggttctcacaaattctcattggaacgttgctgatgtggttg<br>ggtctgaacgcaaagaatggatctatttcccttatgtgcttggccttaggggagtgttgatcttcttatccacagccgtctctgctcagtggaattccactgccttccaccaaactctgcaggatcccag<br>agtcaggggtctgtatcttcctgctggtggctccagttcaggaacagtaaaccctgctccgaatattgcctctcacatctcgtcaatctccgcgaggactggggaccctgtgacgaacatggagaaca<br>tcacatcaggattcctaggacccctgctcgtgttacaggcggggtttttcttgttgacaagaatcctcacaataccgcagagtctagactcgtggtggacttctctcaattttctagggggatctcccgtgt<br>gtcttggccaaaattcgcagtccccaacctccaatcactcaccaacctcctgtcctccaatttgtcctggttatcgctggatgtgtctgcggcgttttatcatattcctcttcatcctgctgctatgcctcatc<br>ttcttattggttcttctggattatcaaggtatgttgcccgtttgtcctctaattccaggatcaacaacaaccagtacgggaccatgcaaaacctgcacgactcctgctcaaggcaactctatgtttccctcatg<br>ttgctgtacaaaacctacggatggaaattgcacctgtattcccatcccatcgtcctgggctttcgcaaaatacctatgggagtgggcctcagtccgtttctcttggctcagtttactagtgccatttgttcag<br>tggttcgtagggctttcccccactgtttggctttcagctatatggatgatgtggtattgggggccaagtctgtacagcatcgtgagtccctttataccgctgttaccaattttcttttgtctctgggtatacat<br>ttaa |
| SEQ ID NO: 50 | Rrgsayymyldmdageaisfpttlgmnkcyiqimdlghtcdatmsyecpmldegvcpddvdcwcnltstwvvygtchhkkgearrsrravtlpshstrklqtrsqtwlesreytklilirve<br>nwifrnpgfalaaaaiawllgsstsqkviylvmilliapays |

TABLE 2-continued

| lists the sequences of the present invention: | |
|---|---|
| SEQ ID NO: 51 | cccgggatcc atgaaaaacc caaaaaagaa atccggagga ttccggattg tcaatatgct aaaacgcgga gtagcccgtg tgagcccctt tgggggcttg aagaggctgc<br>cagccggact tctgctgggt catgggccca tcaggatggt cttggcgatt ctagcctttt tgagattcac ggcaatcaag ccatcactgg gtctcatcaa tagatggggt tcagtgggga<br>aaaaagaggc tatggaaata ataaagaagt tcaagaaaga tctggctgcc atgctgagaa taatcaatgc taggaaggag aagaagagac gaggcgcaga tacaagtgtc<br>ggaattgttg gcctcctgct gaccacagct atggcagcgg aggtcactag acgtgggagt gcatactata tgtacttgga cagaaacgat gctggggagg ccatatcttt tccaaccaca<br>ttggggatga ataagtgtta tatacagatc atggatcttg gacacacgtg tgatgccacc atgagctatg aatgccctat gctggatgag gggtggaac cagatgacgt cgattgttgg<br>tgcaacacga cgtcaacttg ggttgtgtac ggaacctgcc atcacaaaaa aggtgaagca cggagatcta gaagagctgt gacgctcccc tcccattcca ctaggaagct<br>gcaaacgcgg tcgcaaacct ggttggaatc aagagaatac acaaagcact tgattagagt cgaaaattgg atattcagga accctggctt cgcgttagca gcagctgcca tcgcttggct<br>tttgggaagc tcaacgagcc aaaaagtcat atacttggtc atgatactgc tgattgcccc ggcatacagc atcaggtgca taggagtcag caatagggac tttgtggaag gtatgtcagg<br>tgggacttgg gttgatgttg tcttggaaca tggaggttgt gtcactgtaa tggcacagga caaaccgact gtcgacatag agctggttac aacaacagtc agcaacatgg cggaggtaag<br>atcctactgc tatgaggcat caatatcaga catggcttcg gacagccgct gcccaacaca aggtgaagcc taccttgaca agcaatcaga cactcaatat gtctgcaaaa gaacgttagt<br>ggacagaggc tggggaaatg gatgtggact tttggcaaa gggagcctgg tgacatgcgc taagtttgca tgctccaaga aaatgaccgg gaagagcatc cagccagaga<br>atctggagta ccggataatg ctgtcagttc atggctccca gcacagtggg atgatcgtta atgacacagg acatgaaact gatgagaata gagcgaaagt tgagataacg cccaattcac<br>caagagccga agccaccctg ggggggtttg gaagcctagg acttgattgt gaaccgagga caggccttga cttttcagat ttgtattact tgactatgaa taacaagcac tggctggttc<br>acaaggagtg gttccacgac attccattac cttggcacgc tggggcagac accggaactc cacactggaa caacaaagaa gcactggtag agttcaagga cgcacatgcc<br>aaaaggcaaa ctgtcgtggt tctagggagt caagaaggag cagttcacac ggcccttgct ggagctctgg aggctgagat ggatggtgca aagggaaggc tgtcctctgg<br>ccacttgaaa tgtcgcctga aaatggataa acttagattg aagggcgtgt catactcctt gtgtactgca gcgttcacat tcaccaagat cccggctgaa acactgcacg ggacagtcac<br>agtggaggta cagtacgcag ggacagatgg accttgcaag gttccagctc agatggcggt ggacatgcaa actctgaccc cagttgggag gttgataacc gctaaccccg<br>taatcactga aagcactgag aactctaaga tgatgctgga acttgatcca ccatttgggg actcttacat tgtcatagga gtcggggaga agaagatcac ccaccactgg cacaggagtg<br>gcagcaccat tggaaaagca tttgaagcca ctgtgagagg tgccaagaga atggcagtct tgggagacac agcctgggac tttggatcag ttggaggcgc tctcaactca<br>ttgggcaagg gcatccatca aatctttgga gcagctttca aatcattgtt tggaggaatg tcctggttct cacaaattct cattggaacg ttgctgatgt ggttgggtct gaacgcaaag<br>aatggatcta tttcccttat gtgcttggcc ttagggggag tgttgatctt cttatccaca gccgtctctg ctgatgtggg gtagctcsag gatcccggg |
| SEQ ID NO: 52 | gttgttactgttgctgactcagactgcgacagttcgagtttgaagcgaaagctagcaacagtatcaacaggttttatttggatttggaaacgagagtttctggtcatgaaaaacccaaaa<br>ttagaaatccggaggattccggattgtcaatatgctaaaacgcggagtagcccgtgtgagcccctttgggggcttgaagaggctgccagccggacttctgctgggtcatgggcccatcaggatggt<br>cttggcaattctagcctttttgagattcacggcaatcaagccatcactgggtctcatcaatagatggggttcagtggggaaaaaagaggctatggaaataataaagaagttcaagaaagatctggctg<br>ccatgctgagaataatcaatgctaggaaggagaagaagagacggggcgcagatactagtgtcggaattgttggcctcctgctgaccacagctatggcagcggaggtcactagacgtgggagtgc<br>atactatatgtacttggacagaaacgatgctggggaggccatatcttttccaaccacattggggatgaataagtgttatatacagatcatggatcttggacacatgtgtgatgccaccatgagctatgaat<br>gccctatgctggatgaggggggtggaaccagatgacgtcgattgttggtgcaacacgacgtcaacttgggttgtgtacggaacctgccatcacaaaaaaggtgaagcacggagatctagaagagct<br>gtgacgctcccctcccattccactaggaagctgcaaacgcggtcgcaaacctggttggaatcaagagaatacacaaagcacttgattagagtcgaaaattggatattcaggaaccctggcttcgcgt<br>tagcagcagctgccatcgcttggcttttgggaagctcaacgagccaaaaagtcatatacttggtcatgatactgctgattgccccggcatacagcatcaggtgcataggagtcagcaatagggacttt<br>gtggaaggtatgtcaggtgggacttgggttgatattgtcttggaacatggaggttgtgtcaccgtaatggcacaggacaaaccgactgtcgacatagagctggttacaacaacagtcagcaacatgg<br>cggaggtaagatcctactgctatgaggcatcaatatcagacatggcttcggacagccgctgcccaacacaaggtgaagcctaccttgacaagcaatcagacactcaatatgtctgcaaaagaacgt<br>tagtggacagaggctggggaaatggatgtggacttttggcaaagggagtctggtgacatgcgctaagtttgcatgctccaagaaaatgaccgggaagagcatccagccagagaatctggagtac<br>cggataatgctgtcagttcatggctcccagcacagtgggatgatcgttaatgacacaggacatgaaactgatgagaatagagcgaaggttgagataacgcccaattcaccaagagccgaagccac<br>cctgggggggttttggaagcctaggacttgattgtgaaccgaggacaggccttgacttttcagatttgtattacttgactatgaataacaagcactggttggttcacaaggagtggttccacgacattccat<br>taccttggcacgctggggcagacaccggaactccacactggaacaacaaagaagcactggtagagttcaaggacgcacatgccaaaaggcaaactgtcgtggttctagggagtcaagaaggag<br>cagttcacacggcccttgctggagctctggaggctgagatggatggtgcaaagggaaggctgtcctctggccacttgaaatgtcgcctgaaaatg<br>gataaacttagattgaagggcgtgtcatactccttgtgtaccgcagcgttcacattcaccaagatcccggctgaaacactgcacgggacagtcacagtggaggtacagtacgcagggacagatgga<br>ccttgcaaggttccagctcagatggcggtggacatgcaaactctgaccccagttgggaggttgataaccgctaaccccgtaatcactgaaagcactgagaactctaagatgatgctggaacttgatc<br>caccatttggggactcttacattgtcataggagtcggggagaagaagatcacccaccactggcacaggagtggcagcaccattggaaaagcatttgaagccactgtgagaggtgccaagagaatg<br>gcagtcttgggagacacagcctgggactttggatcagttggaggcgctctcaactcattgggcaagggcatccatcaaatttttggagcagctttcaaatcattgtttggaggaatgtcctggttctcac<br>aaattctcattggaacgttgctgatgtggttgggtctgaacacaaagaatggatctatttcccttatgtgcttggccttagggggagtgttgatcttcttatccacagccgtctctgctgatgtggggtgctc<br>ggtggacttctcaaagaaggagacgagatgcggtacaggggtgttcgtctataacgacgttgaagcctggagggacaggtacaagtaccatcctgactccccccgtagattggcagcagcagtca<br>agcaagcctgggaagatggtatctgcgggatctcctctgtttcaagaatggaaaacatcatgtggagatcagtagaaggggagctcaacgcaatcctggaagagaatggagttcaactgacggtc<br>gttgtgggatctgtaaaaaaccccatgtggagaggtccacagagattgcccgtgcctgtgaacgagctgccccacggctggaaggcttgggggaaatcgcacttcgtcagagcagcaaagacaa<br>ataacagctttgtcgtggatggtgacacactgaaggaatgcocactcaaacatagagcatggaacagctttcttgtggaggatcatgggttcggggtatttcacactagtgtctggctcaaggttagag<br>aagattattcattagagtgtgatccagccgttattggaacagctgttaagggaaaggaggctgtacacagtgatctaggctactggattgagagtgagaagaatgacacatggaggctgaagaggg<br>cccatctgatcgagatgaaaacatgtgaatggccaaagtcccacacattgtggacagatggaatagaagagagtgatctgatcatacccaagtctttagctgggccactcagccatcacaataccag<br>agagggctacaggacccaaatgaaagggccatggcacagtgaagagcttgaaattcggtttgaggaatgcccaggcactaaggtccacgtggaggaaacatgtggaacaagaggaccatctct<br>gagatcaaccactgcaagcggaagggtgatcgaggaatggtgctgcagggagtgcacaatgcccccactgtcgttccgggctaaagatggctgttggtatggaatggagataaggcccaggaa<br>agaaccagaaagcaacttagtaaggtcaatggtgactgcaggatcaactgatcacatggatcacttctcccttggagtgcttgtgattctgctcatggtgcaggaagggctgaagaagagaatgacc |

TABLE 2-continued

| lists the sequences of the present invention: |
|---|
| acaaagatcatcataagcacatcaatggcagtgctggtagctatgatcctgggaggattttcaatgagtgacctggctaagcttgcaattttgatgggtgccaccttcgcggaaatgaacactggagg |
| agatgtagctcatctggcgctgatagcggcattcaaagtcagaccagcgttgctggtatctttcatcttcagagctaattggacaccccgtgaaagcatgctgctggccttggcctcgtgtcttttgcaa |
| actgcgatctccgccttggaaggcgacctgatggttctcatcaatggttttgctttggcctggttggcaatacgagcgatggttgttccacgcactgataacatcaccttggcaatcctggctgctctgac |
| accactggcccggggcacactgcttgtggcgtggagagcaggccttgctacttgcggggggtttatgctcctctctctgaagggaaaaggcagtgtgaagaagaacttaccatttgtcatggccctg |
| ggactaaccgctgtgaggctggtcgaccccatcaacgtggtggggctgctgttgctcacaaggagtgggaagcggagctggccccctagcgaagtactcacagctgttggcctgatatgcgcatt |
| ggctggagggttcgccaaggcagatatagagatggctgggcccatggccgcggtcggtctgctaattgtcagttacgtggtctcaggaaagagtgtggacatgtacattgaaagagcaggtgaca |
| tcacatgggaaaaagatgcggaagtcactggaaacagtccccggctcgatgtggcgctagatgagagtggtgatttctccctggtggaggatgacggtcccccatgagagagatcatactcaag |
| gtggtcctgatgaccatctgtggcatgaacccaatagccataccctttgcagctggagcgtggtacgtatacgtgaagactggaaaaaggagtggtgctctatgggatgtgcctgctcccaaggaag |
| taaaaaaggggggagaccacagatggagtgtacagagtaatgactcgtagactgctaggttcaacacaagttggagtgggagttatgcaagaggggtctttcacactatgtggcacgtcacaaaa |
| ggatccgcgctgagaagcggtgaagggagacttgatccatactggggagatgtcaagcaggatctggtgtcatactgtggtccatggaagctagatgccgcctgggacgggcacagcgaggtg |
| cagctcttggccgtgccccccggagagagagcgaggaacatccagactctgcccggaatatttaagacaaaggatggggacattggagcggttgcgctggattacccagcaggaacttcaggat |
| ctccaatcctagacaagtgtgggagagtgataggactttatggcaatggggtcgtgatcaaaaatgggagttatgttagtgccatcacccaagggaggagggaggaagagactcctgttgagtgctt |
| cgagccttcgatgctgaagaagaagcagctaactgtcttagacttgcatcctggagctgggaaaaccaggaga |
| gttcttcctgaaatagtccgtgaagccataaaaacaagactccgtactgtgatcttagctccaaccagggttgtcgctgctgaaatggaggaagcccttagagggcttccagtgcgttatatgacaaca |
| gcagtcaatgtcacccactctggaacagaaatcgtcgacttaatgtgccatgccaccttcacttcacgtctactacagccaatcagagtccccaactataatctgtatattatggatgaggcccacttca |
| cagatccctcaagtatagcagcaagaggatacatttcaacaagggttgagatgggcgaggcggctgccatcttcatgaccgccacgccaccaggaacccgtgacgcatttccggactccaactca |
| ccaattatggacaccgaagtggaagtcccagagagagcctggagctcaggctttgattgggtgacggattattctggaaaaacagtttggtttgttccaagcgtgaggaacggcaatgagatcgca |
| gcttgtctgacaaaggctggaaaacgggtcatacagctcagcagaaagacttttgagacagagttccagaaaacaaaacatcaagagtgggactttgtcgtgacaactgacatttcagagatgggc |
| gccaactttaaagctgaccgtgtcatagattccaggagatgcctaaagccggtcatacttgatggcgagagagtcattctggctggacccatgcctgtcacacatgccagcgctgcccagaggagg |
| gggcgcataggcaggaatcccaacaaacctggagatgagtatctgtatggaggtgggtgcgcagagactgacgaagaccatgcacactggcttgaagcaagaatgctccttgacaatatttacct |
| ccaagatggcctcatagcctcgctctatcgacctgaggccgacaaagtagcagccattgagggagagttcaagcttaggacggagcaaaggaagacctttgtggaactcatgaaaagaggagat |
| cttcctgtttggctggcctatcaggttgcatctgccggaataacctacacagatagaagatggtgctttgatggcacgaccaacaacaccataatggaagacagtgtgccggcagaggtgtggacca |
| gacacggagagaaaagagtgctcaaaccgaggtggatggacgccagagtttgttcagatcatgcggccctgaagtcattcaaggagtttgccgctgggaaaagaggagcggcttttggagtgat |
| ggaagccctgggaacactgccaggacacatgacagagagattccaggaagccattgacaacctcgctgtgctcatgcgggcagagactggaagcaggccttacaaagccgcggcggcccaat |
| tgccggagaccctagagaccattatgcttttggggttgctgggaacagtctcgctgggaatctttttcgtcttgatgaggaacaagggcatagggaagatgggctttggaatggtgactcttggggcc |
| agcgcatggctcatgtggctctcggaaattgagccagccagaattgcatgtgtcctcattgttgtgttcctattgctggtggtgctcatacctgagccagaaaagcaa |
| agatctccccaggacaaccaaatggcaatcatcatcatggtagcagtaggtcttctgggcttgattaccgccaatgaactcggatggttggagagaacaaagagtgacctaagccatctaatgggaa |
| ggagagaggagggggcaaccatgggattctcaatggacattgacctgcggccagcctcagcttgggccatctatgctgccttgacaactttcattaccccagccgtccaacatgcagtgaccacttc |
| atacaacaactactccttaatggcgatggccacgcaagctggagtgttgtttggtatgggcaaagggatgccattctacgcatgggactttggagtcccgctgctaatgataggttgctactcacaatt |
| aacgcccctgaccctaatagtggccatcattttgctcgtggcgcactacatgtacttgatcccagggctgcaggcagcagctgcgcgtgctgcccagaagagaacggcagctggcatcatgaaga |
| accctgttgtggatggaatagtggtgactgacattgacacaatgacaattgacccccaagtggagaaaaagatgggacaggtgctactcatggcagtagccgtctccagcgccatactgtcgcgga |
| ccgcctgggggtgggggaggctggggccctgatcacagccgcaacttccactttgtgggaaggctctccgaacaagtactggaactcctctacagccacttcactgtgtaacatttttaggggaa |
| gttacttggctggagcttctctaatctacacagtaacaagaaacgctggcttggtcaagagacgtgggggtggaacaggagagaccctgggagagaaatggaaggcccgcttgaaccagatgtc |
| ggccctggagttctactcctacaaaaagtcaggcatcaccgaggtgtgcagagaagaggcccgccgcgccctcaaggacggtgtggcaacgggaggccatgctgtgtcccgaggaagtgcaa |
| agctgagatggttggtggagcggggatacctgcagccctatggaaaggtcattgatcttggatgtggcagagggggctggagttactacgccgccaccatccgcaaagttcaagaagtgaaagg |
| atacacaaaaggaggccctggtcatgaagaacccgtgttggtgcaaagctatgggtggaacatagtccgtcttaagagtggggtggacgtctttcatatggcggctgagccgtgtgacacgttgctg |
| tgtgacataggtgagtcatcatctagtcctgaagtggaagaagcacggacgctcagagtcctctccatggtgggggattggcttgaaaaaagaccaggagccttttgtataaaagtgttgtgcccata |
| caccagcactatgatggaaaccctggagcgactgcagcgtaggtatggggggaggactggtcagagtgccactctcccgcaactctacacatgagatgtactgggtctctggagcgaaaagcaac |
| accataaaaagtgtgtccaccacgagccagctcctcttggggcgcatggacgggcctaggaggccagtgaaatatgaggaggatgtgaatctcggctctggcacgcgggctgtggtaagctgcg |
| ctgaagctcccaacatgaagatcattggtaaccgcattgaaaggatccgcagtgagcacgcggaaacgtggttctttgacgagaaccacccatataggacatgggcttaccatggaagctatgagg |
| cccccacacaagggtcagcgtcctctctaataaacggggttgtcaggctcctgtcaaaccctgggatgtggtgactggagtcacaggaatagccatgaccgacaccacaccgtatggtcagcaa |
| agagttttcaaggaaaaagtggacactagggtgccagacccccaagaaggtactcgtcaggttatgagcatggtctcttcctggttgtggaaagagctaggcaaacacaaacggccacgagtctgt |
| accaaagaagagttcatcaacaaggttcgtagcaatgcagcattaggggcaatatttgaagaggaaaaagagtggaagactgcagtggaagctgtgaacgatccaaggttctgggctctagtgga |
| caaggaaagagagcaccacctgagaggagagtgccagagttgtgtgtacaacatgatgggaaaaagagaaaagaaacaaggggaatttggaaaggccaagggcagccgcgccatctggtata |
| tgtggctaggggctagatttctagagttcgaagcccttggattcttgaacgaggatcactggatggggagagagaactcaggaggtggtgttgaagggctgggattacaaagactcggatatgtcct |
| agaagagatgagtcgcataccaggaggaaggatgtatgcagatgacactgctggctgggacacccgcatcagcaggtttgatctggagaatgaagctctaatcaccaaccaaatggagaaaggg |
| cacagggccttggcattggccataatcaagtacacataccaaaacaaagtggtaaaggtccttagaccagctgaaaaagggaaaacagttatggacattatttcgagacaagaccaaagggggag |
| cggacaagttgtcacttacgctcttaacacatttaccaacctagtggtgcaactcattcggaatatggaggctgaggaagtcctagagatgcaagacttgtggctgctgcggaggtcagagaaagtg |
| accaactggttgcagagcaacggatgggataggctcaaacgaatggcagtcagtggagatgattgcgttgtgaagccaattgatgataggtttgcacatgccctcaggttcttgaatgatatgggaa |
| aagttaggaaggacacacaagagtggaaaccctcaactggatgggacaactgggaagaagttccgttttgctcccaccacttcaacaagctccatctcaaggacgggaggtccattgtggttccct |
| gccgccaccaagatgaactgattggccgggcccgcgtctctccaggggcgggatggagcatccgggagactgcttgcctagcaaaatcatatgcgcaaatgtggcagctcctttatttccacaga |

TABLE 2-continued

| lists the sequences of the present invention: | |
|---|---|
| | agggacctccgactgatggccaatgccatttgttcatctgtgccagttgactgggttccaactgggagaactacctggtcaatccatggaaagggagaatggatgaccactgaagacatgcttgtggt<br>gtggaacagagtgtggattgaggagaacgaccacatggaagacaagaccccagttacgaaatggacagacattccctatttgggaaaaagggaagacttgtggtgtggatctctcatagggcaca<br>gaccgcgcaccacctgggctgagaacattaaaaacacagtcaacatggtgcgcaggatcataggtgatgaagaaaagtacatggactacctatccacccaagttcgctacttgggtgaagaaggg<br>tctacacctggagtgctgtaagcaccaatcttaatgttgtcaggcctgctagtcagccacagcttggggaaagctgtgcagcctgtgacccccccaggagaagctgggaaaccaagcctatagtca<br>ggccgagaacgccatggcacggaagaagaatgctgcctgtgagcccctcagaggacactgagtcaaaaaaccccacgcgcttggaggcgcaggatgggaaaagaaggtggcgaccttccc<br>caccccttcaatctggggcctgaactggagatcagctgtggatctccagaagagggactagtggttagaggaga |
| SEQ ID NO: 53 | gatggcggatgtgtgacatacacgacgccaaaagatttgttccagctcctgccacctccgctacgcgagagattaaccacccacgatggccgccaaagtgcatgttgatattgaggctgacagcc<br>cattcatcaagtctttgcagaaggcatttccgtcgttcgaggtggagtcattgcaggtcacaccaaatgaccatgcaaatgccagagcattttcgcacctggctaccaaattgatcgagcaggagact<br>gacaaagacacactcatcttggatatcggcagtgcgccttccaggagaatgatgtctacgcacaaataccactgcgtatgccctatgcgcagcgcagaagaccccgaaaggctcgatagctacgc<br>aaagaaactggcagcggcctccgggaaggtgctggatagagagatcgcaggaaaaatcaccgacctgcagaccgtcatggctacgccagacgctgaatctcctaccttttgcctgcatacagac<br>gtcacgtgtcgtacggcagccgaaatggccgtataccaggacgtgtatgctgtacatgcaccaacatcgctgtaccatcaggcgatgaaaggtgtcagaacggcgtattggattgggtttgacacc<br>accccgtttatgtttgacgcgctagcaggcgcgtatccaacctacgccacaaactgggccgacgagcaggtgttacaggccaggaacataggactgtgtgcagcatccttgactgagggaagact<br>cggcaaactgtccattctccgcaagaagcaattgaaaccttgcgacacagtcatgttctcggtaggatctacattgtacactgagagcagaaagctactgaggagctggcacttaccctccgtattcc<br>acctgaaaggtaaacaatcctttacctgtaggtgcgataccatcgtatcatgtgaagggtacgtagttaagaaaatcactatgtgccccggcctgtacggtaaaacggtagggtacgccgtgacgtat<br>cacgcggagggattcctagtgtgcaagaccacagacactgtcaaaggagaaagagtctcattccctgtatgcacctacgtcccctcaaccatctgtgatcaaatgactggcatactagcgaccgac<br>gtcacaccggaggacgcacagaagttgttagtgggattgaatcagaggatagttgtgaacggaagaacacagcgaaacactaacacgatgaagaactatctgcttccgattgtggccgtcgcat<br>ttagcaagtgggcgagggaatacaaggcagaccttgatgatgaaaaacctctgggtgtccgagagaggtcacttacttgctgctgcttgtgggcatttaaaacgaggaagatgcacaccatgtaca<br>agaaaccagacacccagacaatagtgaaggtgccttcagagtttaactcgttcgtcatcccgagcctatggtctacaggcctcgcaatcccagtcagatcacgcattaagatgcttttggccaagaag<br>accaagcgagagttaatacctgttctcgacgcgtcgtcagccagggatgctgaacaagaggagaaggagaggttggaggccgagctgactagagaagccttaccacccctcgtccccatcgcg<br>ccggcggagacgggagtcgtcgacgtcgacgttgaagaactagagtatcacgcaggtgcaggggtcgtggaaacacctcgcagcgcgttgaaagtcaccgcacagccgaacgacgtactact<br>aggaaattacgtagttctgtccccgcagaccgtgctcaagagctccaagttggcccccgtgcaccctctagcagagcaggtgaaaataataacacataacgggagggccggcggttaccaggtc<br>gacggatatgacggcagggtcctactaccatgtggatcggccattccggtccctgagtttcaagctttgagcgagagcgccactatggtgtacaacgaaagggagttcgtcaacaggaaactatac<br>catattgccgttcacggaccgtcgctgaacaccgacgaggagaactacgagaaagtcagagctgaaagaactgacgccgagtacgtgttcgacgtagataaaaaatgctgcgtcaagagagagg<br>aagcgtcgggtttggtgttggtgggagagctaaccaaccccccgttccatgaattcgcctacgaagggctgaagatcaggccgtcggcaccatataagactacagtagtaggagtctttggggttat<br>gggatcacgcaagtctgctattattaagagcctcgtcaccaaacacaatctgatcaccaacagcaacaaagagaactgccaggaaatagttaacgacgtgaagaagcaccgcgggaaggg<br>gacaagtagggaaaacagtgactccatcctgctaaacgggtgtcgtcgtgccgtggacatcctatatgtggacgaggctttcgcttgccattccggtactctgctggccctaattgctcttgttaaacct<br>cggagcaaagtggtgttatgcggagaccccaagcaatgcggattcttcaatatgatgcagcttaaggtgaacttcaaccacaacatctgcactgaagtatgtcataaaagtatatccagacgttgcac<br>gcgtccagtcacggccatcgtgtctttcgttgcactacggaggcaagatgcgcacgaccaacccgtgcaacaaacccataatcatagacaccacaggacagaccaagcccaagccaggagacat<br>cgtgttaacatgcttccgaggctgggcaaagcagctgcsgttggactaccgtggacacgaagtcatgacagcagcagcatctcagggcctcacccgcaaaggggtatacgccgtaaggcagaa<br>ggtgaatgaaaatcccttgttttgccctgcgtcggagcacgtgaatgtactgctgacgcgcactgaggataggctggtgtggaaaacgctggccggcgatactggattaaggtcctatcaaacat<br>tccacagggtaactttacggccacattggaagaatggcaagaagaacacgacaaaataatgaaggtgattgaaggaccggctgcgcctgtggacgcgttccagaacaaagcgaacgtgtgttgg<br>gcgaaaagcctggtgcctgtcctggacactgccggaatcagattgacagcagaggagtggagcaccataattacagcatttaaggaggacagagcttactctccagtggtggccttgaatgaaattt<br>gcaccaagtactatggagttgacctggacagtggcctgttttctgccccgaaggtgtccctgtattacgagaacaaccactgggataacagacctggtggaaggatgtatggattcaatgccgcaac<br>agctgccaggctggaagctagacataccttcctgaaggggcagtggcatacgggcaagcaggcagttatcgcagaaagaaaaatccaaccgctttctgtgctggacaatgtaattcctatcaaccg<br>caggctgccgcacgccctggtggctgagtacaagacggttaaaggcagtagggttgagtggctggtcaataaagtaagagggtaccacgtcctgctggtgagtgagtacaacctggctttgcctc<br>gacgcagggtcacttggttgtcaccgctgaatgtcacaggcgccgataggtgctacgacctaagtttaggactgccggctgacgccggcaggttcgacttggtctttgtgaacattcacacggaatt<br>cagaatccaccactaccagcagtgtgtcgaccacgccatgaagctgcagatgcttggggggagatgcgctacgactgctaaaacccggcggcatcttgatgagagcttacggatacgccgataaaa<br>tcagcgaagccgttgtttcctccttaagcagaaagttctcgtctgcaagagtgttgcgcccggattgtgtcaccagcaatacagaagtgttcttgctgttctccaactttgacaacggaaagagaccctc<br>tacgctacaccagatgaataccaagctgagtgccgtgtatgccggagaagccatgcacacggccgggtgtgcaccatcctacagagttaagagagcagacatagccacgtgcacagaagcggc<br>tgtggttaacgcagctaacgcccgtggaactgtaggggatggcgtatgcagggccgtggcgaagaaatggccgtcagcctttaagggagcagcaacaccagtgggcacaattaaaacagtcatg<br>tgcggctcgtaccccgtcatccacgctgtagcgcctaatttctctgccacgactgaagcggaaggggaccgcgaattggccgctgtctaccgggcagtggccgccgaagtaaacagactgtcact<br>gagcagcgtagccatcccgctgctgtccacaggagtgttcagcggcggaagagataggctgcagcaatccctcaaccatctattcacagcaatggacgccacggacgctgacgtgaccatctact<br>ggagagtcaaaagttgggagaagaaaatccaggaasccattgacatgaggacggctgtggagtrgctcaatgatgacgtggagctgaccacagacttggtgagagtgcacccggacagcagcc<br>tggtgggtcgtaagggctacagtaccactgacgggtcgctgtactcgtactttgaaggtacgaaattcaaccaggctgctattgatatggcagagatactgacgttgtggcccagactgcaagaggc<br>aaacgaacagatatgcctatacgcgctgggcgaaacaatggacaacatcagatccaaatgtccggtgaacgattccgattcatcaacacctcccaggacagtgccctgcctgtgccgctacgcaat<br>gacagcagaacggatcgcccgccttaggtcacaccaagttaaaagcatggtggtttgctcatcttttcccctcccgaaataccatgtagatggggtgcagaaggtaaagtgcgagaaggttctcctgt<br>tcgacccgacggtaccttcagtggttagtccgcggaagtatgccgcatctacgacggaccactcagatcggtcgttacgagggtttgacttggactggaccaccgactcgtcttccactgccagcga<br>taccatgtagctacccagtttgcagtcgtgtgacatcgactcgatctacgagccaatggctcccatagtagtgacggctgacgtacaccctgaacccgcaggcatcgcggacctggcggcagatgt<br>gcaccctgaacccgcagaccatgtggacctcgagaacccgattcctccaccgcgcccgaagagagctgcataccttgcctcccgcgcggcggagcgaccggtgccggcgccgagaaagccg<br>acgcctgccccaaggactgcgtttaggaacaagctgcctttgacgttcggcgactttgacgagcacgaggtcgatgcgttggcctocgggattactttcggagacttcgacgacgtcctgcgactag |

TABLE 2-continued

| lists the sequences of the present invention: |
|---|
| gccgcgcgggtgcatatatttctcctcggacactggcagcggacatttacaacaaaaatccgttaggcagcacaatctccagtgcgcacaactggatgcggtccaggaggagaaaatgtacccg |
| ccaaaattggatactgagagggagaagctgttgctgctgaaaatgcagatgcacccatcggaggctaataagagtcgataccagtctcgcaaagtggagaacatgaaagccacggtggtggaca |
| ggctcacatcgggggccagattgtacacgggagcggacgtaggccgcataccaacatacgcggttcggtacccccgccccgtgtactcccctaccgtgatcgaaagattctcaagccccgatgta |
| gcaatcgcagcgtgcaacgaatacctatccagaaattacccaacagtggcgtcgtaccagataacagatgaatacgacgcatacttggacatggttgacgggtcggatagttgcttggacaga |
| gcgacatctgcccggcgaagctccggtgctacccgaaacatcatgcgtaccaccagccgactgtacgcagtgccgtcccgtcaccctttcagaacacactacagaacgtgctagcggccgcca |
| ccaagagaaactgcaacgtcacgcaaatgcgagaactacccaccatggactcggcagtgttcaacgtggagtgcttcaagcgctatgcctgctccggagaatattgggaagaatatgctaaacaa |
| cctatccggataaccactgagaacatcactacctatgtgaccaaattgaaaggcccgaaagctgctgccttgttcgctaagacccacaacttggttccgctgcaggaggttcccatggacagattcac |
| ggtcgacatgaaacgagatgtcaaagtcactccagggacgaaacacacagaggaaagacccaaagtccaggtaattcaagcagcggagccaftggcgaccgcttacctgtgcg |
| gcatccacagggaattagtaaggagactaaatgctgtgttacgccctaacgtgcacacattgtttgatatgtcggccgaagactttgacgcgatcatcgcctctcacttccacccaggagacccggtt |
| ctagagacggacattgcatcattcoacaaaagccaggacgactccttggctcttacaggtttaatgatcctcgaagatctaggggtggatcagtacctgctggacttgatcgaggcagcctttgggga |
| aatatccagctgtcacctaccaactggcacgcgcttcaagttcggagctatgatgaaatcggcatgtttctgactttgtttattaacactgttttgaacatcaccatagcaagcagggtactggagcag |
| agactcactgactccgcctgtgcggccttcatcggcgacgacaacatcgttcacggagtgatctccgacaagctgatggcggagaggtgcgcgtcgtgggtcaacatggaggtgaagatcattga |
| cgctgtcatgggcgaaaaacccccatatttttgtgggggattcatagtttttgacagcgtcacacagaccgcctgccgtgtttcagacccacttaagcgcctgttcaagttgggtaagccgctaacagc |
| tgaagacaagcaggacgaagacaggcgacgagcactgagtgacgaggttagcaagtggttccggacaggcttgggggccgaactggaggtggcactaacatctaggtatgaggtagagggct |
| gcaaaagtatcctcatagccatggccaccttggcgagggacattaaggcgtttaagaaattgagaggacctgttatacacctctacggcggtcctagattggtgcgttaatacacagaattctgattgg |
| atcccgggctcgagatgctgagaataatcaatgctaggaaggagaagaagagacgaggcgcagatacaagtgtcggaattgttggcctcctgctgaccacagctatggcagcggaggtcactag |
| acgtgggagtgcatactatatgtacttggctcagaaacgatgctggggaggccatatcttttccaaccacattggggatgaataagtgttatatacagatcatggatcttggacacacgtgtgatgccac |
| catgagctatgaatgccctatgctggatgagggggtggaaccagatgacgtcgattgttggtgcaacacgacgtcaacttgggttgtgtacggaacctgccatcacaaaaaaggtgaagcacgga |
| gatctagaagagctgtgacgctcccctcccattccactaggaagctgcaaacgcggtcgcaaacctggttggaatcaagagaatacacaaagcacttgattagagtcgaaaattggatattcaggaa |
| ccctggcttcgcgttagcagcagctgccatcgcttggcttttgggaagctcaacgagccaaaaagtcatatacttggtcatgatactgctgattgccccggcatacagcatcaggtgcataggagtca |
| gcaatagggactttgtggaaggtatgtcaggtgggacttgggttgatgttgtcttggaacatggaggttgtgtcactgtaatggcacaggacaaaccgactgtcgacatagagctggttacaacaaca |
| gtcagcaacatggcggaggtaagatcctactgctatgaggcatcaatatcagacatggcttcggacagccgctgcccaacacaaggtgaagcctaccttgacaagcaatcagacactcaatatgtc |
| tgcaaaagaacgttagtggacagaggctggggaaatggatgtggactttttggcaaagggagcctggtgacatgcgctaagtttgcatgctccaagaaaatgaccgggaagagcatccagccag |
| agaatctggagtaccggataatgctgtcagttcatggctcccagcacagtgggatgatcgttaatgacacaggacatgaaactgatgagaatagagcgaaagttgagataacgcccaattcaccaa |
| gagccgaagccaccctgggggggtttggaagcctaggacttgattgtgaaccgaggacaggccttgacttttcagatttgtattacttgactatgaataacaagcactggctggttcacaaggagtgg |
| ttccacgacattccattaccttggcacgctggggcagacaccggaactccacactggaacaacaaagaagcactggtagagttcaaggacgcacatgccaaaaggcaaactgtcgtggttctagg |
| gagtcaagaaggagcagttcacacggcccttgctggagctctggaggctgagatggatggtgcaaagggaaggctgtcctctggccacttgaaatgtcgcctgaaaatggataaacttagattgaa |
| gggcgtgtcatactccttgtgtactgcagcgttcacattcaccaagatcccggctgaaacactgcacgggacagtcacagtggaggtacagtacgcagggacagatggaccttgcaaggttccag |
| ctcagatggcggtggacatgcaaactctgaccccagttgggaggttgataaccgctaaccccgtaatcactgaaagcactgagaactctaagatgatgctggaacttgatccaccatttggggactc |
| ttacattgtcataggagtcggggagaagaagatcacccaccactggcacaggagtggcagcaccattggaaaagcatttgaagccactgtgagaggtgccaagagaatggcagtcttgggagac |
| acagcctgggactttggatcagttggaggcgctctcaactcattgggcaagggcatccatcaaatctttggagcagctttcaaatcattgtttggaggaatgtcctggttctcacaaattctcattggaac |
| gttgctgatgtggttgggtctgaacgcaaagaatggatctatttcccttatgtgcttggccttaggggggagtgttgatcttcttatccacagccgtctctgctgagaacatcacatcaggattcctaggacc |
| cctgctcgtgttacaggcggggtttttcttgttgacaagaatcctcacaataccgcagagtctagactcgtggtggacttctctcaattttctagggggatctcccgtgtgtcttggccaaaattcgcagtc |
| cccaacctccaatcactcaccaacctcctgtcctccaatttgtcctggttatcgctggatgtgtctgcggcgttttatcatattcctcttcatcctgctgctatgcctcatcttcttattggttcttctggat |
| tatcaaggtatgttgcccgtttgtcctctaattccaggatcaacaacaaccagtacgggaccatgcaaaacctgcacgactcctgctcaaggcaactctatgtttccctcatgttgctgtacaaaacctacgga |
| tggaaattgcacctgtattcccatcccatcgtcctgggctttcgcaaaatacctatgggagtgggcctcagtccgtttctcttggctcagtttactagtgccatttgttcagtggttcgtagggctttccccca |
| ctgtttggctttcagctatatggatgatgtggtattgggggccaagtctgtacagcatcgtgagtccctttataccgctgttaccaattttcttttgtctctgggtatacatttaactcgagcccgggatcccg |
| ggtaattaattgaattacatccctacgcaaacgttttacggccgccggtggcgcccgcgcccggcggcccgtccttggccgttgcaggccactccggtggctcccgtcgttcccgacttccaggcc |
| cagcagatgcagcaactcatcagcgccgtaaatgcgctgacaatgagacagaacgcaattgctcctgctaggcctcccaaaccaaagaagaagaagacaaccaaaccaaagccgaaaacgca |
| gcccaagaagatcaacggaaaaacgcagcagcaaaagaagaaagacaagcaagccgacaagaagaagaagaaacccggaaaaagagaaagaatgtgcatgaagattgaaaatgactgtatc |
| ttcgtatgcggctagccacagtaacgtagtgtttccagacatgtcgggcaccgcactatcatgggtgcagaaaatctcgggtggtctgggggccttcgcaatcggcgctatcctggtgctggttgtgg |
| tcacttgcattgggctccgcagataagttagggtaggcaatggcattgatatagcaagaaaattgaaaacagaaaaagttagggtaagcaatggcatataaccataactgtataacttgtaacaaagc |
| gcaacaagacctgcgcaattggccccgtggtccgcctcacggaaactcggggcaactcatattgacacattaattggcaataattggaagcttacataagcttaattcgacgaataattggatttttattt |
| tattttgcaattggtttttaatatttccaaaaaaaaaaaaaaaaaaaaaaaaaaaaaaaaaaaaaaaaaaaaaaaaaaaaaaaaaaattcgaaactagtctgcattaatgaatcggcca |
| acgcgcggggagaggttggtttgcgtattgggcgctcttccgcttcctcgctcactgactcgctgcgctcggtcgttcggctgcggcgagcggtatcagctcactcaaaggcggtaatacggttatcc |
| acagaatcaggggataacgcaggaaagaacatgtgagcaaaaggccagcaaaaggccaggaaccgtaaaaaggccgcgttgctggcgtttttccataggctccgcccccctgacgagcatcac |
| aaaaatcgacgctcaagtcagaggtggcgaaacccgacaggactataaagataccaggcgtttccccctggaagctccctcgtgcgctctcctgttccgaccctgccgcttaccggatacctgtcc |
| gcctttctcccttcgggaagcgtggcgctttctcaatgctcgcgctgtaggtatctcagttcggtgtaggtcgttcgctccaagctgggctgtgtgcacgaaccccccgttcagcccgaccgctgcgc |
| cttatccggtaactatcgtcttgagtccaacccggtaagacacgacttatcgccactggcagcagocactggtaacaggattagcagagcgaggtatgtaggcggtgctacagagttcttgaagtgg |
| tggcctaactacggctacactagaaggacagtatttggtatctgcgctctgctgaagccagttaccttcggaaaaagagttggtagctcttgatccggcaaacaaaccaccgctggtagcggtggtttt |
| tttgtttgcaagcagcagattacgcgcagaaaaaaaggatctcaagaagatcctttgatcttttctacggggtctgacgctcagtggaacgaaaactcacgttaagggattttggtcatgagattatcaa |

TABLE 2-continued

| lists the sequences of the present invention: | |
|---|---|
| | aaaggatcttcacctagatccttttaaattaaaaatgaagttttaaatcaatctaaagtatatatgagtaaacttggtctgacagttaccaatgcttaatcagtgaggcacctatctcagcgatctgtctattt<br>cgttcatccatagttgcctgactccccgtcgtgtagataactacgatacgggagggcttaccatctggaccagtgctgcaatgataccgcgagacccacgctcaccggctccagatttatcagcaata<br>aaccagccagccggaagggccgagcgcagaagtggtcctgcaactttatccgcctccatccagtctattaattgttgccgggaagctagagtaagtagttcgccagttaatagtttgcgcaacgttgt<br>tgccattgctacaggcatcgtggtgtcacgctcgtcgtttggtatggcttcattcagctccggttcccaacgatcaaggcgagttacatgatcccccatgttgtgcaaaaaagcggttagctccttcggt<br>cctccgatcgttgtcagaagtaagttggccgcagtgttatcactcatggttatggcagcactgcataattctcttactgtcatgccatccgtaagatgcttttctgtgactggtgagtactcaaaaagtcat<br>tctgagaatagtgtatgcggcgaccgagttgctcttgcccggcgtcaatacgggataataccgcgccacatagcagaactttaaaagtgctcatcattggaaaacgttcttcggggcgaaaactctca<br>aggatcttaccgctgttgagatccagttcgatgtaacccactcgtgcacccaactgatcttcagcatcttttactttcaccagcgtttctgggtgagcaaaaacaggaaggcaaaatgccgcaaaaaag<br>ggaataagggcgacacggaaatgttgaatactcatactcttcctttttcaatattattgaagcatttatcagggttattgtctcatgagcggatacatatttgaatgtatttagaaaaataaacaaataggggt<br>tccgcgcacatttccccgaaaagtgccacctgacgtctaagaaaccattattatcatgacattaacctataaaaataggcgtatcacgaggccctttcgtctcgcgcgtttcggtgatgacggtgaaaa<br>cctctgacacatgcagctcccggagacggtcacagcttctgtctaagcggatgccgggagcagacaagcccgtcagggcgcgtcagcgggtgttggcgggtgtcggggctggcttaactatgcg<br>gcatcagagcagattgtactgagagtgcaccatatcgacgctctcccttatgcgactcctgcattaggaagcagcccagtactaggttgaggccgttgagcaccgccgccgcaaggaatggtgcat<br>gcaaggagatggcgcccaacagtcccccggccacggggcctgccaccatacccacgccgaaacaagcgctcatgagcccgaagtggcgagcccgatcttccccatcggtgatgtcggcgata<br>taggcgccagcaaccgcacctgtggcgccggtgatgccggccacgatgcgtccggcgtagaggatctggctagcgatgaccctgctgattggttcgctgaccatttccggggtgcggaacggcg<br>ttaccagaaactcagaaggttcgtccaaccaaaccgactctgacggcagtttacgagagagatgatagggtctgcttcagtaagccagatgctacacaattaggcttgtacatattgtcgttagaacg<br>cggctacaattaatacataaccttatgtatcatacacatacgatttaggtgacactata |
| SEQ ID NO: 54 | gatggcggatgtgtgacatacacgacgccaaaagatttgttccagctcctgccacctccgctacgcgagagattaaccacccacgatggccgccaaagtgcatgttgatattgaggctgacagcc<br>cattcatcaagtctttgcagaaggcatttccgtcgttcgaggtggagtcattgcaggtcacaccaaatgaccatgcaaatgccagagcattttcgcacctggctaccaaattgatcgagcaggagact<br>gacaaagacacactcatcttggatatcggcagtgcgccttccaggagaatgatgtctacgcacaaataccactgcgtatgccctatgcgcagcgcagaagaccccgaaaggctcgatagctacgc<br>aaagaaactggcagcggcctccgggaaggtgctggatagagagatcgcaggaaaaatcaccgacctgcagaccgtcatggctacgccagacgctgaatctcctaccttttgcctgcatacagac<br>gtcacgtgtcgtacggcagccgaagtggccgtataccaggacgtgtatgctgtacatgcaccaacatcgctgtaccatcaggcgatgaaaggtgtcagaacggcgtattggattgggtttgacacc<br>accccgtttatgtttgacgcgctagcaggcgcgtatccaacctacgccacaaactgggccgacgagcaggtgttacaggccaggaacataggactgtgtgcagcatccttgactgagggaagact<br>cggcaaactgtccattctccgcaagaagcaattgaaaccttgcgacacagtcatgttctcggtaggatctacattgtacactgagagcagaaagctactgaggagctggcacttaccctccgtattcc<br>acctgaaaggtaaacaatcctttacctgtaggtgcgataccatcgtatcatgtgaagggtacgtagttaagaaaatcactatgtgccccggcctgtacggtaaaacggtagggtacgccgtgacgtat<br>cacgcggagggactcctagtgtgcaagaccacagacactgtcaaaggagaaagagtctcattccctgtatgcacctacgtcccctcaaccatctgtgatcaaatgactggcatactagcgaccgac<br>gtcacaccggaggacgcacagaagttgttagtgggattgaatcagaggatagttgtgaacggaagaacacagcgaaacactaacacgatgaagaactatctgcttccgattgtggccgtcgcat<br>ttagcaagtgggcgagggaatacaaggcagaccttgatgatgaaaaacctctgggtgtccgagagaggtcacttacttgctgctgcttgtgggcatttaaaacgaggaagatgcacaccatgtaca<br>agaaaccagacacccagacaatagtgaaggtgccttcagagtttaactcgttcgtcatcccgagcctatggtctacaggcctcgcaatcccagtcagatcacgcattaagatgcttttggccaagaag<br>accaagcgagagttaatacctgttctcgacgcgtcgtcagccagggatgctgaacaagaggagaaggagaggttggaggccgagctgactagagaagccttaccacccctcgtccccatcgcg<br>ccggcggagacgggagtcgtcgacgtcgacgttgaagaactagagtatcacgcaggtgcaggggtcgtggaaacacctcgcagcgcgttgaaagtcaccgcacagccgaacgacgtactact<br>aggaaattacgtagttctgtccccgcagaccgtgctcaagagctccaagttggccccccgtgcaccctctagcagagcaggtgaaaataataacacataacgggagggccggcggttaccaggtc<br>gacggatatgacggcagggtcctactaccatgtggatcggccattccggtccctgagtttcaagctttgagcgagagcgccactatggtgtacaacgaaagggagttcgtcaacaggaaactatac<br>catattgccgttcacggaccgtcgctgaacaccgacgaggagaactacgagaaagtcagagctgaaagaactgacgccgagtacgtgttcgacgtagataaaaaatgctgcgtcaagagagagg<br>aagcgtcgggtttggtgttggtgggagagctaaccaacccccccgttccatgaattcgcctacgaagggctgaagatcaggccgtcggcaccatataagactacagtagtaggagtctttggggttcc<br>gggatcaggcaagtctgctattattaagagcctcgtgaccaaacacgatctggtcaccagcggcaagaaggagaactgccaggaaatagttaacgacgtgaagaagcaccgcgggaaggggac<br>aagtagggaaaacagtgactccatcctgctaaacgggtgtcgtcgtgccgtggacatcctatatgtggacgaggctttcgcttgccattccggtactctgctggccctaattgctcttgttaaacctcgg<br>agcaaagtggtgttatgcggagaccccaagcaatgcggattcttcaatatgatgcagcttaaggtgaacttcaaccacaacatctgcactgaagtatgtcataaaagtatatccagacgttgcacgcgt<br>ccagtcacggccatcgtgtctacgttgcactacggaggcaagatgcgcacgaccaacccgtgcaacaaacccataatcatagacaccacaggacagaccaagcccaagccaggagacatcgtg<br>ttaacatgcttccgaggctgggcaaagcagctgcagttggactaccgtggacacgaagtcatgacagcagcagcatctcagggcctcacccgcaaaggggtatacgccgtaaggcagaaggtg<br>aatgaaaatcccttgtatgcccctgcgtcggagcacgtgaatgtactgctgacgcgcactgaggataggctggtgtggaaaacgctggccggcgatccctggattaaggtcctatcaaacattccac<br>agggtaactttacggccacattggaagaatggcaagaagaacacgacaaaataatgaaggtgattgaaggaccggctgcgcctgtggacgcgttccagaacaaagcgaacgtgtgttgggcgaa<br>aagcctggtgcctgtcctggacactgccggaatcagattgacagcagaggagtggagcaccataattacagcatttaaggaggacagagcttactctccagtggtggccttgaatgaaatttgcacc<br>aagtactatggagttgacctggacagtggcctgttttctgccccgaaggtgtccctgtattacgagaacaaccactgggataacagacctggtggaaggatgtatggattcaatgccgcaacagctg<br>ccaggctggaagctagacataccttcctgaaggggcagtggcatacgggcaagcaggcagttatcgcagaaagaaaaatccaaccgctttctgtgctggacaatgtaattcctatcaaccgcagg<br>ctgccgcacgccctggtggctgagtacaagacggttaaaggcagtagggttgagtggctggtcaataaagtaagagggtaccacgtcctgctggtgagtgagtacaacctggctttgcctcg<br>acgcagggtcacttggttgtcaccgctgaatgtcacaggcgccgataggtgctacgacctaagtttaggactgccggctgacgccggcaggttcgacttggtctttgtgaacattcacacggaattca<br>gaatccaccactaccagcagtgtgtcgaccacgccatgaagctgcagatgcttggggagatgcgctacgactgctaaaacccggcggcatcttgatgagagcttacggatacgccgataaaatc<br>agcgaagccgttgtttcctccttaagcagaaagttctcgtctgcaagagtgttgcgcccggattgtgtcaccagcaatacagaagtgttcttgctgttctccaactttgacaacggaaagagaccctcta<br>cgctacaccagatgaataccaagctgagtgccgtgtatgccggagaagccatgcacacggccgggtgtgcaccatcctacagagttaagagagcagacatagccacgtgcacagaagcggctg<br>tggttaacgcagctaacgcccgtggaactgtaggggatggcgtatgcagggccgtggcgaagaaatggccgtcagcctttaagggagcagcaacaccagtgggcacaattaaaacagtcatgtg<br>cggctcgtaccccgtcatccacgctgtagcgcctaatttctctgccacgactgaagcggaaggggaccgcgaattggccgctgtctaccgggcagtggccgccgaagtaaacagactgtcactga |

TABLE 2-continued

| lists the sequences of the present invention: |
| --- |
| gcagcgtagccatcccgctgctgtccacaggagtgttcagcggcggaagagataggctgcagcaatccctcaaccatctattcacagcaatggacgccacggacgctgacgtgaccatctactgc agagacaaaagttgggagaagaaaatccaggaagccattgacatgaggacggctgtggagttgctcaatgatgacgtggagctgaccacagacttggtgagagtgcacccggacagcagcctg gtgggtcgtaagggctacagtaccactgacgggtcgctgtactcgtactttgaaggtacgaaattcaaccaggctgctattgatatggcagagatactgacgttgtggcccagactgcaagaggcaa acgaacagatatgcctatacgcgctgggcgaaacaatggacaacatcagatccaaatgtccggtgaacgattccgattcatcaacacctcccaggacagtgccctgcctgtgccgctacgcaatga cagcagaacggatcgcccgccttaggtcacaccaagttaaaagcatggtggtttgctcatcttttcccctcccgaaataccatgtagatggggtgcagaaggtaaagtgcgagaaggttctcctgttc gacccgacggtaccttcagtggttagtccgcggaagtatgccgcatctacgacggaccactcagatcggtcgctacgagggtttgacttggactggaccaccgactcgtcttccactgccagcgata ccatgtcgctacccagtttgcagtcgtgtgacatcgactcgatctacgagccaatggctcccatagtagtgacggctgacgtacaccctgaacccgcaggcatcgcggacctggcggcagatgtgc accctgaacccgcagaccatgtggacctcgagaacccgattcctccaccgcgcccgaagagagctgcataccttgcctcccgcgcggcggagcgaccggtgccggcgccgagaaagccgac gcctgccccaaggactgcgtttaggaacaagctgcctttgacgttcggcgactttgacgagcacgaggtcgatgcgttggcctccgggattactttcggagacttcgacgacgtcctgcgactaggc cgcgcgggtgcatatatttctcctcggacactggcagcggacatttacaacaaaaatccgttaggcagcacaatctccagtgcgcacaactggatgcggtccaggaggagaaaatgtacccgcca aaactggatactgagagggagaagctgttgctgctgaaaatgcagatgcacccatcggaggctaataagagtcgataccagtctcgcaaagtggagaacatgaaagccacggtggtggacaggc tcacatcgggggccagactgtacacgggagcggacgtaggccgcataccaacatacgcggctcggtaccccgccccgtgtactcccctaccgtgatcgaaagactctcaagccccgatgtagca atcgcagcgtgcaacgaatacctattcagaaactacccaacagtggcgtcgtaccagataacagatgaatacgacgcatacctggacatggttgacgggtcggatagctgcctggacagagcgaca ttctgcccggcgaagctccggtgctacccgaaacatcatgcgtaccaccagccgactgtacgcagtgccgtcccgtcaccctttcagaacacactacagaacgtgctagcggccgccaccaaga gaaactgcaacgtcacgcaaatgcgagaactacccaccatggactcggcagtgttcaacgtggagtgcttcaagcgctatgcctgctccggagaatattgggaagaatatgctaaacaacctatcc ggataaccactgagaacatcactacctatgtgaccaaattgaaaggcccgaaagctgctgccttgttcgctaagacccacaacttggttccgctgcaggaggttcccatggacagattcacggtcga catgaaacgagatgtcaaagtcactccagggacgaaacacacagaggaaagacccaaagtccaggtaattcaagcagcggagccattggcgaccgcttacctgtgcggcatccacagggaatt agtaaggagactaaatgctgtgttacgccctaacgtgcacacattgtttgatatgtcggccgaagactttgacgcgatcatcgcctctcactttccacccaggagacccggttctagagacggacattg catcattcgacaaaagccaggacgactccttggctcttacaggtttaatgatcctcgaagatctaggggtggatcagtacctgctggacttgatcgaggcagcctttggggaaatatccagctgtcac ctaccaactggcacgcgcttcaagttcggagctatgatgaaatcgggcatgtttctgactttgtttattaacactgttttgaacatcaccatagcaagcagggtactggagcagagactcactgactccg cctgtgcggccttcatcggcgacgacaacatcgttcacggagtgatctccgacaagctgatggcggagaggtgcgcgtcgtgggtcaacatggaggtgaagatcattgacgctgtcatgggcgaa aaacccccatatttttgtgggggattcatagtttttgacagcgtcacacagaccgcctgccgtgtttcagacccacttaagcgcctgttcaagttgggtaagccgctaacagctgaagacaagcagga cgaagacaggcgacgagcactgagtgacgaggttagcaagtggttccggacaggcttgggggccgaactggaggtggcactaacatctaggtatgaggtagagggctgcaaaagtatcctcat agccatggccaccttggcgagggacattaaggcgtttaagaaattgagaggacctgttatacacctctacggcggtcctagattggtgcgttaatacacagaattctgattggatcccgggctcgaga tgctgagaataatcaatgctaggaaggagaagaagagacgaggcgcagatacaagtgtcggaattgttggcctcctgctgaccacagctatggcagcggaggtcactagacgtgggagtgcata ctatatgtacttggacagaaacgatgctggggaggccatatcttttccaaccacattggggatgaataagtgttatatacagatcatggatcttggacacacgtgtgatgccaccatgagctatgaatgc cctatgctggatgagggggtggaaccagatgacgtcgattgttggtgcaacacgacgtcaacttgggttgtgtacggaacctgccatcacaaaaaaggtgaagcacggagatctagaagagctgt gacgctcccctcccattccactaggaagctgcaaacgcggtcgcaaacctggttggaatcaagagaatacacaaagcacttgattagagtcgaaaattggatattcaggaaccctggcttcgcgtta gcagcagctgccatcgcttggcttttgggaagctcaacgagccaaaaagtcatatacttggtcatgatactgctgattgccccggcatacagcatcaggtgcataggagtcagcaatagggactttgt ggaaggtatgtcaggtgggacttgggttgatgttgtcttggaacatggaggttgtgtcactgtaatggcacaggacaaaccgactgtcgacatagagctggttacaacaacagtcagcaacatggcg gaggtaagatcctactgctatgaggcatcaatatcagacatggcttcggacagccgctgcccaacacaaggtgaagcctaccttgacaagcaatcagacactcaatatgtctgcaaaagaacgtta gtggacagaggctggggaaatggatgtggactttttggcaaagggagcctggtgacatgcgctaagtttgcatgctccaagaaaatgaccgggaagagcatccagccagagaatctggagtacc ggataatgctgtcagttcatggctcccagcacagtgggatgatcgttaatgacacaggacatgaaactgatgagaatagagcgaaagttgagataacgcccaattcaccaagagccgaagccacc ctgggggggtttggaagcctaggacttgattgtgaaccgaggacaggccttgacttttcagatttgtattacttgactatgaataacaagcactggctggttcacaaggagtggttccacgacattcc attaccttggcacgctggggcagacaccggaactccacactggaacaacaaagaagcactggtagagttcaaggacgcacatgccaaaaggcaaactgtcgtggttctagggagtcaagaagg agcagttcacacggcccttgctggagctctggaggctgagatggatggtgcaaagggaaggctgtcctctggccacttgaaatgtcgcctgaaaatggataaacttagattgaagggcgtgtcata ctccttgtgtactgcagcgttcacattcaccaagatcccggctgaaacactgcacgggacagtcacagtggaggtacagtacgcagggacagatggaccttgcaaggttccagctcagatggcgg tggacatgcaaactctgaccccagttgggaggttgataaccgctaaccccgtaatcactgaaagcactgagaactctaagatgatgctggaacttgatccaccatttggggactcttacattgtcatag gagtcggggagaagaagatcacccaccactgacacaggagtggcagcaccattggaaaagcatttgaagccactgtgagaggtgccaagagaatggcagtcttgggagacacagcctgggac tttggatcagttggaggcgctctcaactcattgggcaagggcatccatcaaatctttggagcagctttcaaatcattgtttggaggaatgtcctggttctcacaaattctcattggaacgttgctgatgtgg ttgggtctgaacgcaaagaatggatctagaatcctcacaataccgcagagtctagactcgtggtggacttctctcaattttctaggggatctcccgtgtgtcttggccaaaattcgcagtccccaacct ccaatcactcaccaacctcctgtcctccaatttgtcctggttatcgctggatgtgtctgcggcgttttatcatattcctcttcatcctgctgctatgcctcatcttcttattggttcttctggattatcaagg tatgttgcccgtttgtcctctaattccaggatcaacaacaaccagtacgggaccatgcaaaacctgcacgactcctgctcaaggcaactctatgtttccctcatgttgctgtacaaaacctacggatggaaatt gcacctgtattcccatcccatcgtcctgggctttcgcaaaatacctatgggagtgggcctcagtccgtttctcttggctcagtttactagtgccatttgttcagtggttcgtagggctttcccccactgtttgg ctttcagctatatggatgatgtggtattgggggccaagtctgtacagcatcgtgagtccctttataccgctgttaccaattttcttttgtctctgggtatacatttaactcgagcccgggatcccgggtaatta attgaattacatccctacgcaaacgttttacggccgccggtggcgcccgcgcccggcggcccgtccttggccgttgcaggccactccggtggctcccgtcgtccccgacttccaggcccagcagat gcagcaactcatcagcgccgtaaatgcgctgacaatgagacagaacgcaattgctcctgctaggcctcccaaaccaaagaagaagaagacaaccaaaccaaagccgaaaacgcagcccaaga agatcaacggaaaaacgcagcagcaaaagaagaaagacaagcaagccgacaagaagaagaagaaacccggaaaaagagaaagaatgtgcatgaagattgaaaatgactgtatcttcgtatgc ggctagccacagtaacgtagtgtttccagacatgtcgggcaccgcactatcatgggtgcagaaaatctcgggtggtctgggggccttcgcaatcggcgctatcctggtgctggttgtggtcacttgc attgggctccgcagataagttagggtaggcaatggcattgatatagcaagaaaattgaaaacagaaaaagttagggtaagcaatggcatataaccataactgtataacttgtaacaaagcgcaacaa gacctgcgcaattggccccgtggtccgcctcacggaaactcggggcaactcatattgacacattaattggcaataattggaagcttacataagcttaattcgacgaataattggattttatttatttgca |

TABLE 2-continued

| lists the sequences of the present invention: | |
|---|---|
| | attggtttttaatatttccaaaaaaaaaaaaaaaaaaaaaaaaaaaaaaaaaaaaaaaaaaaaaaaaaaaaaaaaaaaaaattcgaaactagtctgcattaatgaatcggccaacgcgcg<br>gggagaggcggtttgcgtattgggcgctcttccgcttcctcgctcactgactcgctgcgctcggtcgttcggctgcggcgagcggtatcagctcactcaaaggcggtaatacggttatccacagaat<br>caggggataacgcaggaaagaacatgtgagcaaaaggccagcaaaaggccaggaaccgtaaaaaggccgcgttgctggcgtttttccataggctccgcccccctgacgagcatcacaaaaatc<br>gacgctcaagtcagaggtggcgaaacccgacaggactataaagataccaggcgtttccccctggaagctccctcgtgcgctctcctgttccgaccctgccgcttaccggatacctgtccgcctttct<br>cccttcgggaagcgtggcgctttctcaatgctcgcgctgtaggtatctcagttcggtgtaggtcgttcgctccaagctgggctgtgtgcacgaaccccccgttcagcccgaccgctgcgccttatccg<br>gtaactatcgtcttgagtccaacccggtaagacacgacttatcgccactggcagcagccactggtaacaggattagcagagcgaggtatgtaggcggtgctacagagttcttgaagtggtggccta<br>actacggctacactagaaggacagtatttggtatctgcgctctgctgaagccagttaccttcggaaaaagagttggtagctcttgatccggcaaacaaaccaccgctggtagcggtggtttttttgtttg<br>caagcagcagattacgcgcagaaaaaaaggatctcaagaagatcctttgatcttttctacggggtctgacgctcagtggaacgaaaactcacgttaagggattttggtcatgagattatcaaaaagga<br>tcttcacctagatccttttaaattaaaaatgaagttttaaatcaatctaaagtatatatgagtaaacttggtctgacagttaccaatgcttaatcagtgaggcacctatctcagcgatctgtctatttcgttca<br>tccatagttgcctgactccccgtcgtgtagataactacgatacgggagggcttaccatctggccccagtgctgcaatgataccgcgagacccacgctcaccggctccagatttatcagcaataaaccag<br>ccagccggaagggccgagcgcagaagtggtcctgcaactttatccgcctccatccagtctattaattgttgccgggaagctagagtaagtagttcgccagttaatagtttgcgcaacgttgttgccatt<br>gctacaggcatcgtggtgtcacgctcgtcgtttggtatggcttcattcagctccggttcccaacgatcaaggcgagttacatgatcccccatgttgtgcaaaaaagcggttagctccttcggtcctccga<br>tcgttgtcagaagtaagttggccgcagtgttatcactcatggttatggcagcactgcataattctcttactgtcatgccatccgtaagatgcttttctgtgactggtgagtactcaaccaagtcattctgaga<br>atagtgtatgcggcgaccgagttgctcttgcccggcgtcaatacgagataataccgcgccacatagcagaactttaaaagtgctcatcattggaaaacgttcttcggggcgaaaactctcaaggatct<br>taccgctgttgagatccagttcgatgtaacccactcgtgcacccaactgatcttcagcatcttttactttcaccagcgtttctgggtgagcaaaaacaggaaggcaaaatgccgcaaaaaagggaata<br>agggcgacacggaaatgttgaatactcatactcttcctttttcaatattattgaagcatttatcagggttattgtctcatgagcggatacatatttgaatgtatttagaaaaataaacaaataggggttccgcg<br>cacatttccccgaaaagtgccacctgacgtctaagaaaccattattatcatgacattaacctataaaaataggcgtatcacgaggccctttcgtctcgcgcgtttcggtgatgacggtgaaaacctctga<br>cacatgcagctcccggagacggtcacagcttctgtctaagcggatgccgggagcagacaagcccgtcagggcgcgtcagcgggtgttggcgggtgtcggggctggcttaactatgcggcatca<br>gagcagattgtactgagagtgcaccatatcgacgctctcccttatgcgactcctgcattaggaagcagcccagtactaggttgaggccgttgagcaccgccgccgcaaggaatggtgcatgcaag<br>gagatggcgcccaacagtcccccggccacggggcctgccaccatacccacgccgaaacaagcgctcatgagcccgaagtggcgagcccgatcttccccatcggtgatgtcggcgatataggc<br>gccagcaacgcacctgtggcgccggtgatgccggccacgatgcgtccggcgtagaggatctggctagcgatgaccctgctgattggttcgctgaccatttccggggtgcggaacggcgttacc<br>agaaactcagaaggttcgtccaaccaaaccgactctgacggcagtttacgagagagatgatagggtctgcttcagtaagccagatgctacacaattaggcttgtacatattgtcgttagaacgcggct<br>acaattaatacataaccttatgtatcatacacatacgatttaggtgacactata |
| SEQ ID NO: 55 | gatggcggatgtgtgacatacacgacgccaaaagatttgttccagctcctgccacctccgctacgcgagagattaaccacccacgatggccgccaaagtgcatgttgatattgaggctgacagcc<br>cattcatcaagtctttgcagaaggcatttccgtcgttcgaggtggagtcattgcaggtcacaccaaatgaccatgcaaatgccagagcattttcgcacctggctaccaaattgatcgagcaggagact<br>gacaaagacacactcatcttggatatcggcagtgcgccttccaggagaatgatgtctacgcacaaataccactgcgtatgccctatgcgcagcgcagaagaccccgaaaggctcgatagctacgc<br>aaagaaactggcagcggcctccgggaaggtgctggatagagagatcgcaggaaaaatcaccgacctgcagaccgtcatggctacgccagacgctgaatctcctacctttttgcctgcatacagac<br>gtcacgtgtcgtacggcagccgaagtggccgtataccaggacgtgtatgctgtacatgcaccaacatcgctgtaccatcaggcgatgaaaggtgtcagaacggcgtattggattgggtttgacacc<br>accccgtttatgtttgacgcgctagcaggcgcgtatccaacctacgccacaaactgggccgacgagcaggtgttacaggccaggaacataggactgtgtgcagcatccttgactgagggaagact<br>cggcaaactgtccattctccgcaagctagcaattgaaaccttgcgacacagtcatgttctcggtaggatctacattgtacactgagagcagaaagctactgaggagctggcacttaccctocgtattcc<br>acctgaaaggtaaacaatcctttacctgtaggtgcgataccatcgtatcatgtgaagggtacgtagttaagaaaatcactatgtgccccggcctgtacggtaaaacggtagggtacgccgtgacgtat<br>cacgcggagggattcctagtgtgcaagaccacagacactgtcaaaggagaaagagtctcattccctgtatgcacctacgtcccctcaaccatctgtgatcaaatgactggcatactagcgaccgac<br>gtcacaccggaggacgcacagaagttgttagtgggattgaatcagaggatagttgtgaacggaagaacacagcgaaacactaacacgatgaagaactatctgcttccgattgtggccgtcgcat<br>ttagcaagtgggcgagggaatacaaggcagaccttgatgatgaaaaacctctgggtgtccgagagaggtcacttacttgctgctgcttgtgggcatttaaaacgaggaagatgcacaccatgtaca<br>agaaaccagacacccagacaatagtgaaggtgccttcagagtttaactcgttcgtcatcccgagcctatggtctacaggcctcgcaatcccagtcagatcacgcattaagatgcttttggccaagaag<br>accaagcgagagttaatacctgttctcgacgcgtcgtcagccagggatgctgaacaagaggagaaggagaggttggaggccgagctgactagagaagccttaccacccctcgtccccatcgcg<br>ccggcggagacgggagtcgtcgacgtcgacgttgaagaactagagtatcacgcaggtgcaggggtcgtggaaacacctcgcagcgcgttgaaagtcaocgcacagccgaacgacgtactact<br>aggaaattacgtagttctgtccccgcagaccgtgctcaagagctccaagttggcccccgtgcaccctctagcagagcaggtgaaaataataacacataacgggagggccggcggttaccaggtc<br>gacggatatgacggcagggtcctactaccatgtggatcggccattccggtccctgagtttcaagctttgagcgagagcgccactatggtgtacaacgaaagggagttcgtcaacaggaaactatac<br>catattgccgttcacggaccgtcgctgaacaccgacgaggagaactacgagaaagtcagagctgaaagaactgacgccgagtacgtgttcgacgtagataaaaaaatgctgcgtcaagagagagg<br>aagcgtcgggtttggtgttggtgggagagctaaccaacccccgttccatgaattcgcctacgaagggctgaagatcaggccgtcggcaccatataagactacagtagtaggagtctttggggtta<br>gggatcaggcaagtctgctattattaagagcctcgtgaccaaacacgatctggtcaccagcggcaagaaggagaactgccaggaaatagttaacgacgtgaagaagcaccgcgggaaggggac<br>aagtagggaaaacagtgactccatcctgctaaacgggtgtcgtcgtgccgtggacatcctatatgtggacgaggctttcgcttgccattccggtactctgctggccctaattgctcttgttaaacctcgg<br>agcaaagtggtgttatgcggagaccccaagcaatgcggattcttcaatatgatgcagcttaaggtgaacttcaaccacaacatctgcactgaagtatgtcataaaagtatatccagacgttgcacgcgt<br>ccagtcacggccatcgtgtctacgttgcactacggaggcaagatgcgcacgaccaacccgtgcaacaaacccataatcatagacaccacaggacagaccaagcccaagccaggagacatcgtg<br>ttaacatgcttccgaggctgggcaaagcagctgcagttggactaccgtggacacgaagtcatgacagcagcagcatctcagggcctcacccgcaaaggggtatacgccgtaaggcagaaggtg<br>aatgaaaatcccttgtatgcccctgcgtcggagcacgtgaatgtactgctgacgcgcactgaggataggctggtgtggaaaacgctggccggcgatccctggattaaggtcctatcaaacat<br>tccacagggtaactttacggccacattggaagaatggcaagaagaacacgacaaaataatgaaggtgattgaaggaccggctgcgcctgtggacgcgttccagaacaaagcgaacgtgtgttgg<br>gcgaaaagcctggtgcctgtcctggacactgccggaatcagattgacagcagaggagtggagcaccataattacagcatttaaggaggacagagcttactctccagtggtggccttgaatgaaattt<br>gcaccaagtactatggagttgacctggacagtggcctgttttctgccccgaaggtgtccctgtattacgagaacaaccactgggataacagacctggtggaaggatgtatggattcaatgccgcaac |

TABLE 2-continued

| lists the sequences of the present invention: |
| --- |
| agctgccaggctggaagctagacataccttcctgaaggggcagtggcatacgggcaagcaggcagttatcgcagaaagaaaaatccaaccgctttctgtgctggacaatgtaattcctatcaaccg |
| caggctgccgcacgccctggtggctgagtacaagacggttaaaggcagtagggttgagtggctggtcaataaagtaagagggtaccacgtcctgctggtgagtgagtacaacctggctttgcctc |
| gacgcagggtcacttggttgtcaccgctgaatgtcacaggcgccgataggtgctacgacctaagtttaggactgccggctgacgccggcaggttcgacttggtctttgtgaacattcacacggaatt |
| cagaatccaccactaccagcagtgtgtcgaccacgccatgaagctgcagatgcttggggagatgcgctacgactgctaaaacccggcggcatcttgatgagagcttacggatacgccgataaaa |
| tcagcgaagccgttgtttcctccttaagcagaaagttctcgtctgcaagagtgctgcgcccggattgtgtcaccagcaatacagaagtgttcttgctgttctccaactttgacaacggaaagagaccctc |
| tacgctacaccagatgaataccaagctgagtgccgtgtatgccggagaagccatgcacacggccgggtgtgcaccatcctacagagttaagagagcagacatagccacgtgcacagaagcggc |
| tgtggttaacgcagctaacgcccgtggaactgtaggggatggcgtatgcagggccgtggcgaagaaatggccgtcagcctttaagggagcagcaacaccagtgggcacaattaaaacagtcatg |
| tgcggctcgtaccccgtcatccacgctgtagcgcctaatttctctgccacgactgaagcggaaggggaccgcgaattggccgctgtctaccgggcagtggccgccgaagtaaacagactgtcact |
| gagcagcgtagccatcccgctgctgtccacaggagtgttcagcggcggaagagataggctgcagcaatccctcaaccatctattcacagcaatggacgccacggacgctgacgtgaccatctact |
| gcagagacaaaagttgggagaagaaaatccaggaagccattgacatgaggacggctgtggagttgctcaatgatgacgtggagctgaccacagacttggtgagagtgcacccggacagcagcc |
| tggtgggtcgtaagggctacagtaccactgacgggtcgctgtactcgtactttgaaggtacgaaattcaaccaggctgctattgatatggcagagatactgacgttgtggcccagactgcaagaggc |
| aaacgaacagatatgcctatacgcgctgggcgaaacaatggacaacatcagatccaaatgtccggtgaacgattccgattcatcaacacctcccaggacagtgccctgcctgtgccgctacgcaat |
| gacagcagaacggatcgcccgccttaggtcacaccaagttaaaagcatggtggtttgctcatcttttcccctcccgaaataccatgtagatggggtgcagaaggtaaagtgcgagaaggttctcctgt |
| tcgacccgacggtaccttcagtggttagtccgcggaagtatgccgcatctacgacggaccactcagatcggtcgttacgagggtttgacttggactggaccaccgactcgtcttccactgccagcga |
| taccatgtcgctacccagtttgcagtcgtgtgacatcgactcgatctacgagccaatggctcccatagtagtgacggctgacgtacaccctgaacccgcaggcatcgcggacctggcggcagatgt |
| gcaccctgaacccgcagaccatgtggacctcgagaacccgattcctccaccgcgcccgaagagagctgcataccttgcctcccgcgcggcggagcgaccggtgccggcgccgagaaagccg |
| acgcctgccccaaggactgcgtttaggaacaagctgcctttgacgttcggcgactttgacgagcacgaggtcgatgcgttggcctccgggattactttcggagacttcgacgacgtcctgcgactag |
| gccgcgcgggtgcatatatttctcctcggacactggcagcggacatttacaacaaaaatccgttaggcagcacaatctccagtgcgcacaactggatgcggtccaggaggagaaaatgtacccg |
| ccaaaactggatactgagagggagaagctgctgctgctgaaaatgcagatgcacccatcggaggctaataagagtcgataccagtctcgcaaagtggagaacatgaaagccacggtggtggaca |
| ggctcacatcgggggccagattgtacacgggagcggacgtaggccgcataccaacatacgcggttcggtaccccgccccgtgtactcccctaccgtgatcgaaagattctcaagccccgatgta |
| gcaatcgcagcgtgcaacgaatacctatccagaaattacccaacagtggcgtcgtaccagataacagatgaatacgacgcatacttggacatggttgacgggtcggatagttgcttggacagagcg |
| acattctgcccggcgaagctccggtgctacccgaaacatcatgcgtaccaccagccgactgtacgcagtgccgtcccgtcaccctttcagaacacactacagaacgtgctagcggccgccaccaa |
| gagaaactgcaacgtcacgcaaatgcgagaactacccaccatggactcggcagtgttcaacgtggagtgcttcaagcgctatgcctgctccggagaatattgggaagaatatgctaaacaacctat |
| ccggataaccactgagaacatcactacctatgtgaccaaattgaaaggcccgaaagctgctgccttgttcgctaagacccacaacttggttccgctgcaggaggttcccatggacagattcacggtc |
| gacatgaaacgagatgtcaaagtcactccagggacgaaacacacagaggaaagacccaaagtccaggtaactcaagcagcggagccactggcgaccgcttacctgtgcggcatccacaggga |
| attagtaaggagactaaatgctgtgttacgccctaacgtgcacacattgtttgatatgtcggccgaagactttgacgcgatcatcgcctctcacttccacccaggagacccggttctagagacggac |
| attgcatcattcgacaaaagccaggacgactccttggctcttacaggtttaatgatcctcgaagatctaggggtggatcagtacctgctggacttgatcgaggcagcctttggggaaatatccagctgt |
| cacctaccaactggcacgcgcttcaagttcggagctatgatgaaatcgggcatgtttctgactttgtttattaacactgttttgaacatcaccatagcaagcagggtactggagcagagactcactgact |
| ccgcctgtgcggccttcatcggcgacgacaacatcgttcacggagtgatctccgacaagctgatggcggagaggtgcgcgtcgtgggtcaacatggaggtgaagatcattgacgctgtcatgggc |
| gaaaaaccccatatttttgtggggggattcatagtttttgacagcgtcacacagaccgcctgccgtgtttcagacccacttaagcgcctgttcaagttgggtaagccgctaacagctgaagacaagca |
| ggacgaagacaggcgacgagcactgagtgacgaggttagcaagtggttccggacaggcttgggggccgaactggaggtggcactaacatctaggtatgaggtagagggctgcaaaagt |
| atcctcatagccatggccaccttggcgagggacattaaggcgtttaagaaattgagaggacctgttatacacctctacggcggtcctagattggtgcgttaatacacagaattctgattggatcccggg |
| ctcgagatgctgagaataatcaatgctaggaaggagaagaagagacgaggcgcagatacaagtgtcggaattgttggcctcctgctgaccacagctatggcagcggaggtcactagacgtggga |
| gtgcatactatatgtacttggacagaaacgatgctggggaggccatatcttttccaaccacattggggatgaataagtgttatatacagatcatggatcttggacacacgtgtgatgccaccatgagcta |
| tgaatgccctatgctggatgagggggtggaaccagatgacgtcgattgttggtgcaacacgacgtcaacttgggttgtgtacggaacctgccatcacaaaaaaggtgaagcacggagatctagaa |
| gagctgtgacgctcccctcccattccactaggaagctgcaaacgcggtcgcaaacctggttggaatcaagagaatacacaaagcacttgattagagtcgaaaattggatattcaggaaccct |
| ggcttcgcgttagcagcagctgccatcgcttggcttttgggaagctcaacgagccaaaaagtcatatacttggtcatgatactgctgattgccccggcatacagcatcaggtgcataggagtcagcaa |
| tagggaccttgtggaaggtatgtcaggtgggacctgggctgatgttgtcctggaacatggaggctgtgtcactgtaatggcacaggacaaaccgactgtcgacatagagctggctacaacaacagtca |
| gcaacatggcggaggtaagatcctactgctatgaggcatcaatatcagacatggcttcggacagccgctgcccaacacaaggtgaagcctaccttgacaagcaatcagacactcaatatgtctgca |
| aaagaacgctagtggacagaggctggggaaatggatgtggacctcttggcaaagggagcctggtgacatgcgctaagcttgcatgctccaagaaaatgaccgggaagagcatccagccagagaa |
| tctggagtaccggataatgctgtcagctcatggctcccagcacagtgggatgatcgctaatgacacaggacatgaaactgatgagaatagagcgaaagctgagataacgcccaactcaccaaga |
| gccgaagccaccctgggggggcttggaagcctaggacctgattgtgaaccgaggacaggccctgacctctcagatctgtattacctgactatgaataacaagcactggctggctcacaaggagtggctc |
| cacgacattccattaccttggcacgctggggcagacaccggaactccacactggaacaacaaagaagcactggtagagttcaaggacgcacatgccaaaaggcaaactgtcgtggttctaggga |
| gtcaagaaggagcagctcacacggcccctgctggagctctggaggctgagatggatggtgcaaagggaaggctgtcctctggccacctgaaatgtcgcctgaaaatggataaacctagattgaagg |
| gcgtgtcatactccttgtgtactgcagcgttcacattcaccaagatcccggctgaaacactgcacgggacagtcacagtggaggtacagtacgcagggacagatggaccttgcaaggttccagctc |
| agatggcggtggacatgcaaactctgaccccagttgggaggctgataaccgctaaccccgtaatcactgaaagcactgagaactctaagatgatgctggaacttgatccaccacttggggactct |
| tacactgtcataggagtcggggagaagaagatcacccaccactggcacaggagtggcagcaccactggaaaagcatctgaagccactgtgagaggtgccaagagaatggcagtcctgggagaca |
| cagcctgggaccttggatcagctggaggcgctctcaactcactgggcaagggcatccatcaaatccttggagcagccttcaaatcactgcttggaggaatgtcctggctctcacaaactctcattggaacg |
| ctgctgatgtggctgggtctgaacgcaaagaatggatctattttccctatgtgcctggccctaggggagtgctgatcctcttatccacagccgtctctgctcagtggaactccactgccctccaccaaactc |
| tgcaggatcccagagtcaggggtctgtatcctcctgctggtggctccagctcaggaacagtaaaccctgctccgaatactgcctctcacatctcgtcaatctccgcgaggactggggaccctgtgacg |
| aacatggagaacatcacatcaggattcctaggacccctgctcgtgctacaggcggggttcttcctgttgacaagaatcctcacaataccgcagagtctagactcgtggtggacctctctcaactctctagg |

TABLE 2-continued

| | lists the sequences of the present invention: |
|---|---|
| | gggatctcccgtgtgtcctggccaaaactcgcagtocccaacctccaatcactcaccaacctcctgtcctccaatctgtcctggttatcgctggatgtgtctgcggcgttctatcatattcctcttcatcctgc<br>tgctatgcctcatcttcttattggctcctctggattatcaaggtatgctggcgtctgtcctctaactccaggatcaacaacaaccagtacgggaccatgcaaaacctgcacgactcctgctcaaggca<br>actctatgtttccctcatgttgctgtacaaaacctacggatggaaattgcacctgtattcccatcccatcgtcctgggctttcgcaaaatacctatgggagtgggcctcagtccgtttctcttggctcagttt<br>actagtgccatttgttcagtggttcgtagggctttcccccactgtttggctttcagctatatggatgatgtggtattgggggccaagtctgtacagcatcgtgagtccctttataccgctgttaccaattttct<br>tttgtctctgggtatacatttaactcgagcccgggatcccgggtaattaattgaattacatccctacgcaaacgttttacggccgccggtggcgcccgcgcccggcggcccgtccttggccgttgcagg<br>ccactccggtggctcccgtcgtccccgacttccaggcccagcagatgcagcaactcatcagcgccgtaaatgcgctgacaatgagacagaacgcaattgctcctgctaggcctcccaaaccaaag<br>aagaagaagacaaccaaactaaagccgaaaacgcagcccaagaagatcaacggaaaaacgcagcagcaaaagaagaaagacaagcaagccgacaagaagaagaagaaacccggaaaaa<br>gagaaagaatgtgcatgaagattgaaaatgactgtatcttcgtatgcggctagccacagtaacgtagtgtttccagacatgtcgggcaccgcactatcatgggtgcagaaaatctcgggtggtctgg<br>gggccttcgcaatcggcgctatcctggtgctggttgtggtcacttgcattgggctccgcagataagttagggtaggcaatggcattgatatagcaagaaaattgaaaacagaaaaagttagggtaag<br>caatggcatataaccataactgtataacttgtaacaaagcgcaacaagacctgcgcaattggccccgtggtccgcctcacggaaactcggggcaactcatattgacacattaattggcaataattgga<br>agcttacataagcttaattcgacgaataattggattttttatttatttgcaattggtttttaatatttccaaaaaaaaaaaaaaaaaaaaaaaaaaaaaaaaaaaaaaaaaaaaaaaaaaaaaaaaaa<br>aaaaaaaattcgaaactagtctgcattaatgaatcggccaacgcgcggggagaggcggtttgcgtattgggcgctcttccgcttcctcgctcactgactcgctgcgctcggtcgttcggctgcggcg<br>agcggtatcagctcactcaaaggcggtaatacggttatccacagaatcaggggataacgcaggaaagaacatgtgagcaaaaggccagcaaaaggccaggaaccgtaaaaaggccgcgttgct<br>ggcgtttttccataggctccgcccccctgacgagcatcacaaaaatcgacgctcaagtcagaggtggcgaaacccgacaggactataaagataccaggcgtttccccctggaagctccctcgtgc<br>gctctcctgttccgaccctgccgcttaccggatacctgtccgcctttctcccttcgggaagcgtggcgctttctcaatgctcgcgctgtaggtatctcagttcggtgtaggtcgttcgctccaagctggg<br>ctgtgtgcacgaaccccccgttcagcccgaccgctgcgccttatccggtaactatcgtcttgagtccaacccggtaagacacgacttatcgccactggcagcagccactggtaacaggattagcag<br>agcgaggtatgtaggcggtgctacagagttcttgaagtggtggcctaactacggctacactagaaggacagtatttggtatctgcgctctgctgaagccagttaccttcggaaaaagagttggtagct<br>cttgatccggcaaacaaaccaccgctggtagcggtggtttttttgtttgcaagcagcagattacgcgcagaaaaaaaggatctcaagaagatcctttgatcttttctacggggtctgacgctcagtgga<br>acgaaaactcacgttaagggattttggtcatgagattatcaaaaaggatcttcacctagatccttttaaattaaaaatgaagttttaaatcaatctaaagtatatatgagtaaacttggtctgacagtt<br>accaatgcttaatcagtgaggcacctatctcagcgatctgtctatttcgttcatccatagttgcctgactccccgtcgtgtagataactacgatacgggagggcttaccatctggccccagtgctgcaat<br>gataccgcgagacccacgctcaccggctccagatttatcagcaataaaccagccagccggaagggccgagcgcagaagtggtcctgcaactttatccgcctccatccagtctattaattgttgccg<br>ggaagctagagtaagtagttcgccagttaatagtttgcgcaacgttgttgccattgctacaggcatcgtggtgtcacgctcgtcgtttggtatggcttcattcagctccggttcccaacgatcaaggcga<br>gttacatgatcccccatgttgtgcaaaaaagcggttagctccttcggtcctccgatcgttgtcagaagtaagttggccgcagtgttatcactcatggttatggcagcactgcataattctcttactgtcatg<br>ccatccgtaagatgcttttctgtgactggtgagtactcaaccaagtcattctgagaatagtgtatgcggcgaccgagttgctcttgcccggcgtcaatacgggataataccgcgccacatagcagaact<br>ttaaaagtgctcatcattggaaaacgttcttcggggcgaaaactctcaaggatcttaccgctgttgagatccagttcgatgtaacccactcgtgcacccaactgatcttcagcatcttttactttcaccagc<br>gtttctgggtgagcaaaaacaggaaggcaaaatgccgcaaaaaagggaataagggcgacacggaaatgttgaatactcatactcttcctttttcaatattattgaagcatttatcagggttattgtctcat<br>gagcggatacatatttgaatgtatttagaaaaataaacaaataggggttccgcgcacatttccccgaaaagtgccacctgacgtctaagaaaccattattatcatgacattaacctataaaaataggcgt<br>atcacgaggccctttcgtctcgcgcgtttcggtgatgacggtgaaaacctctgacacatgcagctcccggagacggtcacagcttctgtctaagcggatgccgggagcagacaagcccgtcaggg<br>cgcgtcagcgggtgttggcgggtgtcggggctggcttaactatgcggcatcagagcagattgtactgagagtgcaccatatcgacgctctcccttatgcgactcctgcattaggaagcagcccagt<br>actaggttgaggccgttgagcaccgccgccgcaaggaatggtgcatgcaaggagatggcgcccaacagtcccccggccacggggcctgccaccatacccacgccgaaacaagcgctcatga<br>gcccgaagtggcgagcccgatcttccccatcggtgatgtcggcgatataggcgccagcaaccgcacctgtggcgccggtgatgccggccacgatgcgtccggcgtagaggatctggctagcga<br>tgaccctgctgattggttcgctgaccatttccggggtgcggaacggcgttaccagaaactcagaaggttcgtccaaccaaaccgactctgacggcagtttacgagagagatgatagggtctgcttca<br>gtaagccagatgctacacaattaggcttgtacatattgtcgttagaacgcggctacaattaatacataaccttatgtatcatacacatacgatttaggtgacactata |
| SEQ ID NO: 56 | ttaattccgtgtattctatagtgtcacctaaatcgtatgtgtatgatacataaggttatgtattaattgtagccgcgttctaacgacaatatgtacaagcctaattgtgtagcatctggcttactgaagcagac<br>cctatcatctctctcgtaaactgccggcagagtcggtttggttggacgaaccttctgagtttctggtaacgccgtcccgcacccggaaatggtcagcgaaccaatcagcagggtcatcgctagccagat<br>cctctacgccggacgcatcgtggccggcatcaccggcgccacaggtgcggttgctggcgcctatatcgccgacatcaccgatggggaagatcgggctcgccacttcgggctcatgagcgcttgtt<br>tcggcgtgggtatggtggcaggccccgtggccgggggactgttgggcgccatctccttgcatgcaccattccttgcggcggcggtsctcaacggcctcaacctactactgggctgcttcctaatgc<br>aggagtcgcataagggagagcgtcgaatggtgcactctcagtacaatctgctctgatgccgcatagttaagccagccccgacacccgccaacacccgctgacgcgccctgacgggc<br>ttgtctgctcccggcatccgcttacagacaagctgtgaccgtctccgggagctgcatgtgtcagaggttttcaccgtcatcaccgaaacgcgcgagacgaaagggcctcgtgatacgcctatttttat<br>aggttaatgtcatgataataatggtttcttagacgtcaggtggcacttttcggggaaatgtgcgcggaacccctatttgtttatttttctaaatacattcaaatatgtatccgctcatgagacaataaccctga<br>taaatgcttcaataatattgaaaaaggaagagtatgagtactcaacatttccgtgtcgcccttattcccttttttgcggcattttgccttcctgtttttgctcacccagaaacgctggtgaaagtaaaagatgc<br>tgaagatcagttgggtgcacgagtgggttacatcgaactggatctcaacagcggtaagatccttgagagttttcgccccgaagaacgttttccaatgatgagcacttttaaagttctgctatgtggcgcg<br>gtattatcccgtattgacgccgggcaagagcaactcggtcgccgcatacactattctcagaatgacttggttgagtactcaccagtcacagaaaagcatcttacggatggcatgacagtaagagaatt<br>atgcagtgctgccataaccatgagtgataacactgcggccaacttacttctgacaacgatcggaggaccgaaggagctaaccgcttttttgcacaacatgggggatcatgtaactcgccttgatcgtt<br>gggaaccggagctgaatgaagccataccaaacgacgagcgtgacaccacgatgcctgtagcaatggcaacaacgttgcgcaaactattaactggcgaactacttactctagcttcccggcaacaa<br>ttaatagactggatggaggcggataaagttgcaggaccacttctgcgctcggcccttccggctggctggtttattgctgataaatctggagccggtgagcgtgggtctcgcggtatcattgcagcact<br>ggggccagatggtaagccctcocgtatcgtagttatctacacgacggggagtcaggcaactatggatgaacgaaatagacagatcgctgagataggtgcctcactgattaagcattggtaactgtca<br>gaccaagtttactcatatatactttagattgatttaaaacttcatttttaatttaaaaggatctaggtgaagatcctttttgataatctcatgaccaaaatcccttaacgtgagttttcgttccactgagcgt<br>cagaccccgtagaaaagatcaaaggatcttcttgagatcctttttttctgcgcgtaatctgctgcttgcaaacaaaaaaaccaccgctaccagcggtggtttgtttgccggatcaagagctaccaactctttt<br>tccgaaggtaactggcttcagcagagcgcagataccaaatactgtccttctagtgtagccgtagttaggccaccacttcaagaactctgtagcaccgcctacatacctcgctctgctaatcctgttaccagt |

TABLE 2-continued

| lists the sequences of the present invention: |
|---|
| ggctgctgccagtggcgataagtcgtgtcttaccgggttggactcaagacgatagttaccggataaggcgcagcggtcgggctgaacggggggttcgtgcacacagcccagcttggagcg<br>aacgacctacaccgaactgagatacctacagcgtgagcattgagaaagcgccacgcttcccgaagggagaaaggcggacaggtatccggtaagcggcagggtcggaacaggagagcgcac<br>gagggagcttccagggggaaacgcctggtatctttatagtcctgtcgggtttcgccacctctgacttgagcgtcgatttttgtgatgctcgtcaggggggcggagcctatggaaaaacgccagcaac<br>gcggcctttttacggttcctggccttttgctggccttttgctcacatgttctttcctgcgttatcccctgattctgtggataaccgtattaccgcctttgagtgagctgataccgctcgccgcagccgaacga<br>ccgagcgcagcgagtcagtgagcgaggaagcggaagagcgcccaatacgcaaaccgcctctccccgcgcgttggccgattcattaatgcagctgtggaatgtgtgtcagttagggtgtggaaag<br>tccccaggctccccagcaggcagaagtatgcaaagcatgcatctcaattagtcagcaaccaggtgtggaaagtccccaggctccccagcaggcagaagtatgcaaagcatgcatctcaattagtc<br>agcaaccatagtcccgcccctaactccgcccatcccgcccctaactccgcccagttccgcccattctccgccccatggctgactaattttttttatttatgcagaggccgaggccgcctcggcctctga<br>gctattccagaagtagtgaggaggcttttttggaggcctaggcttttgcaaaaagcttggacacaagacaggcttgcgagatatgtttgagaataccactttatcccgcgtcagggagaggcagtgcg<br>taaaaagacgcggactcatgtgaaatactggtttttagtgcgccagatctctataatctcgcgcaacctattttcccctcgaacacttttttaagccgtagataaacaggctgggacacttcacatgagcg<br>aaaaatacatcgtcacctgggacatgttgcagatccatgcacgtaaactcgcaagccgactgatgccttctgaacaatggaaaggcattattgccgtaagccgtggcggtctgtaccgggtgcgtta<br>ctggcgcgtgaactgggtattcgtcatgtcgataccgtttgtatttccagctacgatcacgacaaccagcgcgagcttaaagtgctgaaacgcgcagaaggcgatggcgaaggcttcatcgttattga<br>tgacctggtggataccggtggtactgcggttgcgattcgtgaaatgtatccaaaagcgcactttgtcaccatcttcgcaaaaccggctggtcgtccgctggttgatgactatgttgttgatatcccgca<br>agatacctggattgaacagccgtgggatatgggcgtcgtattcgtcccgccaatctccggtcgctaatcttttcaacgcctggcactgccgggcgttgttctttttaacttcaggcgggttacaatagttt<br>ccagtaagtattctggaggctgcatccatgacacaggcaaacctgagcgaaaccctgttcaaaccccgctttaaacatcctgaaacctcgacgctagtccgccgctttaatcacggcgcacaaccg<br>cctgtgcagtcggcccttgatggtaaaaccatccctcactggtatcgcatgattaaccgtctgatgtggatctggcgcggcattgacccacgcgaaatcctcgacgtccaggcacgtattgtgatgag<br>cgatgccgaacgtaccgacgatgatttatacgatacggtgattggctaccgtggcggcaactggatttatgagtgggccccggatctttgtgaaggaaccttacttctgtggtgtgacataattggaca<br>aactacctacagagatttaaagctctaaggtaaatataaaatttttaagtgtataatgtgttaaactactgattctaattgtttgtgtattttagattccaacctatggaactgatgaatgggagcagtggtgg<br>aatgcctttaatgaggaaaacctgttttgctcagaagaaatgccatctagtgatgatgaggctactgctgactctcaacattctactcctccaaaaaagaagagaaaggtagaagaccccaaggactttc<br>cttcagaattgctaagtttttgagtcatgctgtgtttagtaatagaactcttgcttgctttgctatttacaccacaaaggaaaaagctgcactgctatacaagaaaattatggaaaaatattctgtaacct<br>ttataagtaggcataacagttataatcataacatactgttttttcttactccacacaggcatagagtgtctgctattaataactatgctcaaaaattgtgtacctttagctttttaatttgtaaaggggttaa<br>taaggaatatttgatgtatagtgccttgactagagatcataatcagccataccacatttgtagaggttttacttgctttaaaaaacctcccacacctccccctgaacctgaaacataaaatgaatgcaattgtt<br>gttgttaacttgtttattgcagcttataatggttacaaataaagoaatagcatcacaaatttcacaaataaagcatttttttcactgcattctagttgtggtttgtccaaatttcatcaatgtatcttatcatg<br>tctggatcaactggataactcaagctaaccaaaatcatcccaaacttcccaccccataccctattaccactgccaattacctagtggtttcatttactctaaacctgtgattcctctgaattattttcattta<br>aagaaattgtatttgttaaatatgtactacaaacttagtagttggaagggctaattcactcccaaagaagacaagatatccttgatctgtggatctaccacacacaaggctacttccctgattagcagaacta<br>cacaccagggccaggggtcagatatccactgacctttggatggtgctacaagctagtaccagttgagccagataaggtagaagaggccaataaaggagagaacaccagcttgttacaccctgtgagcctgcat<br>gggatggatgacccggagagagaagtgttagagtggaggtttgacagccgcctagcatttcatcacgtggcccgagagctgcatccggagtacttcaagaactgctgatatcgagcttgctacaag<br>ggactttccgctggggactttccagggaggcgtggcctgggcgggactggggagtggcgagccctcagatcctgcatataagcagctgctttttgcctgtactgggtctctctggttagaccag<br>atctgagcctgggagctctctggctaactagggaacccactgcttaagcctcaataaagcttgccttgagtgcttcaagtagtgtgtgcccgtctgttgtgtgactctggtaactagagatccctcagac<br>ccttttagtcagtgtggaaaatctctagcagtggcgcccgaacagggacttgaaagcgaaagggaaaccagaggagctctctcgacgcaggactcggcttgctgaagcgcgcacggcaagagg<br>cgaggggcggcgactggtgagtacgccaaaaattttgactagcggaggctagaaggagagagatgggtgcgagagcgtcagtattaagcgggggagaattagatcgcgatgggaaaaaattc<br>ggttaaggccagggggaaagaaaaaatataaattaaaacatatagtatgggcaagcagggagctagaacgattcgcagttaatcctggcctgttagaaacatcagaaggctgtagacaaatactgg<br>gacagctacaaccatcccttcagacaggatcagaagaacttagatcattatataatacagtagcaaccctctattgtgtgcatcaaaggatagagataaaagacaccaaggaagctttagacaagata<br>gaggaagagcaaaacaaaagtaagaccaccgcacagcaagcggccgctgatcttcagacctggaggaggagatatgagggacaattggagaagtgaattatataaatataaagtagtaaaaatt<br>gaaccattaggagtagcacccaccaaggcaaagagaagagtggtgcagagagaaaaaagagcagtgggaataggagctttgttccttgggttcttgggagcagcaggaagcactatgggcgca<br>gcgtcaatgacgctgacggtacaggccagacaattattgtctggtatagtgcagcagcagaacaatttgctgagggctattgaggcgcaacagcatctgttgcaactcacagtctggggcatcaagc<br>agctccaggcaagaatcctggctgtggaaagatacctaaaggatcaacagctcctggggatttggggttgctctggaaaactcatttgcaccactgctgtgccttggaatgctagttggagtaataaat<br>ctctggaacagatttggaatcacacgacctggatggagtgggacagagaaattaacaattacacaagcttaatacactccttaattgaagaatcgcaaaaccagcaagaaaagaatgaacaagaatt<br>attggaattagataaatgggcaagtttgtggaattggtttaacataacaaattggctgtggtatataaaattattcataatgatagtaggaggcttggtaggtttaagaatagtttttgctgtactttctatag<br>tgaatagagttaggcagggatattcaccattatcgtttcagacccacctcccaaccccgaggggacccgacaggcccgaaggaatagaagaagaaggtggagagagagacagagacagatccatt<br>cgattagtgaacggatctcgacggtatcgccgaattcacaaatggcagtattcatccacaattttaaaagaaaaggggggattggggggtacagtgcaggggaaagaatagtagacataatagcaa<br>cagacatacaaactaaagaattacaaaaacaaattacaaaaattcaaaattttcgggtttattacagggacagcagagatccactttatcgataagcttgggagttccgcgttacataacttacggtaaat<br>ggcccgcctggctgaccgcccaacgacccccgcccattgacgtcaataatgacgtatgttcccatagtaacgccaatagggactttccattgacgtcaatgggtggaatatttacggtaaactgccc<br>acttggcagtacatcaagtgtatcatatgccaagtacgccccctattgacgtcaatgacggtaaatggcccgcctggcattatgcccagtacatgaccttacgggactttcctacttggcagtacatc<br>tacgtattagtcatcgctattaccatggtgatgcggttttggcagtacaccaatgggcgtggatagcggtttgactcacggggatttccaagtctccaccccattgacgtcaatgggagtttgttttggca<br>ccaaaatcaacgggactttccaaaatgtcgtaacaactccgccccattgacgcaaatgggcggtaggcgtgtacggtgggaggtctata!aagcagagctcgtttagtgaaccg!cagatcgcctg<br>gagacgccatccacgctgttttgacctccatagaagacaccgactctagctagaggatcccgggctcgagatgctgagaataatcaatgctaggaaggagaagaagagacgaggcgcagataca<br>agtgtcggaattgttggcctcctgctgaccacagctatggcagcggaggtcactagacgtgggagtgcatactatatgtacttggacagaaacgatgctggggaggccatatcttttccaaccacatt<br>ggggatgaataagtgttatatacagatcatggatcttggacacacgtgtgatgccaccatgagctatgaatgccctatgctggatgagggggtggaaccagatgacgtcgattgttggtgcaacacg<br>acgtcaacttgggttgtgtacggaacctgccatcacaaaaaaggtgaagcacggagatctagaagagctgtgacgctcccctcccattccactaggaagctgcaaacgcggtcgcaaacctggtt<br>ggaatcaagagaatacacaaagcacttgattagagtcgaaaattggatattcaggaaccctggcttcgcgttagcagcagctgccatcgcttggcttttgggaagctcaacgagccaaaaagtcatat<br>acttggtcatgatactgctgattgccccggcatacagcatcaggtgcataggagtcagcaatagggactttgtggaaggtatgtcaggtgggacttgggttgatgttgtcttggaacatggaggttgtg |

TABLE 2-continued

| lists the sequences of the present invention: | |
| --- | --- |
| | tcactgtaatggcacaggacaaaccgactgtcgacatagagctggttacaacaacagtcagcaacatggcggaggtaagatcctactgctatgaggcatcaatatcagacatggcttcggacagcc<br>gctgcccaacacaaggtgaagcctaccttgacaagcaatcagacactcaatatgtctgcaaaagaacgttagtggacagaggctggggaaatggatgtggactttttggcaaagggagcctggtg<br>acatgcgctaagtttgcatgctccaagaaaatgaccgggaagagcatccagccagagaatctggagtaccggataatgctgtcagttcatggctcccagcacagtgggatgatcgttaatgacaca<br>ggacatgaaactgatgagaatagagcgaaagttgagataacgcccaattcaccaagagccgaagccaccctggggggggtttggaagcctaggacttgattgtgaaccgaggacaggccttgact<br>tttcagatttgtattacttgactatgaataacaagcactggctggttcacaaggagtggttccacgacattccattaccttggcacgctggggcagacaccggaactccacactggaacaacaaagaa<br>gcactggtagagttcaaggacgcacatgccaaaaggcaaactgtcgtggttctagggagtcaagaaggagcagttcacacggcccttgctggagctctggaggctgagatggatggtgcaaagg<br>gaaggctgtcctctggccacttgaaatgtcgcctgaaaatggataaacttagattgaagggcgtgtcatactccttgtgtactgcagcgttcacattcaccaagatcccggctgaaacactgcacggg<br>acagtcacagtggaggtacagtacgcagggacagatggaccttgcaaggttccagctcagatggcggtggacatgcaaactctgaccccagttgggaggttgataaccgctaaccccgtaatcac<br>tgaaagcactgagaactctaagatgatgctggaacttgatccaccatttggggactcttacattgtcataggagtcggggagaagaagatcacccaccactggcacaggagtggcagcaccattgg<br>aaaagcatttgaagccactgtgagaggtgccaagagaatggcagtcttgggagacacagcctgggactttggatcagttggaggcgctctcaactcattgggcaaggcatccatcaaatctttgg<br>agcagctttcaaatcattgtttggaggaatgtcctggttctcacaaattctcattggaacgttgctgatgtggttgggtctgaacgcaaagaatggatctatttcccttatgtgcttggccttagggggagt<br>gttgatcttcttatccacagccgtctctgctgagaacatcacatcaggattcctaggacccctgctcgtgttacaggcggggtttttcttgttgacaagaatcctcacaataccgcagagtctagactcgt<br>ggtggacttctctcaattttctagggggatotcccgtgtgtcttggccaaaattcgcagtccccaacctccaatcactcaccaacctcctgtcctccaatttgtcctggttatcgctggatgtgtctgcggc<br>gttttatcatattcctcttcatcctgctgctatgcctcatcttcttattggttcttctggattatcaaggtatgttgcccgtttgtcctctaattccaggatcaacaacaaccagtacgggaccatgcaaaac<br>ctgcacgactcctgctcaaggcaactctatgtttccctcatgttgctgtacaaaacctacggatggaaattgcacctgtattcccatcccatcgtcctgggctttcgcaaaatacctatgggagtgggcctca<br>gtccgtttctcttggctcagtttactagtgccatttgttcagtggttcgtagggctttcccccactgtttggctttcagctatatggatgatgtggtattgggggccaagtctgtacagcatcgtgagtccctt<br>tataccgctgttaccaattttcttttgtctctgggtatacatttaactcgagcccgggatccggactagtaactcgaggcccctctccctcccccccccctaacgttactggccgaagccgcttggaataa<br>ggccggtgtgcgtttgtctatatgttattttccaccatattgccgtcttttggcaatgtgagggcccggaaacctggccctgtcttcttgacgagcattcctaggggtctttcccctctcgccaaaggaatg<br>caaggtctgttgaatgtcgtgaaggaagcagttcctctggaagcttcttgaagacaaacaacgtctgtagcgaccctttgcaggcagcggaaccccccacctggcgacaggtgcctctgcggccaa<br>aagccacgtgtataagatacacctgcaaaggcggcacaaccccagtgccacgttgtgagttggatagttgtggaaagagtcaaatggctctcctcaagcgtattcaacaaggggctgaaggatgcc<br>cagaaggtaccccattgtatgggatctgatctggggcctcggtacacatgctttacatgtgtttagtcgaggttaaaaaaacgtctaggccccccgaaccacggggacgtggttttcctttgaaaaaca<br>cgatgataatatggccacaaccttggatgaccgagtacaagcccacggtgcgcctcgccacccgcgacgacgtcccccgggccgtacgcaccctcgccgccgcgttcgccgactaccccgcca<br>cgcgccacaccgtcgacccggaccgccacatcgagcgggtcaccgagctgcaagaactcttcctcacgcgcgtcgggctcgacatcggcaaggtgtgggtcgcggacgacggcgccgcggt<br>ggcggtctggaccacgccggagagcgtcgaagcgggggcggtgttcgccgagatcggcccgcgcatggccgagttgagcggttcccggctggccgcgcagcaacagatggaaggcctcct<br>ggcgccgcaccggcccaaggagcccgcgtggttcctggccaccgtcggcgtctcgcccgaccaccagggcaagggtctgggcagcgccgtcgtgctccccggagtggaggcggccgagcg<br>cgccggggtgcccgccttcctggagacctccgcgccccgcaacctcccctttctacgagcggctcggcttcaccgtcaccgccgacgtcgaggtgcccgaaggaccgcgcacctggtgcatgac<br>ccgcaagcccggtgcctgataaggtacctttaagaccaatgacttacaaggcagctgtagatcttagccactttttaaaagaaaaggggggactggaagggctaattcactcccaacgaagacaag<br>atctttttgcttgtactgggtctctctggttagaccagatctgagcctgggagctctctggctaactagggaacccactgcttaagcctcaataaagcttgccttgagtgcttcaagtagtgtgtgcccgtc<br>tgttgtgtgactctggtaactagagatccctcagacccttttagtcagtgtggaaaatctctaga |
| SEQ ID NO: 57 | ttaattccgtgtattctatagtgtcacctaaatcgtatgtgtatgatacataaggttatgtattaattgtagccgcgttctaacgacaatatgtacaagcctaattgtgtagcatctggcttactgaagcagac<br>cctatcatctctctcgtaaactgccgtcagagtcggtttggttggacgaaccttctgagtttctggtaacgccgtcccgcacccggaaatggtcagcgaaccaatcagcagggtcatcgctagccagat<br>cctctacgccggacgcatcgtggccggcatcaccggcgccacaggtgcggttgctggcgcctatatcgccgacatcaccgatggggaagatcgggctcgccacttcgggctcatgagcgcttgtt<br>tcggcgtgggtatggtggcaggccccgtggccgggggactgttgggcgccatctccttgcatgcaccattccttgcggcggcggtgctcaacggcctcaacctactactgggctgcttcctaatgc<br>aggagtcgcataagggagagcgtcgaatggtgcactctcagtacaatctgctctgatgccgcatagttaagccagccccgacacccgccaacacccgctgacgcgccctgacgggcttgtctgct<br>cccggcatccgcttacagacaagctgtgaccgtctccgggagctgcatgtgtcagaggttttcaccgtcatcaccgaaacgcgcgagacgaaagggcctcgtgatacgcctatttttataggttaatg<br>tcatgataataatggtttcttagacgtcaggtggcacttttcggggaaatgtgcgcggaacccctatttgtttatttttctaaatacattcaaatatgtatccgctcatgagacaataaccctgataaatgctt<br>caataatattgaaaaaggaagagtatgagtattcaacatttccgtgtcgcccttattcccttttttgcggcattttgccttcctgtttttgctcacccagaaacgctggtgaaagtaaaagatgctgaagatca<br>gttgggtgcacgagtgggttacatcgaactggatctcaacagcggtaagatccttgagagttttcgccccgaagaacgttttccaatgatgagcacttttaaagttctgctatgtggcgcggtattatcc<br>cgtattgacgccgggcaagagcaactcggtcgccgcatacactattctcagaatgacttggttgagtactcaccagtcacagaaaagcatcttacggatggcatgacagtaagagaattatgcagtg<br>ctgccataaccatgagtgataacactgcggccaacttacttctgacaacgatcggaggaccgaaggagctaaccgcttttttgcacaacatgggggatcatgtaactcgccttgatcgttgggaacc<br>ggagctgaatgaagccataccaaacgacgagcgtgacaccacgatgcctstagcaatggcaacaacgttgcgcaaactattaactggcgaactacttactctagcttcccggcaacaattaataga<br>ctggatggaggcggataaagttgcaggaccacttctgcgctcggcccttccggctggctggtttattgctgataaatctggagccggtgagcgtgggtctcgcggtatcattgcagcactggggcca<br>gatggtaagccctcccgtatcgtagttatctacacgacggggagtcaggcaactatggatgaacgaaatagacagatcgctgagataggtgcctcactgattaagcattggtaactgtcagaccaag<br>tttactcatatatactttagattgatttaaaacttcatttttaatttaaaaggatctaggtgaagatcctttttgataatctcatgaccaaaatcccttaacgtgagttttcgttccactgagcgtcagacccc<br>gtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggt<br>aactggcttcagcagagcgcagataccaaatactgtccttctagtgtagccgtagttaggccaccacttcaagaactctgtagcaccgcctacatacctcgctctgctaatcctgttaccagtggctgct<br>gccagtggcgataagtcgtgtcttaccgggttggactcaagacgatagttaccggataaggcgcagcggtcgggctgaacggggggttcgtgcacacagcccagcttggagcgaacgacctac<br>accgaactgagatacctacagcgtgagcattgagaaagcgccacgcttcccgaagggagaaaggcggacaggtatccggtaagcggcagggtcggaacaggagagcgcacgagggagctt<br>ccagggggaaacgcctggtatctttatagtcctgtcgggtttcgccacctctgacttgagcgtcgatttttgtgatgctcgtcaggggggcggagcctatggaaaaacgccagcaacgcggcctttttt<br>acggttcctggccttttgctggccttttgctcacatgttctttcctgcgttatcccctgattctgtggataaccgtattaccgcctttgagtgagctgataccgctcgccgcagccgaacgaccgagcgca |

TABLE 2-continued lists the sequences of the present invention:

gcgagtcagtgagcgaggaagcggaagagcgcccaatacgcaaaccgcctctccccgcgcgttggccgattcattaatgcagctgtggaatgtgtgtcagttagggtgtggaaagtccccaggc
tccccagcaggcagaagtatgcaaagcatgcatctcaattagtcagcaaccaggtgtggaaagtccccaggctccccagcaggcagaagtatgcaaagcatgcatctcaattagtcagcaaccat
agtcccgcccctaactccgcccatcccgcccctaactccgcccagttccgcccattctccgccccatggctgactaattttttttatttatgcagaggccgaggccgcctcggcctctgagctattccag
aagtagtgaggaggcttttttggaggcctaggcttttgcaaaaagcttggacacaagacaggcttgcgagatatgtttgagaataccactttatcccgcgtcagggagaggcagtgcgtaaaaagac
gcggactcatgtgaaatactggttttagtgcgccagatctctataatctcgcgcaacctattttcccctcgaacacttttaagccgtagataaacaggctgggacacttcacatgagcgaaaaatacat
cgtcacctgggacatgttgcagatccatgcacgtaaactcgcaagccgactgatgccttctgaacaatggaaaggcattattgccgtaagccgtggcggtctgtaccgggtgcgttactggcgcgtg
aactgggtattcgtcatgtcgataccgtttgtatttccagctacgatcacgacaaccagcgcgagcttaaagtgctgaaacgcgcagaaggcgatggcgaaggcttcatcgttattgatgacctggtg
gataccggtggtactgcggttgcgattcgtgaaatgtatccaaaagcgcactttgtcaccatcttcgcaaaaccggctggtcgtccgctggttgatgactatgttgttgatatcccgcaagatacctgga
ttgaacagccgtgggatatgggcgtcgtattcgtcccgccaatctccggtcgctaatcttttcaacgcctggcactgccgggcgttgttctttttaacttcaggcgggttacaatagtttccagtaagt
attctggaggctgcatccatgacacaggcaaacctgagcgaaaccctgttcaaaccccgctttaaacatcctgaaacctcgacgctagtccgccgctttaatcacggcgcacaaccgcctgtgcagt
cggcccttgatggtaaaaccatccctcactggtatcgcatgattaaccgtctgatgtggatctggcgcggcattgacccacgcgaaatcctcgacgtccaggcacgtattgtgatgagcgatgccga
acgtaccgacgatgatttatacgatacggtgattggctaccgtggcggcaactggatttatgagtgggccccggatctttgtgaaggaaccttacttctgtggtgtgacataattggacaaactacctac
agagatttaaagctctaaggtaaatataaaatttttaagtgtataatgtgttaaactactgattctaattgtttgtgtattttagattccaacctatggaactgatgaatgggagcagtggtggaatgccttta
atgaggaaaacctgtttgctcagaagaaatgccatctagtgatgatgaggctactgctgactctcaacattctactcctccaaaaaagaagagaaaggtagaagaccccaaggactttccttcagaatt
gctaagtttttgagtcatgctgtgtttagtaatagaactcttgcttgctttgctatttacaccacaaaggaaaaagctgcactgctatacaagaaaattatggaaaaatattctgtaacctttataagtaggc
ataacagttataatcataacatactgtttttttcttactccacacaggcatagagtgtctgctattaataactatgctcaaaaattgtgtacctttagctttttaatttgtaaaggggttaataaggaatatttg
atgtatagtgccttgactagagatcataatcagccataccacatttgtagaggttttacttgctttaaaaaacctcccacacctccccctgaacctgaaacataaaatgaatgcaattgttgttgttaacttgt
ttattgcagcttataatggttacaaataaagcaatagcatcacaaatttcacaaataaagcatttttttcactgcattctagttgtggtttgtccaaactcatcaatgtatcttatcatgtctggatcaactgg
ataactcaagctaaccaaaatcatcccaaacttcccaccccataccctattaccactgccaattacctagtggtttcatttactctaaacctgtgattcctctgaattattttcattttaaagaaattgtattt
gttaaatatgtactacaaacttagtagttggaagggctaattcactcccaaagaagacaagatatccttgatctgtggatctaccacacacaaggctacttccctgattagcagaactacacaccagggccagg
ggtcagatatccactgacctttggatggtgctacaagctagtaccagttgagccagataaggtagaagaggccaataaaggagagaacaccagcttgttacaccctgtgagcctgcatgggatgga
tgacccggagagagaagtgttagagtggaggtttgacagccgcctagcatttcatcacgtggcccgagagctgcatccggagtacttcaagaactgctgatatcgagcttgctacaagggactttcc
gctggggactttccagggaggcgtggcctgggcgggactggggagtggcgagccctcagatcctgcatataagcagctgctttttgcctgtactgggtctctctggttagaccag
atctgagcctgggagctctctggctaactagggaacccactgcttaagcctcaataaagcttgccttgagtgcttcaagtagtgtgtgcccgtctgttgtgtgactctggtaactagagatccctcagac
ccttttagtcagtgtggaaaatctctagcagtggcgcccgaacagggacttgaaagcgaaagggaaaccagaggagctctctcgacgcaggactcggcttgctgaagcgcgcacggcaagagg
cgaggggcggcgactggtgagtacgccaaaaattttgactagcggaggctagaaggagagagatgggtgcgagagcgtcagtattaagcgggggagaattagatcgcgatgggaaaaaattc
ggttaaggccagggggaaagaaaaaatataaattaaaacatatagtatgggcaagcagggagctagaacgattcgcagttaatcctggcctgttagaaacatcagaaggctgtagacaaatactgg
gacagctacaaccatcccttcagacaggatcagaagaacttagatcattatataatacagtagcaaccctctattgtgtgcatcaaaggatagagataaaagacaccaaggaagctttagacaagata
gaggaagagcaaaacaaaagtaagaccaccgcacagcaagcggccgctgatcttcagacctggaggaggagatatgagggacaattggagaagtgaattatataaatataaagtagtaaaaatt
gaaccattaggagtagcacccaccaaggcaaagagaagagtggtgcagagagaaaaaagagcagtgggaataggagctttgttccttgggttcttgggagcagcaggaagcactatgggcgca
gcgtcaatgacgctgacggtacaggccagacaattattgtctggtatagtgcagcagcagaacaatttgctgagggctattgaggcgcaacagcatctgttgcaactcacagtctggggcatcaagc
agctccaggcaagaatcctggctgtggaaagatacctaaaggatcaacagctcctggggatttggggttgctctggaaaactcatttgcaccactgctgtgccttggaatgctagttggagtaataaat
ctctggaacagatttggaatcacacgacctggatggagtgggacagagaaattaacaattacacaagcttaatacactccttaattgaagaatcgcaaaaccagcaagaaaagaatgaacaagaatt
attggaattagataaatgggcaagtttgtggaattggtttaacataacaaattggctgtggtatataaaattattcataatgatagtaggaggcttggtaggtttaagaatagtttttgctgtactttctatag
tgaatagagttaggcagggatattcaccattatcgtttcagacccacctcccaaccccgaggggacccgacaggcccgaaggaatagaagaagaaggtggagagagagacagagacagatccatt
cgattagtgaacggatctcgacggtatcgccgaattcacaaatggcagtattcatccacaattttaaaagaaaaggggggattggggggtacagtgcaggggaaagaatagtagacataatagcaa
cagacatacaaactaaagaattacaaaaacaaattacaaaaattcaaaatt!tcgggtttattacagggacagcagagatccactttatcgataagcttgggagttccgcgttacataacttacggtaaat
ggcccgcctggctgaccgcccaacgacccccgcccattgacgtcaataatgacgtatgttcccatagtaacgccaatagggactttccattgacgtcaatgggtggagtatttacggtaaactgccc
acttggcagtacatcaagtgtatcatatgccaagtacgccccctattgacgtcaatgacggtaaatggcccgcctggcattatgcccagtacatgaccttacgggactttcctacttggcagtacatc
tacgtattagtcatcgctattaccatggtgatgcggttttggcagtacaccaatgggcgtggatagcggtttgactcacggggatttccaagtctccaccccattgacgtcaatgggagtttgttttggca
ccaaaatcaacgggactttccaaaatgtcgtaacaactccgccccattgacgcaaatgggcggtaggcgtgtacggtgggaggtctatataagcagagctcgtttagtgaaccgtcagatcgcctg
gagacgccatccacgctgttttgacctccatagaagacaccgactctagctagaggatcccgggctcgagatgctgagaataatcaatgctaggaaggagaagaagagacgaggcgcagataca
agtgtcggaattgttggcctcctgctgaccacagctatggcagcggaggtcactagacgtgggagtgcatactatatgtacttggacagaaacgatgctggggaggccatatcttttccaaccacatt
ggggatgaataagtgttatatacagatcatggatcttggacacacgtgtgatgccaccatgagctatgaatgccctatgctggatgagggggtggaaccagatgacgtcgattgttggtgcaacacg
acgtcaacttgggttgtgtacggaacctgccatcacaaaaaaggtgaagcacggagatctagaagagctgtgacgctcccctcccattccactaggaagctgcaaacgcggtcgcaaacctggtt
ggaatcaagagaatacacaaagcacttgattagagtcgaaaattggatattcaggaaccctggcttcgcgttagcagcagctgccatcgcttggcttttgggaagctcaacgagccaaaaagtcatat
acttggtcatgatactgctgattgccccggcatacagcatcaggtgcataggagtcagcaatagggactttgtggaaggtatgtcaggtgggacttgggttgatgttgtcttggaacatggaggttgtg
tcactgtaatggcacaggacaaaccgactgtcgacatagagctggttacaacaacagtcagcaacatggcggaggtaagatcctactgctatgaggcatcaatatcagacatggcttcggacagcc
gctgcccaacacaaggtgaagcctaccttgacaagcaatcagacactcaatatgtctgcaaaagaacgttagtggacagaggctggggaaatggatgtggactttctggcaaagggagcctggtg
acatgcgctaagtttgcatgctccaagaaaatgaccgggaagagcatccagccagagaatctggagtaccggataatgctgtcagttcatggctcccagcacagtgggatgatcgttaatgacaca
ggacatgaaactgatgagaatagagcgaaagttgagataacgcccaattcaccaagagccgaagccaccctggggggggtttggaagcctaggacttgattgtgaaccgaggacaggccttgact TABLE 2-continued

| | lists the sequences of the present invention: |
|---|---|
| | tttcagatttgtattacttgactatgaataacaagcactggctggttcacaaggagtggttccacgacattccattaccttggcacgctggggcagacaccggaactccacactagaacaacaaagaa<br>gcactggtagagttcaaggacgcacatgccaaaaggcaaactgtcgtggttctagggagtcaagaaggagcagttcacacggcccttgctggagctctggaggctgagatggatggtgcaaagg<br>gaaggctgtcctctggccacttgaaatgtcgcctgaaaatggataaacttagattgaagggcgtgtcatactccttgtgtactgcagcgttcacattcaccaagatcccggctgaaacactgcacggg<br>acagtcacagtggaggtacagtacgcagggacagatggaccttgcaaggttccagctcagatggcggtggacatgcaaactctgaccccagttgggaggttgataaccgctaaccccgtaatcac<br>tgaaagcactgagaactctaagatgatgctggaacttgatccaccatttggggactcttacattgtcataggagtcggggagaagaagatcacccaccactggcacaggagtggcagcaccattgg<br>aaaagcatttgaagccactgtgagaggtgccaagagaatggcagtcttgggagacacagcctgggactttggatcagttggaggcgctctcaactcattgggcaagggcatccatcaaatctttgg<br>agcagctttcaaatcattgtttggaggaatgtcctggttctcacaaattctcattggaacgttgctgatgtggttgggtctgaacgcaaagaatggatctagaatcctcacaataccgcagagtctagact<br>cgtggtggacttctctcaattttctaggggatctcccgtgtgtcttggccaaaattcgcagtccccaacctccaatcactcaccaacctcctgtcctccaatttgtcctggttatcgctggatgtgtctgc<br>ggcgttttatcatattcctcttcatcctgctgctatgcctcatcttcttattggttcttctggattatcaaggtatgttgcccgtttgtcctctaattccaggatcaacaacaaccagtacgggaccatgcaaa<br>acctgcacgactcctgctcaaggcaactctatgtttccctcatattgctgtacaaaacctacggatggaaattgcacctgtattcccatcccatcgtcctgggctttcgcaaaatacctatgggagtgggc<br>ctcagtccgtttctcttggctcagtttactagtgccatttgttcagtggttcgtagggctttcccccactgtttggctttcagctatatggatgatgtggtattgggggccaagtctgtacagcatcgtgagtc<br>cctttataccgctgttaccaattttcttttgtctctgggtatacatttaactcgagcccgggatccggactagtaactcgaggcccctctccctcccccccccctaacgttactggccgaagccgcttgga<br>ataaggccggtgtgcgtttgtctatatgttattttccaccatattgccgtcttttggcaatgtgagggcccggaaacctggccctgtcttcttgacgagcattcctaggggtctttcccctctcgccaaagg<br>aatgcaaggtctgttgaatgtcgtgaaggaagcagttcctctggaagcttcttgaagacaaacaacgtctgtagcgaccctttgcaggcagcggaaccccccacctggcgacaggtgcctctgcgg<br>ccaaaagccacgtgtataagatacacctgcaaaggcggcacaaccccagtgccacgttgtgagttggatagttgtggaaagagtcaaatggctctcctcaagcgtattcaacaaggggctgaagg<br>atgcccagaaggtaccccattgtatgggatctgatctggggcctcggtacacatgctttacatgtgtttagtcgaggttaaaaaaacgtctaggccccccgaaccacggggacgtggttttcctttgaa<br>aaacacgatgataatatggccacaaccttggatgaccgagtacaagcccacggtgcgcctcgccacccgcgacgacgtcccccgggccgtacgcaccctcgccgccgcgttcgccgactaccc<br>cgccacgcgaacaccgtcgacccggaccgccacatcgagcgggtcaccgagctgcaagaactcttcctcacgcgcgtcgggctcgacatcggcaaggtgtgggtcgcggacgacggcgcc<br>gcggtggcggtctggaccacgccggagagcgtcgaagcgggggcggtgttcgccgagatcggcccgcgcatggccgagttgagcggttcccggctggccgcgcagcaacagatggaaggc<br>ctcctggcgccgcaccggcccaaggagcccgcgtggttcctggccaccgtcggcgtctcgcccgaccaccagggcaagggtctgggcagcgccgtcgtgctccccggagtggaggcggccg<br>agcgcgccggggtgcccgccttcctggagacctccgcgccccgcaacctccccttctacgagcggctcggcttcaccgtcaccgccgacgtcgaggtgcccgaaggaccgcgcacctggtgc<br>atgacccgcaagcccggtgcctgataaggtacctttaagaccaatgacttacaaggcagctgtagatcttagccactttttaaaagaaaaggggggactggaagggctaattcactcccaacgaag<br>acaagatctttttgcttgtactgggtctctctggttagaccagatctgagcctgggagctctctggctaactagggaacccactgcttaagcctcaataaagcttgccttgagtgcttcaagtagtgtgtg<br>cccgtctgttgtgtgactctggtaactagagatccctcagacccttttagtcagtgtggaaaatctctaga |
| SEQ ID NO: 58 | ttaattccgtgtattctatagtgtcacctaaatcgtatgtgtatgatacataaggttatgtattaattgtagccgcgttctaacgacaatatgtacaagcctaattgtgtagcatctggcttactgaagcagac<br>cctatcatctctctcgtaaactgccgtcagagtcggtttggttggacgaaccttctgagtttctggtaacgccgtcccgcacccggaaatggtcagcgaaccaatcagcagggtcatcgctagccagat<br>cctctacgccggacgcatcgtggccggcatcaccggcgccacaggtgcggttgctggcgcctatatcgccgacatcaccgatggggaagatcgggctcgccacttcgggctcatgagcgcttgtt<br>tcggcgtgggtatggtggcaggccccgtggccgggggactgttgggcgccatctccttgcatgcaccattccttgcggcggcggtgctcaacggcctcaacctactactgggctgcttcctaatgc<br>aggagtcgcataagggagagcgtcgaatggtgcactctcagtacaatctgctctgatgccgcatagttaagccagccccgacacccgccaacacccgctgacgcgccctgacgggcttgtctgct<br>cccggcatccgcttacagacaagctgtgaccgtctccgggagctgcatgtgtcagaggttttcaccgtcatcaccgaaacgcgcgagacgaaagggcctcgtgatacgcctatttttataggttaatg<br>tcatgataataatggtttcttagacgtcaggtggcacttttcggggaaatgtgcgcggaacccctatttgtttatttttctaaatacattcaaatatgtatccgctcatgagacaataaccctgataaatgctt<br>caataatattgaaaaaggaagagtatgagtattcaacatttccgtgtcgcccttattcccttttttgcggcattttgccttcctgtttttgctcacccagaaacgctggtgaaagtaaaagatgctgaagatca<br>gttgggtgcacgagtgggttacatcgaactggatctcaacagcggtaagatccttgagagttttcgccccgaagaacgttttccaatgatgagcacttttaaagttctgctatgtggcgcggtattatcc<br>cgtattgacgccgggcaagagcaactcggtcgccgcatacactattctcagaatgacttggttgagtactcaccagtcacagaaaagcatcttacggatggcatgacagtaagagaattatgcagtg<br>ctgccataaccatgagtgataacactgcggccaacttacttctgacaacgatcggaggaccgaaggagctaaccgcttttttgcacaacatgggggatcatgtaactcgccttgatcgttgggaacc<br>ggagctgaatgaagccataccaaacgacgagcgtgacaccacgatgcctgtagcaatggcaacaacgttgcgcaaactattaactggcgaactacttactctagcttcccggcaacaattaataga<br>ctggatggaggcggataaagttgcaggaccacttctgcgctcggcccttccggctggctggtttattgctgataaatctggagccggtgagcgtgggtctcgcggtatcattgcagcactggggcca<br>gatggtaagccctcccgtatcgtagttatctacacgacggggagtcaggcaactatggatgaacgaaatagacagatcgctgagataggtgcctcactgattaagcattggtaactgtcagaccaag<br>tttactcatatatactttagattgatttaaaacttcatttttaatttaaaaggatctaggtgaagatcctttttgataatctcatgaccaaaatcccttaacgtgagttttcgttccactgagcgtcagaccc<br>cgtagaaaagatcaaaggatcttcttgagatcctttttttctgcgcgtaatctgctgcttgcaaacaaaaaaaccaccgctaccagcggtggtttgtttgccggatcaagagctaccaactctttttccgaagg<br>taactggcttcagcagagcgcagataccaaatactgtccttctagtgtagccgtagttaggccaccacttcaagaactctgtagcaccgcctacatacctcgctctgctaatcctgttaccagtggctgct<br>gccagtggcgataagtcgtgtcttaccgggttggactcaagacgatagttaccggataaggcgcagcggtcgggctgaacggggggttcgtgcacacagcccagcttggagcgaacgacctac<br>accgaactgagatacctacagcgtgagcattgagaaagcgccacgcttcccgaagggagaaaggcggacaggtatccggtaagcggcagggtcggaacaggagagcgcacgagggagctt<br>ccagggggaaacgcctggtatctttatagtcctgtcgggtttcgccacctctgacttgagcgtcgatttttgtgatgctcgtcaggggggcggagcctatggaaaaacgccagcaacgcggcctttt<br>acggttcctggccttttgctggccttttgctcacatgttctttcctgcgttatcccctgattctgtggataaccgtattaccgcctttgagtgagctgataccgctcgccgcagccgaacgaccgagcgca<br>gcgagtcagtgagcgaggaagcggaagagcgcccaatacgcaaaccgcctctccccgcgcgttggccgattcattaatgcagctgtggaatgtgtgtcagttagggtgtggaaagtccccaggc<br>tccccagcaggcagaagtatgcaaagcatgcatctcaattagtcagcaaccaggtgtggaaagtccccaggctccccagcaggcagaagtatgcaaagcatgcatctcaattagtcagcaaccat<br>agtcccgcccctaactccgcccatcccgcccctaactccgcccagttccgcccattctccgccccatggctgactaattttttttatttatgcagaggccgaggccgcctcggcctctgagctattccag<br>aagtagtgaggaggcttttttggaggcctaggcttttgcaaaaagcttggacacaagacaggcttgcgagatatgtttgagaataccactttatcccgcgtcagggagaggcagtgcgtaaaaagac<br>gcggactcatgtgaaatactggttttagtgcgccagatctctataatctcgcgcaacctattttcccctcgaacactttttaagccgtagataaacaggctgggacacttcacatgagcgaaaaatacat |

TABLE 2-continued

| lists the sequences of the present invention: |
|---|
| cgtcacctgggacatgttgcagatccatgcacgtaaactcgcaagccgactgatgccttctgaacaatggaaaggcattattgccgtaagccgtggcggtctgtaccgggtgcgttactggcgcgtg<br>aactgggtattcgtcatgtcgataccgtttgtatttccagctacgatcacgacaaccagcgcgagcttaaagtgctgaaacgcgcagaaggcgatggcgaaggcttcatcgttattgatgacctggtg<br>gataccggtggtactgcggttgcgattcgtgaaatgtatccaaaagcgcactttgtcaccatcttcgcaaaaccggctggtcgtccgctggttgatgactatgttgttgatatcccgcaagatacctgga<br>ttgaacagccgtgggatatgggcgtcgtattcgtcccgccaatctccggtcgctaatcttttcaacgcctggcactgccgggcgttgttctttttaacttcaggcgggttacaatagtttccagtaagt<br>attctggaggctgcatccatgacacaggcaaacctgagcgaaaccctgttcaaaccccgctttaaacatcctgaaacctcgacgctagtccgccgctttaatcacggcgcacaaccgcctgtgcagt<br>cggcccttgatggtaaaaccatccctcactggtatcgcatgattaaccgtctgatgtggatctggcgcggcattgacccacgcgaaatcctcgacgtccaggcacgtattgtgatgagcgatgccga<br>acgtaccgacgatgatttatacgatacggtgattggctaccgtggcggcaactggatttatgagtgggccccggatctttgtgaaggaaccttacttctgtggtgtgacataattggacaaactacctac<br>agagatttaaagctctaaggtaaatataaaatttttaagtgtataatgtgttaaactactgattctaattgtttgtgtattttagattccaacctatggaactgatgaatgggagcagtggtggaatgcctttta<br>atgaggaaaacctgttttgctcagaagaaatgccatctagtgatgatgaggctactgctgactctcaacattctactcctccaaaaaagaagagaaaggtagaagaccccaaggactttccttcagaatt<br>gctaagtttttgagtcatgctgtgtttagtaatagaactcttgcttgctttgctatttacaccacaaaggaaaaagctgcactgctatacaagaaaattatggaaaaatattctgtaacctttataagtaggc<br>ataacagttataatcataacatactgtttttttcttactccacacaggcatagagtgtctgctattaataactatgctcaaaaattgtgtacctttagctttttaatttgtaaaggggttaataaggaatatttg<br>atgtatagtgccttgactagagatcataatcagccataccacatttgtagaggttttacttgctttaaaaaacctcccacacctccccctgaacctgaaacataaaatgaatgcaattgttgttgttaacttgt<br>ttattgcagcttataatggttacaaataaagcaatagcatcacaaatttcacaaataaagcatttttttcactgcattctagttgtggtttgtccaaactcatcaatgtatcttatcatgtctggatcaactgg<br>ataactcaagctaaccaaaatcatcccaaacttcccaccccataccctattaccactgccaattacctagtggtttcatttactctaaacctgtgattcctctgaattattttcattttaaagaaattgtattt<br>gttaaatatgtactacaaacttagtagttggaagggctaattcactcccaaagaagacaagatatccttgatctgtggatctaccacacacaaggctacttccctgattagcagaactacacaccagggccagg<br>ggtcagatatccactgacctttggatggtgctacaagctagtaccagttgagccagataaggtagaagaggccaataaaggagagaacaccagcttgttacaccctgtgagcctgcatgggatgga<br>tgacccggagagagaagtgttagagtggaggtttgacagccgcctagcatttcatcacgtggcccgagagctgcatccggagtacttcaagaactgctgatatcgagcttgctacaagggactttcc<br>gctggggactttccagggaggcgtggcctgggcgggactggggagtggcgagccctcagatcctgcatataagcagctgctttttgcctgtactgggtctctctggttagaccagatctgagcctg<br>ggagctctctggctaactagggaacccactgcttaagcctcaataaagcttgccttgagtgcttcaagtagtgtgtgcccgtctgttgtgtgactctggtaactagagatccctcagacccttttagtc<br>agtgtggaaaatctctagcagtggcgcccgaacagggacttgaaagcgaaagggaaaccagaggagctctctcgacgcaggactcggcttgctgaagcgcgcacggcaagaggcgaggggc<br>ggcgactggtgagtacgccaaaaattttgactagcggaggctagaaggagagagatgggtgcgagagcgtcagtattaagcgggggagaattagatcgcgatgggaaaaaattcggttaaggc<br>caggggggaaagaaaaaatataaattaaaacatatagtatgggcaagcagggagctagaacgattcgcagttaatcctggcctgttagaaacatcagaaggctgtagacaaatactgggacagctac<br>aaccatcccttcagacaggatcagaagaacttagatcattatataatacagtagcaaccctctattgtgtgcatcaaaggatagagataaaagacaccaaggaagctttagacaagatagaggaaga<br>gcaaaacaaaagtaagaccaccgcacagcaagcggccgctgatcttcagacctggaggaggagatatgagggacaattggagaagtgaattatataaatataaagtagtaaaaattgaaccatta<br>ggagtagcacccaccaaggcaaagagaagagtggtgcagagagaaaaaagagcagtgggaataggagctttgttccttgggttcttgggagcagcaggaagcactatgggcgcagcgtcaatg<br>acgctgacggtacaggccagacaattattgtctggtatagtgcagcagcagaacaatttgctgagggctattgaggcgcaacagcatctgttgcaactcacagtctggggcatcaagcagctccag<br>gcaagaatcctggctgtggaaagatacctaaaggatcaacagctcctggggatttggggttgctctggaaaactcatttgcaccactgctgtgccttggaatgctagttggagtaataaatctctggaa<br>cagatttggaatcacacgacctggatggagtgggacagagaaattaacaattacacaagcttaatacactccttaattgaagaatcgcaaaaccagcaagaaaagaatgaacaagaattattggaatt<br>agataaatgggcaagtttgtggaattggtttaacataacaaattggctgtggtatataaaattattcataatgatagtaggaggcttggtaggtttaagaatagtttttgctgtactttctatagtgaatag<br>agttaggcagggatattcaccattatcgtttcagacccacctcccaaccccgaggggacccgacaggcccgaaggaatagaagaagaaggtggagagagagacagagacagatccattcgatt<br>agtgaacggatctcgacggtatcgccgaattcacaaatggcagtattcatccacaattttaaaagaaaaggggggattggggggtacagtgcaggggaaagaatagtagacataatagcaacaga<br>catacaaactaaagaattacaaaaacaaattacaaaaattcaaaattttcgggtttattacagggacagcagagatccactttatcgataagcttgggagttccgcgttacataacttacggtaaatggcc<br>cgcctggctgaccgcccaacgacccccgcccattgacgtcaataatgacgtatgttcccatagtaacgccaatagggactttccattgacgtcaatgggtggagtatttacggtaaactgcccacttg<br>gcagtacatcaagtgtatcatatgccaagtacgccccctattgacgtcaatgacggtaaatggcccgcctggcattatgcccagtacatgaccttacgggactttcctacttggcagtacatctacgtat<br>tagtcatcgctattaccatggtgatgcggttttggcagtacaccaatgggcgtggatagcggtttgactcacggggatttccaagtctccaccccaKgacgtcaatgggagtttgttttggcaccaaaa<br>tcaacgggactttccaaaatgtcgtaacaactccgccccattgacgcaaatgggcggtaggcgtgtacggtgggaggtctatataagcagagctcgtttagtgaaccgtcagatcgcctggagacg<br>ccatccacgctgttttgacctccatagaagacaccgactctagctagaggatcccgggctcgagatgctgagaataatcaatgctaggaaggagaagaagagacgaggcgcagatacaagtgtc<br>ggaattgttggcctcctgctgaccacagctatggcagcggaggtcactagacgtgggagtgcatactatatgtacttggacagaaacgatgctggggaggccatatcttttccaaccacattgggga<br>tgaataagtgttatatacagatcatggatcttggacacacgtgtgatgccaccatgagctatgaatgccctatgctggatgaggggggtggaaccagatgacgtcgattgttggtgcaacacgacgtca<br>acttgggttgtgtacggaacctgccatcacaaaaaaaggtgaagcacggagatctagaagagctgtgacgctcccctcccattccactaggaagctgcaaacgcggtcgcaaacctggttggaatc<br>aagagaatacacaaagcacttgattagagtcgaaaattggatattcaggaaccctggcttcgcgttagcagcagctgccatcgcttggcttttgggaagctcaacgagccaaaaagtcatatacttgg<br>tcatgatactgctgattgccccggcatacagcatcaggtgcataggagtcagcaatagggactttgtggaaggtatgtcaggtgggacttgggttgatgttgtcttggaacatggaggttgtgtcactg<br>taatggcacaggacaaaccgactgtcgacatagagctggttacaacaacagtcagcaacatggcggaggtaagatcctactgctatgaggcatcaatatcagacatggcttcggacagccgctgc<br>ccaacacaaggtgaagcctaccttgacaagcaatcagacactcaatatgtctgcaaaagaacgttagtggacagaggctggggaaatggatgtggactttttggcaaagggagcctggtgacatg<br>cgctaagtttgcatgctccaagaaaatgaccgggaagagcatccagccagagaatctggagtaccggataatgctgtcagttcatggctcccagcacagtgggatgatcgttaatgacacaggaca<br>tgaaactgatgagaatagagcgaaagttgagataacgcccaattcaccaagagccgaagccaccctgggggggtttggaagcctaggacttgattgtgaaccgaggacaggccttgacttttcag<br>atttgtattacttgactatgaataacaagcactggctggttcacaaggagtggttccacgacattccattaccttggcacgctggggcagacaccggaactccacactggaacaacaaagaagcact<br>ggtagagttcaaggacgcacatgccaaaaggcaaactgtcgtggttctagggagtcaagaaggagcagttcacacggcccttgctggagctctggaggctgagatggatggtgcaaagggaag<br>gctgtcctctggccacttgaaatgtcgcctgaaaatggataaacttagattgaagggcgtgtcatactccttgtgtactgcagcgttcacattcaccaagatcccggctgaaacactgcacgggacagt<br>cacagtggaggtacagtacgcagggacagatggaccttgcaaggttccagctcagatggcggtggacatgcaaactctgaccccagttgggaggttgataaccgctaaccccgtaatcactgaaa<br>gcactgagaactctaagatgatgctggaacttgatccaccatttggggactcttacattgtcataggagtcggggagaagaagatcacccaccactggcacaggagtggcagcaccattggaaaag |

TABLE 2-continued

| | lists the sequences of the present invention: |
|---|---|
| | catttgaagccactgtgagaggtgccaagagaatggcagtcttgggagacacagcctgggactttggatcagttggaggcgctctcaactcattgggcaagggcatccatcaaatctttggagcag<br>ctttcaaatcattgtttggaggaatgtcctggttctcacaaattctcattggaacgttgctgatgtggttgggtctgaacgcaaagaatggatctatttcccttatgtgcttggccttagggggagtgttgatc<br>ttcttatccacagccgtctctgctcagtggaattccactgccttccaccaaactctgcaggatcccagagtcaggggtctgtatcttcctgctggtggctccagttcaggaacagtaaaccctgctccga<br>atattgcctctcacatctcgtcaatctccgcgaggactggggaccctgtgacgaacatggagaacatcacatcaggattcctaggacccctgctcgtgttacaggcggggtttttcttgttgacaagaa<br>tcctcacaataccgcagagtctagactcgtggtggacttctctcaattttctagggggatctcccgtgtgtcttggccaaaattcgcagtccccaacctccaatcactcaccaacctcctgtcctc<br>caatttgtcctggttatcgctggatgtgtctgcggcgttttatcatattcctcttcatcctgctgctatgcctcatcttcttattggttcttctggattatcaaggtatgttgcccgtttgtcctctaattcca<br>ggatcaacaacaaccagtacgggaccatgcaaaacctgcacgactcctgctcaaggcaactctatgtttccctcatgttgctgtacaaaacctacggatggaaattgcacctgtattcccatcccatcgtcctg<br>ggctttcgcaaaatacctatgggagtgggcctcagtccgtttctcttggctcagtttactagtgccatttgttcagtggttcgtagggctttcccccactgtttggctttcagctatatggatgatgtggtatt<br>gggggccaagtctgtacagcatcgtgagtccctttataccgctgttaccaattttcttttgtctctgggtatacatttaactcgagcccgggatccggactagtaactcgaggcccctctccctcccccc<br>ccctaacgttactggccgaagccgcttggaataaggccggtgtgcgtttgtctatatgttattttccaccatattgccgtcttttggcaatgtgagggcccggaaacctggccctgtcttcttgacgagca<br>ttcctaggggtctttcccctctcgccaaaggaatgcaaggtctgttgaatgtcgtgaaggaagcagttcctctggaagcttcttgaagacaaacaacgtctgtagcgaccctttgcaggcagcggaac<br>cccccacctggcgacaggtgcctctgcggccaaaagccacgtgtataagatacacctgcaaaggcggcacaaccccagtgccacgttgtgagttggatagttgtggaaagagtcaaatggctctc<br>ctcaagcgtattcaacaaggggctgaaggatgcccagaaggtaccccattgtatgggatctgatctggggcctcggtacacatgctttacatgtgtttagtcgaggttaaaaaaacgtctaggccccc<br>cgaaccacggggacgtggttttcctttgaaaaacacgatgataatatggccacaaccttggatgaccgagtacaagcccacggtgcgcctcgccacccgcgacgacgtcccccgggccgtacgc<br>accctcgccgccgcgttcgccgactaccccgccacgcgccacaccgtcgacccggaccgccacatcgagcgggtcaccgagctgcaagaactcttcctcacgcgcgtcgggctcgacatcgg<br>caaggtgtgggtcgcggacgacggcgccgcggtggcggtctggaccacgccggagagcgtcgaagcgggggcggtgttcgccgagatcggcccgcgcatggccgagttgagcggttcccg<br>gctggccgcgcagcaacagatggaaggcctcctggcgccgcaccggcccaaggagcccgcgtggttcctggccaccgtcggcgtctcgcccgaccaccagggcaagggtctgggcagcgc<br>cgtcgtgctccccggagtggaggcggccgagcgcgccggggtgcccgccttcctggagacctccgcgccccgcaacctccccttctacgagcggctcggcttcaccgtcaccgccgacgtcg<br>aggtgcccgaaggaccgcgcacctggtgcatgacccgcaagcccggtgcctgataaggtacctttaagaccaatgacttacaaggcagctgtagatcttagccactttttaaaagaaaagggggg<br>actggaagggctaattcactcccaacgaagacaagatctggtgcttgtactgggtctctctggttagaccagatctgagcctgggagctctctggctaactagggaacccactgcttaagcctcaataa<br>agcttgccttgagtgcttcaagtagtgtgtgcccgtctgttgtgtgactctggtaactagagatccctcagacccttttagtcagtgtggaaaatctctaga |
| SEQ ID NO: 59 | agttgttgatctgtgtgaatcagactgcgacagttcgagtttgaagcgaaagctagcaacagtatcaacaggttttattttggatttggaaacgagagtttctggtcatgaaaaacccaaaaaagaaatc<br>cggaggattccggattgtcaatatgctaaaacgcggagtagcccgtgtgagcccctttgggggcttgaagaggctgccagccggacttctgctgggtcatgggcccatcaggatggtcttggcgat<br>tctagcctttttgagattcacggcaatcaagccatcactgggtctcatcaatagatggggttcagtggggaaaaaagaggctatggaaataataaagaagttcaagaaagatctggctgccatgctga<br>gaataatcaatgctaggaaggagaagaagagacgaggcgcagatactagtgtcggaattgttggcctcctgctgaccacagctatggcagcggaggtcactagacgtgggagtgcatactatatg<br>tacttggacagaaacgacgctggggaggccatatcttttccaaccacattggggatgaataagtgttatatacagatcatggatcttggacacatgtgtgatgccaccatgagctatgaatgccctatg<br>ctggatgaggggggtggaaccagatgacgtcgattgttggtgcaacacgacgtcaacttgggttgtgtacggaacctgccatcacaaaaaaggtgaagcacggagatctagaagagctgtgacgct<br>cccctcccattccactaggaagctgcaaacgcggtcgcaaacctggttggaatcaagagaatacacaaagcacttgattagagtcgaaaattggatattcaggaaccctggcttcgcgttagcagca<br>gctgccatcgcttggcttttgggaagctcaacgagccaaaaagtcatatacttggtcatgatactgctgattgccccggcatacagcatcaggtgcataggagtcagcaatagggactttgtggaagg<br>tatgtcaggtgggacttgggttgatgttgtcttggaacatggaggttgtgtcaccgtaatggcacaggacaaaccgactgtcgacatagagctggttacaacaacagtcagcaacatggcggaggta<br>agatcctactgctatgaggcatcaatatcggacatggcttcggacagccgctgcccaacacaaggtgaagcctaccttgacaagcaatcagacactcaatatgtctgcaaaagaacgttagtggac<br>agaggctggggaaatggatgtggactttttggcaaagggagcctggtgacatgcgctaagtttgcatgctccaagaaaatgaccgggaagagcatccagccagagaatctggagtaccggataat<br>gctgtcagttcatggctcccagcacagtgggatgatcgttaatgacacaggacatgaaactgatgagaatagagcgaaggttgagataacgcccaattcaccaagagccgaagccaccctgggg<br>ggttttggaagcctaggacttgattgtgaaccgaggacaggccttgacttttcagatttgtattacttgactatgaataacaagcactggttggttcacaaggagtggttccacgacattccattaccttgg<br>cacgctggggcagacaccggaactccacactggaacaacaaagaagcactggtagagttcaaggacgcacatgccaaaaggcaaactgtcgtggttctagggagtcaagaaggagcagttcac<br>acggcccttgctggagctctggaggctgagatggatggtgcaaagggaaggctgtcctctggccacttgaaatgtcgcctgaaaatggataaacttagattgaagggcgtgtcatactccttgtgtac<br>cgcagcgttcacattcaccaagatcccggctgaaacactgcacgggacagtcacagtggaggtacagtacgcagggacagatggaccttgcaaggttccagctcagatggcggtggacatgca<br>aactctgaccccagttgggaggttgataaccgctaaccccgtaatcactgaaagcactgagaactctaagatgatgctggaacttgatccaccatttggggactcttacattgtcataggagtcgggg<br>agaagaagatcacccaccactggcacaggagtggcagcaccattggaaaagcatttgaagccactgtgagaggtgccaagagaatggcagtcttgggagacacagcctgggactttggatcagt<br>tggaggcgctctcaactcattgggcaagggcatccatcaaatttttggagcagctttcaaatcattgtttggaggaatgtcctggttctcacaaattctcattggaacgttgctgatgtggttgggtctgaa<br>cacaaagaatggatctatttcccttatgtgcttggccttaggggggagtgttgatcttcttatccacagctgtctctgctgatgtggggtgctcggtggacttctcaaagaaggagacgagatgcggtaca<br>ggggtgttcgtctataacgacgttgaagcctggagggacaggtacaagtaccatcctgactccccccgtagattggcagcagcagtcaagcaagcctgggaagatggtatctgtgggatc<br>tcctctgtttcaagaatggaaaacatcatgtggagatcagtagaaggggagctcaacgcaatcctggaagagaatggagttcaactgacggtcgttgtgggatctgtaaaaaaccccatgtggaga<br>ggtccacagagattgcccgtgcctgtgaacgagctgccccacggctggaaggcttgggggaaatcgtacttcgtcagagcagcaaagacaaataacagctttgtcgtggatggtgacacactgaa<br>ggaatgcccactcaaacatagagcatggaacagctttcttgtggaggatcatgggttcggggtatttcacactagtgtctggctcaaggttagagaagattattcattagagtgtgatccagccgttatt<br>ggaacagctgttaagggaaaggaggctgtacacagtgatctaggctactggattgagagtgagaagaatgacacatggaggttgaagagggcccatctgatcgagatgaaaacatgtgaatggc<br>caaagtcccacacattgtggacagatggaatagaagagagtgatctgatcatacccaagtctttagctgggccactcagccatcacaataccagagagggctacaggacccaaatgaaagggcca<br>tggcacagtgaagagcttgaaattcggtttgaggaatgcccaggcactaaggtccacgtggaggaaacatgtggaacaagaggaccatctctgagatcaaccactgcaagcggaagggtgatcg<br>aggaatggtgctgcagggagtgcacaatgcccccactgtcgttccgggctaaagatggctgttggtatggaatggagataaggcccaggaaagaaccagaaagtaacttagtaaggtcaatggtg<br>actgcaggatcaactgatcacatggatcacttctcccttggagtgcttgtgattctgctcatggtgcaggaagggctgaagaagagaatgaccacaaagatcatcataagcacatcgatggcagtgct |

TABLE 2-continued

| lists the sequences of the present invention: |
|---|
| ggtagctatgatcctgggaggattttcaatgagtgacctggctaagcttgcaattttgatgggtgccaccttcgcggaaatgaacactggaggagatgtagctcatctggcgctgatagcggcattca |
| aagtcagaccagcgttgctggtatctttcatcttcagagctaattggacaccccgtgaaagcatgctgctggccttggcctcgtgtcttttgcaaactgcgatctccgccttggaaggcgacctgatggt |
| tctcatcaatggttttgctttggcctggttggcaatacgagcgatggttgttccacgcactgataacatcaccttggcaatcctggctgctctgacaccactggcccggggcacactgcttgtggcgtgg |
| agagcaggccttgctacttgcgggggtttatgctcctctctctgaagggaaaaggcagtgtgaagaagaacttaccatttgtcatggccctgggactaaccgctgtgaggctggtcgaccccatca |
| acgtggtgggactgctgttgctcacaaggagtgggaagcggagctggcccccctagcgaagtactcacagctgttggcctgatatgcgcattggctggagggttcgccaaggcagatatagagatg |
| gctgggcccatggccgcggtcggtctgctaattgtcagttacgtggtctcaggaaagagtgtggacatgtacattgaaagagcaggtgacatcacatgggaaaaagatgcggaagtcactggaaa |
| cagtccccggctcgatgtggcgctagatgagagtggtgatttctccctggtggaggatgacggtcccccccatgagagagatcatactcaaggtggtcctgatgaccatctgtggcatgaacccaata |
| gccataccctttgcagctggagcgtggtacgtatacgtgaagactggaaaaaggagtggtgctctatgggatgtgcctgctcccaaggaagtaaaaaaggggggagaccacagatggagtgtaca |
| gagtaatgactcgtagactgctaggttcaacacaagttggagtgggagttatgcaagagggggtctttcacactatgtggcacgtcacaaaaggatccgcgctgagaagcggtgaagggagactt |
| gatccatactggggagatgtcaagcaggatctggtgtcatactgtggtccatggaagctagatgccgcctgggacgggcacagcgaggtgcagctcttggccgtgccccccggagagagagcg |
| aggaacatccagactctgcccggaatatttaagacaaaggatggggacattggagcggttgcgctggattacccagcaggaacttcaggatctccaatcctagacaagtgtgggagagtgatagg |
| actttatggcaatggggtcgtgatcaaaaatgggagttatgttagtgccatcacccaagggaggagggaggaagagactcctgttgagtgcttcgagccttcgatgctgaagaagaagcagcta |
| actgtcttagacttgcatcctggagctgggaaaaccaggagagttcttcctgaaatagtccgtgaagccataaaaacaagactccgtactgtgatcttagctccaaccagggttgtcgctgctgaaatg |
| gaggaagcccttagagggcttccagtgcgttatatgacaacagcagtcaatgtcacccactctggaacagaaatcgtcgacttaatgtgccatgccaccttcacttcacgtctactacagccaatcag |
| agtccccaactataatctgtatattatggatgaggcccacttcacagatccctcaagtatagcagcaagaggatacatttcaacaagggttgagatgggcgaggcggctgccatcttcatgaccgcca |
| cgccaccaggaacccgtgacgcatttccggactccaactcaccaattatggacaccgaagtggaagtcccagagagagcctggagctcaggctttgattgggtgacggatcattctggaaaaaca |
| gtttggtttgttccaagcgtgaggaacggcaatgagatcgcagcttgtctgacaaaggctggaaaacgggtcatacagctcagcagaaagacttttgagacagagttccagaaaacaaaacatcaa |
| gagtgggactttgtcgtgacaactgacatttcagagatgggcgccaactttaaagctgaccgtgtcatagattccaggagatgcctaaagccggtcatacttgatggcgagagagtcattctggctgg |
| acccatgcctgtcacacatgccagcgctgcccagaggagggggcgcataggcaggaatcccaacaaacctggagatgagtatctgtatggaggtgggtgcgcagagactgacgaagaccatg |
| cacactggcttgaagcaagaatgctccttgacaatatttacctccaagatggcctcatagcctcgctctatcgacctgaggccgacaaagtagcagccattgagggagagttcaagcttaggacgga |
| gcaaaggaagacctttgtggaactcatgaaaagaggagatcttcctgtttggctggcctatcaggttgcatctgccggaataacctacacagatagaagatggtgctttgatggcacgaccaacaac |
| accataatggaagacagtgtgccggcagaggtgtggaccagacacggagagaaaagagtgctcaaaccgaggtggatggacgccagagtttgttcagatcatgcggccctgaagtcatttt |
| aaggagtttgccgctgggaaaagaggagcggcttttggagtgatggaagccctgggaacactgccaggacacatgacagagagattccaggaagccattgacaacctcgctgtgctcatgcggg |
| cagagactggaagcaggccttacaaagccgcggcggcccaattgccggagaccctagagaccattatgcttttggggttgctgggaacagtctcgctgggaatctttttcgtcttgatgaggaacaa |
| gggcatagggaagatgggctttggaatggtgactcttggggccagcgcatggctcatgtggctctcggaaattgagccagccagaattgcatgtgtcctcattgttgtgttcctattgctggtggtgct |
| catacctgagccagaaaagcaaagatctccccaggacaaccaaatggcaatcatcatcatggtagcagtaggtcttctgggcttgattaccgccaatgaactcggatggttggagagaacaaagag |
| tgacctaagccatctaatgggaaggagagaggagggggcaaccataggattctcaatggacattgacctgcggccagcctcagcttgggccatctatgctgccttgacaactttcattacccca |
| gccgtccaacatgcagtgaccacttcatacaacaactactccttaatggcgatggccacgcaagctggagtgttgtttggtatgggcaaagggatgccattctacgcatgggactttggagtcccgct |
| gctaatgataggttgctactcacaattaacacccctgaccctaatagtggccatcattttgctcgtggcgcactacatgtacttgatcccagggctgcaggcagcagctgcgcgtgctgcccagaaga |
| gaacggcagctggcatcatgaagaaccctgttgtggatggaatagtggtgactgacattgacacaatgacaattgaccccaagtggagaaaaagatgggacaggtgctactcatagcagtagcc |
| gtctccagcgccatactgtcgcggaccgcctgggggtggggggaggctggggccctgatcacagcggcaacttccactttgtgggaaggctctccgaacaagtactggaactcctctacagcca |
| cttcactgtgtaacatttttaggggaagttacttggctggagcttctctaatctacacagtaacaagaaacgctggcttggtcaagagacgtgggggtggaacaggagagaccctgggagagaaa |
| tggaaggcccgcttgaaccagatgtcggccctggagttctactcctacaaaaagtcaggcatcaccgaggtgtgcagagaagaggcccgccgcgccctcaaggacggtgtggcaacgggagg |
| ccatgctgtgtcccgaggaagtgcaaagctgagatggttggtggagcggggatacctacagccctatggaaaggtcattgatcttggatgtggcagaggggggctggagttactacgccgccacca |
| tccgcaaagttcaagaagtgaaaggatacacaaaaggaggccctggtcatgaagaacccatgttggtgcaaagctatgggtggaacatagtccgtcttaagagtggggtggacgtctttcatatgg |
| cggctgagccgtgtgacacgttgctgtgtgacataggtgagtcatcatctagtcctgaagtggaagaagcacggacgctcagagtcctctccatggtgggggattggcttgaaaaaagaccagga |
| gccttttgtataaaagtgttgtgcccatacaccagcactatgatggaaaccctggagcgactgcagcgtaggtatgggggaggactggtcagagtgccactctcccgcaactctacacatgagatgt |
| actgggtctctggagcgaaaagcaacaccataaaaagtgtgtccaccacgagccagctcctcttggggcgcatggacgggcccaggaggccagtgaaatatgaggaggatgtgaatctcggctc |
| tggcacgcgggctgtggtaagctgcgctgaagctcccaacatgaagatcattggtaaccgcattgaaaggatccgcagtgagcacgcggaaacgtggttctttgacgagaaccacccatatagga |
| catgggcttaccatggaagctatgaggcccccacacaagggtcagcgtcctctctaataaacggggttgtcaggctcctgtcaaaaccctgggatgtggtgactggagtcacaggaatagccatga |
| ccgacaccacaccgtatggtcagcaaagagttttcaaggaaaaagtggacactagggtgccagaccccccaagaaggcactcgtcaggttatgagcatggtctcttcctggttgtggaaagagctag |
| gcaaacacaaacggccacgagtctgtaccaaagaagagttcatcaacaaggttcgtagcaatgcagcattaggggcaatatttgaagaggaaaaagagtggaagactgcagtggaagctgtgaa |
| cgatccaaggttctgggctctagtggacaaggaaagagagcaccacctgagaggagagtgccagagttgtgtgtacaacatgatgggaaaaagagaaaagaaacaaggggaatttggaaaggc |
| caagggcagccgcgccatctggtatatgtggctaggggctagatttctagagttcgaagcccttggattcttgaacgaggatcactggatggggagagagaactcaggaggtggtgttgaagggct |

TABLE 2-continued

| lists the sequences of the present invention: |
|---|
| gggattacaaagactcggatatgtcctagaagagatgagtcgcataccaggaggaaggatgtatgcagatgacactgctggctgggacacccgcatcagcaggtttgatctggagaatgaagctc |
| taatcaccaaccaaatggagaaagggcacagggccttggcattggccataatcaagtacacataccaaaacaaagtggtaaaggtccttagaccagctgaaaaagggaagacagttatggacatt |
| atttcgagacaagaccaaaggggggagcggacaagttgtcacttacgctcttaacacatttaccaacctagtggtgcaactcattcggaatatggaggctgaggaagttctagagatgcaagacttgtg |
| gctgctgcggaggtcagagaaagtgaccaactggttgcagagcaacggatgggataggctcaaacgaatggcagtcagtggagatgattgcgttgtgaagccaattgatgataggtttgcacatg |
| ccctcaggttcttgaatgatatgggaaaagttaggaaggacacacaagagtggaaaccctcaactggatgggacaactgggaagaagttccgttttgctcccaccacttcaacaagctccatctcaa |
| ggacgggaggtccattgtggttccctgccgccaccaagatgaactgattggccgggcccgcgtctctccaggggcgggatggagcatccgggagactgcttgcctagcaaaatcatatgcgcaa |
| atgtggcagctcctttatttccacagaagggacctccgactgatggccaatgccatttgttcatctgtgccagttgactgggttccaactgggagaactacctggtcaatccatggaaagggagaat |
| ggatgaccactgaagacatgcttgtggtgtggaacagagtgtggattgaggagaacgaccacatggaagacaagaccccagttacgaaatggacagacattccctatttgggaaaaagggaaga |
| cttgtggtgtggatctctcatagggcacagaccgcgcaccacctgggctgagaacattaaaaacacagtcaacatggtgcgcaggatcataggtgatgaagaaaagtacatggactacctatccac |
| ccaagttcgctacttgggtgaagaagggtctacacctggagtgctgtaagcaccaatcttagtgttgtcaggcctgctagtcagccacagcttggggaaagctgtgcagcctgtgaccccccagg |
| agaagctgggaaaccaagcctatagtcaggccgagaacgccatggcacggaagaagccatgctgcctgtgagcccctcagaggacactgagtcaaaaaaccccacgcgcttggaggcgcag |
| gatgggaaaagaaggtggcgaccttccccacccttcaatctggggcctgaactggagatcagctgtggatctccagaagagggactagtggttagaggagacccccggaaaacgcaaaacag |
| catattgacgctgggaaagaccagagactccatgagtttccaccacgctggccgccaggcacagatcgccgaatagcggcggccggtgtggggaaatccatgggtct |

The invention will be better illustrated through the following examples and Figures. The examples to follow aim to clarify the object of the invention and illustrate advantageous embodiments, but in no way intend to restrict the range of the invention.

FIGURE LEGEND

FIG. 1 illustrates the wild-type protein S of the HBV, which notably comprises four transmembrane domains, represented by black vertical rectangles; the N and C-terminal ends thereof are oriented towards the light of the endoplasmic reticulum (ER). In the case of the HBVadw isolate, this protein of approximately 45 kD comprises 226 amino acid residues.

Figure 2A:
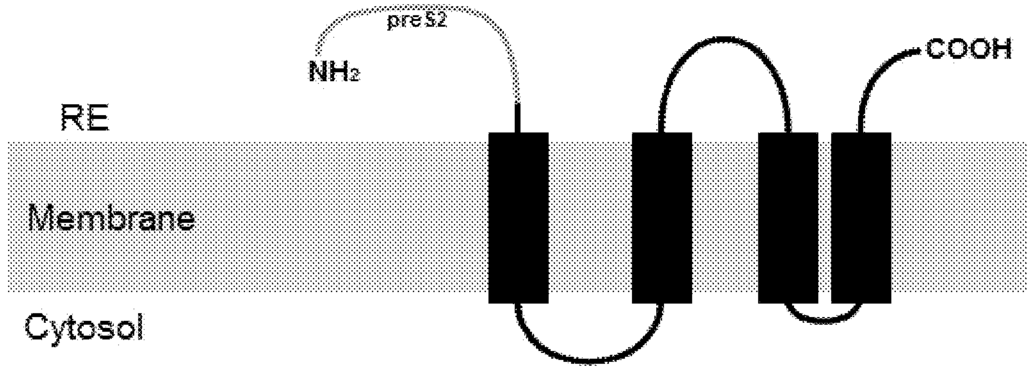

FIG. 2A illustrates the wild-type protein M of the HBV, which notably comprises four transmembrane domains, represented by black vertical rectangles; the N and C-terminal ends thereof are oriented towards the light of the endoplasmic reticulum (ER). In the case of the HBVadw isolate, this protein of approximately 33 kD comprises 281 amino acid residues. This FIG. 2A presents a first transmembrane topology of the protein M.

Figure 2B:
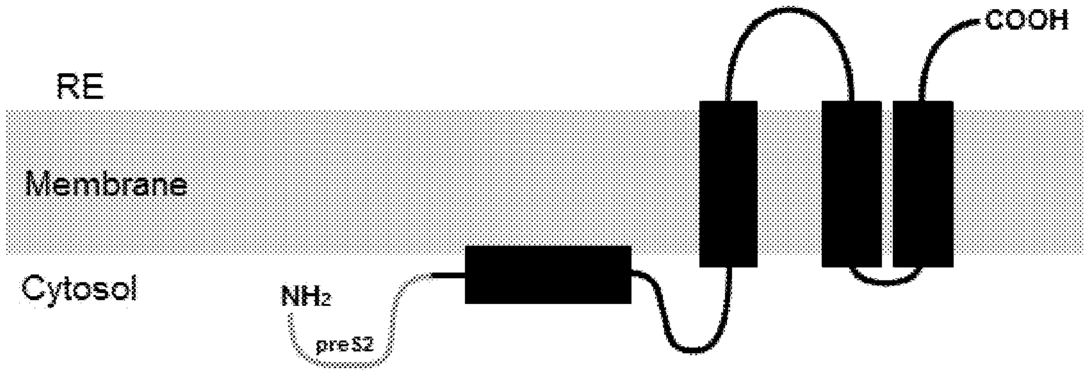

FIG. 2B illustrates the protein M of the HBV, which comprises three transmembrane domains, represented by black vertical triangles; the C-terminal end thereof is oriented towards the light of the endoplasmic reticulum (ER). Unlike FIG. 2A, the N-terminal end is oriented towards the cytosol, and as a result thereof, the first transmembrane domain located on the N-terminal side is represented by a black horizontal rectangle. This FIG. 2B presents a second transmembrane typology of the protein M.

Figure 3:
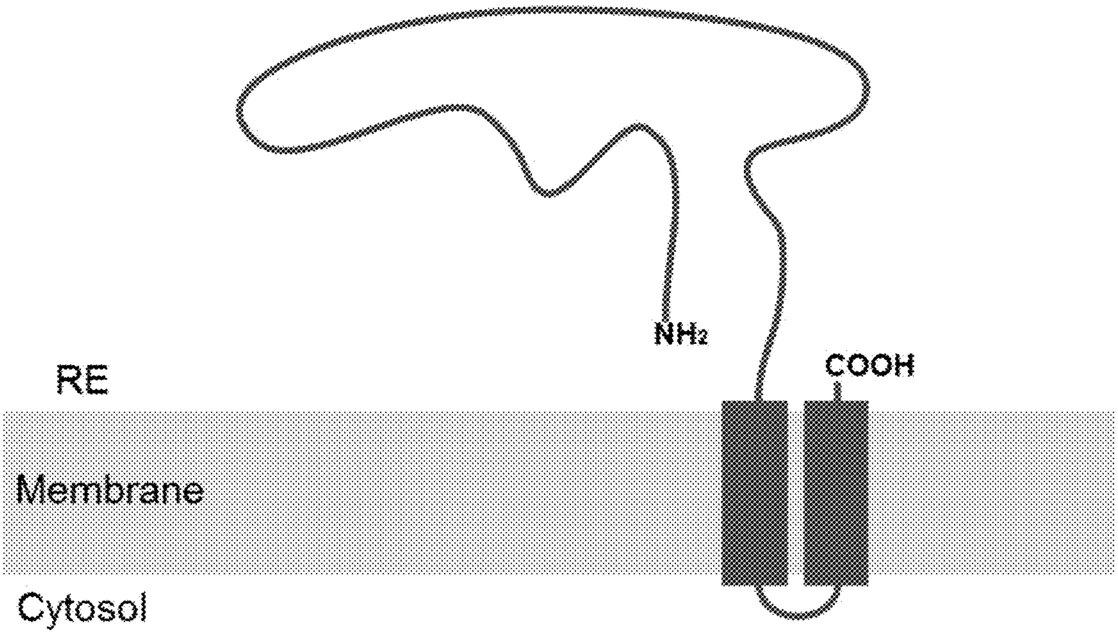

FIG. 3 illustrates the wild-type envelope protein E of the Zika virus, which notably comprises two transmembrane domains, represented by dark gray vertical rectangles; the N-terminal end thereof is in the light of the endoplasmic reticulum (ER), but is oriented towards the cytosol, and the C-terminal end thereof is oriented towards the light of the endoplasmic reticulum (ER). This protein of approximately 54 kD comprises 504 amino acid residues.

Figure 4:
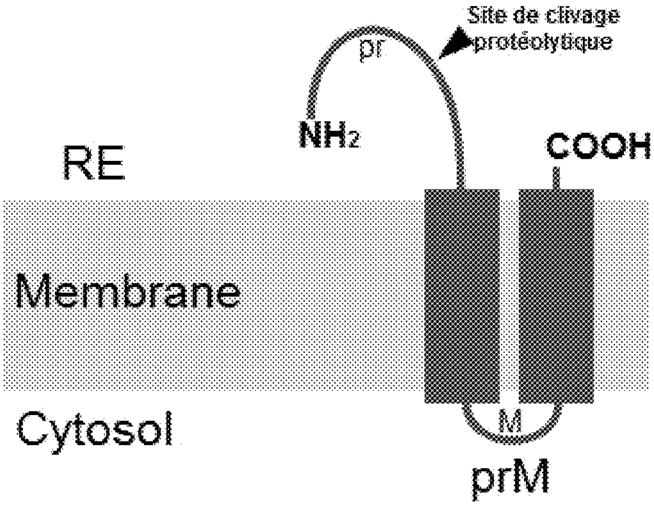

FIG. 4 illustrates the wild-type protein prM of the Zika virus, which notably comprises two transmembrane domain, represented by gray vertical rectangles; the N-terminal end thereof is in the light of the endoplasmic reticulum (ER) but is oriented towards the cytosol, and the C-terminal end thereof is oriented towards the light of the endoplasmic reticulum (ER). This protein of approximately 18 kD comprises 164 amino acid residues. The proteolytic cleavage site, allowing the pr portion and the M portion of the protein prM to be cleaved, is also indicated.

Figure 5:
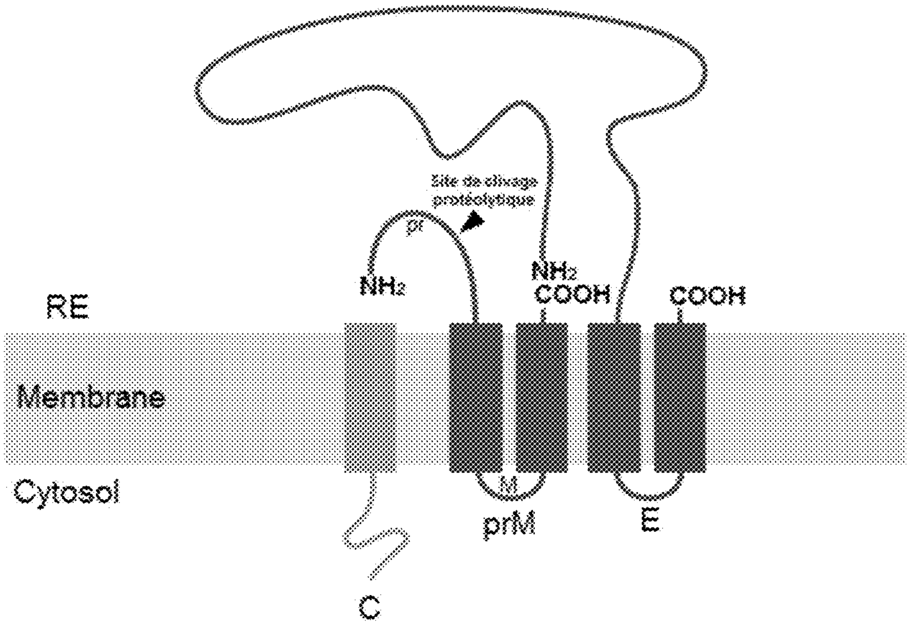

FIG. 5 illustrates the configuration of certain proteins of the Zika virus, and notably the configuration of the capsid protein (C), of the protein prM (pr and M) and of the envelope protein E (E) in relation to the membrane.

The capsid protein (C) comprises, on the C-terminal side, a transmembrane domain, represented by a light gray vertical rectangle; the N-terminal end thereof is oriented towards the cytosol.

The proteins E and prM are as described in the legends of FIGS. 3 and 4.

FIG. 6 illustrates the cartography of the synthesis gene allowing the fusion peptides prM+E to be obtained, i.e. a fusion peptide comprising the envelope protein E and the protein prM of Zika. The position of the transmembrane domains of the protein C, of the protein prM and of the envelope protein E is represented by short dark gray arrows.

Figure 7:
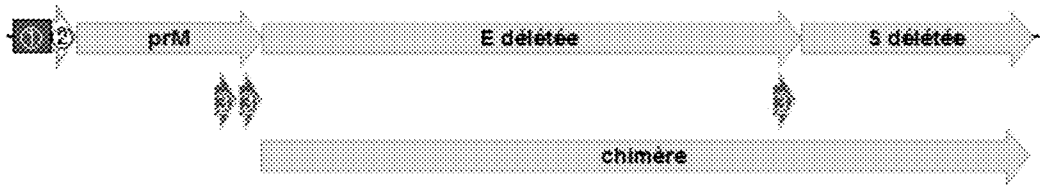

FIG. 7 illustrates the cartography of the synthesis gene allowing the fusion protein "prM+deleted E+deleted S" to be obtained, i.e. the fusion protein comprising the protein prM, the protein E deleted from a transmembrane domain and the protein S deleted from a transmembrane domain, and notably the fusion protein represented by SEQ ID NO. 8 or SEQ ID NO. 35 or SEQ ID NO. 18 or SEQ ID NO. 43. The position of the transmembrane domains of the protein prM and of the envelope protein E is represented by short arrows (indicated by the number 3 and in dark gray). The position of the initiation sequence is represented by a dark gray rectangle indicated by the number 1 and the position of the transfer initiation peptide is represented by a white arrow indicated by the number 2.

Figure 8:
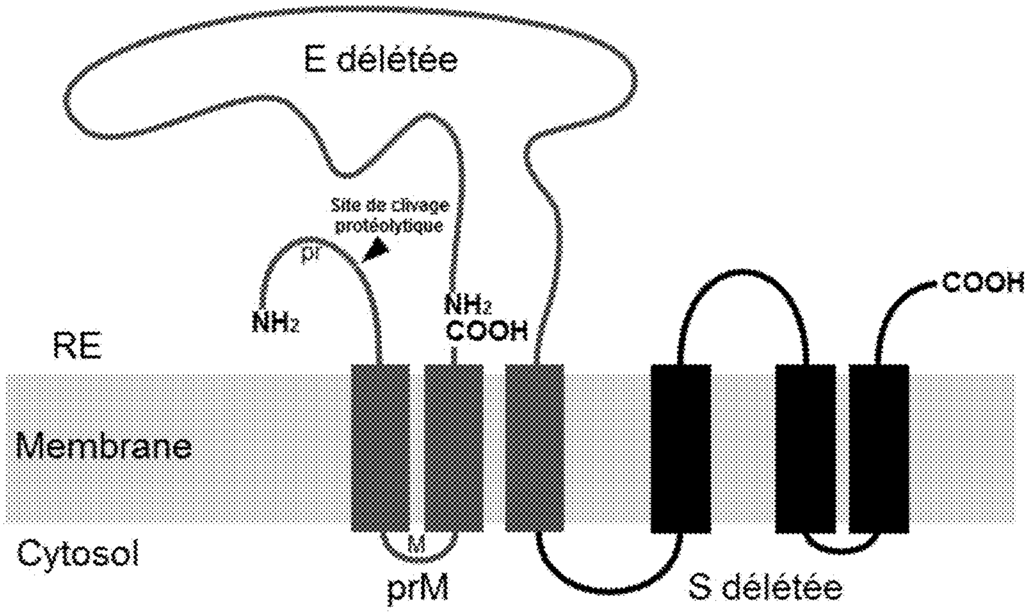

FIG. 8 illustrates the transmembrane topology of the fusion protein "prM+deleted E+deleted 5," i.e. the fusion protein comprising the protein prM, the protein E deleted from a transmembrane domain and the protein S deleted from a transmembrane domain, and notably the fusion protein represented by SEQ ID NO. 8 or SEQ ID NO. 35 or SEQ ID NO. 18 or SEQ ID NO. 43.

Figure 9:
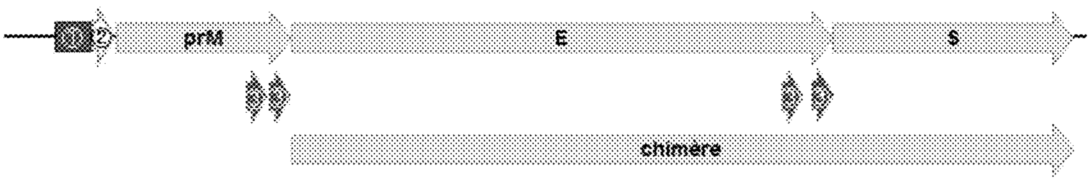

FIG. 9 illustrates the cartography of the synthesis gene allowing the fusion protein "prM+E+5" to be obtained, i.e. the fusion protein comprising the protein prM, the protein E and the protein S, and notably the fusion protein represented by SEQ ID NO. 10 or SEQ ID NO. 37 or SEQ ID NO. 20 or SEQ ID NO. 45. The position of the transmembrane domains of the protein prM and the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 10:
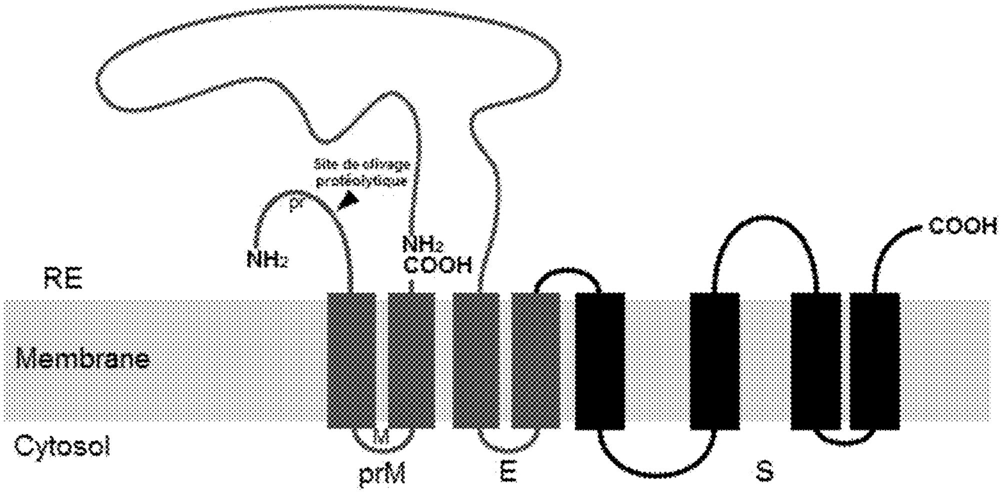

FIG. 10 illustrates the transmembrane topology of the fusion protein "prM+E+5," i.e. the fusion protein comprising the protein prM, the protein E and the protein S, and notably the fusion protein represented by SEQ ID NO. 10 or SEQ ID NO. 37 or SEQ ID NO. 20 or SEQ ID NO. 45.

Figure 11:
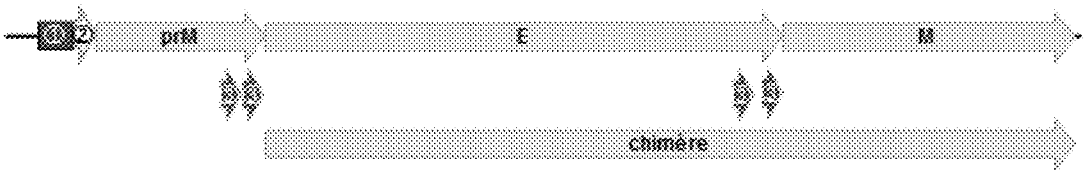

FIG. 11 illustrates the cartography of the synthesis gene allowing the fusion protein "prM+E+M" to be obtained, i.e. the fusion protein comprising the protein prM, the protein E and the protein M, and notably the fusion protein represented by SEQ ID NO. 14 or SEQ ID NO. 41 or SEQ ID NO. 24 or SEQ ID NO. 49. The position of the transmembrane domains of the protein prM and of the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 12:
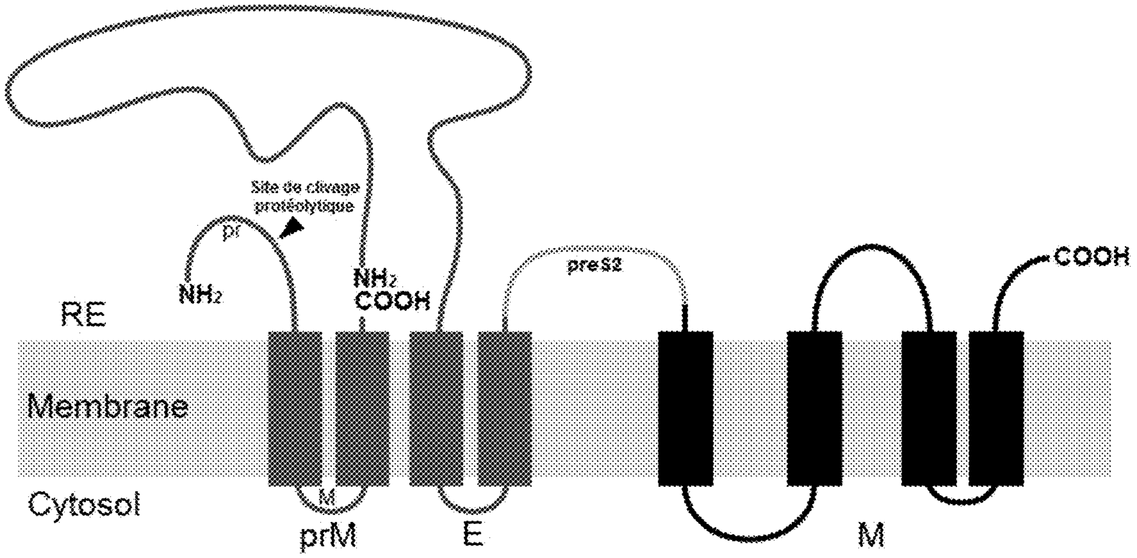

FIG. 12 illustrates the transmembrane topology of the fusion protein "prM+E+M," i.e. the fusion protein comprising the protein prM, the protein E and the protein M, and notably the fusion protein represented by SEQ ID NO. 14 or SEQ ID NO. 41 or SEQ ID NO. 24 or SEQ ID NO. 49.

Figure 13:
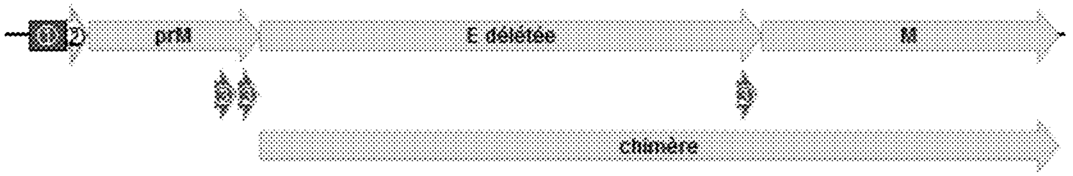

FIG. 13 illustrates the cartography of the synthesis gene allowing the fusion protein "prM+deleted E+M" to be obtained, i.e. the fusion protein comprising the protein prM, the protein E deleted from a transmembrane domain and the protein M, and notably the fusion protein represented by SEQ ID NO. 12 or SEQ ID NO. 39 or SEQ ID NO. 22 or SEQ ID NO. 47. The position of the transmembrane domains of the protein prM and of the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 14:
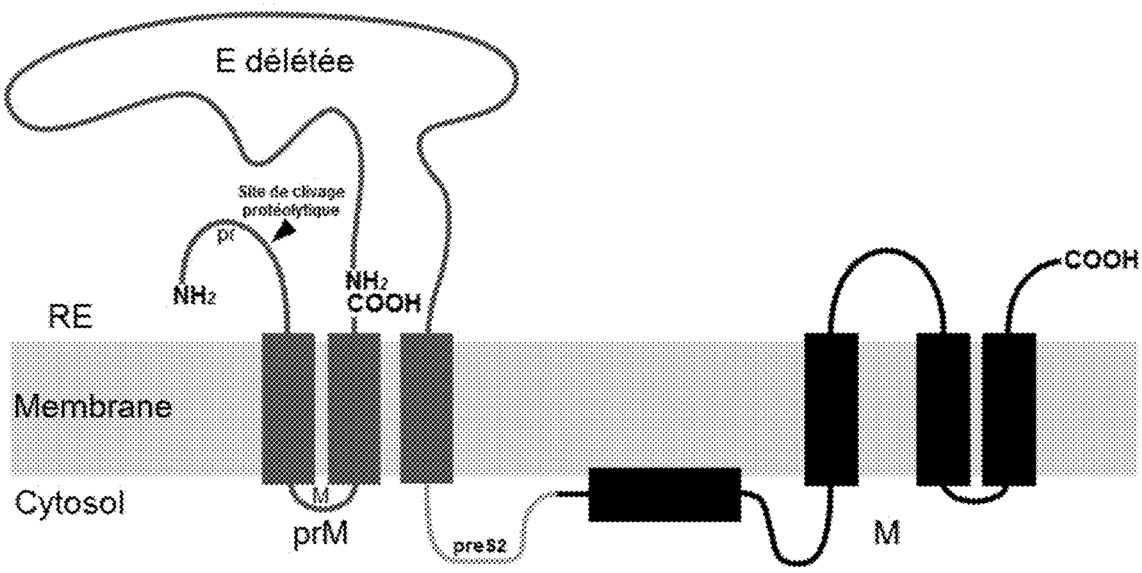

FIG. 14 illustrates the transmembrane topology of the fusion protein "prM+deleted E+M," i.e. the fusion protein comprising the protein prM, the protein E deleted from a transmembrane domain and the protein M, and notably the fusion protein represented by SEQ ID NO. 12 or SEQ ID NO. 39 or SEQ ID NO. 22 or SEQ ID NO. 47.

Figure 15:

FIG. 15 illustrates the cartography of the synthesis gene allowing the fusion protein "deleted E+deleted 5" to be obtained, i.e. the fusion protein comprising the protein E deleted from a transmembrane domain and the protein S deleted from a transmembrane domain, and notably the fusion protein represented by SEQ ID NO. 7 or SEQ ID NO. 37 or SEQ ID NO. 17 or SEQ ID NO. 42. The position of the transmembrane domain of the envelope protein E is represented by a short arrow (indicated by the number 3 and in dark gray). The position of the initiation sequence is represented by a gray rectangle indicated by the number 1 and the position of the transfer initiation peptide is represented by a white arrow indicated by the number 2.

Figure 16:
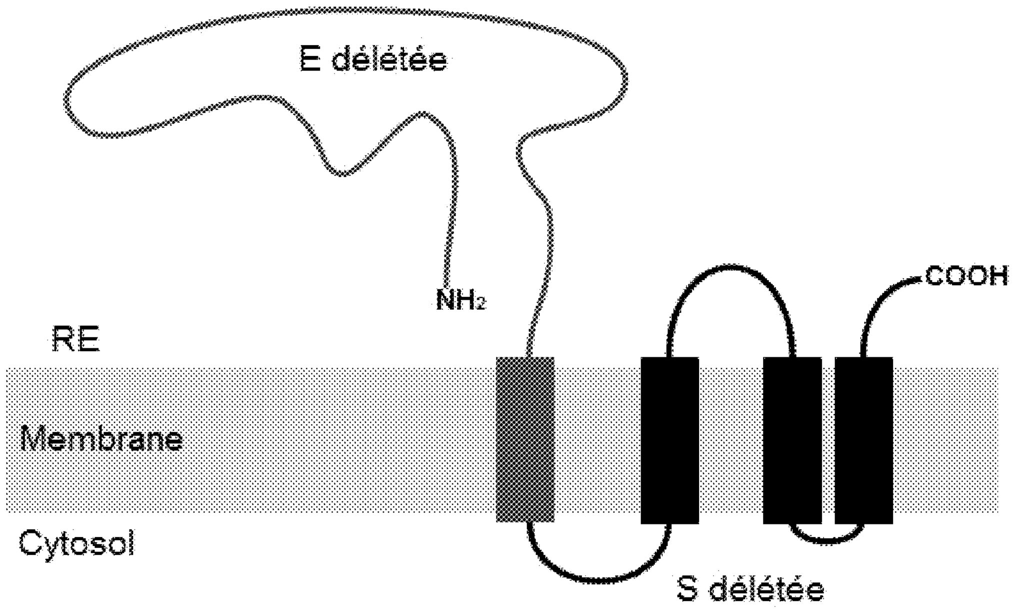

FIG. 16 illustrates the transmembrane topology of the fusion protein "deleted E+deleted 5," i.e. the fusion protein comprising the protein E deleted from a transmembrane domain and the protein S deleted from a transmembrane domain, and notably the fusion protein represented by SEQ ID NO. 7 or SEQ ID NO. 34 or SEQ ID NO. 17 or SEQ ID NO. 42.

Figure 17:
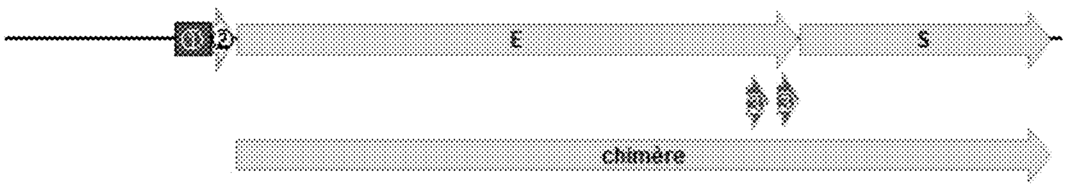

FIG. 17 illustrates the cartography of the synthesis gene allowing the fusion protein "E+5" to be obtained, i.e. the fusion protein comprising the protein E and the protein S, and notably the fusion protein represented by SEQ ID NO. 9 or SEQ ID NO. 36 or SEQ ID NO. 19 or SEQ ID NO. 44. The position of the two transmembrane domains of the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 18:
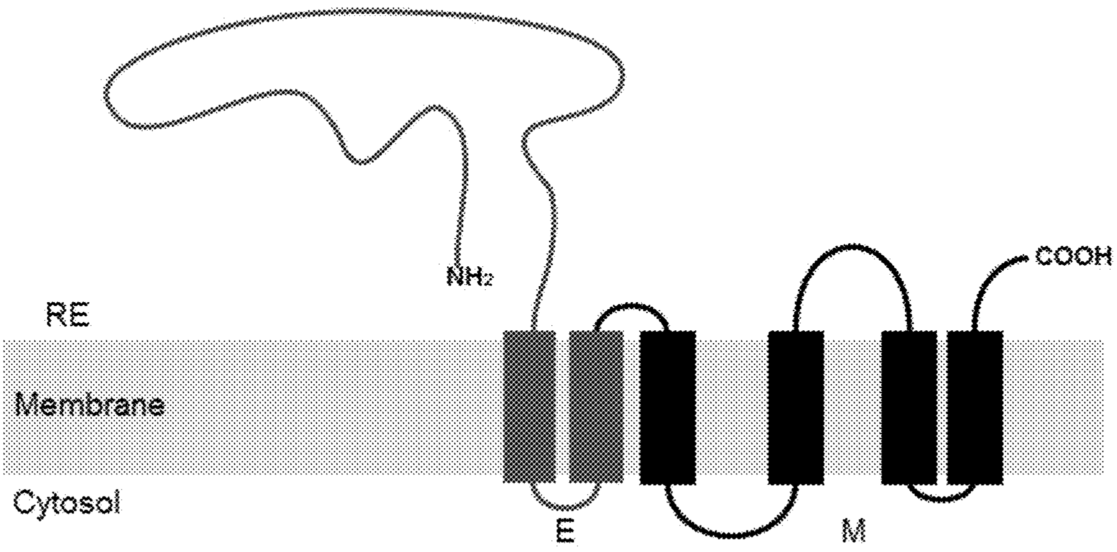

FIG. 18 illustrates the transmembrane topology of the fusion protein "E+S," i.e. the fusion protein comprising the protein E and the protein S, and notably the fusion protein represented by SEQ ID NO. 9 or SEQ ID NO. 36 or SEQ ID NO. 19 or SEQ ID NO. 44.

Figure 19:
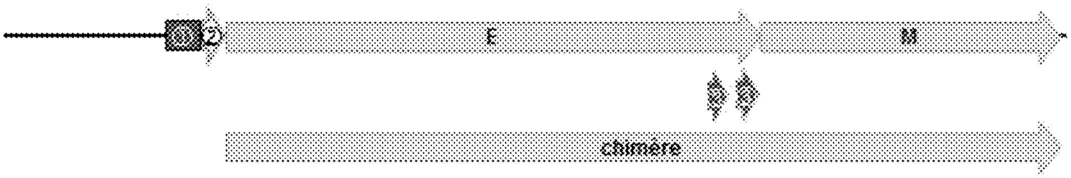

FIG. 19 illustrates the cartography of the synthesis gene allowing the fusion protein "E+M" to be obtained, i.e. the fusion protein comprising the protein E and the protein M, and notably the fusion protein represented by SEQ ID NO. 13 or SEQ ID NO. 40 or SEQ ID NO. 23 or SEQ ID NO. 48. The position of the two transmembrane domains of the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 20:
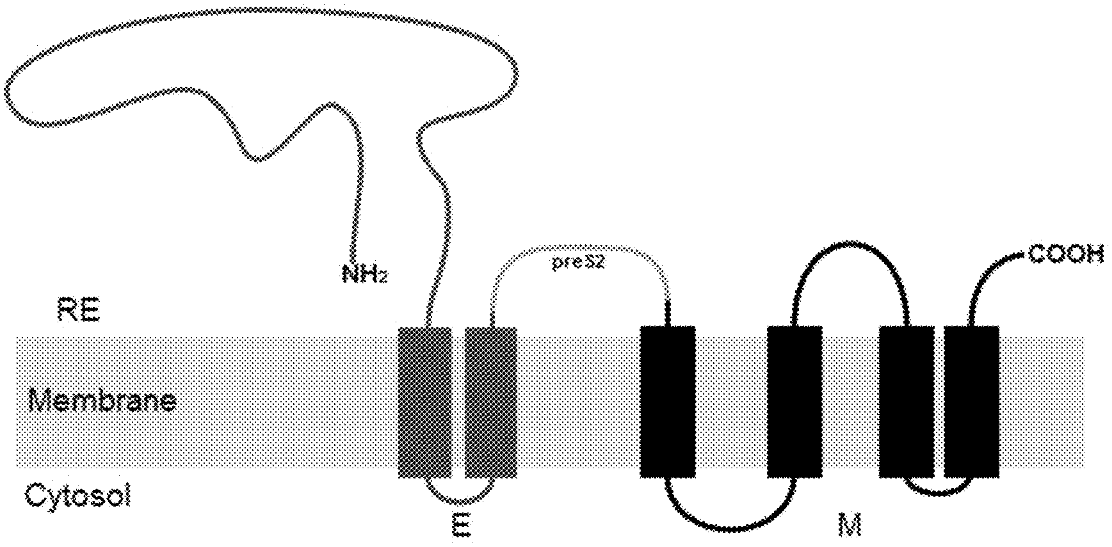

FIG. 20 illustrates the transmembrane topology of the fusion protein "E+M," i.e. the fusion protein comprising the protein E and the protein M, and notably the fusion protein represented by SEQ ID NO. 13 or SEQ ID NO. 40 or SEQ ID NO. 23 or SEQ ID NO. 48.

Figure 21:
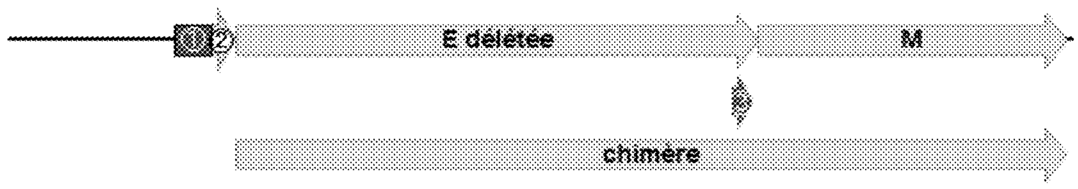

FIG. 21 illustrates the cartography of the synthesis gene allowing the fusion protein "deleted E+M" to be obtained, i.e. the fusion protein comprising the protein E deleted from a transmembrane domain and the protein M, and notably the fusion protein represented by SEQ ID NO. 11 or SEQ ID NO. 38 or SEQ ID NO. 21 or SEQ ID NO. 46. The position of the two transmembrane domains of the envelope protein E is represented by short arrows (indicated by the number 3 and in dark gray). The position of the initiation sequence is represented by a gray rectangle indicated by the number 1 and the position of the transfer initiation peptide is represented by a white arrow indicated by the number 2.

Figure 22:
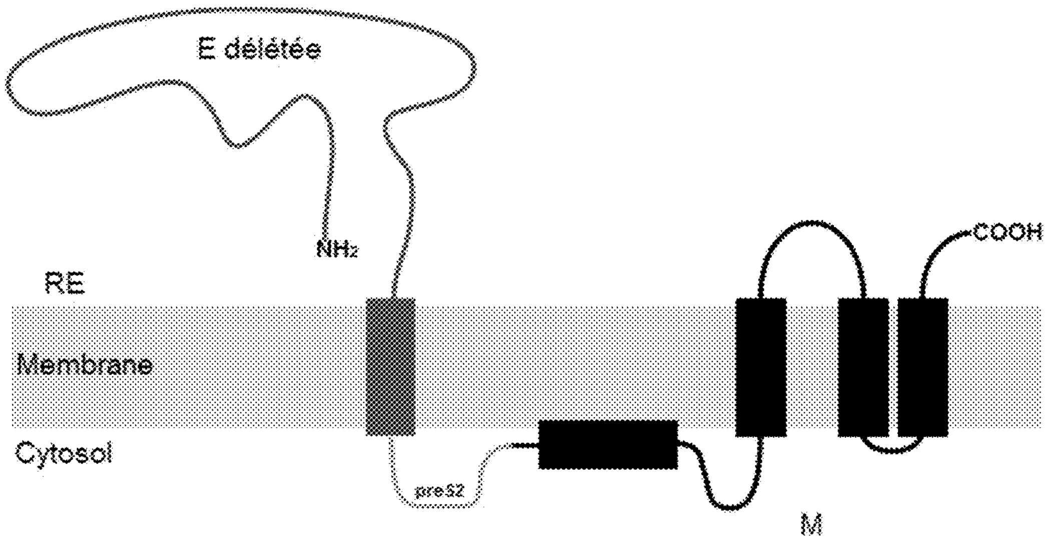

FIG. 22 illustrates the transmembrane topology of the fusion protein "deleted E+M," i.e. the fusion protein comprising the protein E deleted from a transmembrane domain and the protein M, and notably the fusion protein represented by SEQ ID NO. 11 or SEQ ID NO. 38 or SEQ ID NO. 21 or SEQ ID NO. 46.

Figure 23:
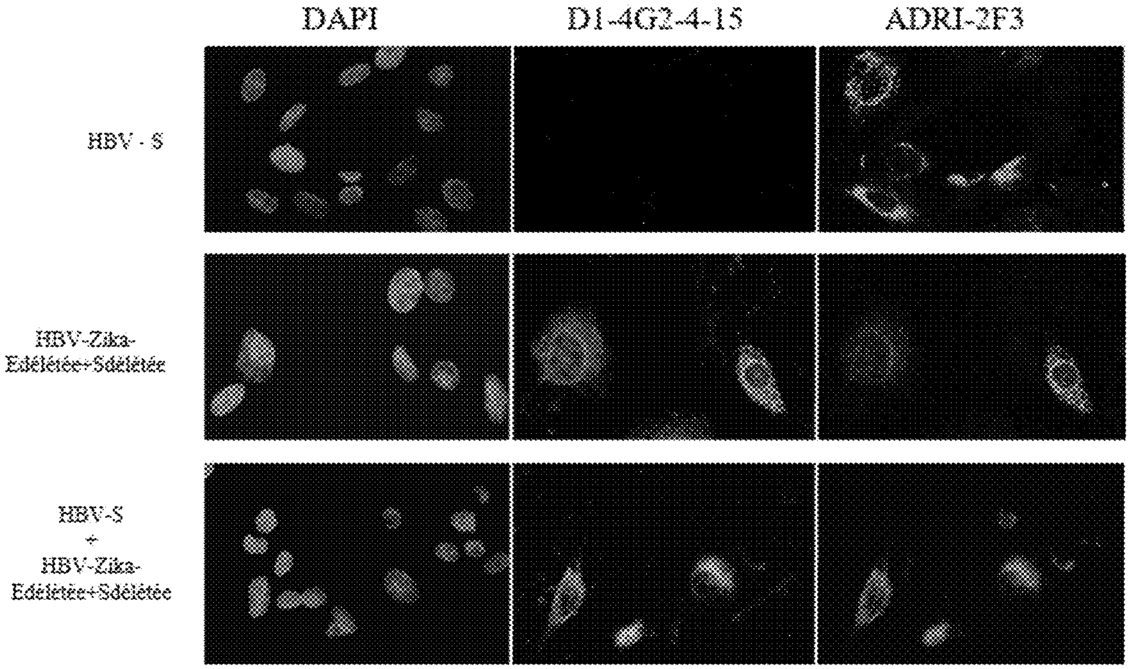

FIG. 23 illustrates the immunofluorescence of cells transfected by the RNA transcribed in vitro from the plasmids pSFV1-HBV-S and/or pSFV1-prM+deleted E+deleted S and revealed by an anti-HBV-S antibody (ADRI-2F3) or an anti-Zika antibody (D1-4G2-4-15). In particular, the chimeric protein HBV-Zika-deleted E+deleted S is detected with comparable efficacy either by the antibody recognizing the envelope protein of the Zika virus or by the antibody recognizing the protein HBV-S (line 2). These two fluorescence signals are perfectly co-localized, which shows that the chimeric protein HBV-Zika-deleted E+deleted S is not degraded or cleaved during its expression.

Figure 24:
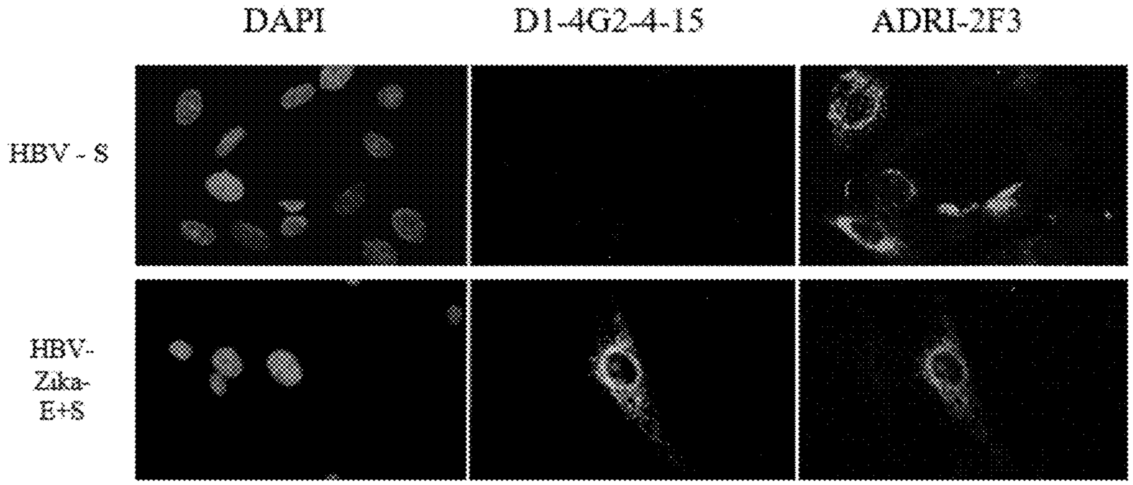

FIG. 24 illustrates the immunofluorescence of cells transfected by the RNA transcribed in vitro from the plasmids pSFV1-HBV-S and/or pSFV1-prM+E+S and revealed by an anti-HBV-S antibody (ADRI-2F3) or an anti-Zika antibody (D1-4G2-4-15). In particular, the chimeric protein HBV-Zika-E+S is detected with comparable efficacy either by the antibody recognizing the envelope protein of the Zika virus or by the antibody recognizing the protein HBV-S. These two fluorescence signals are perfectly co-localized, which shows that the chimeric protein HBV-Zika-E+S is not degraded or cleaved during its expression.

Figure 25:
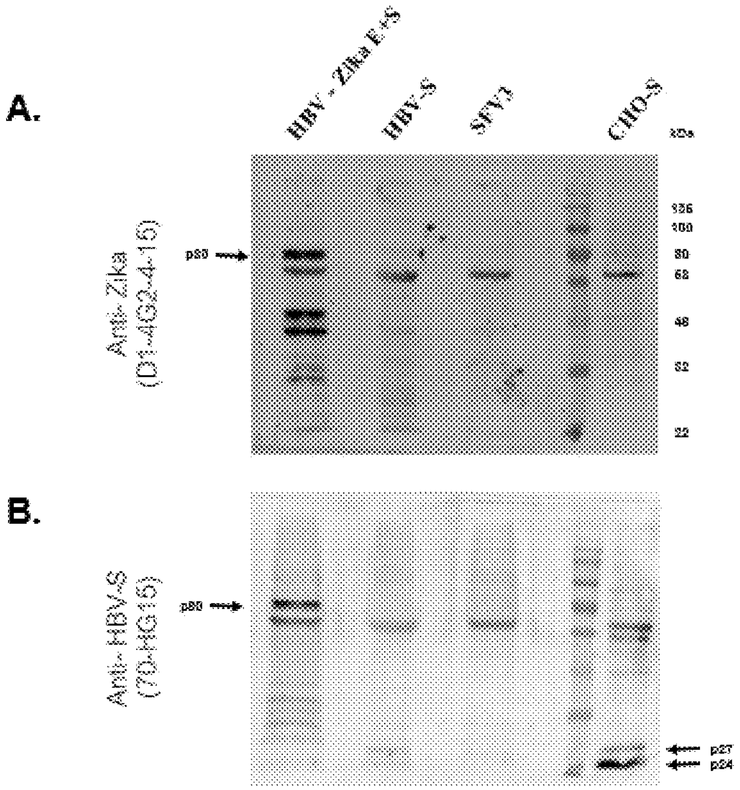

FIG. 25 illustrates a western blot revealed by the anti-Zika antibody D1-4G2-4-15 (A) or the anti-HBV-S antibody 70-HG15 (B), on the lysates of cells transfected by the RNA transcribed in vitro from the plasmids pSFV1-prM+E+S, pSFV1-HBV-S or pSFV3. The lysate CHO-S is used as a positive control. The two glycolized forms of the protein HBV-S (p24 and p27) are specifically detected on the immunoblot incubated with the anti-HBV-S antibody. The chimeric protein HBV-Zika-E+S is specifically detected by the two antibodies, with the expected theoretical size of 80 kDa (p80). This confirms a satisfactory production as well as the integration of the chimeric protein HBV-Zika-E+S, which does not undergo cleavage during its expression.

Figure 26:
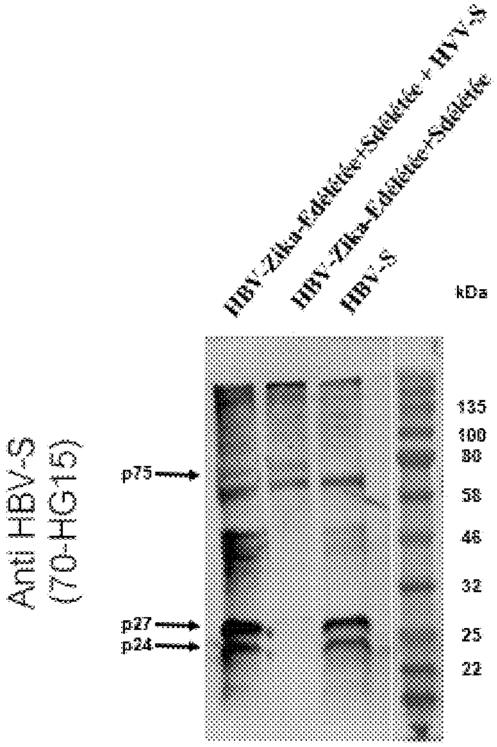

FIG. 26 illustrates a western blot revealed by the anti-HBV-S antibody (70-HG15) on the lysates of cells transfected by the RNA transcribed from the plasmids pSFV1-prM+deleted E+deleted S and/or pSFV1-HBV-S. The specific detection of the chimeric protein HBV-Zika-deleted E+deleted S with an expected theoretical size of 75 kDa (p75) shows that it is not degraded or cleaved during its expression. The protein HBV-S is also detected in its two glycosylation forms (p24 and p27).

Figure 27:
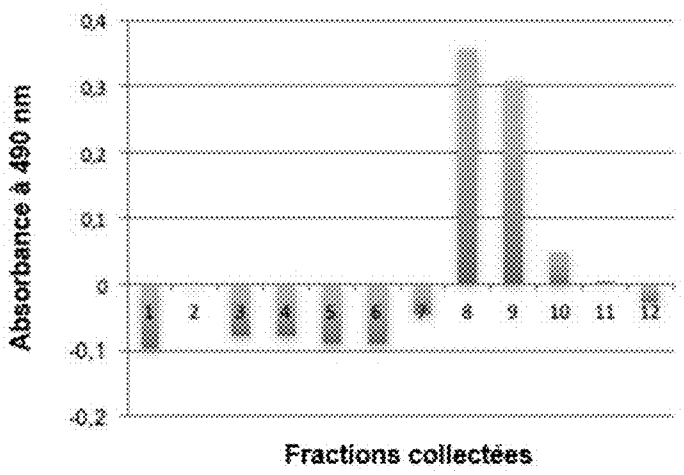

FIG. 27 corresponds to an ELISA analysis (HBV-S detection) of the fractions collected after differential ultracentrifugation of the lysates of the cells expressing the RNA transcribed in vitro from the plasmids pSFV1-prM+E+S and pSFV1-HBV-S. The chimeric particle-enriched fractions 8 and 9 were collected, dialyzed then observed through negative staining (FIGS. 28 and 29).

Figure 28:
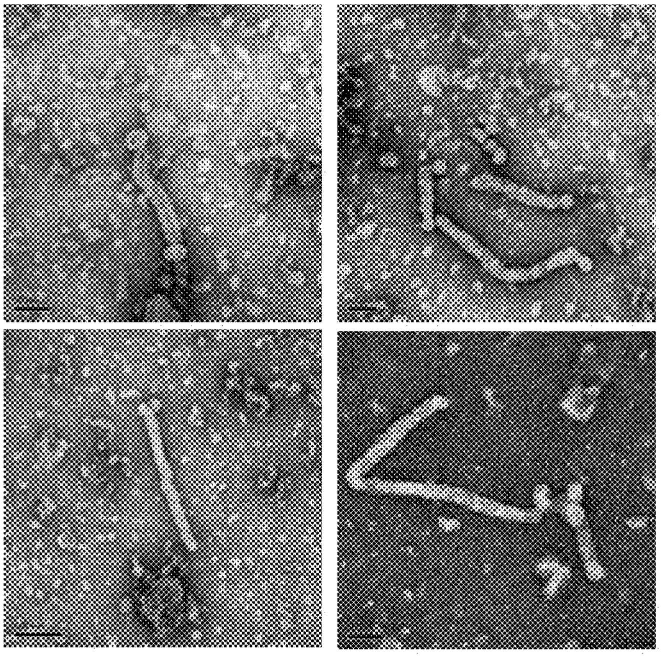

FIG. 28 corresponds to a transmission electron microscopy observation with negative staining performed on the chimeric particles purified from the co-expression of the RNA transcribed from the plasmids pSFV-1-prM+E+S and pSFV1-HBV-S in BHK-21 cells. These chimeric particles are present in the form of bands and beads characteristic in size and structure of the assembly of the envelope proteins of the HBV (Patient R, Hourioux C, Sizaret P Y, Trassard S, Sureau C, Roingeard P. J Virol. 2007 April; 81(8):3842-51).

Figure 29:
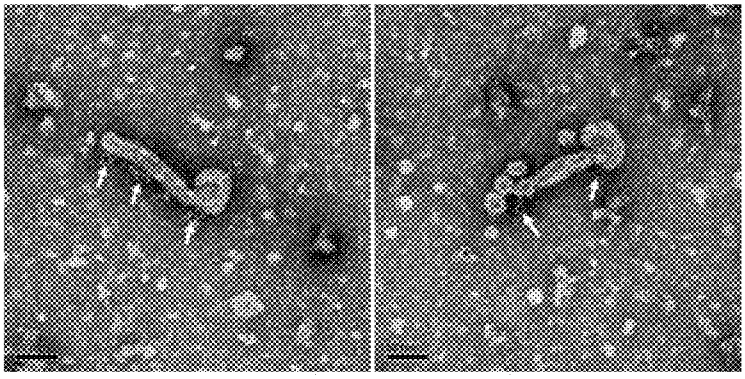

FIG. 29 corresponds to a transmission electron microscopy observation with negative staining performed on the chimeric particles purified from the co-expression of the RNA transcribed from the plasmids pSFV-1-prM+E+S and pSFV1-HBV-S in BHK-21 cells. Immunolabeling (immunogold) by the anti-Zika antibody D1-4G2-15 demonstrates the effective incorporation of the chimeric protein HBV-Zika-E+S in the vaccine particles (presence of gold beads at the surface of particles, arrows).

Figure 30:
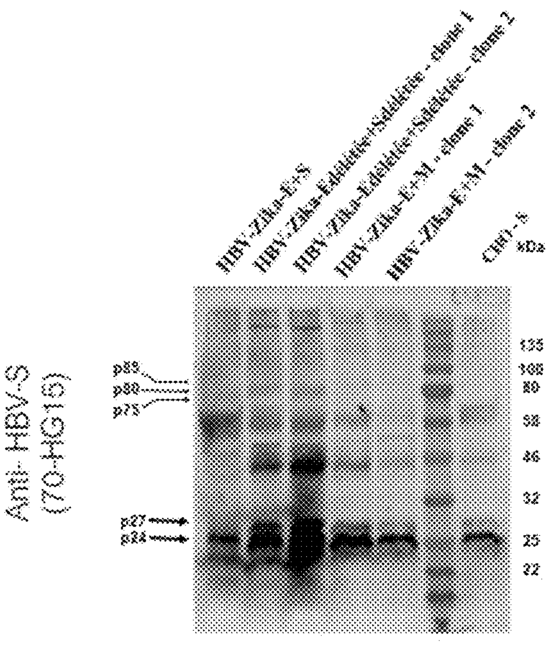

FIG. 30 illustrates a western blot revealed by the anti-HBV-S antibody 70-HG15 on the lysates of CHO-S cells transduced by pHR'$^{puro}$-HBV-Zika-prM+E+S, pHR'$^{puro}$-HBV-Zika-prM+deleted E+deleted S (clones 1 and 2) and pHR'$^{puro}$-HBV-Zika-prM+E+M (clones 1 and 2). The clone CHO-S is used as a positive control.

Figure 31:
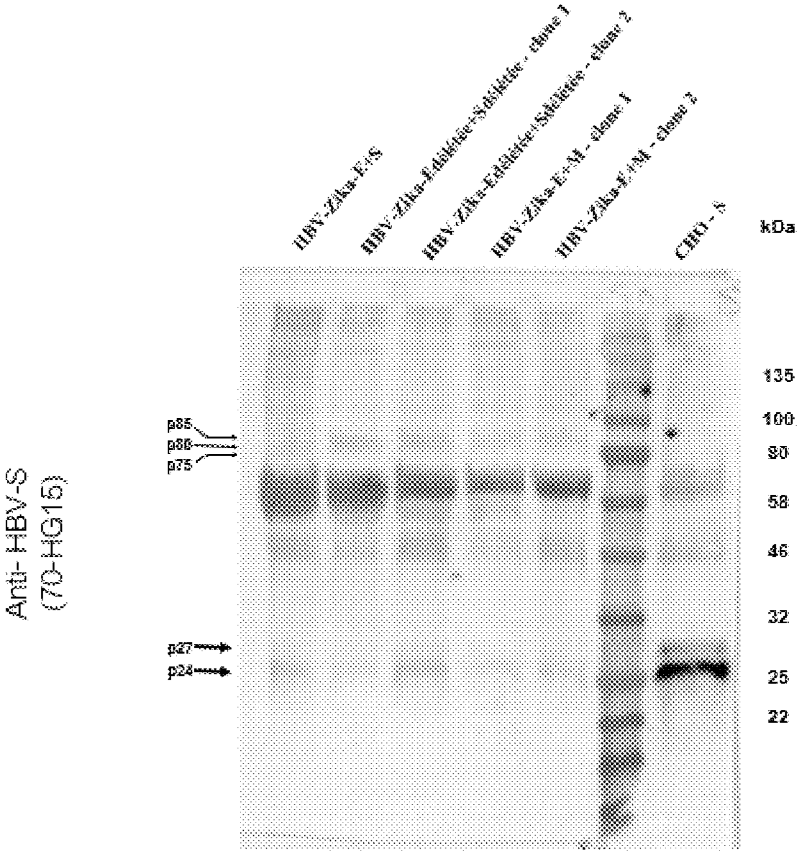

FIG. 31 illustrates a western blot revealed by the anti-HBV-S antibody 70-HG15 on the supernatants of CHO-S cells transduced by pHR'$^{puro}$-HBV-Zika-prM+E+S, pHR'$^{puro}$-HBV-Zika-prM+deleted E+deleted S (clones 1 and 2) and pHR'$^{puro}$-HBV-Zika-prM+E+M (clones 1 and 2). The clone CHO-S is used as a positive control.

EXAMPLES

Example 1: Stable Production of the Wild-Type Envelope Protein S of Wild-Type HBV-S and of the Chimeric Protein HBV-Zika in Clones of the Cellular Line CHO Ovary cells of Chinese hamsters (CHO) are stably transduced using a strategy based on the lentiviral expression vector pHR' (described by Dull et al., A third-generation lentivirus vector with a conditional packaging system, 1998, Journal of Virology, vol. 72, pp 8463-8471). The strategy based on the lentiviral expression vector pHR' was described in the article Patient et al., Chimeric Hepatitis B and C viruses envelope proteins can form subviral particles: implications for the design of new vaccine strategies, 2009, New Biotechnology, vol. 25, no. 4, pp 226-234.

The DNA sequence of the chimeric HBV-Zika envelope proteins is transferred to the restriction site BamH1 and/or XH01 of the plasmid pHR'$^{gfp}$ (constructed from the plasmid pHR' and coding the GFP as a screening marker) to generate the plasmids pHR'$^{gfp}$-HBV-Zika. The lentiviruses are produced in the HEK-293T cells (human embryo kidney cells), kept in Dulbecco's Modified Eagle Medium (DMEM).

Twenty-four hours before the transfection, $3\times10^6$ cells are used to inoculate a culture dish measuring 75 $cm^2$ (Falcon®). The cells are transfected with an equimolar mixture (1 pmol of each) of plasmid pHR'$^{gfP}$-HBV-Zika, of plasmid pHCMVG (referenced in the ATCC under the reference pHCMV-G (ATCC® 754971) coding the VSV-G (envelope glycoprotein of the vesicular stomatitis virus) and the packaging construction p8.74 through the calcium phosphate method.

The following day, the transfection solution is eliminated and replaced with the fresh complete medium.

After 24 and 48 hours of culture, the supernatant is collected, filtered through a low protein binding filter with pores measuring 0.45 μm (Sartorius) and concentrated through centrifugation on a 20% saccharose cushion at 4° C. for 90 minutes at 100,000×g.

The residue is resuspended in 500 μL of PBS and stored at −80° C. until use.

The transduction unit (TU) titer is determined by quantifying the protein p24 (Innotest® HIV Antigen mAb Kit, Innogenetics).

The clone CHO-S (stably producing the protein HBV-S, previously described in the article Patient et al., Chimeric Hepatitis B and C viruses envelope proteins can form subviral particles: implications for the design of new vaccine strategies, 2009, New Biotechnology, vol. 25, no. 4, pp 226-234), cultivated in the DMEM-F12 (commercialized by Fisher Scientific) is transduced with the recombining lentivectors HRR'$^{gfp}$-HBV-Zika.

One day before transduction, $10^5$ CHO-S cells/well are used to inoculate a six-well cellular culture plate (Falcon®).

The cells are incubated with the vectors HR'$^{gfp}$-HBV-Zika (infection multiplicity: 2.5) and 4 μg/mL of polybrene (Sigma) in the fresh complete medium.

Three days after transduction, the cells are used to inoculate a 96-well cellular culture plate (Falcon®) with a density of 1 cell/well.

The plates are incubated for 3 weeks.

The positive cellular clones of the GFP, named CHO-S+Zika-S or CHO-S+Zika-M are isolated and amplified.

The intracellular production of the proteins HBV-S and chimeric HBV-Zika is analyzed with a western blot of the cellular lysates, as previously described in the article Patient et al., Chimeric Hepatitis B and C viruses envelope proteins can form subviral particles: implications for the design of new vaccine strategies, 2009, New Biotechnology, vol. 25, no. 4, pp 226-234.

The membranes are incubated for one night at 4° C. with a polyclonal rabbit anti-HBsAg antibody (R247) or the monoclonal antibody directed to the Zika envelope protein (4G2).

Example 2: Analysis of the Supernatant of Cells Stably Coproducing the Envelope Proteins HBV-S and Chimeric HBV-Zika The subviral envelope particles secreted are purified from the supernatant of the cells through gradient centrifugation of cesium chloride (CsCl), as previously described in the article Patient et al., Chimeric Hepatitis B and C viruses envelope proteins can form subviral particles: implications for the design of new vaccine strategies, 2009, New Biotechnology, vol. 25, no. 4, pp 226-234.

To summarize, 200 mL of supernatant are clarified and the total proteins are precipitated through the addition of a 45% solution of $(NH_4)_2SO_4$ (pH 7.5).

The precipitate is collected through centrifugation at 4° C. for 15 minutes at 10,000×g and the residue is dissolved in a minimum volume of Tris-NaCl-EDTA (TNE) pad (10 mM Tris/HCl pH 7.5/100 mM NaCl/1 mM EDTA).

The solution is dialyzed against the TNE pad and cesium chloride is added until a density of 1.22 g/$cm^3$ is achieved.

Two successive cycles of isopycnic centrifugation are performed at 15° C. for 24 hours at 40,000 rpm in a 45Ti rotor (Beckman).

The fractions are collected from above and tested for the HBsAg antigen using an ELISA test. The peak fractions are collected and dialyzed at 4° C. against the TNE pad.

The final preparations are analyzed through negative staining electron microscopy and western blot as previously described.

Example 3: Transitory Production of the Wild-Type HBV Envelope Protein S (HBV-S) and the Chimeric HBV-Zika Protein (HBV-Zika-E+S, HBV-Zika-E+M or HBV-Zika-Deleted E+Deleted S) in Clones of the BKH-21 Cellular Line I.1) Construction of the Plasmids pSFV1-prM+E+S and pSFV1-prM+Deleted E+Deleted S The vector pSFV1 (Invitrogen) having a bicistronic structure of 11033 pb is used for the following constructions. This vector has a promoter sequence of SP6-ARN polymerase, inserted in 5' of the first cistron, to initiate the synthesis of a complete RNA with a positive polarity (RNA named 42S(+)) through in-vitro transcription. After transfection into mammal cells, these recombining RNA capped in vitro self-replicate in the presence of the replicase nsP1-4 of the SFV (Semliki Forest Virus) and serve to produce proteins of interest through the intermediate secondary mRNA named 26S(+).

I.1.1) Cloning Sequences of Chimeric Proteins HBV-Zika-prM+E+S and HBV-Zika-prM+Deleted E+Deleted S in the Vector pSFV1

The fragments of hybrid nucleic acid molecules are cloned at the BamHI site of the plasmid pSFV1, previously linearized with this enzyme. The different plasmids comprising the fusion proteins of the invention (notably the plasmids pSFV1-prM+E+S and pSFV1-prM+deleted E+deleted S) are magnified through bacterial transformation, then purified with DNA Maxiprep using phenol/chloroform. The orientation of the insertion is verified through enzyme restriction and all of the constructions are verified through sequencing.

I.2) Obtaining of the Transitorily Transfected Cells by the RNA of Different Constructions Derived from the SFV The newborn hamster kidney cell (BHK-21) culture procedures as well as the in-vitro transcription protocols of the matrix plasmids SFV and the transfection plasmids of the self-replicating recombining RNA are identical to those previously described [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8):3842-51]. The construction pSFV—HBV—S, expressing the wild-type HBV protein S and previously described in the aforementioned article, was used as a control.

I.3) Analysis of the Intracellular Production of the Wild-Type and Chimeric Envelope Proteins The procedures for the biochemical analysis of the proteins of interest (notably HBV—S, HBV-Zika-E+S and HBV-Zika-deleted E+deleted S, HBV-Zika-E+M, etc.) through confocal microscopy immunofluorescence and western blot, the procedures for the ultrastructural analysis of the transfected cells with transmission electron microscopy as well as the procedures for the quantification (ELISA)/purification (sucrose gradient then dialysis) of the subviral particles of chimeric envelope HBV-Zika (HBV-Zika-E+S, HBV-Zika-deleted E+deleted S, HBV-Zika-E+M) are those previously described [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8):3842-51].

The proteins HBV-S, HBV-Zika-E+S, HBV-Zika-deleted E+deleted S were detected with the anti-HBV-S antibody 70-HG15 (interchim), the anti-Zika antibody D1-4G2-15 (millipore) for western blog analyses. The proteins HBV-S, HBV-Zika-E+S, HBV-Zika-deleted E+deleted S were detected with the anti-HBV-S antibody ADRI-2F3 (Cerino A. et al., 2015, 10(4): e0125704) and the anti-Zika antibody D1-4G2-15 for immunofluorescence analyses.

I.4) Analysis of the Culture Supernatant

After transfection, the culture supernatant of approximately $10^7$ transfected cells is cleared via centrifugation for 10 minutes at 1500 g then ultracentrifuged at 4° C. for 16 hours at 35,000 rpm using an SW41 rotor (L70 Ultracentrifuge, Beckman). The residue is resuspended with 50 μL of the lysis pad, then analyzed with a western blot.

I.5) Production of the Fusion Proteins HBV-Zika-E+S and HBV-Zika-Deleted E+Deleted S of the Invention Sixteen hours after the transfection by the SFV RNA comprising the hybrid nucleic acid molecules of the invention and transcribed from the plasmids pSFV1-prM+E+S and pSFV1-prM+deleted E+deleted S, the BHK-21 cells were lysed then analyzed with a western blot using the antibodies D1-4G2-4-15 and 70-HG15. After transitory production in the BHK-21 cell, the size of the fusion proteins HBV-Zika-E+S and HBV-Zika-deleted E+deleted S is detected at around 80 kD for the protein HBV-Zika-E+S and at around 75 kD for the protein HBV-Zika-deleted E+deleted S, i.e. precisely at the sizes corresponding to those theoretically determined. These results show, moreover, that the cleavage between prM and the chimeric proteins is efficacious. Furthermore, the perfect co-localization of the immunofluorescence signals obtained through the detection of said fusion proteins of the invention with the anti-HBV-S antibody ADRI-2F3 and anti-Zika antibody D1-4G2-15 show that they are correctly produced in the cells and do not or only slightly undergo internal cleavage to their sequence after their translation (FIGS. 23, 24, 25A and B and 26).

To restore the secretion abilities of the different fusion proteins of the invention (HBV-Zika-E+S and HBV-Zika-deleted E+deleted S), co-transfections are performed by providing the wild-type form of the protein HBV-S in trans to each of the fusion proteins of the invention (HBV-Zika-E+S and HBV-Zika-deleted E+deleted S). Sixteen hours after the transfection, the co-transfected cells are crushed and the intracellular subviral particles were purified through a sucrose gradient then affinity chromatography [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8):3842-51]. After detection through specific ELISA of the protein HBV-S and collection of the fractions enriched in subviral particles (FIG. 27), these particles are studied with a western blot using the anti-HBS antibody (70-HG-15) and electron microscopy with, if necessary, immunodetection using the antibody D1-4G2-1. The antibodies are as previously described in the example 1.3 (FIGS. 26, 28 and 29).

The transmission electron microscopy images show that in all these experiments co-producing the wild-type protein HBV-S with one of the fusion proteins from the invention (HBV-Zika-E+S and HBV-Zika-deleted E+deleted S), it is possible to produce a significant quantity of spherical and filamentous subviral particles (FIG. 28). The western blot analyses show that these more or less filamentous subviral particles are rich in fusion proteins from the invention (HBV-Zika-E+S, HBV-Zika-deleted E+deleted S), which is confirmed, moreover, by the anti-Zika immunostaining (immunogold) specifically observed on the negative stainings presented in FIG. 29.

The implementation of the present invention in an "SFV" system shows that the fusion proteins of the invention (HBV-Zika-E+S and HBV-Zika-deleted E+deleted S) containing nearly all or all of the protein E of the Zika virus gather into chimeric subviral particles of the same type as the subviral particles used in the production of vaccines against hepatitis B, thus facilitating the purification of said chimeric subviral particles from the invention and potentially the development of an industrial application of a vaccine against the Zika virus in perfect harmony with that of the vaccine against the HBV.

Example 4: Obtaining of Subviral Envelope Particles from the Zika Virus in a Lentiviral System Chinese hamster ovary cells (CHO) are stably transduced using a strategy based on the lentiviral expression vector pHR' (described by Dull et al., A third-generation lentivirus vector with a conditional packaging system, 1998, Journal of Virology, vol. 72, pp 8463-8471). The strategy based on the lentiviral expression vector pHR' was described in the article Patient et al., Chimeric Hepatitis B and C viruses envelope proteins can form subviral particles: implications for the design of new vaccine strategies, 2009, New Biotechnology, vol. 25, no. 4, pp 226-234.

The DNA sequence of the chimeric envelope proteins HBV-Zika (prM+E+S, prM+E+M or prM+deleted E+deleted S) is introduced at the restriction site BamH1 of the linearized plasmid pHR,$^{puro}$ (constructed from the plasmid pHR', and coding the puromycin as a selection gene) to generate the chimeric plasmids pHR'$^{puro}$-HBV-Zika (pHR'$^{puro}$-HBV-prM+E+S, pHR'$^{puro}$-HBV-prM+deleted E+deleted S and pHR'$^{puro}$-HBV-prM+E+M). The lentiviruses are produced in the HEK-293T cells (human embryo kidney cells) and kept in the Dulbecco's Modified Eagle Medium (DMEM).

Twenty-four hours before transfection, $3\times10^6$ cells are used to inoculate a culture dish measuring 75 $cm^2$ (Falcon®). The cells are transfected with an equimolar mixture (1 pmol of each) of chimeric plasmid pHR'Puro_HBV-Zika (pHR'$^{puro}$-HBV-prM+E+S, pHR'$^{puro}$-HBV-prM+deleted E+deleted S and pHR'$^{puro}$-HBV-prM+E+M), of plasmid pHCMVG (referenced in the ATCC under the reference pHCMV-G (ATCC® 754971) coding the VSV-G (envelope glycoprotein of the vesicular stomatitis virus) and the encapsidation construction pCMVR8.74 (Addgene, reference #22036) using the calcium phosphate method.

The following day, the transfection solution is eliminated and replaced by a fresh complete medium.

After 24 and 48 hours of culture, the supernatant is collected, filtered through a low protein binding filter with pores measuring 0.45 μm (Sartorius) and concentrated through centrifugation on a 20% saccharose cushion at 4° C. for 90 minutes at 26,000×g.

The residue is resuspended in 500 μL of PBS and stored at −80° C. until use.

The transduction unit (TU) titer is determined by quantifying the protein p24 (Innotest® HIV Antigen mAb Kit, Innogenetics).

The clone CHO-S (stably producing the protein HBV-S, previously described in the article Patient et al., Chimeric Hepatitis B and C viruses envelope proteins can form subviral particles: implications for the design of new vaccine strategies, 2009, New Biotechnology, vol. 25, no. 4, pp 226-234), cultivated in the medium DMEM-F12 (commercialized by Fisher Scientific), is transduced with the recombining lentivectors chimeric HR'$^{puro}$-HBV-Zika (obtained from the plasmids pHR'$^{puro}$-HBV-prM+E+S, pHR'$^{puro}$-HBV-prM+deleted E+deleted S and pHR'$^{puro}$-HBV-prM+E+M).

One day before transduction, $10^5$ CHO-S cells/well are used to inoculate a six-well cellular culture plate (Falcon®).

The cells are incubated with the vectors chimeric pHR'$^{puro}$-HBV-Zika defined above (infection multiplicity: 2.5) and 4 μg/mL of polybrene (Sigma) in the fresh complete medium.

Three days after transduction, the cells are used to inoculate a 96-well cellular culture plate (Falcon®) with a density of 1 cell/well.

The plates are incubated for 3 weeks with puromycin selection (2.5 μg/ml at the end in the culture supernatant).

The cellular clones from the puromycin selection, named CHO-S+Zika-prM+E+S, CHO-S+Zika-prM+deleted E+deleted S or CHO-S+Zika-prM+E+M are isolated and amplified. The expression of HBV-S and chimeric HBV-Zika (HBV-Zika+E+S, HBV-Zika-deleted E+deleted S and HBV-Zika-E+M) is analyzed using immunofluorescence with a human monoclonal anti-HBs antibody and an anti-Zika antibody, as described in example 1.3.

The intracellular production of the proteins HBV-S and chimeric HBV-Zika (HBV-Zika-E+S, HBV-Zika-deleted E+deleted S and HBV-Zika-E+M) is analyzed with a western blot of the cellular lysates, as previously described in the article Patient et al., Chimeric Hepatitis B and C viruses envelope proteins can form subviral particles: implications for the design of new vaccine strategies, 2009, New Biotechnology, vol. 25, no. 4, pp 226-234.

The membranes are incubated for one night at 4° C. with an anti-HBV-S antibody (70-HG15) or the monoclonal antibody directed at the Zika envelope protein (D1-4G2-4-15). The sizes of the fusion proteins HBV-Zika-E+S and HBV-Zika-deleted E+deleted S are approximately 80 kD for the protein HBV-Zika-E+S and approximately 75 kD for the protein HBV-Zika-deleted E+deleted S and 85 kD for the protein HBV-Zika-E+M. These results show, moreover, that the cleavage between prM and the chimeric proteins is efficacious. The protein HBV-S presents two sizes based on its level of glycosylation, one shape of 24 kD (non-glycosylated) and one of 27 kD (glycosylated). These results, correlated with the intense immunofluorescence obtained through the detection of said fusion proteins from the invention with the anti-HBV-S antibody (ADRI-2F3) show that they are correctly produced (FIG. 30).

Example 5: Analysis of the Supernatant of Cells Stably Coproducing the Envelope Proteins HBV-S and Chimeric HBV-Zika (HBV-Zika-E+S, HBV-Zika-E+M or HBV-Zika-Deleted E+Deleted S)

The supernatant is collected, filtered through a low protein binding filter with pores measuring 0.45 μm (Sartorius) and concentrated through centrifugation on a 20% saccharose cushion at 4° C. for 90 minutes at 26,000×g. The residue is resuspended in a minimum volume of PBS then undergoes a western blot analysis. The incubation of the antibody 70-HG15 shows that the chimeric proteins HBV- Zika are detected and consequently have co-assembled with the protein HBV-S into subviral particles (FIG. 31).

Example 6: Analysis of the Intracellular and Extracellular Production of Chimeric Envelope Proteins The procedures for the biochemical analysis of the proteins of interest (notably HBV-Zika-E+S, HBV-Zika-deleted E+deleted S and HBV-Zika-E+M) through confocal microscopy immunofluorescence and western blot, the procedures for the ultrastructural analysis of the transfected cells with transmission electron microscopy as well as the procedures for the quantification (ELISA)/purification (sucrose gradient then affinity chromatography) of the subviral particles of chimeric envelope HBV-Zika (HBV-Zika-E+S, HBV-Zika-deleted E+deleted S and HBV-Zika-E+M) are evaluated for their reactivity towards anti-Zika envelope antibodies. For example, the antibodies commercialized by Biofront Technologies (http://www.biofronttech.com/), like the antibodies from family 1176 (1176-46, 1176-56, 1176-66, 1176-76, 1176-86), or the antibodies 7E5 or 7G6 are used for qualitative analyses (immunofluorescence, immunomicroscopy, electronic/immunogold), qualitative and semi-qualitative analyses using western blot tests (analysis of the size of the proteins of interest and their production level) and quantitative analysis using a sandwich ELISA test allowing the quantity of proteins of interest secreted in the culture supernatant to be determined. The detection of the dimeric conformation of the protein sequence of the Zika envelope is evaluated through immunofluorescence detection using specific reference antibodies 747(4)B7, 752-2C8, 753(3) C10 and 747(4)A11 commercialized by the company Absolute antibody (http://absoluteantibody.com). The detection of the protein prM in the cells producing the chimeric proteins or in the subviral chimeric envelope particles of chimeric HBV-Zika is notably evaluated with the antibody GTX133305 commercialized by GeneTex (http://www-.genetex.com).

Example 7: Immunization Assay in Small Animals and Analysis of the Immune Response A. Immunization Protocol Immunizations are performed in GLP conditions (good laboratory practices). The New Zealand rabbits are naïve of all experimental protocols, in particular any previous immunization test. They are young and female, with homogeneous ages and weights. The animals are monitored with a daily clinical examination, monitoring of their mortality and weekly weighing.

Batches of six animals are immunized for each vaccine preparation comprising the chimeric HBV-Zika proteins (HBV-Zika-E+M), HBV-Zika-E+S and HBV-Zika-deleted E+deleted S). A batch of 6 animals is used as a control, 3 animals receiving only the adjuvant and three animals receiving the control vaccine constituted of a commercial anti-HBV vaccine (preparation with only HBV-S protein). The injection is performed subcutaneously with a maximum volume not exceeding 1 ml.

The vaccination schema comprises an initial injection on day 0 (D0) followed by two boosters on days D14 and D28. Three blood samples of at least 5 ml are taken from the animals before each injection; the sample on D0 is used as a negative control before immunization (pre-immune serum).

To complete the study of the immune response development kinetics, samples are taken on D42, D56 and D70. The two animals in each batch that respond best to the anti-Zika and/or anti-HBV-S antibodies receive a fourth vaccine injection on D70, then are exsanguinated on D85.

B. Analyses of the Anti-Zika and Anti-HBV Immune Response Induced in the Small Animal The analysis of the immune response takes place in vitro using standardized productions of authentic Zika virus. The cross-neutralization with other flaviviruses is measured in the same way with preparations of authentic dengue and West Nile viruses.

1. Production of Standardized Batches of Zika, Dengue and West Nile Viruses on Vero Cells These three viruses are produced in a BSL3 environment (Biosafety level 3). The Vero line (ATCC® CCL81™) is infected with each of the three viruses and the culture supernatants containing the virus are collected at different times ranging from 3 days (Zika virus), 4 days (West Nile virus) to 7 days for the dengue virus. For example, in the case of the Zika virus, the strain H/PF/2013 (genbank accession number: KJ776791) is used to infect sub confluent cells due to an MOI (multiplicity of infection) of 0.01 in the DMEM deprived of fetal bovine serum (FBS). After 24 h, the culture mediums are replaced by a complete nutritive medium (notably comprising 10% FBS). After 3 days of culture, the supernatants of these cells are collected, then clarified with centrifugation at 300×g, and finally possibly ultracentrifuged on a saccharose gradient. The viral titers are determined with the cellular method (determination of the viral dose infecting 50% of the cellular tissues; $TCID5_0$), according to the method described by Spearman-Karber (Kärber, G. Archiv f. experiment. Pathol. u. Pharmakol. 1931; 162: 480), possibly completed with a specific quantitative method Q-RT-PCR.

2. Kinetics Analysis of the Reactivity of the Antibodies Induced in the Small Animal.

The serums of the animals before and after immunization are dosed with the ELISA method to determine their reactivity to the Zika virus. For this, the ELISA anti-Zika virus test kit (IgA/IgG/IgM), commercialized by EUROIMMUN (euroimmun.com) is used to immunocapture anti-Zika antibodies in rabbits, which are then revealed using an anti-rabbit antibody coupled with peroxidase. The colorimetric revelation and the reading of the optical density (OD) allow the evolution of this anti-Zika response to be compared over time (D14 and D28, D42, D56, D70). The pre-immune serums as well as the serums of animals vaccinated only with the adjuvant or the anti-HBV commercial specialty are used as controls.

All of the rabbit serums are also dosed for their anti-HBV reactivity. This is achieved using the commercial anti-HBs Architect System kit (Abbott laboratories).

3. Analysis of the Neutralizing Ability of the Antibodies Induced in the Small Animal Against the Zika Virus Infection Vero cells naïve of all infection are inoculated 24 h before infection onto a 96-well plate at $2\times10^3$ cells/well. Before infection, serum dilutions (e.g. 1/5, 1/25, 1/125, 1/625 and 1/3125) are incubated with constant virus quantities ($1\times10^3$) produced according to paragraph 1 for one hour at 37° C. These serum+virus mixtures are then deposited on the naïve Vero cells and then cultured for 72 h. For each of the infection conditions with virus+serum dilution mixtures, the effective infection of the cell layer is measured through visual determination of the cytopathogenic effect (presence of cell lysis plaques). The results of three independent experiments are then considered to determine the neutralization percentage. This neutralization percentage, determined for each serum dilution, is defined according to the following method: 100% neutralization is determined when no lysis plaque is detected in any of the wells for a single dilution; 50% neutralization corresponds to the identification of lysis plaques in 50% of the wells. When all of the wells present lysis plaques, the neutralization percentage is 0%. For these experiments, different controls are implemented, like virus pre-incubation in the presence of pre-immune serums, virus pre-incubation with the serums of rabbits immunized only with the adjuvant and infection of the cell layer with the virus in the absence of pre-incubation with rabbit serums.

The invention claimed is:

1. An immunogenic fusion protein comprising at least two peptides:

a) on the C-terminal side, a first peptide which consists of:

an amino acid sequence of the protein S or the protein M of a human hepatitis B virus (HBV) isolate, wherein the sequence of the protein S is chosen from the group consisting of SEQ ID NO: 1 and 2, and the sequence of the protein M is chosen from the group consisting of SEQ ID NO: 3 and 4, or an amino acid sequence with a percent identity of at least 95% with said amino acid sequence of the protein S or the protein M, provided that said amino acid sequence maintains the ability to form subviral, non-infectious particles and/or immunogenic properties against the HBV virus, or, and b) on the N-terminal side, a second peptide which consists of:

a sequence of amino acids comprising at least one transmembrane domain and the ectodomain of at least one protein of a Zika virus isolate, or an amino acid sequence with a percent identity of at least 95% with said amino acid sequence of at least one transmembrane domain and the ectodomain of at least one protein of a Zika virus isolate, provided that said amino acid sequence maintains the ability to form subviral, non-infectious particles and/or immunogenic properties against the Zika virus, said protein of a Zika virus isolate being chosen from among the envelope protein E represented by SEQ ID NO. 15 or a fusion peptide comprising the envelope protein E and the protein prM represented by SEQ ID NO. 50.

2. An immunogenic fusion protein according to claim 1, wherein the first peptide located on the C-terminal side thereof consists of:

the amino acid sequence of the protein S of a human HBV isolate, wherein the sequence of the protein S is represented by of SEQ ID NO: 1, or an amino acid sequence presenting a percent identity of at least 95% with said amino acid sequence of the protein S represented by of SEQ ID NO: 1, provided that said amino acid sequence maintains the ability to form subviral, non-infectious particles and/or the immunogenic properties against the human HBV.

3. An immunogenic fusion protein according to claim 1, wherein the first peptide located on the C-terminal side thereof consists of:

the amino acid sequence of the protein S of a human HBV isolate, wherein the sequence of the protein S is represented by of SEQ ID NO: 2, or an amino acid sequence presenting a percent identity of at least 95% with said amino acid sequence of the protein S represented by of SEQ ID NO: 2, provided that said amino acid sequence maintains the ability to form subviral, non-infectious particles and/or the immunogenic properties against the human HBV.

4. An immunogenic fusion protein according to claim 1, wherein the first peptide located on the C-terminal side thereof consists of:

the amino acid sequence of the protein M of a human HBV isolate, wherein the sequence of the protein M is represented by of SEQ ID NO: 3, or an amino acid sequence presenting a percent identity of at least 95% with said amino acid sequence of the protein M deleted from a sequence of 1 to 54 amino acids located at the N-terminal end thereof, provided that said amino acid sequence maintains the ability to form subviral, non-infectious particles and/or the immunogenic properties against the human HBV.

5. An immunogenic fusion protein according to claim 1, wherein the first peptide located on the C-terminal side thereof consists of:

the amino acid sequence of the protein M of a human HBV isolate, wherein the sequence of the protein M is represented by of SEQ ID NO: 4, or an amino acid sequence presenting a percent identity of at least 95% with said amino acid sequence of the protein M not deleted from a sequence of 1 to 54 amino acids located at the N-terminal end thereof, provided that said amino acid sequence maintains the ability to form subviral, non-infectious particles and/or the immunogenic properties against the human HBV.

6. An immunogenic fusion protein according to claim 1, wherein the second peptide located on the N-terminal side thereof consists of:

the amino acid sequence of at least one transmembrane domain and the ectodomain of the envelope protein E of a Zika virus isolate, or an amino acid sequence presenting an identity percent of at least 95%, with said amino acid sequence of at least one transmembrane domain and the ectodomain of the envelope protein E of a Zika virus isolate, provided that said amino acid sequence maintains the ability to form subviral, non-infectious particles and/or the immunogenic properties against the Zika virus.

7. An immunogenic fusion protein according to claim 1, wherein the second peptide located on the N-terminal side thereof consists of:

the amino acid sequence of a fusion peptide comprising at least one transmembrane domain and the ectodomain of the envelope protein E of a Zika virus isolate and the protein prM of a Zika virus isolate, wherein said amino acid sequence is chosen from among the envelope protein E represented by SEQ ID NO. 15 or a fusion peptide comprising the envelope protein E and the protein prM represented by SEQ ID NO. 50, or an amino acid sequence presenting an identity percent of at 95%, with said amino acid sequence of said fusion peptide, provided that said amino acid sequence maintains the ability to form subviral, non-infectious particles and/or the immunogenic properties against the Zika virus.

8. An immunogenic fusion protein according to claim 1, wherein said fusion protein comprises:

the amino acid sequence represented by:

SEQ ID NO. 7 or SEQ ID NO. 17, or
SEQ ID NO. 8 or SEQ ID NO. 18, or
SEQ ID NO. 9 or SEQ ID NO. 19, or
SEQ ID NO. 10 or SEQ ID NO. 20, or
SEQ ID NO. 11 or SEQ ID NO. 21, or
SEQ ID NO. 12 or SEQ ID NO. 22, or
SEQ ID NO. 13 or SEQ ID NO. 23, or
SEQ ID NO. 14 or SEQ ID NO. 24, or an amino acid sequence presenting an identity percent of at least 95% with said SEQ ID NO. 7, SEQ ID NO. 17, SEQ ID NO. 8, SEQ ID NO. 18, SEQ ID NO. 9, SEQ ID NO. 19, SEQ ID NO. 10, SEQ ID NO. 20, SEQ ID NO. 11, SEQ ID NO. 21, SEQ ID NO. 12, SEQ ID NO. 22, SEQ ID NO. 13, SEQ ID NO. 23, SEQ ID NO. 14, SEQ ID NO. 24, provided that said amino acid sequence maintains the ability to form subviral, non-infectious particles and/or the immunogenic properties against the human HBV and/or the Zika virus, or the amino acid sequence of a synthetic variant derived from said SEQ ID NO. 7, SEQ ID NO. 17, SEQ ID NO. 8, SEQ ID NO. 18, SEQ ID NO. 9, SEQ ID NO. 19, SEQ ID NO. 10, SEQ ID NO. 20, SEQ ID NO. 11, SEQ ID NO. 21, SEQ ID NO. 12, SEQ ID NO. 22, SEQ ID NO. 13, SEQ ID NO. 23, SEQ ID NO. 14, SEQ ID NO. 24, provided that said amino acid sequence maintains the ability to form subviral, non-infectious particles and/or the immunogenic properties against the human HBV and/or the Zika virus.

9. Nucleic acid molecules coding a fusion protein according to claim 1.

10. A subviral, non-infectious and immunogenic particle comprising the following proteins:

a protein comprising the wild-type domain S of the surface antigen of a hepatitis B virus isolate, and the fusion protein according to claim 1.

11. An immunogenic fusion protein according to claim 1, for its use as a medication, notably as a vaccine.

12. An immunogenic fusion protein according to claim 1, for its use in preventing and/or treating hepatitis B and/or Zika virus infections.

13. An immunogenic fusion protein according to claim 1, wherein the second peptide located on the N-terminal side thereof consists of:

the sequence of amino acids of at least one transmembrane domain chosen from the group consisting of the amino acid sequences between positions 456-484 of SEQ ID NO: 15, 485-504 of SEQ ID NO: 15, 124-143 of SEQ ID NO: 50, and 150-164 of SEQ ID NO: 50, and the amino acid sequence of the ectodomain chosen from the group consisting of the amino acid sequences between positions 1-455 of SEQ ID NO: 15 and 1-123 of SEQ ID NO: 50 of at least one protein of a Zika virus isolate, or an amino acid sequence with a percent identity of at least 95% with said amino acid sequence of at least one transmembrane domain and the ectodomain of at least one protein of a Zika virus isolate, provided that said amino acid sequence maintains the ability to form subviral, non-infectious particles and/or immunogenic properties against the Zika virus, said protein of a Zika virus isolate being chosen from among the envelope protein E represented by SEQ ID NO. 15 and a fusion peptide comprising the envelope protein E and the protein prM represented by SEQ ID NO. 50.

* * * * *

SEQUENCE LISTING

<160> NUMBER OF SEQ ID NOS: 59

<210> SEQ ID NO 1
<211> LENGTH: 203
<212> TYPE: PRT
<213> ORGANISM: Artificial sequence
<220> FEATURE:
<223> OTHER INFORMATION: S deleted

<400> SEQUENCE: 1

Arg Ile Leu Thr Ile Pro Gln Ser Leu Asp Ser Trp Trp Thr Ser Leu
1 5 10 15

Asn Phe Leu Gly Gly Ser Pro Val Cys Leu Gly Gln Asn Ser Gln Ser
20 25 30

Pro Thr Ser Asn His Ser Pro Thr Ser Cys Pro Pro Ile Cys Pro Gly
35 40 45

Tyr Arg Trp Met Cys Leu Arg Arg Phe Ile Ile Phe Leu Phe Ile Leu
50 55 60

Leu Leu Cys Leu Ile Phe Leu Leu Val Leu Leu Asp Tyr Gln Gly Met
65 70 75 80

Leu Pro Val Cys Pro Leu Ile Pro Gly Ser Thr Thr Thr Ser Thr Gly
85 90 95

Pro Cys Lys Thr Cys Thr Thr Pro Ala Gln Gly Asn Ser Met Phe Pro
100 105 110

Ser Cys Cys Cys Thr Lys Pro Thr Asp Gly Asn Cys Thr Cys Ile Pro
115 120 125

Ile Pro Ser Ser Trp Ala Phe Ala Lys Tyr Leu Trp Glu Trp Ala Ser
130 135 140

Val Arg Phe Ser Trp Leu Ser Leu Leu Val Pro Phe Val Gln Trp Phe
145 150 155 160

Val Gly Leu Ser Pro Thr Val Trp Leu Ser Ala Ile Trp Met Met Trp
165 170 175

Tyr Trp Gly Pro Ser Leu Tyr Ser Ile Val Ser Pro Phe Ile Pro Leu
180 185 190

Leu Pro Ile Phe Phe Cys Leu Trp Val Tyr Ile
195 200

<210> SEQ ID NO 2
<211> LENGTH: 226
<212> TYPE: PRT
<213> ORGANISM: Hepatitis B virus

<400> SEQUENCE: 2

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Ser Pro Val Cys
35 40 45

Leu Gly Gln Asn Ser Gln Ser Pro Thr Ser Asn His Ser Pro Thr Ser
50 55 60

-continued

```
Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225


<210> SEQ ID NO 3
<211> LENGTH: 227
<212> TYPE: PRT
<213> ORGANISM: Artificial sequence
<220> FEATURE:
<223> OTHER INFORMATION: M deleted

<400> SEQUENCE: 3

Asn Met Glu Asn Ile Thr Ser Gly Phe Leu Gly Pro Leu Leu Val Leu
1               5                   10                  15

Gln Ala Gly Phe Phe Leu Leu Thr Arg Ile Leu Thr Ile Pro Gln Ser
            20                  25                  30

Leu Asp Ser Trp Trp Thr Ser Leu Asn Phe Leu Gly Gly Ser Pro Val
        35                  40                  45

Cys Leu Gly Gln Asn Ser Gln Ser Pro Thr Ser Asn His Ser Pro Thr
    50                  55                  60

Ser Cys Pro Pro Ile Cys Pro Gly Tyr Arg Trp Met Cys Leu Arg Arg
65                  70                  75                  80

Phe Ile Ile Phe Leu Phe Ile Leu Leu Leu Cys Leu Ile Phe Leu Leu
                85                  90                  95

Val Leu Leu Asp Tyr Gln Gly Met Leu Pro Val Cys Pro Leu Ile Pro
            100                 105                 110

Gly Ser Thr Thr Thr Ser Thr Gly Pro Cys Lys Thr Cys Thr Thr Pro
        115                 120                 125

Ala Gln Gly Asn Ser Met Phe Pro Ser Cys Cys Cys Thr Lys Pro Thr
    130                 135                 140

Asp Gly Asn Cys Thr Cys Ile Pro Ile Pro Ser Ser Trp Ala Phe Ala
145                 150                 155                 160

Lys Tyr Leu Trp Glu Trp Ala Ser Val Arg Phe Ser Trp Leu Ser Leu
                165                 170                 175

Leu Val Pro Phe Val Gln Trp Phe Val Gly Leu Ser Pro Thr Val Trp
            180                 185                 190
```

```
Leu Ser Ala Ile Trp Met Met Trp Tyr Trp Gly Pro Ser Leu Tyr Ser
        195                 200                 205

Ile Val Ser Pro Phe Ile Pro Leu Leu Pro Ile Phe Phe Cys Leu Trp
    210                 215                 220

Val Tyr Ile
225


<210> SEQ ID NO 4
<211> LENGTH: 281
<212> TYPE: PRT
<213> ORGANISM: hepatitis B virus

<400> SEQUENCE: 4

Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ser Pro Val Cys Leu Gly Gln Asn Ser Gln Ser Pro Thr
            100                 105                 110

Ser Asn His Ser Pro Thr Ser Cys Pro Pro Ile Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Asn Ser Met Phe Pro Ser Cys
            180                 185                 190

Cys Cys Thr Lys Pro Thr Asp Gly Asn Cys Thr Cys Ile Pro Ile Pro
        195                 200                 205

Ser Ser Trp Ala Phe Ala Lys Tyr Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Ala Ile Trp Met Met Trp Tyr Trp
                245                 250                 255

Gly Pro Ser Leu Tyr Ser Ile Val Ser Pro Phe Ile Pro Leu Leu Pro
            260                 265                 270

Ile Phe Phe Cys Leu Trp Val Tyr Ile
        275                 280


<210> SEQ ID NO 5
<211> LENGTH: 484
<212> TYPE: PRT
<213> ORGANISM: Artificial sequence
<220> FEATURE:
<223> OTHER INFORMATION: E deleted
```

<400> SEQUENCE: 5

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg

-continued 405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Ala Lys
465 470 475 480

Asn Gly Ser Asp

<210> SEQ ID NO 6
<211> LENGTH: 648
<212> TYPE: PRT
<213> ORGANISM: Artificial sequence
<220> FEATURE:
<223> OTHER INFORMATION: prM + E deleted

<400> SEQUENCE: 6

Arg Arg Gly Ser Ala Tyr Tyr Met Tyr Leu Asp Arg Asn Asp Ala Gly
1 5 10 15

Glu Ala Ile Ser Phe Pro Thr Thr Leu Gly Met Asn Lys Cys Tyr Ile
20 25 30

Gln Ile Met Asp Leu Gly His Thr Cys Asp Ala Thr Met Ser Tyr Glu
35 40 45

Cys Pro Met Leu Asp Glu Gly Val Glu Pro Asp Asp Val Asp Cys Trp
50 55 60

Cys Asn Thr Thr Ser Thr Trp Val Val Tyr Gly Thr Cys His His Lys
65 70 75 80

Lys Gly Glu Ala Arg Arg Ser Arg Arg Ala Val Thr Leu Pro Ser His
85 90 95

Ser Thr Arg Lys Leu Gln Thr Arg Ser Gln Thr Trp Leu Glu Ser Arg
100 105 110

Glu Tyr Thr Lys His Leu Ile Arg Val Glu Asn Trp Ile Phe Arg Asn
115 120 125

Pro Gly Phe Ala Leu Ala Ala Ala Ala Ile Ala Trp Leu Leu Gly Ser
130 135 140

Ser Thr Ser Gln Lys Val Ile Tyr Leu Val Met Ile Leu Leu Ile Ala
145 150 155 160

Pro Ala Tyr Ser Ile Arg Cys Ile Gly Val Ser Asn Arg Asp Phe Val
165 170 175

Glu Gly Met Ser Gly Gly Thr Trp Val Asp Val Val Leu Glu His Gly
180 185 190

Gly Cys Val Thr Val Met Ala Gln Asp Lys Pro Thr Val Asp Ile Glu
195 200 205

Leu Val Thr Thr Thr Val Ser Asn Met Ala Glu Val Arg Ser Tyr Cys
210 215 220

Tyr Glu Ala Ser Ile Ser Asp Met Ala Ser Asp Ser Arg Cys Pro Thr
225 230 235 240

Gln Gly Glu Ala Tyr Leu Asp Lys Gln Ser Asp Thr Gln Tyr Val Cys
245 250 255

Lys Arg Thr Leu Val Asp Arg Gly Trp Gly Asn Gly Cys Gly Leu Phe
260 265 270

Gly Lys Gly Ser Leu Val Thr Cys Ala Lys Phe Ala Cys Ser Lys Lys
275 280 285

-continued

Met Thr Gly Lys Ser Ile Gln Pro Glu Asn Leu Glu Tyr Arg Ile Met
    290                 295                 300

Leu Ser Val His Gly Ser Gln His Ser Gly Met Ile Val Asn Asp Thr
305                 310                 315                 320

Gly His Glu Thr Asp Glu Asn Arg Ala Lys Val Glu Ile Thr Pro Asn
                325                 330                 335

Ser Pro Arg Ala Glu Ala Thr Leu Gly Gly Phe Gly Ser Leu Gly Leu
            340                 345                 350

Asp Cys Glu Pro Arg Thr Gly Leu Asp Phe Ser Asp Leu Tyr Tyr Leu
        355                 360                 365

Thr Met Asn Asn Lys His Trp Leu Val His Lys Glu Trp Phe His Asp
    370                 375                 380

Ile Pro Leu Pro Trp His Ala Gly Ala Asp Thr Gly Thr Pro His Trp
385                 390                 395                 400

Asn Asn Lys Glu Ala Leu Val Glu Phe Lys Asp Ala His Ala Lys Arg
                405                 410                 415

Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495

Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Asp
                645

<210> SEQ ID NO 7
<211> LENGTH: 686
<212> TYPE: PRT
<213> ORGANISM: Artificial sequence
<220> FEATURE:
<223> OTHER INFORMATION: E deleted + S deleted

<400> SEQUENCE: 7

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Arg Ile Leu Thr Ile Pro Gln Ser Leu Asp Ser Trp Trp
                485                 490                 495

Thr Ser Leu Asn Phe Leu Gly Gly Ser Pro Val Cys Leu Gly Gln Asn
            500                 505                 510

Ser Gln Ser Pro Thr Ser Asn His Ser Pro Thr Ser Cys Pro Pro Ile
        515                 520                 525

Cys Pro Gly Tyr Arg Trp Met Cys Leu Arg Arg Phe Ile Ile Phe Leu
    530                 535                 540

Phe Ile Leu Leu Leu Cys Leu Ile Phe Leu Leu Val Leu Leu Asp Tyr
545                 550                 555                 560

Gln Gly Met Leu Pro Val Cys Pro Leu Ile Pro Gly Ser Thr Thr Thr
                565                 570                 575

Ser Thr Gly Pro Cys Lys Thr Cys Thr Thr Pro Ala Gln Gly Asn Ser
            580                 585                 590

Met Phe Pro Ser Cys Cys Cys Thr Lys Pro Thr Asp Gly Asn Cys Thr
        595                 600                 605

Cys Ile Pro Ile Pro Ser Ser Trp Ala Phe Ala Lys Tyr Leu Trp Glu
    610                 615                 620

Trp Ala Ser Val Arg Phe Ser Trp Leu Ser Leu Leu Val Pro Phe Val
625                 630                 635                 640

Gln Trp Phe Val Gly Leu Ser Pro Thr Val Trp Leu Ser Ala Ile Trp
                645                 650                 655

Met Met Trp Tyr Trp Gly Pro Ser Leu Tyr Ser Ile Val Ser Pro Phe
            660                 665                 670

Ile Pro Leu Leu Pro Ile Phe Phe Cys Leu Trp Val Tyr Ile
        675                 680                 685
```

<210> SEQ ID NO 8
<211> LENGTH: 850
<212> TYPE: PRT
<213> ORGANISM: Artificial sequence
<220> FEATURE:
<223> OTHER INFORMATION: prM + E deleted + S deleted

<400> SEQUENCE: 8

```
Arg Arg Gly Ser Ala Tyr Tyr Met Tyr Leu Asp Arg Asn Asp Ala Gly
1               5                   10                  15

Glu Ala Ile Ser Phe Pro Thr Thr Leu Gly Met Asn Lys Cys Tyr Ile
            20                  25                  30

Gln Ile Met Asp Leu Gly His Thr Cys Asp Ala Thr Met Ser Tyr Glu
        35                  40                  45

Cys Pro Met Leu Asp Glu Gly Val Glu Pro Asp Asp Val Asp Cys Trp
    50                  55                  60

Cys Asn Thr Thr Ser Thr Trp Val Val Tyr Gly Thr Cys His His Lys
65                  70                  75                  80

Lys Gly Glu Ala Arg Arg Ser Arg Arg Ala Val Thr Leu Pro Ser His
                85                  90                  95
```

-continued

```
Ser Thr Arg Lys Leu Gln Thr Arg Ser Gln Thr Trp Leu Glu Ser Arg
            100                 105                 110

Glu Tyr Thr Lys His Leu Ile Arg Val Glu Asn Trp Ile Phe Arg Asn
        115                 120                 125

Pro Gly Phe Ala Leu Ala Ala Ala Ala Ile Ala Trp Leu Leu Gly Ser
    130                 135                 140

Ser Thr Ser Gln Lys Val Ile Tyr Leu Val Met Ile Leu Leu Ile Ala
145                 150                 155                 160

Pro Ala Tyr Ser Ile Arg Cys Ile Gly Val Ser Asn Arg Asp Phe Val
                165                 170                 175

Glu Gly Met Ser Gly Gly Thr Trp Val Asp Val Val Leu Glu His Gly
            180                 185                 190

Gly Cys Val Thr Val Met Ala Gln Asp Lys Pro Thr Val Asp Ile Glu
        195                 200                 205

Leu Val Thr Thr Thr Val Ser Asn Met Ala Glu Val Arg Ser Tyr Cys
    210                 215                 220

Tyr Glu Ala Ser Ile Ser Asp Met Ala Ser Asp Ser Arg Cys Pro Thr
225                 230                 235                 240

Gln Gly Glu Ala Tyr Leu Asp Lys Gln Ser Asp Thr Gln Tyr Val Cys
                245                 250                 255

Lys Arg Thr Leu Val Asp Arg Gly Trp Gly Asn Gly Cys Gly Leu Phe
            260                 265                 270

Gly Lys Gly Ser Leu Val Thr Cys Ala Lys Phe Ala Cys Ser Lys Lys
        275                 280                 285

Met Thr Gly Lys Ser Ile Gln Pro Glu Asn Leu Glu Tyr Arg Ile Met
    290                 295                 300

Leu Ser Val His Gly Ser Gln His Ser Gly Met Ile Val Asn Asp Thr
305                 310                 315                 320

Gly His Glu Thr Asp Glu Asn Arg Ala Lys Val Glu Ile Thr Pro Asn
                325                 330                 335

Ser Pro Arg Ala Glu Ala Thr Leu Gly Gly Phe Gly Ser Leu Gly Leu
            340                 345                 350

Asp Cys Glu Pro Arg Thr Gly Leu Asp Phe Ser Asp Leu Tyr Tyr Leu
        355                 360                 365

Thr Met Asn Asn Lys His Trp Leu Val His Lys Glu Trp Phe His Asp
    370                 375                 380

Ile Pro Leu Pro Trp His Ala Gly Ala Asp Thr Gly Thr Pro His Trp
385                 390                 395                 400

Asn Asn Lys Glu Ala Leu Val Glu Phe Lys Asp Ala His Ala Lys Arg
                405                 410                 415

Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495

Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
```

```
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Arg Ile Leu Thr Ile Pro Gln Ser Leu
                645                 650                 655

Asp Ser Trp Trp Thr Ser Leu Asn Phe Leu Gly Gly Ser Pro Val Cys
            660                 665                 670

Leu Gly Gln Asn Ser Gln Ser Pro Thr Ser Asn His Ser Pro Thr Ser
        675                 680                 685

Cys Pro Pro Ile Cys Pro Gly Tyr Arg Trp Met Cys Leu Arg Arg Phe
    690                 695                 700

Ile Ile Phe Leu Phe Ile Leu Leu Leu Cys Leu Ile Phe Leu Leu Val
705                 710                 715                 720

Leu Leu Asp Tyr Gln Gly Met Leu Pro Val Cys Pro Leu Ile Pro Gly
                725                 730                 735

Ser Thr Thr Thr Ser Thr Gly Pro Cys Lys Thr Cys Thr Thr Pro Ala
            740                 745                 750

Gln Gly Asn Ser Met Phe Pro Ser Cys Cys Cys Thr Lys Pro Thr Asp
        755                 760                 765

Gly Asn Cys Thr Cys Ile Pro Ile Pro Ser Ser Trp Ala Phe Ala Lys
    770                 775                 780

Tyr Leu Trp Glu Trp Ala Ser Val Arg Phe Ser Trp Leu Ser Leu Leu
785                 790                 795                 800

Val Pro Phe Val Gln Trp Phe Val Gly Leu Ser Pro Thr Val Trp Leu
                805                 810                 815

Ser Ala Ile Trp Met Met Trp Tyr Trp Gly Pro Ser Leu Tyr Ser Ile
            820                 825                 830

Val Ser Pro Phe Ile Pro Leu Leu Pro Ile Phe Phe Cys Leu Trp Val
        835                 840                 845

Tyr Ile
    850


<210> SEQ ID NO 9
<211> LENGTH: 729
<212> TYPE: PRT
<213> ORGANISM: Artificial sequence
<220> FEATURE:
<223> OTHER INFORMATION: E + S

<400> SEQUENCE: 9

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

-continued

```
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala Glu Asn Ile Thr Ser Gly Phe Leu
            500                 505                 510

Gly Pro Leu Leu Val Leu Gln Ala Gly Phe Phe Leu Leu Thr Arg Ile
        515                 520                 525

Leu Thr Ile Pro Gln Ser Leu Asp Ser Trp Trp Thr Ser Leu Asn Phe
    530                 535                 540

Leu Gly Gly Ser Pro Val Cys Leu Gly Gln Asn Ser Gln Ser Pro Thr
545                 550                 555                 560

Ser Asn His Ser Pro Thr Ser Cys Pro Pro Ile Cys Pro Gly Tyr Arg
                565                 570                 575

Trp Met Cys Leu Arg Arg Phe Ile Ile Phe Leu Phe Ile Leu Leu Leu
            580                 585                 590

Cys Leu Ile Phe Leu Leu Val Leu Leu Asp Tyr Gln Gly Met Leu Pro
        595                 600                 605

Val Cys Pro Leu Ile Pro Gly Ser Thr Thr Thr Ser Thr Gly Pro Cys
    610                 615                 620

Lys Thr Cys Thr Thr Pro Ala Gln Gly Asn Ser Met Phe Pro Ser Cys
625                 630                 635                 640

Cys Cys Thr Lys Pro Thr Asp Gly Asn Cys Thr Cys Ile Pro Ile Pro
                645                 650                 655

Ser Ser Trp Ala Phe Ala Lys Tyr Leu Trp Glu Trp Ala Ser Val Arg
            660                 665                 670

Phe Ser Trp Leu Ser Leu Leu Val Pro Phe Val Gln Trp Phe Val Gly
        675                 680                 685

Leu Ser Pro Thr Val Trp Leu Ser Ala Ile Trp Met Met Trp Tyr Trp
    690                 695                 700

Gly Pro Ser Leu Tyr Ser Ile Val Ser Pro Phe Ile Pro Leu Leu Pro
705                 710                 715                 720

Ile Phe Phe Cys Leu Trp Val Tyr Ile
                725
```

<210> SEQ ID NO 10
<211> LENGTH: 893
<212> TYPE: PRT
<213> ORGANISM: Artificial sequence
<220> FEATURE:
<223> OTHER INFORMATION: prM + E + S

<400> SEQUENCE: 10

```
Arg Arg Gly Ser Ala Tyr Tyr Met Tyr Leu Asp Arg Asn Asp Ala Gly
1               5                   10                  15

Glu Ala Ile Ser Phe Pro Thr Thr Leu Gly Met Asn Lys Cys Tyr Ile
            20                  25                  30

Gln Ile Met Asp Leu Gly His Thr Cys Asp Ala Thr Met Ser Tyr Glu
        35                  40                  45

Cys Pro Met Leu Asp Glu Gly Val Glu Pro Asp Asp Val Asp Cys Trp
    50                  55                  60

Cys Asn Thr Thr Ser Thr Trp Val Val Tyr Gly Thr Cys His His Lys
65                  70                  75                  80
```

-continued

```
Lys Gly Glu Ala Arg Arg Ser Arg Arg Ala Val Thr Leu Pro Ser His
                85                  90                  95

Ser Thr Arg Lys Leu Gln Thr Arg Ser Gln Thr Trp Leu Glu Ser Arg
            100                 105                 110

Glu Tyr Thr Lys His Leu Ile Arg Val Glu Asn Trp Ile Phe Arg Asn
        115                 120                 125

Pro Gly Phe Ala Leu Ala Ala Ala Ala Ile Ala Trp Leu Leu Gly Ser
    130                 135                 140

Ser Thr Ser Gln Lys Val Ile Tyr Leu Val Met Ile Leu Leu Ile Ala
145                 150                 155                 160

Pro Ala Tyr Ser Ile Arg Cys Ile Gly Val Ser Asn Arg Asp Phe Val
                165                 170                 175

Glu Gly Met Ser Gly Gly Thr Trp Val Asp Val Val Leu Glu His Gly
            180                 185                 190

Gly Cys Val Thr Val Met Ala Gln Asp Lys Pro Thr Val Asp Ile Glu
        195                 200                 205

Leu Val Thr Thr Thr Val Ser Asn Met Ala Glu Val Arg Ser Tyr Cys
    210                 215                 220

Tyr Glu Ala Ser Ile Ser Asp Met Ala Ser Asp Ser Arg Cys Pro Thr
225                 230                 235                 240

Gln Gly Glu Ala Tyr Leu Asp Lys Gln Ser Asp Thr Gln Tyr Val Cys
                245                 250                 255

Lys Arg Thr Leu Val Asp Arg Gly Trp Gly Asn Gly Cys Gly Leu Phe
            260                 265                 270

Gly Lys Gly Ser Leu Val Thr Cys Ala Lys Phe Ala Cys Ser Lys Lys
        275                 280                 285

Met Thr Gly Lys Ser Ile Gln Pro Glu Asn Leu Glu Tyr Arg Ile Met
    290                 295                 300

Leu Ser Val His Gly Ser Gln His Ser Gly Met Ile Val Asn Asp Thr
305                 310                 315                 320

Gly His Glu Thr Asp Glu Asn Arg Ala Lys Val Glu Ile Thr Pro Asn
                325                 330                 335

Ser Pro Arg Ala Glu Ala Thr Leu Gly Gly Phe Gly Ser Leu Gly Leu
            340                 345                 350

Asp Cys Glu Pro Arg Thr Gly Leu Asp Phe Ser Asp Leu Tyr Tyr Leu
        355                 360                 365

Thr Met Asn Asn Lys His Trp Leu Val His Lys Glu Trp Phe His Asp
    370                 375                 380

Ile Pro Leu Pro Trp His Ala Gly Ala Asp Thr Gly Thr Pro His Trp
385                 390                 395                 400

Asn Asn Lys Glu Ala Leu Val Glu Phe Lys Asp Ala His Ala Lys Arg
                405                 410                 415

Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495
```

-continued

```
Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Ile Ser Leu Met Cys Leu Ala Leu Gly
                645                 650                 655

Gly Val Leu Ile Phe Leu Ser Thr Ala Val Ser Ala Glu Asn Ile Thr
            660                 665                 670

Ser Gly Phe Leu Gly Pro Leu Leu Val Leu Gln Ala Gly Phe Phe Leu
        675                 680                 685

Leu Thr Arg Ile Leu Thr Ile Pro Gln Ser Leu Asp Ser Trp Trp Thr
    690                 695                 700

Ser Leu Asn Phe Leu Gly Gly Ser Pro Val Cys Leu Gly Gln Asn Ser
705                 710                 715                 720

Gln Ser Pro Thr Ser Asn His Ser Pro Thr Ser Cys Pro Pro Ile Cys
                725                 730                 735

Pro Gly Tyr Arg Trp Met Cys Leu Arg Arg Phe Ile Ile Phe Leu Phe
            740                 745                 750

Ile Leu Leu Leu Cys Leu Ile Phe Leu Leu Val Leu Leu Asp Tyr Gln
        755                 760                 765

Gly Met Leu Pro Val Cys Pro Leu Ile Pro Gly Ser Thr Thr Thr Ser
    770                 775                 780

Thr Gly Pro Cys Lys Thr Cys Thr Thr Pro Ala Gln Gly Asn Ser Met
785                 790                 795                 800

Phe Pro Ser Cys Cys Cys Thr Lys Pro Thr Asp Gly Asn Cys Thr Cys
                805                 810                 815

Ile Pro Ile Pro Ser Ser Trp Ala Phe Ala Lys Tyr Leu Trp Glu Trp
            820                 825                 830

Ala Ser Val Arg Phe Ser Trp Leu Ser Leu Leu Val Pro Phe Val Gln
        835                 840                 845

Trp Phe Val Gly Leu Ser Pro Thr Val Trp Leu Ser Ala Ile Trp Met
    850                 855                 860

Met Trp Tyr Trp Gly Pro Ser Leu Tyr Ser Ile Val Ser Pro Phe Ile
865                 870                 875                 880

Pro Leu Leu Pro Ile Phe Phe Cys Leu Trp Val Tyr Ile
                885                 890
```

<210> SEQ ID NO 11
<211> LENGTH: 763
<212> TYPE: PRT

<213> ORGANISM: Artificial sequence
<220> FEATURE:
<223> OTHER INFORMATION: E deleted + M

<400> SEQUENCE: 11

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
```

```
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Gln Trp Asn Ser Thr Ala Phe His Gln Thr Leu Gln Asp
                485                 490                 495

Pro Arg Val Arg Gly Leu Tyr Leu Pro Ala Gly Gly Ser Ser Ser Gly
            500                 505                 510

Thr Val Asn Pro Ala Pro Asn Ile Ala Ser His Ile Ser Ser Ile Ser
        515                 520                 525

Ala Arg Thr Gly Asp Pro Val Thr Asn Met Glu Asn Ile Thr Ser Gly
    530                 535                 540

Phe Leu Gly Pro Leu Leu Val Leu Gln Ala Gly Phe Phe Leu Leu Thr
545                 550                 555                 560

Arg Ile Leu Thr Ile Pro Gln Ser Leu Asp Ser Trp Trp Thr Ser Leu
                565                 570                 575

Asn Phe Leu Gly Gly Ser Pro Val Cys Leu Gly Gln Asn Ser Gln Ser
            580                 585                 590

Pro Thr Ser Asn His Ser Pro Thr Ser Cys Pro Pro Ile Cys Pro Gly
        595                 600                 605

Tyr Arg Trp Met Cys Leu Arg Arg Phe Ile Ile Phe Leu Phe Ile Leu
    610                 615                 620

Leu Leu Cys Leu Ile Phe Leu Leu Val Leu Leu Asp Tyr Gln Gly Met
625                 630                 635                 640

Leu Pro Val Cys Pro Leu Ile Pro Gly Ser Thr Thr Thr Ser Thr Gly
                645                 650                 655

Pro Cys Lys Thr Cys Thr Thr Pro Ala Gln Gly Asn Ser Met Phe Pro
            660                 665                 670

Ser Cys Cys Cys Thr Lys Pro Thr Asp Gly Asn Cys Thr Cys Ile Pro
        675                 680                 685

Ile Pro Ser Ser Trp Ala Phe Ala Lys Tyr Leu Trp Glu Trp Ala Ser
    690                 695                 700

Val Arg Phe Ser Trp Leu Ser Leu Leu Val Pro Phe Val Gln Trp Phe
705                 710                 715                 720

Val Gly Leu Ser Pro Thr Val Trp Leu Ser Ala Ile Trp Met Met Trp
                725                 730                 735

Tyr Trp Gly Pro Ser Leu Tyr Ser Ile Val Ser Pro Phe Ile Pro Leu
            740                 745                 750

Leu Pro Ile Phe Phe Cys Leu Trp Val Tyr Ile
        755                 760
```

<210> SEQ ID NO 12
<211> LENGTH: 927
<212> TYPE: PRT
<213> ORGANISM: Artificial sequence
<220> FEATURE:
<223> OTHER INFORMATION: prM + E deleted + M -continued

<400> SEQUENCE: 12

```
Arg Arg Gly Ser Ala Tyr Tyr Met Tyr Leu Asp Arg Asn Asp Ala Gly
1               5                   10                  15

Glu Ala Ile Ser Phe Pro Thr Thr Leu Gly Met Asn Lys Cys Tyr Ile
            20                  25                  30

Gln Ile Met Asp Leu Gly His Thr Cys Asp Ala Thr Met Ser Tyr Glu
        35                  40                  45

Cys Pro Met Leu Asp Glu Gly Val Glu Pro Asp Asp Val Asp Cys Trp
    50                  55                  60

Cys Asn Thr Thr Ser Thr Trp Val Val Tyr Gly Thr Cys His His Lys
65                  70                  75                  80

Lys Gly Glu Ala Arg Arg Ser Arg Arg Ala Val Thr Leu Pro Ser His
                85                  90                  95

Ser Thr Arg Lys Leu Gln Thr Arg Ser Gln Thr Trp Leu Glu Ser Arg
            100                 105                 110

Glu Tyr Thr Lys His Leu Ile Arg Val Glu Asn Trp Ile Phe Arg Asn
        115                 120                 125

Pro Gly Phe Ala Leu Ala Ala Ala Ala Ile Ala Trp Leu Leu Gly Ser
    130                 135                 140

Ser Thr Ser Gln Lys Val Ile Tyr Leu Val Met Ile Leu Leu Ile Ala
145                 150                 155                 160

Pro Ala Tyr Ser Ile Arg Cys Ile Gly Val Ser Asn Arg Asp Phe Val
                165                 170                 175

Glu Gly Met Ser Gly Gly Thr Trp Val Asp Val Val Leu Glu His Gly
            180                 185                 190

Gly Cys Val Thr Val Met Ala Gln Asp Lys Pro Thr Val Asp Ile Glu
        195                 200                 205

Leu Val Thr Thr Thr Val Ser Asn Met Ala Glu Val Arg Ser Tyr Cys
    210                 215                 220

Tyr Glu Ala Ser Ile Ser Asp Met Ala Ser Asp Ser Arg Cys Pro Thr
225                 230                 235                 240

Gln Gly Glu Ala Tyr Leu Asp Lys Gln Ser Asp Thr Gln Tyr Val Cys
                245                 250                 255

Lys Arg Thr Leu Val Asp Arg Gly Trp Gly Asn Gly Cys Gly Leu Phe
            260                 265                 270

Gly Lys Gly Ser Leu Val Thr Cys Ala Lys Phe Ala Cys Ser Lys Lys
        275                 280                 285

Met Thr Gly Lys Ser Ile Gln Pro Glu Asn Leu Glu Tyr Arg Ile Met
    290                 295                 300

Leu Ser Val His Gly Ser Gln His Ser Gly Met Ile Val Asn Asp Thr
305                 310                 315                 320

Gly His Glu Thr Asp Glu Asn Arg Ala Lys Val Glu Ile Thr Pro Asn
                325                 330                 335

Ser Pro Arg Ala Glu Ala Thr Leu Gly Gly Phe Gly Ser Leu Gly Leu
            340                 345                 350

Asp Cys Glu Pro Arg Thr Gly Leu Asp Phe Ser Asp Leu Tyr Tyr Leu
        355                 360                 365

Thr Met Asn Asn Lys His Trp Leu Val His Lys Glu Trp Phe His Asp
    370                 375                 380

Ile Pro Leu Pro Trp His Ala Gly Ala Asp Thr Gly Thr Pro His Trp
385                 390                 395                 400

Asn Asn Lys Glu Ala Leu Val Glu Phe Lys Asp Ala His Ala Lys Arg
                405                 410                 415
```

```
Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495

Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Gln Trp Asn Ser Thr Ala Phe His Gln
                645                 650                 655

Thr Leu Gln Asp Pro Arg Val Arg Gly Leu Tyr Leu Pro Ala Gly Gly
            660                 665                 670

Ser Ser Ser Gly Thr Val Asn Pro Ala Pro Asn Ile Ala Ser His Ile
        675                 680                 685

Ser Ser Ile Ser Ala Arg Thr Gly Asp Pro Val Thr Asn Met Glu Asn
    690                 695                 700

Ile Thr Ser Gly Phe Leu Gly Pro Leu Leu Val Leu Gln Ala Gly Phe
705                 710                 715                 720

Phe Leu Leu Thr Arg Ile Leu Thr Ile Pro Gln Ser Leu Asp Ser Trp
                725                 730                 735

Trp Thr Ser Leu Asn Phe Leu Gly Gly Ser Pro Val Cys Leu Gly Gln
            740                 745                 750

Asn Ser Gln Ser Pro Thr Ser Asn His Ser Pro Thr Ser Cys Pro Pro
        755                 760                 765

Ile Cys Pro Gly Tyr Arg Trp Met Cys Leu Arg Arg Phe Ile Ile Phe
    770                 775                 780

Leu Phe Ile Leu Leu Leu Cys Leu Ile Phe Leu Leu Val Leu Leu Asp
785                 790                 795                 800

Tyr Gln Gly Met Leu Pro Val Cys Pro Leu Ile Pro Gly Ser Thr Thr
                805                 810                 815

Thr Ser Thr Gly Pro Cys Lys Thr Cys Thr Thr Pro Ala Gln Gly Asn
            820                 825                 830
```

```
Ser Met Phe Pro Ser Cys Cys Cys Thr Lys Pro Thr Asp Gly Asn Cys
        835                 840                 845

Thr Cys Ile Pro Ile Pro Ser Ser Trp Ala Phe Ala Lys Tyr Leu Trp
    850                 855                 860

Glu Trp Ala Ser Val Arg Phe Ser Trp Leu Ser Leu Leu Val Pro Phe
865                 870                 875                 880

Val Gln Trp Phe Val Gly Leu Ser Pro Thr Val Trp Leu Ser Ala Ile
                885                 890                 895

Trp Met Met Trp Tyr Trp Gly Pro Ser Leu Tyr Ser Ile Val Ser Pro
            900                 905                 910

Phe Ile Pro Leu Leu Pro Ile Phe Phe Cys Leu Trp Val Tyr Ile
        915                 920                 925


<210> SEQ ID NO 13
<211> LENGTH: 784
<212> TYPE: PRT
<213> ORGANISM: Artificial sequence
<220> FEATURE:
<223> OTHER INFORMATION: E + M

<400> SEQUENCE: 13

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270
```

-continued

```
Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala Gln Trp Asn Ser Thr Ala Phe His
            500                 505                 510

Gln Thr Leu Gln Asp Pro Arg Val Arg Gly Leu Tyr Leu Pro Ala Gly
        515                 520                 525

Gly Ser Ser Ser Gly Thr Val Asn Pro Ala Pro Asn Ile Ala Ser His
    530                 535                 540

Ile Ser Ser Ile Ser Ala Arg Thr Gly Asp Pro Val Thr Asn Met Glu
545                 550                 555                 560

Asn Ile Thr Ser Gly Phe Leu Gly Pro Leu Leu Val Leu Gln Ala Gly
                565                 570                 575

Phe Phe Leu Leu Thr Arg Ile Leu Thr Ile Pro Gln Ser Leu Asp Ser
            580                 585                 590

Trp Trp Thr Ser Leu Asn Phe Leu Gly Gly Ser Pro Val Cys Leu Gly
        595                 600                 605

Gln Asn Ser Gln Ser Pro Thr Ser Asn His Ser Pro Thr Ser Cys Pro
    610                 615                 620

Pro Ile Cys Pro Gly Tyr Arg Trp Met Cys Leu Arg Arg Phe Ile Ile
625                 630                 635                 640

Phe Leu Phe Ile Leu Leu Leu Cys Leu Ile Phe Leu Leu Val Leu Leu
                645                 650                 655

Asp Tyr Gln Gly Met Leu Pro Val Cys Pro Leu Ile Pro Gly Ser Thr
            660                 665                 670

Thr Thr Ser Thr Gly Pro Cys Lys Thr Cys Thr Thr Pro Ala Gln Gly
        675                 680                 685

Asn Ser Met Phe Pro Ser Cys Cys Cys Thr Lys Pro Thr Asp Gly Asn
```

-continued

```
    690                 695                 700

Cys Thr Cys Ile Pro Ile Pro Ser Ser Trp Ala Phe Ala Lys Tyr Leu
705                 710                 715                 720

Trp Glu Trp Ala Ser Val Arg Phe Ser Trp Leu Ser Leu Leu Val Pro
                725                 730                 735

Phe Val Gln Trp Phe Val Gly Leu Ser Pro Thr Val Trp Leu Ser Ala
            740                 745                 750

Ile Trp Met Met Trp Tyr Trp Gly Pro Ser Leu Tyr Ser Ile Val Ser
        755                 760                 765

Pro Phe Ile Pro Leu Leu Pro Ile Phe Phe Cys Leu Trp Val Tyr Ile
    770                 775                 780


<210> SEQ ID NO 14
<211> LENGTH: 948
<212> TYPE: PRT
<213> ORGANISM: Artificial sequence
<220> FEATURE:
<223> OTHER INFORMATION: prM + E + M

<400> SEQUENCE: 14

Arg Arg Gly Ser Ala Tyr Tyr Met Tyr Leu Asp Arg Asn Asp Ala Gly
1               5                   10                  15

Glu Ala Ile Ser Phe Pro Thr Thr Leu Gly Met Asn Lys Cys Tyr Ile
            20                  25                  30

Gln Ile Met Asp Leu Gly His Thr Cys Asp Ala Thr Met Ser Tyr Glu
        35                  40                  45

Cys Pro Met Leu Asp Glu Gly Val Glu Pro Asp Asp Val Asp Cys Trp
    50                  55                  60

Cys Asn Thr Thr Ser Thr Trp Val Val Tyr Gly Thr Cys His His Lys
65                  70                  75                  80

Lys Gly Glu Ala Arg Arg Ser Arg Arg Ala Val Thr Leu Pro Ser His
                85                  90                  95

Ser Thr Arg Lys Leu Gln Thr Arg Ser Gln Thr Trp Leu Glu Ser Arg
            100                 105                 110

Glu Tyr Thr Lys His Leu Ile Arg Val Glu Asn Trp Ile Phe Arg Asn
        115                 120                 125

Pro Gly Phe Ala Leu Ala Ala Ala Ala Ile Ala Trp Leu Leu Gly Ser
    130                 135                 140

Ser Thr Ser Gln Lys Val Ile Tyr Leu Val Met Ile Leu Leu Ile Ala
145                 150                 155                 160

Pro Ala Tyr Ser Ile Arg Cys Ile Gly Val Ser Asn Arg Asp Phe Val
                165                 170                 175

Glu Gly Met Ser Gly Gly Thr Trp Val Asp Val Val Leu Glu His Gly
            180                 185                 190

Gly Cys Val Thr Val Met Ala Gln Asp Lys Pro Thr Val Asp Ile Glu
        195                 200                 205

Leu Val Thr Thr Thr Val Ser Asn Met Ala Glu Val Arg Ser Tyr Cys
    210                 215                 220

Tyr Glu Ala Ser Ile Ser Asp Met Ala Ser Asp Ser Arg Cys Pro Thr
225                 230                 235                 240

Gln Gly Glu Ala Tyr Leu Asp Lys Gln Ser Asp Thr Gln Tyr Val Cys
                245                 250                 255

Lys Arg Thr Leu Val Asp Arg Gly Trp Gly Asn Gly Cys Gly Leu Phe
            260                 265                 270

Gly Lys Gly Ser Leu Val Thr Cys Ala Lys Phe Ala Cys Ser Lys Lys
```

-continued

```
        275                 280                 285

Met Thr Gly Lys Ser Ile Gln Pro Glu Asn Leu Glu Tyr Arg Ile Met
    290                 295                 300

Leu Ser Val His Gly Ser Gln His Ser Gly Met Ile Val Asn Asp Thr
305                 310                 315                 320

Gly His Glu Thr Asp Glu Asn Arg Ala Lys Val Glu Ile Thr Pro Asn
                325                 330                 335

Ser Pro Arg Ala Glu Ala Thr Leu Gly Gly Phe Gly Ser Leu Gly Leu
            340                 345                 350

Asp Cys Glu Pro Arg Thr Gly Leu Asp Phe Ser Asp Leu Tyr Tyr Leu
        355                 360                 365

Thr Met Asn Asn Lys His Trp Leu Val His Lys Glu Trp Phe His Asp
    370                 375                 380

Ile Pro Leu Pro Trp His Ala Gly Ala Asp Thr Gly Thr Pro His Trp
385                 390                 395                 400

Asn Asn Lys Glu Ala Leu Val Glu Phe Lys Asp Ala His Ala Lys Arg
                405                 410                 415

Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495

Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Ile Ser Leu Met Cys Leu Ala Leu Gly
                645                 650                 655

Gly Val Leu Ile Phe Leu Ser Thr Ala Val Ser Ala Gln Trp Asn Ser
            660                 665                 670

Thr Ala Phe His Gln Thr Leu Gln Asp Pro Arg Val Arg Gly Leu Tyr
        675                 680                 685

Leu Pro Ala Gly Gly Ser Ser Ser Gly Thr Val Asn Pro Ala Pro Asn
    690                 695                 700
```

```
Ile Ala Ser His Ile Ser Ser Ile Ser Ala Arg Thr Gly Asp Pro Val
705                 710                 715                 720

Thr Asn Met Glu Asn Ile Thr Ser Gly Phe Leu Gly Pro Leu Leu Val
                725                 730                 735

Leu Gln Ala Gly Phe Phe Leu Leu Thr Arg Ile Leu Thr Ile Pro Gln
            740                 745                 750

Ser Leu Asp Ser Trp Trp Thr Ser Leu Asn Phe Leu Gly Gly Ser Pro
        755                 760                 765

Val Cys Leu Gly Gln Asn Ser Gln Ser Pro Thr Ser Asn His Ser Pro
    770                 775                 780

Thr Ser Cys Pro Pro Ile Cys Pro Gly Tyr Arg Trp Met Cys Leu Arg
785                 790                 795                 800

Arg Phe Ile Ile Phe Leu Phe Ile Leu Leu Leu Cys Leu Ile Phe Leu
                805                 810                 815

Leu Val Leu Leu Asp Tyr Gln Gly Met Leu Pro Val Cys Pro Leu Ile
            820                 825                 830

Pro Gly Ser Thr Thr Thr Ser Thr Gly Pro Cys Lys Thr Cys Thr Thr
        835                 840                 845

Pro Ala Gln Gly Asn Ser Met Phe Pro Ser Cys Cys Cys Thr Lys Pro
    850                 855                 860

Thr Asp Gly Asn Cys Thr Cys Ile Pro Ile Pro Ser Ser Trp Ala Phe
865                 870                 875                 880

Ala Lys Tyr Leu Trp Glu Trp Ala Ser Val Arg Phe Ser Trp Leu Ser
                885                 890                 895

Leu Leu Val Pro Phe Val Gln Trp Phe Val Gly Leu Ser Pro Thr Val
            900                 905                 910

Trp Leu Ser Ala Ile Trp Met Met Trp Tyr Trp Gly Pro Ser Leu Tyr
        915                 920                 925

Ser Ile Val Ser Pro Phe Ile Pro Leu Leu Pro Ile Phe Phe Cys Leu
    930                 935                 940

Trp Val Tyr Ile
945
```

<210> SEQ ID NO 15
<211> LENGTH: 504
<212> TYPE: PRT
<213> ORGANISM: Zika virus

<400> SEQUENCE: 15

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
```

-continued

```
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 16
<211> LENGTH: 668
<212> TYPE: PRT
<213> ORGANISM: Artificial sequence
<220> FEATURE:
<223> OTHER INFORMATION: prM + E

<400> SEQUENCE: 16

Arg Arg Gly Ser Ala Tyr Tyr Met Tyr Leu Asp Arg Asn Asp Ala Gly
1 5 10 15

Glu Ala Ile Ser Phe Pro Thr Thr Leu Gly Met Asn Lys Cys Tyr Ile
20 25 30

Gln Ile Met Asp Leu Gly His Thr Cys Asp Ala Thr Met Ser Tyr Glu
35 40 45

Cys Pro Met Leu Asp Glu Gly Val Glu Pro Asp Asp Val Asp Cys Trp
50 55 60

Cys Asn Thr Thr Ser Thr Trp Val Val Tyr Gly Thr Cys His His Lys
65 70 75 80

Lys Gly Glu Ala Arg Arg Ser Arg Arg Ala Val Thr Leu Pro Ser His
85 90 95

Ser Thr Arg Lys Leu Gln Thr Arg Ser Gln Thr Trp Leu Glu Ser Arg
100 105 110

Glu Tyr Thr Lys His Leu Ile Arg Val Glu Asn Trp Ile Phe Arg Asn
115 120 125

Pro Gly Phe Ala Leu Ala Ala Ala Ala Ile Ala Trp Leu Leu Gly Ser
130 135 140

Ser Thr Ser Gln Lys Val Ile Tyr Leu Val Met Ile Leu Leu Ile Ala
145 150 155 160

Pro Ala Tyr Ser Ile Arg Cys Ile Gly Val Ser Asn Arg Asp Phe Val
165 170 175

Glu Gly Met Ser Gly Gly Thr Trp Val Asp Val Val Leu Glu His Gly
180 185 190

Gly Cys Val Thr Val Met Ala Gln Asp Lys Pro Thr Val Asp Ile Glu
195 200 205

Leu Val Thr Thr Thr Val Ser Asn Met Ala Glu Val Arg Ser Tyr Cys
210 215 220

Tyr Glu Ala Ser Ile Ser Asp Met Ala Ser Asp Ser Arg Cys Pro Thr
225 230 235 240

Gln Gly Glu Ala Tyr Leu Asp Lys Gln Ser Asp Thr Gln Tyr Val Cys
245 250 255

Lys Arg Thr Leu Val Asp Arg Gly Trp Gly Asn Gly Cys Gly Leu Phe
260 265 270

Gly Lys Gly Ser Leu Val Thr Cys Ala Lys Phe Ala Cys Ser Lys Lys
275 280 285

Met Thr Gly Lys Ser Ile Gln Pro Glu Asn Leu Glu Tyr Arg Ile Met
290 295 300

Leu Ser Val His Gly Ser Gln His Ser Gly Met Ile Val Asn Asp Thr
305 310 315 320

Gly His Glu Thr Asp Glu Asn Arg Ala Lys Val Glu Ile Thr Pro Asn
325 330 335

Ser Pro Arg Ala Glu Ala Thr Leu Gly Gly Phe Gly Ser Leu Gly Leu
340 345 350

Asp Cys Glu Pro Arg Thr Gly Leu Asp Phe Ser Asp Leu Tyr Tyr Leu
355 360 365

Thr Met Asn Asn Lys His Trp Leu Val His Lys Glu Trp Phe His Asp
370 375 380

Ile Pro Leu Pro Trp His Ala Gly Ala Asp Thr Gly Thr Pro His Trp
385 390 395 400

```
Asn Asn Lys Glu Ala Leu Val Glu Phe Lys Asp Ala His Ala Lys Arg
                405                 410                 415

Gln Thr Val Val Val Leu Gly Ser Gln Glu Gly Ala Val His Thr Ala
            420                 425                 430

Leu Ala Gly Ala Leu Glu Ala Glu Met Asp Gly Ala Lys Gly Arg Leu
        435                 440                 445

Ser Ser Gly His Leu Lys Cys Arg Leu Lys Met Asp Lys Leu Arg Leu
    450                 455                 460

Lys Gly Val Ser Tyr Ser Leu Cys Thr Ala Ala Phe Thr Phe Thr Lys
465                 470                 475                 480

Ile Pro Ala Glu Thr Leu His Gly Thr Val Thr Val Glu Val Gln Tyr
                485                 490                 495

Ala Gly Thr Asp Gly Pro Cys Lys Val Pro Ala Gln Met Ala Val Asp
            500                 505                 510

Met Gln Thr Leu Thr Pro Val Gly Arg Leu Ile Thr Ala Asn Pro Val
        515                 520                 525

Ile Thr Glu Ser Thr Glu Asn Ser Lys Met Met Leu Glu Leu Asp Pro
    530                 535                 540

Pro Phe Gly Asp Ser Tyr Ile Val Ile Gly Val Gly Glu Lys Lys Ile
545                 550                 555                 560

Thr His His Trp His Arg Ser Gly Ser Thr Ile Gly Lys Ala Phe Glu
                565                 570                 575

Ala Thr Val Arg Gly Ala Lys Arg Met Ala Val Leu Gly Asp Thr Ala
            580                 585                 590

Trp Asp Phe Gly Ser Val Gly Gly Ala Leu Asn Ser Leu Gly Lys Gly
        595                 600                 605

Ile His Gln Ile Phe Gly Ala Ala Phe Lys Ser Leu Phe Gly Gly Met
    610                 615                 620

Ser Trp Phe Ser Gln Ile Leu Ile Gly Thr Leu Leu Met Trp Leu Gly
625                 630                 635                 640

Leu Asn Ala Lys Asn Gly Ser Ile Ser Leu Met Cys Leu Ala Leu Gly
                645                 650                 655

Gly Val Leu Ile Phe Leu Ser Thr Ala Val Ser Ala
            660                 665


<210> SEQ ID NO 17
<211> LENGTH: 710
<212> TYPE: PRT
<213> ORGANISM: Artificial sequence
<220> FEATURE:
<223> OTHER INFORMATION: TIP + E deleted + S deleted

<400> SEQUENCE: 17

Met Leu Gly Ser Ser Thr Ser Gln Lys Val Ile Tyr Leu Val Met Ile
1               5                   10                  15

Leu Leu Ile Ala Pro Ala Tyr Ser Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95
```

-continued

```
Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480

Phe Gly Gly Met Ser Trp Phe Ser Gln Ile Leu Ile Gly Thr Leu Leu
                485                 490                 495

Met Trp Leu Gly Leu Asn Ala Lys Asn Gly Ser Arg Ile Leu Thr Ile
            500                 505                 510
```

-continued

Pro Gln Ser Leu Asp Ser Trp Trp Thr Ser Leu Asn Phe Leu Gly Gly
515 520 525

Ser Pro Val Cys Leu Gly Gln Asn Ser Gln Ser Pro Thr Ser Asn His
530 535 540

Ser Pro Thr Ser Cys Pro Pro Ile Cys Pro Gly Tyr Arg Trp Met Cys
545 550 555 560

Leu Arg Arg Phe Ile Ile Phe Leu Phe Ile Leu Leu Leu Cys Leu Ile
565 570 575

Phe Leu Leu Val Leu Leu Asp Tyr Gln Gly Met Leu Pro Val Cys Pro
580 585 590

Leu Ile Pro Gly Ser Thr Thr Thr Ser Thr Gly Pro Cys Lys Thr Cys
595 600 605

Thr Thr Pro Ala Gln Gly Asn Ser Met Phe Pro Ser Cys Cys Cys Thr
610 615 620

Lys Pro Thr Asp Gly Asn Cys Thr Cys Ile Pro Ile Pro Ser Ser Trp
625 630 635 640

Ala Phe Ala Lys Tyr Leu Trp Glu Trp Ala Ser Val Arg Phe Ser Trp
645 650 655

Leu Ser Leu Leu Val Pro Phe Val Gln Trp Phe Val Gly Leu Ser Pro
660 665 670

Thr Val Trp Leu Ser Ala Ile Trp Met Met Trp Tyr Trp Gly Pro Ser
675 680 685

Leu Tyr Ser Ile Val Ser Pro Phe Ile Pro Leu Leu Pro Ile Phe Phe
690 695 700

Cys Leu Trp Val Tyr Ile
705 710

<210> SEQ ID NO 18
<211> LENGTH: 886
<212> TYPE: PRT
<213> ORGANISM: Artificial sequence
<220> FEATURE:
<223> OTHER INFORMATION: TIP + prM + E deleted + S deleted

<400> SEQUENCE: 18

Met Leu Arg Ile Ile Asn Ala Arg Lys Glu Lys Lys Arg Arg Gly Ala
1 5 10 15

Asp Thr Ser Val Gly Ile Val Gly Leu Leu Leu Thr Thr Ala Met Ala
20 25 30

Ala Glu Val Thr Arg Arg Gly Ser Ala Tyr Tyr Met Tyr Leu Asp Arg
35 40 45

Asn Asp Ala Gly Glu Ala Ile Ser Phe Pro Thr Thr Leu Gly Met Asn
50 55 60

Lys Cys Tyr Ile Gln Ile Met Asp Leu Gly His Thr Cys Asp Ala Thr
65 70 75 80

Met Ser Tyr Glu Cys Pro Met Leu Asp Glu Gly Val Glu Pro Asp Asp
85 90 95

Val Asp Cys Trp Cys Asn Thr Thr Ser Thr Trp Val Val Tyr Gly Thr
100 105 110

Cys His His Lys Lys Gly Glu Ala Arg Arg Ser Arg Arg Ala Val Thr
115 120 125

Leu Pro Ser His Ser Thr Arg Lys Leu Gln Thr Arg Ser Gln Thr Trp
130 135 140

Leu Glu Ser Arg Glu Tyr Thr Lys His Leu Ile Arg Val Glu Asn Trp
145 150 155 160

-continued

```
Ile Phe Arg Asn Pro Gly Phe Ala Leu Ala Ala Ala Ala Ile Ala Trp
                165                 170                 175

Leu Leu Gly Ser Ser Thr Ser Gln Lys Val Ile Tyr Leu Val Met Ile
            180                 185                 190

Leu Leu Ile Ala Pro Ala Tyr Ser Ile Arg Cys Ile Gly Val Ser Asn
        195                 200                 205

Arg Asp Phe Val Glu Gly Met Ser Gly Gly Thr Trp Val Asp Val Val
    210                 215                 220

Leu Glu His Gly Gly Cys Val Thr Val Met Ala Gln Asp Lys Pro Thr
225                 230                 235                 240

Val Asp Ile Glu Leu Val Thr Thr Thr Val Ser Asn Met Ala Glu Val
                245                 250                 255

Arg Ser Tyr Cys Tyr Glu Ala Ser Ile Ser Asp Met Ala Ser Asp Ser
            260                 265                 270

Arg Cys Pro Thr Gln Gly Glu Ala Tyr Leu Asp Lys Gln Ser Asp Thr
        275                 280                 285

Gln Tyr Val Cys Lys Arg Thr Leu Val Asp Arg Gly Trp Gly Asn Gly
    290                 295                 300

Cys Gly Leu Phe Gly Lys Gly Ser Leu Val Thr Cys Ala Lys Phe Ala
305                 310                 315                 320

Cys Ser Lys Lys Met Thr Gly Lys Ser Ile Gln Pro Glu Asn Leu Glu
                325                 330                 335

Tyr Arg Ile Met Leu Ser Val His Gly Ser Gln His Ser Gly Met Ile
            340                 345                 350

Val Asn Asp Thr Gly His Glu Thr Asp Glu Asn Arg Ala Lys Val Glu
        355                 360                 365

Ile Thr Pro Asn Ser Pro Arg Ala Glu Ala Thr Leu Gly Gly Phe Gly
    370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala
        435                 440                 445

His Ala Lys Arg Gln Thr Val Val Val Leu Gly Ser Gln Glu Gly Ala
    450                 455                 460

Val His Thr Ala Leu Ala Gly Ala Leu Glu Ala Glu Met Asp Gly Ala
465                 470                 475                 480

Lys Gly Arg Leu Ser Ser Gly His Leu Lys Cys Arg Leu Lys Met Asp
                485                 490                 495

Lys Leu Arg Leu Lys Gly Val Ser Tyr Ser Leu Cys Thr Ala Ala Phe
            500                 505                 510

Thr Phe Thr Lys Ile Pro Ala Glu Thr Leu His Gly Thr Val Thr Val
        515                 520                 525

Glu Val Gln Tyr Ala Gly Thr Asp Gly Pro Cys Lys Val Pro Ala Gln
    530                 535                 540

Met Ala Val Asp Met Gln Thr Leu Thr Pro Val Gly Arg Leu Ile Thr
545                 550                 555                 560

Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
```

-continued

```
            580                 585                 590

Glu Lys Lys Ile Thr His His Trp His Arg Ser Gly Ser Thr Ile Gly
        595                 600                 605

Lys Ala Phe Glu Ala Thr Val Arg Gly Ala Lys Arg Met Ala Val Leu
    610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Arg Ile Leu Thr Ile
        675                 680                 685

Pro Gln Ser Leu Asp Ser Trp Trp Thr Ser Leu Asn Phe Leu Gly Gly
    690                 695                 700

Ser Pro Val Cys Leu Gly Gln Asn Ser Gln Ser Pro Thr Ser Asn His
705                 710                 715                 720

Ser Pro Thr Ser Cys Pro Pro Ile Cys Pro Gly Tyr Arg Trp Met Cys
                725                 730                 735

Leu Arg Arg Phe Ile Ile Phe Leu Phe Ile Leu Leu Leu Cys Leu Ile
            740                 745                 750

Phe Leu Leu Val Leu Leu Asp Tyr Gln Gly Met Leu Pro Val Cys Pro
        755                 760                 765

Leu Ile Pro Gly Ser Thr Thr Thr Ser Thr Gly Pro Cys Lys Thr Cys
    770                 775                 780

Thr Thr Pro Ala Gln Gly Asn Ser Met Phe Pro Ser Cys Cys Cys Thr
785                 790                 795                 800

Lys Pro Thr Asp Gly Asn Cys Thr Cys Ile Pro Ile Pro Ser Ser Trp
                805                 810                 815

Ala Phe Ala Lys Tyr Leu Trp Glu Trp Ala Ser Val Arg Phe Ser Trp
            820                 825                 830

Leu Ser Leu Leu Val Pro Phe Val Gln Trp Phe Val Gly Leu Ser Pro
        835                 840                 845

Thr Val Trp Leu Ser Ala Ile Trp Met Met Trp Tyr Trp Gly Pro Ser
    850                 855                 860

Leu Tyr Ser Ile Val Ser Pro Phe Ile Pro Leu Leu Pro Ile Phe Phe
865                 870                 875                 880

Cys Leu Trp Val Tyr Ile
                885


<210> SEQ ID NO 19
<211> LENGTH: 753
<212> TYPE: PRT
<213> ORGANISM: Artificial sequence
<220> FEATURE:
<223> OTHER INFORMATION: TIP + E + S

<400> SEQUENCE: 19

Met Leu Gly Ser Ser Thr Ser Gln Lys Val Ile Tyr Leu Val Met Ile
1               5                   10                  15

Leu Leu Ile Ala Pro Ala Tyr Ser Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
```

-continued

```
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480
```

Phe Gly Gly Met Ser Trp Phe Ser Gln Ile Leu Ile Gly Thr Leu Leu
485 490 495

Met Trp Leu Gly Leu Asn Ala Lys Asn Gly Ser Ile Ser Leu Met Cys
500 505 510

Leu Ala Leu Gly Gly Val Leu Ile Phe Leu Ser Thr Ala Val Ser Ala
515 520 525

Glu Asn Ile Thr Ser Gly Phe Leu Gly Pro Leu Leu Val Leu Gln Ala
530 535 540

Gly Phe Phe Leu Leu Thr Arg Ile Leu Thr Ile Pro Gln Ser Leu Asp
545 550 555 560

Ser Trp Trp Thr Ser Leu Asn Phe Leu Gly Gly Ser Pro Val Cys Leu
565 570 575

Gly Gln Asn Ser Gln Ser Pro Thr Ser Asn His Ser Pro Thr Ser Cys
580 585 590

Pro Pro Ile Cys Pro Gly Tyr Arg Trp Met Cys Leu Arg Arg Phe Ile
595 600 605

Ile Phe Leu Phe Ile Leu Leu Leu Cys Leu Ile Phe Leu Leu Val Leu
610 615 620

Leu Asp Tyr Gln Gly Met Leu Pro Val Cys Pro Leu Ile Pro Gly Ser
625 630 635 640

Thr Thr Thr Ser Thr Gly Pro Cys Lys Thr Cys Thr Thr Pro Ala Gln
645 650 655

Gly Asn Ser Met Phe Pro Ser Cys Cys Cys Thr Lys Pro Thr Asp Gly
660 665 670

Asn Cys Thr Cys Ile Pro Ile Pro Ser Ser Trp Ala Phe Ala Lys Tyr
675 680 685

Leu Trp Glu Trp Ala Ser Val Arg Phe Ser Trp Leu Ser Leu Leu Val
690 695 700

Pro Phe Val Gln Trp Phe Val Gly Leu Ser Pro Thr Val Trp Leu Ser
705 710 715 720

Ala Ile Trp Met Met Trp Tyr Trp Gly Pro Ser Leu Tyr Ser Ile Val
725 730 735

Ser Pro Phe Ile Pro Leu Leu Pro Ile Phe Phe Cys Leu Trp Val Tyr
740 745 750

Ile

<210> SEQ ID NO 20
<211> LENGTH: 929
<212> TYPE: PRT
<213> ORGANISM: Artificial sequence
<220> FEATURE:
<223> OTHER INFORMATION: TIP + prM + E + S

<400> SEQUENCE: 20

Met Leu Arg Ile Ile Asn Ala Arg Lys Glu Lys Lys Arg Arg Gly Ala
1 5 10 15

Asp Thr Ser Val Gly Ile Val Gly Leu Leu Leu Thr Thr Ala Met Ala
20 25 30

Ala Glu Val Thr Arg Arg Gly Ser Ala Tyr Tyr Met Tyr Leu Asp Arg
35 40 45

Asn Asp Ala Gly Glu Ala Ile Ser Phe Pro Thr Thr Leu Gly Met Asn
50 55 60

Lys Cys Tyr Ile Gln Ile Met Asp Leu Gly His Thr Cys Asp Ala Thr
65 70 75 80

-continued

```
Met Ser Tyr Glu Cys Pro Met Leu Asp Glu Gly Val Glu Pro Asp Asp
                85                  90                  95

Val Asp Cys Trp Cys Asn Thr Thr Ser Thr Trp Val Val Tyr Gly Thr
            100                 105                 110

Cys His His Lys Lys Gly Glu Ala Arg Arg Ser Arg Arg Ala Val Thr
        115                 120                 125

Leu Pro Ser His Ser Thr Arg Lys Leu Gln Thr Arg Ser Gln Thr Trp
    130                 135                 140

Leu Glu Ser Arg Glu Tyr Thr Lys His Leu Ile Arg Val Glu Asn Trp
145                 150                 155                 160

Ile Phe Arg Asn Pro Gly Phe Ala Leu Ala Ala Ala Ala Ile Ala Trp
                165                 170                 175

Leu Leu Gly Ser Ser Thr Ser Gln Lys Val Ile Tyr Leu Val Met Ile
            180                 185                 190

Leu Leu Ile Ala Pro Ala Tyr Ser Ile Arg Cys Ile Gly Val Ser Asn
        195                 200                 205

Arg Asp Phe Val Glu Gly Met Ser Gly Gly Thr Trp Val Asp Val Val
    210                 215                 220

Leu Glu His Gly Gly Cys Val Thr Val Met Ala Gln Asp Lys Pro Thr
225                 230                 235                 240

Val Asp Ile Glu Leu Val Thr Thr Thr Val Ser Asn Met Ala Glu Val
                245                 250                 255

Arg Ser Tyr Cys Tyr Glu Ala Ser Ile Ser Asp Met Ala Ser Asp Ser
            260                 265                 270

Arg Cys Pro Thr Gln Gly Glu Ala Tyr Leu Asp Lys Gln Ser Asp Thr
        275                 280                 285

Gln Tyr Val Cys Lys Arg Thr Leu Val Asp Arg Gly Trp Gly Asn Gly
    290                 295                 300

Cys Gly Leu Phe Gly Lys Gly Ser Leu Val Thr Cys Ala Lys Phe Ala
305                 310                 315                 320

Cys Ser Lys Lys Met Thr Gly Lys Ser Ile Gln Pro Glu Asn Leu Glu
                325                 330                 335

Tyr Arg Ile Met Leu Ser Val His Gly Ser Gln His Ser Gly Met Ile
            340                 345                 350

Val Asn Asp Thr Gly His Glu Thr Asp Glu Asn Arg Ala Lys Val Glu
        355                 360                 365

Ile Thr Pro Asn Ser Pro Arg Ala Glu Ala Thr Leu Gly Gly Phe Gly
    370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala
        435                 440                 445

His Ala Lys Arg Gln Thr Val Val Val Leu Gly Ser Gln Glu Gly Ala
    450                 455                 460

Val His Thr Ala Leu Ala Gly Ala Leu Glu Ala Glu Met Asp Gly Ala
465                 470                 475                 480

Lys Gly Arg Leu Ser Ser Gly His Leu Lys Cys Arg Leu Lys Met Asp
                485                 490                 495

Lys Leu Arg Leu Lys Gly Val Ser Tyr Ser Leu Cys Thr Ala Ala Phe
```

-continued

```
            500                 505                 510

Thr Phe Thr Lys Ile Pro Ala Glu Thr Leu His Gly Thr Val Thr Val
        515                 520                 525

Glu Val Gln Tyr Ala Gly Thr Asp Gly Pro Cys Lys Val Pro Ala Gln
    530                 535                 540

Met Ala Val Asp Met Gln Thr Leu Thr Pro Val Gly Arg Leu Ile Thr
545                 550                 555                 560

Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
            580                 585                 590

Glu Lys Lys Ile Thr His His Trp His Arg Ser Gly Ser Thr Ile Gly
        595                 600                 605

Lys Ala Phe Glu Ala Thr Val Arg Gly Ala Lys Arg Met Ala Val Leu
    610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Ile Ser Leu Met Cys
        675                 680                 685

Leu Ala Leu Gly Gly Val Leu Ile Phe Leu Ser Thr Ala Val Ser Ala
    690                 695                 700

Glu Asn Ile Thr Ser Gly Phe Leu Gly Pro Leu Leu Val Leu Gln Ala
705                 710                 715                 720

Gly Phe Phe Leu Leu Thr Arg Ile Leu Thr Ile Pro Gln Ser Leu Asp
                725                 730                 735

Ser Trp Trp Thr Ser Leu Asn Phe Leu Gly Gly Ser Pro Val Cys Leu
            740                 745                 750

Gly Gln Asn Ser Gln Ser Pro Thr Ser Asn His Ser Pro Thr Ser Cys
        755                 760                 765

Pro Pro Ile Cys Pro Gly Tyr Arg Trp Met Cys Leu Arg Arg Phe Ile
    770                 775                 780

Ile Phe Leu Phe Ile Leu Leu Leu Cys Leu Ile Phe Leu Leu Val Leu
785                 790                 795                 800

Leu Asp Tyr Gln Gly Met Leu Pro Val Cys Pro Leu Ile Pro Gly Ser
                805                 810                 815

Thr Thr Thr Ser Thr Gly Pro Cys Lys Thr Cys Thr Thr Pro Ala Gln
            820                 825                 830

Gly Asn Ser Met Phe Pro Ser Cys Cys Cys Thr Lys Pro Thr Asp Gly
        835                 840                 845

Asn Cys Thr Cys Ile Pro Ile Pro Ser Ser Trp Ala Phe Ala Lys Tyr
    850                 855                 860

Leu Trp Glu Trp Ala Ser Val Arg Phe Ser Trp Leu Ser Leu Leu Val
865                 870                 875                 880

Pro Phe Val Gln Trp Phe Val Gly Leu Ser Pro Thr Val Trp Leu Ser
                885                 890                 895

Ala Ile Trp Met Met Trp Tyr Trp Gly Pro Ser Leu Tyr Ser Ile Val
            900                 905                 910

Ser Pro Phe Ile Pro Leu Leu Pro Ile Phe Phe Cys Leu Trp Val Tyr
        915                 920                 925
```

Ile

<210> SEQ ID NO 21
<211> LENGTH: 787
<212> TYPE: PRT
<213> ORGANISM: Artificial sequence
<220> FEATURE:
<223> OTHER INFORMATION: TIP + E deleted + M

<400> SEQUENCE: 21

Met Leu Gly Ser Ser Thr Ser Gln Lys Val Ile Tyr Leu Val Met Ile
1 5 10 15

Leu Leu Ile Ala Pro Ala Tyr Ser Ile Arg Cys Ile Gly Val Ser Asn
20 25 30

Arg Asp Phe Val Glu Gly Met Ser Gly Gly Thr Trp Val Asp Val Val
35 40 45

Leu Glu His Gly Gly Cys Val Thr Val Met Ala Gln Asp Lys Pro Thr
50 55 60

Val Asp Ile Glu Leu Val Thr Thr Thr Val Ser Asn Met Ala Glu Val
65 70 75 80

Arg Ser Tyr Cys Tyr Glu Ala Ser Ile Ser Asp Met Ala Ser Asp Ser
85 90 95

Arg Cys Pro Thr Gln Gly Glu Ala Tyr Leu Asp Lys Gln Ser Asp Thr
100 105 110

Gln Tyr Val Cys Lys Arg Thr Leu Val Asp Arg Gly Trp Gly Asn Gly
115 120 125

Cys Gly Leu Phe Gly Lys Gly Ser Leu Val Thr Cys Ala Lys Phe Ala
130 135 140

Cys Ser Lys Lys Met Thr Gly Lys Ser Ile Gln Pro Glu Asn Leu Glu
145 150 155 160

Tyr Arg Ile Met Leu Ser Val His Gly Ser Gln His Ser Gly Met Ile
165 170 175

Val Asn Asp Thr Gly His Glu Thr Asp Glu Asn Arg Ala Lys Val Glu
180 185 190

Ile Thr Pro Asn Ser Pro Arg Ala Glu Ala Thr Leu Gly Gly Phe Gly
195 200 205

Ser Leu Gly Leu Asp Cys Glu Pro Arg Thr Gly Leu Asp Phe Ser Asp
210 215 220

Leu Tyr Tyr Leu Thr Met Asn Asn Lys His Trp Leu Val His Lys Glu
225 230 235 240

Trp Phe His Asp Ile Pro Leu Pro Trp His Ala Gly Ala Asp Thr Gly
245 250 255

Thr Pro His Trp Asn Asn Lys Glu Ala Leu Val Glu Phe Lys Asp Ala
260 265 270

His Ala Lys Arg Gln Thr Val Val Val Leu Gly Ser Gln Glu Gly Ala
275 280 285

Val His Thr Ala Leu Ala Gly Ala Leu Glu Ala Glu Met Asp Gly Ala
290 295 300

Lys Gly Arg Leu Ser Ser Gly His Leu Lys Cys Arg Leu Lys Met Asp
305 310 315 320

Lys Leu Arg Leu Lys Gly Val Ser Tyr Ser Leu Cys Thr Ala Ala Phe
325 330 335

Thr Phe Thr Lys Ile Pro Ala Glu Thr Leu His Gly Thr Val Thr Val
340 345 350

```
Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480

Phe Gly Gly Met Ser Trp Phe Ser Gln Ile Leu Ile Gly Thr Leu Leu
                485                 490                 495

Met Trp Leu Gly Leu Asn Ala Lys Asn Gly Ser Gln Trp Asn Ser Thr
            500                 505                 510

Ala Phe His Gln Thr Leu Gln Asp Pro Arg Val Arg Gly Leu Tyr Leu
        515                 520                 525

Pro Ala Gly Gly Ser Ser Ser Gly Thr Val Asn Pro Ala Pro Asn Ile
    530                 535                 540

Ala Ser His Ile Ser Ser Ile Ser Ala Arg Thr Gly Asp Pro Val Thr
545                 550                 555                 560

Asn Met Glu Asn Ile Thr Ser Gly Phe Leu Gly Pro Leu Leu Val Leu
                565                 570                 575

Gln Ala Gly Phe Phe Leu Leu Thr Arg Ile Leu Thr Ile Pro Gln Ser
            580                 585                 590

Leu Asp Ser Trp Trp Thr Ser Leu Asn Phe Leu Gly Gly Ser Pro Val
        595                 600                 605

Cys Leu Gly Gln Asn Ser Gln Ser Pro Thr Ser Asn His Ser Pro Thr
    610                 615                 620

Ser Cys Pro Pro Ile Cys Pro Gly Tyr Arg Trp Met Cys Leu Arg Arg
625                 630                 635                 640

Phe Ile Ile Phe Leu Phe Ile Leu Leu Leu Cys Leu Ile Phe Leu Leu
                645                 650                 655

Val Leu Leu Asp Tyr Gln Gly Met Leu Pro Val Cys Pro Leu Ile Pro
            660                 665                 670

Gly Ser Thr Thr Thr Ser Thr Gly Pro Cys Lys Thr Cys Thr Thr Pro
        675                 680                 685

Ala Gln Gly Asn Ser Met Phe Pro Ser Cys Cys Cys Thr Lys Pro Thr
    690                 695                 700

Asp Gly Asn Cys Thr Cys Ile Pro Ile Pro Ser Ser Trp Ala Phe Ala
705                 710                 715                 720

Lys Tyr Leu Trp Glu Trp Ala Ser Val Arg Phe Ser Trp Leu Ser Leu
                725                 730                 735

Leu Val Pro Phe Val Gln Trp Phe Val Gly Leu Ser Pro Thr Val Trp
            740                 745                 750

Leu Ser Ala Ile Trp Met Met Trp Tyr Trp Gly Pro Ser Leu Tyr Ser
        755                 760                 765

Ile Val Ser Pro Phe Ile Pro Leu Leu Pro Ile Phe Phe Cys Leu Trp
```

770 775 780

Val Tyr Ile
785

<210> SEQ ID NO 22
<211> LENGTH: 963
<212> TYPE: PRT
<213> ORGANISM: Artificial sequence
<220> FEATURE:
<223> OTHER INFORMATION: TIP + prM + E deleted + M

<400> SEQUENCE: 22

Met Leu Arg Ile Ile Asn Ala Arg Lys Glu Lys Lys Arg Arg Gly Ala
1 5 10 15

Asp Thr Ser Val Gly Ile Val Gly Leu Leu Leu Thr Thr Ala Met Ala
20 25 30

Ala Glu Val Thr Arg Arg Gly Ser Ala Tyr Tyr Met Tyr Leu Asp Arg
35 40 45

Asn Asp Ala Gly Glu Ala Ile Ser Phe Pro Thr Thr Leu Gly Met Asn
50 55 60

Lys Cys Tyr Ile Gln Ile Met Asp Leu Gly His Thr Cys Asp Ala Thr
65 70 75 80

Met Ser Tyr Glu Cys Pro Met Leu Asp Glu Gly Val Glu Pro Asp Asp
85 90 95

Val Asp Cys Trp Cys Asn Thr Thr Ser Thr Trp Val Val Tyr Gly Thr
100 105 110

Cys His His Lys Lys Gly Glu Ala Arg Arg Ser Arg Arg Ala Val Thr
115 120 125

Leu Pro Ser His Ser Thr Arg Lys Leu Gln Thr Arg Ser Gln Thr Trp
130 135 140

Leu Glu Ser Arg Glu Tyr Thr Lys His Leu Ile Arg Val Glu Asn Trp
145 150 155 160

Ile Phe Arg Asn Pro Gly Phe Ala Leu Ala Ala Ala Ala Ile Ala Trp
165 170 175

Leu Leu Gly Ser Ser Thr Ser Gln Lys Val Ile Tyr Leu Val Met Ile
180 185 190

Leu Leu Ile Ala Pro Ala Tyr Ser Ile Arg Cys Ile Gly Val Ser Asn
195 200 205

Arg Asp Phe Val Glu Gly Met Ser Gly Gly Thr Trp Val Asp Val Val
210 215 220

Leu Glu His Gly Gly Cys Val Thr Val Met Ala Gln Asp Lys Pro Thr
225 230 235 240

Val Asp Ile Glu Leu Val Thr Thr Thr Val Ser Asn Met Ala Glu Val
245 250 255

Arg Ser Tyr Cys Tyr Glu Ala Ser Ile Ser Asp Met Ala Ser Asp Ser
260 265 270

Arg Cys Pro Thr Gln Gly Glu Ala Tyr Leu Asp Lys Gln Ser Asp Thr
275 280 285

Gln Tyr Val Cys Lys Arg Thr Leu Val Asp Arg Gly Trp Gly Asn Gly
290 295 300

Cys Gly Leu Phe Gly Lys Gly Ser Leu Val Thr Cys Ala Lys Phe Ala
305 310 315 320

Cys Ser Lys Lys Met Thr Gly Lys Ser Ile Gln Pro Glu Asn Leu Glu
325 330 335

Tyr Arg Ile Met Leu Ser Val His Gly Ser Gln His Ser Gly Met Ile

-continued

```
            340                 345                 350

Val Asn Asp Thr Gly His Glu Thr Asp Glu Asn Arg Ala Lys Val Glu
        355                 360                 365

Ile Thr Pro Asn Ser Pro Arg Ala Glu Ala Thr Leu Gly Gly Phe Gly
    370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala
        435                 440                 445

His Ala Lys Arg Gln Thr Val Val Val Leu Gly Ser Gln Glu Gly Ala
    450                 455                 460

Val His Thr Ala Leu Ala Gly Ala Leu Glu Ala Glu Met Asp Gly Ala
465                 470                 475                 480

Lys Gly Arg Leu Ser Ser Gly His Leu Lys Cys Arg Leu Lys Met Asp
                485                 490                 495

Lys Leu Arg Leu Lys Gly Val Ser Tyr Ser Leu Cys Thr Ala Ala Phe
            500                 505                 510

Thr Phe Thr Lys Ile Pro Ala Glu Thr Leu His Gly Thr Val Thr Val
        515                 520                 525

Glu Val Gln Tyr Ala Gly Thr Asp Gly Pro Cys Lys Val Pro Ala Gln
    530                 535                 540

Met Ala Val Asp Met Gln Thr Leu Thr Pro Val Gly Arg Leu Ile Thr
545                 550                 555                 560

Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
            580                 585                 590

Glu Lys Lys Ile Thr His His Trp His Arg Ser Gly Ser Thr Ile Gly
        595                 600                 605

Lys Ala Phe Glu Ala Thr Val Arg Gly Ala Lys Arg Met Ala Val Leu
    610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Gln Trp Asn Ser Thr
        675                 680                 685

Ala Phe His Gln Thr Leu Gln Asp Pro Arg Val Arg Gly Leu Tyr Leu
    690                 695                 700

Pro Ala Gly Gly Ser Ser Ser Gly Thr Val Asn Pro Ala Pro Asn Ile
705                 710                 715                 720

Ala Ser His Ile Ser Ser Ile Ser Ala Arg Thr Gly Asp Pro Val Thr
                725                 730                 735

Asn Met Glu Asn Ile Thr Ser Gly Phe Leu Gly Pro Leu Leu Val Leu
            740                 745                 750

Gln Ala Gly Phe Phe Leu Leu Thr Arg Ile Leu Thr Ile Pro Gln Ser
        755                 760                 765
```

```
Leu Asp Ser Trp Trp Thr Ser Leu Asn Phe Leu Gly Gly Ser Pro Val
    770                 775                 780

Cys Leu Gly Gln Asn Ser Gln Ser Pro Thr Ser Asn His Ser Pro Thr
785                 790                 795                 800

Ser Cys Pro Pro Ile Cys Pro Gly Tyr Arg Trp Met Cys Leu Arg Arg
                805                 810                 815

Phe Ile Ile Phe Leu Phe Ile Leu Leu Leu Cys Leu Ile Phe Leu Leu
            820                 825                 830

Val Leu Leu Asp Tyr Gln Gly Met Leu Pro Val Cys Pro Leu Ile Pro
        835                 840                 845

Gly Ser Thr Thr Thr Ser Thr Gly Pro Cys Lys Thr Cys Thr Thr Pro
    850                 855                 860

Ala Gln Gly Asn Ser Met Phe Pro Ser Cys Cys Cys Thr Lys Pro Thr
865                 870                 875                 880

Asp Gly Asn Cys Thr Cys Ile Pro Ile Pro Ser Ser Trp Ala Phe Ala
                885                 890                 895

Lys Tyr Leu Trp Glu Trp Ala Ser Val Arg Phe Ser Trp Leu Ser Leu
            900                 905                 910

Leu Val Pro Phe Val Gln Trp Phe Val Gly Leu Ser Pro Thr Val Trp
        915                 920                 925

Leu Ser Ala Ile Trp Met Met Trp Tyr Trp Gly Pro Ser Leu Tyr Ser
    930                 935                 940

Ile Val Ser Pro Phe Ile Pro Leu Leu Pro Ile Phe Phe Cys Leu Trp
945                 950                 955                 960

Val Tyr Ile


<210> SEQ ID NO 23
<211> LENGTH: 808
<212> TYPE: PRT
<213> ORGANISM: Artificial sequence
<220> FEATURE:
<223> OTHER INFORMATION: TIP + E + M

<400> SEQUENCE: 23

Met Leu Gly Ser Ser Thr Ser Gln Lys Val Ile Tyr Leu Val Met Ile
1               5                   10                  15

Leu Leu Ile Ala Pro Ala Tyr Ser Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160
```

-continued

```
Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480

Phe Gly Gly Met Ser Trp Phe Ser Gln Ile Leu Ile Gly Thr Leu Leu
                485                 490                 495

Met Trp Leu Gly Leu Asn Ala Lys Asn Gly Ser Ile Ser Leu Met Cys
            500                 505                 510

Leu Ala Leu Gly Gly Val Leu Ile Phe Leu Ser Thr Ala Val Ser Ala
        515                 520                 525

Gln Trp Asn Ser Thr Ala Phe His Gln Thr Leu Gln Asp Pro Arg Val
    530                 535                 540

Arg Gly Leu Tyr Leu Pro Ala Gly Gly Ser Ser Ser Gly Thr Val Asn
545                 550                 555                 560

Pro Ala Pro Asn Ile Ala Ser His Ile Ser Ser Ile Ser Ala Arg Thr
                565                 570                 575

Gly Asp Pro Val Thr Asn Met Glu Asn Ile Thr Ser Gly Phe Leu Gly
```

```
            580                 585                 590

Pro Leu Leu Val Leu Gln Ala Gly Phe Phe Leu Leu Thr Arg Ile Leu
        595                 600                 605

Thr Ile Pro Gln Ser Leu Asp Ser Trp Trp Thr Ser Leu Asn Phe Leu
    610                 615                 620

Gly Gly Ser Pro Val Cys Leu Gly Gln Asn Ser Gln Ser Pro Thr Ser
625                 630                 635                 640

Asn His Ser Pro Thr Ser Cys Pro Pro Ile Cys Pro Gly Tyr Arg Trp
                645                 650                 655

Met Cys Leu Arg Arg Phe Ile Ile Phe Leu Phe Ile Leu Leu Leu Cys
            660                 665                 670

Leu Ile Phe Leu Leu Val Leu Leu Asp Tyr Gln Gly Met Leu Pro Val
        675                 680                 685

Cys Pro Leu Ile Pro Gly Ser Thr Thr Thr Ser Thr Gly Pro Cys Lys
    690                 695                 700

Thr Cys Thr Thr Pro Ala Gln Gly Asn Ser Met Phe Pro Ser Cys Cys
705                 710                 715                 720

Cys Thr Lys Pro Thr Asp Gly Asn Cys Thr Cys Ile Pro Ile Pro Ser
                725                 730                 735

Ser Trp Ala Phe Ala Lys Tyr Leu Trp Glu Trp Ala Ser Val Arg Phe
            740                 745                 750

Ser Trp Leu Ser Leu Leu Val Pro Phe Val Gln Trp Phe Val Gly Leu
        755                 760                 765

Ser Pro Thr Val Trp Leu Ser Ala Ile Trp Met Met Trp Tyr Trp Gly
    770                 775                 780

Pro Ser Leu Tyr Ser Ile Val Ser Pro Phe Ile Pro Leu Leu Pro Ile
785                 790                 795                 800

Phe Phe Cys Leu Trp Val Tyr Ile
                805


<210> SEQ ID NO 24
<211> LENGTH: 984
<212> TYPE: PRT
<213> ORGANISM: Artificial sequence
<220> FEATURE:
<223> OTHER INFORMATION: TIP + prM + E + M

<400> SEQUENCE: 24

Met Leu Arg Ile Ile Asn Ala Arg Lys Glu Lys Lys Arg Arg Gly Ala
1               5                   10                  15

Asp Thr Ser Val Gly Ile Val Gly Leu Leu Leu Thr Thr Ala Met Ala
            20                  25                  30

Ala Glu Val Thr Arg Arg Gly Ser Ala Tyr Tyr Met Tyr Leu Asp Arg
        35                  40                  45

Asn Asp Ala Gly Glu Ala Ile Ser Phe Pro Thr Thr Leu Gly Met Asn
    50                  55                  60

Lys Cys Tyr Ile Gln Ile Met Asp Leu Gly His Thr Cys Asp Ala Thr
65                  70                  75                  80

Met Ser Tyr Glu Cys Pro Met Leu Asp Glu Gly Val Glu Pro Asp Asp
                85                  90                  95

Val Asp Cys Trp Cys Asn Thr Thr Ser Thr Trp Val Val Tyr Gly Thr
            100                 105                 110

Cys His His Lys Lys Gly Glu Ala Arg Arg Ser Arg Arg Ala Val Thr
        115                 120                 125

Leu Pro Ser His Ser Thr Arg Lys Leu Gln Thr Arg Ser Gln Thr Trp
```

```
    130                 135                 140

Leu Glu Ser Arg Glu Tyr Thr Lys His Leu Ile Arg Val Glu Asn Trp
145                 150                 155                 160

Ile Phe Arg Asn Pro Gly Phe Ala Leu Ala Ala Ala Ala Ile Ala Trp
                165                 170                 175

Leu Leu Gly Ser Ser Thr Ser Gln Lys Val Ile Tyr Leu Val Met Ile
            180                 185                 190

Leu Leu Ile Ala Pro Ala Tyr Ser Ile Arg Cys Ile Gly Val Ser Asn
        195                 200                 205

Arg Asp Phe Val Glu Gly Met Ser Gly Gly Thr Trp Val Asp Val Val
    210                 215                 220

Leu Glu His Gly Gly Cys Val Thr Val Met Ala Gln Asp Lys Pro Thr
225                 230                 235                 240

Val Asp Ile Glu Leu Val Thr Thr Thr Val Ser Asn Met Ala Glu Val
                245                 250                 255

Arg Ser Tyr Cys Tyr Glu Ala Ser Ile Ser Asp Met Ala Ser Asp Ser
            260                 265                 270

Arg Cys Pro Thr Gln Gly Glu Ala Tyr Leu Asp Lys Gln Ser Asp Thr
        275                 280                 285

Gln Tyr Val Cys Lys Arg Thr Leu Val Asp Arg Gly Trp Gly Asn Gly
    290                 295                 300

Cys Gly Leu Phe Gly Lys Gly Ser Leu Val Thr Cys Ala Lys Phe Ala
305                 310                 315                 320

Cys Ser Lys Lys Met Thr Gly Lys Ser Ile Gln Pro Glu Asn Leu Glu
                325                 330                 335

Tyr Arg Ile Met Leu Ser Val His Gly Ser Gln His Ser Gly Met Ile
            340                 345                 350

Val Asn Asp Thr Gly His Glu Thr Asp Glu Asn Arg Ala Lys Val Glu
        355                 360                 365

Ile Thr Pro Asn Ser Pro Arg Ala Glu Ala Thr Leu Gly Gly Phe Gly
    370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala
        435                 440                 445

His Ala Lys Arg Gln Thr Val Val Val Leu Gly Ser Gln Glu Gly Ala
    450                 455                 460

Val His Thr Ala Leu Ala Gly Ala Leu Glu Ala Glu Met Asp Gly Ala
465                 470                 475                 480

Lys Gly Arg Leu Ser Ser Gly His Leu Lys Cys Arg Leu Lys Met Asp
                485                 490                 495

Lys Leu Arg Leu Lys Gly Val Ser Tyr Ser Leu Cys Thr Ala Ala Phe
            500                 505                 510

Thr Phe Thr Lys Ile Pro Ala Glu Thr Leu His Gly Thr Val Thr Val
        515                 520                 525

Glu Val Gln Tyr Ala Gly Thr Asp Gly Pro Cys Lys Val Pro Ala Gln
    530                 535                 540

Met Ala Val Asp Met Gln Thr Leu Thr Pro Val Gly Arg Leu Ile Thr
545                 550                 555                 560
```

-continued

```
Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
            580                 585                 590

Glu Lys Lys Ile Thr His His Trp His Arg Ser Gly Ser Thr Ile Gly
        595                 600                 605

Lys Ala Phe Glu Ala Thr Val Arg Gly Ala Lys Arg Met Ala Val Leu
    610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Ile Ser Leu Met Cys
        675                 680                 685

Leu Ala Leu Gly Gly Val Leu Ile Phe Leu Ser Thr Ala Val Ser Ala
    690                 695                 700

Gln Trp Asn Ser Thr Ala Phe His Gln Thr Leu Gln Asp Pro Arg Val
705                 710                 715                 720

Arg Gly Leu Tyr Leu Pro Ala Gly Gly Ser Ser Ser Gly Thr Val Asn
                725                 730                 735

Pro Ala Pro Asn Ile Ala Ser His Ile Ser Ser Ile Ser Ala Arg Thr
            740                 745                 750

Gly Asp Pro Val Thr Asn Met Glu Asn Ile Thr Ser Gly Phe Leu Gly
        755                 760                 765

Pro Leu Leu Val Leu Gln Ala Gly Phe Phe Leu Leu Thr Arg Ile Leu
    770                 775                 780

Thr Ile Pro Gln Ser Leu Asp Ser Trp Trp Thr Ser Leu Asn Phe Leu
785                 790                 795                 800

Gly Gly Ser Pro Val Cys Leu Gly Gln Asn Ser Gln Ser Pro Thr Ser
                805                 810                 815

Asn His Ser Pro Thr Ser Cys Pro Pro Ile Cys Pro Gly Tyr Arg Trp
            820                 825                 830

Met Cys Leu Arg Arg Phe Ile Ile Phe Leu Phe Ile Leu Leu Leu Cys
        835                 840                 845

Leu Ile Phe Leu Leu Val Leu Leu Asp Tyr Gln Gly Met Leu Pro Val
    850                 855                 860

Cys Pro Leu Ile Pro Gly Ser Thr Thr Thr Ser Thr Gly Pro Cys Lys
865                 870                 875                 880

Thr Cys Thr Thr Pro Ala Gln Gly Asn Ser Met Phe Pro Ser Cys Cys
                885                 890                 895

Cys Thr Lys Pro Thr Asp Gly Asn Cys Thr Cys Ile Pro Ile Pro Ser
            900                 905                 910

Ser Trp Ala Phe Ala Lys Tyr Leu Trp Glu Trp Ala Ser Val Arg Phe
        915                 920                 925

Ser Trp Leu Ser Leu Leu Val Pro Phe Val Gln Trp Phe Val Gly Leu
    930                 935                 940

Ser Pro Thr Val Trp Leu Ser Ala Ile Trp Met Met Trp Tyr Trp Gly
945                 950                 955                 960

Pro Ser Leu Tyr Ser Ile Val Ser Pro Phe Ile Pro Leu Leu Pro Ile
                965                 970                 975
```

Phe Phe Cys Leu Trp Val Tyr Ile
980

<210> SEQ ID NO 25
<211> LENGTH: 19
<212> TYPE: PRT
<213> ORGANISM: Artificial sequence
<220> FEATURE:
<223> OTHER INFORMATION: transfer initiation peptide

<400> SEQUENCE: 25

Thr Ser Val Gly Ile Val Gly Leu Leu Leu Thr Thr Ala Met Ala Ala
1 5 10 15

Glu Val Thr

<210> SEQ ID NO 26
<211> LENGTH: 15
<212> TYPE: PRT
<213> ORGANISM: Artificial sequence
<220> FEATURE:
<223> OTHER INFORMATION: transfer initiation peptide

<400> SEQUENCE: 26

Val Ile Tyr Leu Val Met Ile Leu Leu Ile Ala Pro Ala Tyr Ser
1 5 10 15

<210> SEQ ID NO 27
<211> LENGTH: 17
<212> TYPE: PRT
<213> ORGANISM: Artificial sequence
<220> FEATURE:
<223> OTHER INFORMATION: Initiation sequence

<400> SEQUENCE: 27

Met Leu Arg Ile Ile Asn Ala Arg Lys Glu Lys Lys Arg Arg Gly Ala
1 5 10 15

Asp

<210> SEQ ID NO 28
<211> LENGTH: 9
<212> TYPE: PRT
<213> ORGANISM: Artificial sequence
<220> FEATURE:
<223> OTHER INFORMATION: Initiation sequence

<400> SEQUENCE: 28

Met Leu Gly Ser Ser Thr Ser Gln Lys
1 5

<210> SEQ ID NO 29
<211> LENGTH: 10374
<212> TYPE: DNA
<213> ORGANISM: Zika virus

<400> SEQUENCE: 29
acaggtttta ttttggattt ggaaacgaga gtttctggtc atgaaaaacc caaaaaagaa 60
atccggagga ttccggattg tcaatatgct aaaacgcgga gtagcccgtg tgagcccctt 120
tgggggcttg aagaggctgc cagccggact tctgctgggt catgggccca tcaggatggt 180
cttggcgatt ctagcctttt tgagattcac ggcaatcaag ccatcactgg gtctcatcaa 240
tagatggggt tcagtgggga aaaaagaggc tatggaaata ataaagaagt tcaagaaaga 300
tctggctgcc atgctgagaa taatcaatgc taggaaggag aagaagagac gaggcgcaga 360

-continued

```
tactagtgtc ggaattgttg gcctcctgct gaccacagct atggcagcgg aggtcactag    420
acgtgggagt gcatactata tgtacttgga cagaaacgat gctggggagg ccatatcttt    480
tccaaccaca ttggggatga ataagtgtta tatacagatc atggatcttg gacacacgtg    540
tgatgccacc atgagctatg aatgccctat gctggatgag ggggtggaac cagatgacgt    600
cgattgttgg tgcaacacga cgtcaacttg ggttgtgtac ggaacctgcc atcacaaaaa    660
aggtgaagca cggagatcta gaagagctgt gacgctcccc tcccattcca ctaggaagct    720
gcaaacgcgg tcgcaaacct ggttggaatc aagagaatac acaaagcact tgattagagt    780
cgaaaattgg atattcagga accctggctt cgcgttagca gcagctgcca tcgcttggct    840
tttgggaagc tcaacgagcc aaaaagtcat atacttggtc atgatactgc tgattgcccc    900
ggcatacagc atcaggtgca taggagtcag caatagggac tttgtggaag gtatgtcagg    960
tgggacttgg gttgatgttg tcttggaaca tggaggttgt gtcactgtaa tggcacagga   1020
caaaccgact gtcgacatag agctggttac aacaacagtc agcaacatgg cggaggtaag   1080
atcctactgc tatgaggcat caatatcaga catggcttcg gacagccgct gcccaacaca   1140
aggtgaagcc taccttgaca agcaatcaga cactcaatat gtctgcaaaa gaacgttagt   1200
ggacagaggc tggggaaatg gatgtggact tttggcaaa gggagcctgg tgacatgcgc   1260
taagtttgca tgctccaaga aaatgaccgg gaagagcatc cagccagaga atctggagta   1320
ccggataatg ctgtcagttc atggctccca gcacagtggg atgatcgtta atgacacagg   1380
acatgaaact gatgagaata gagcgaaagt tgagataacg cccaattcac caagagccga   1440
agccaccctg ggggggtttg gaagcctagg acttgattgt gaaccgagga caggccttga   1500
cttttcagat ttgtattact tgactatgaa taacaagcac tggctggttc acaaggagtg   1560
gttccacgac attccattac cttggcacgc tggggcagac accggaactc cacactggaa   1620
caacaaagaa gcactggtag agttcaagga cgcacatgcc aaaaggcaaa ctgtcgtggt   1680
tctagggagt caagaaggag cagttcacac ggcccttgct ggagctctgg aggctgagat   1740
ggatggtgca aagggaaggc tgtcctctgg ccacttgaaa tgtcgcctga aaatggataa   1800
acttagattg aagggcgtgt catactcctt gtgtactgca gcgttcacat tcaccaagat   1860
cccggctgaa acactgcacg ggacagtcac agtggaggta cagtacgcag ggacagatgg   1920
accttgcaag gttccagctc agatggcggt ggacatgcaa actctgaccc cagttgggag   1980
gttgataacc gctaaccccg taatcactga aagcactgag aactctaaga tgatgctgga   2040
acttgatcca ccatttgggg actcttacat tgtcatagga gtcggggaga agaagatcac   2100
ccaccactgg cacaggagtg gcagcaccat tggaaaagca tttgaagcca ctgtgagagg   2160
tgccaagaga atggcagtct tgggagacac agcctgggac tttggatcag ttggaggcgc   2220
tctcaactca ttgggcaagg gcatccatca aatctttgga gcagctttca aatcattgtt   2280
tggaggaatg tcctggttct cacaaattct cattggaacg ttgctgatgt ggttgggtct   2340
gaacgcaaag aatggatcta tttcccttat gtgcttggcc ttagggggag tgttgatctt   2400
cttatccaca gccgtctctg ctgatgtggg gtgctcggtg gacttctcaa agaaggagac   2460
gagatgcggt acaggggtgt tcgtctataa cgacgttgaa gcctggaggg acaggtacaa   2520
gtaccatcct gactcccccc gtagattggc agcagcagtc aagcaagcct gggaagatgg   2580
tatctgcggg atctcctctg tttcaagaat ggaaaacatc atgtggagat cagtagaagg   2640
ggagctcaac gcaatcctgg aagagaatgg agttcaactg acggtcgttg tgggatctgt   2700
aaaaaacccc atgtggagag gtccacagag attgcccgtg cctgtgaacg agctgcccca   2760
```

-continued

```
cggctggaag gcttggggga aatcgtactt cgtcagagca gcaaagacaa ataacagctt   2820
tgtcgtggat ggtgacacac tgaaggaatg cccactcaaa catagagcat ggaacagctt   2880
tcttgtggag gatcatgggt tcggggtatt tcacactagt gtctggctca aggttagaga   2940
agattattca ttagagtgtg atccagccgt tattggaaca gctgttaagg gaaaggaggc   3000
tgtacacagt gatctaggct actggattga gagtgagaag aatgacacat ggaggctgaa   3060
gagggcccat ctgatcgaga tgaaaacatg tgaatggcca aagtcccaca cattgtggac   3120
agatggaata gaagagagtg atctgatcat acccaagtct ttagctgggc cactcagcca   3180
tcacaatacc agagagggct acaggaccca aatgaaaggg ccatggcaca gtgaagagct   3240
tgaaattcgg tttgaggaat gcccaggcac taaggtccac gtggaggaaa catgtggaac   3300
gagaggacca tctctgagat caaccactgc aagcggaagg gtgatcgagg aatggtgctg   3360
cagggagtgc acaatgcccc cactgtcgtt ccgggctaaa gatggctgtt ggtatggaat   3420
ggagataagg cccaggaaag aaccagaaag caacttagta aggtcaatgg tgactgcagg   3480
atcaactgat cacatggacc acttctccct tggagtgctt gtgattctgc tcatggtgca   3540
ggaagggttg aagaagagaa tgaccacaaa gatcatcata agcacatcaa tggcagtgct   3600
ggtagctatg atcctgggag gattttcaat gagtgacctg gctaagcttg caattttgat   3660
gggtgccacc ttcgcggaaa tgaacactgg aggagatgta gctcatctgg cgctgatagc   3720
ggcattcaaa gtcagaccag cgttgctggt atctttcatc ttcagagcta attggacacc   3780
ccgtgaaagc atgctgctgg ccttggcctc gtgtcttttg caaactgcga tctccgcctt   3840
ggaaggcgac ctgatggttc tcatcaatgg ttttgctttg gcctggttgg caatacgagc   3900
gatggttgtt ccacgcactg ataacatcac cttggcaatc ctggctgctc tgacaccact   3960
ggcccggggc acactgcttg tggcgtggag agcaggcctt gctacttgcg gggggtttat   4020
gctcctctct ctgaagggaa aaggcagtgt gaagaagaac ttaccatttg tcatggccct   4080
gggactaacc gctgtgaggc tggtcgaccc catcaacgtg gtgggactgc tgttgctcac   4140
aaggagtggg aagcggagct ggccccctag cgaagtactc acagctgttg gcctgatatg   4200
cgcattggct ggagggttcg ccaaggcaga tatagagatg gctgggccca tggccgcggt   4260
cggtctgcta attgtcagtt acgtggtctc aggaaagagt gtggacatgt acattgaaag   4320
agcaggtgac atcacatggg aaaaagatgc ggaagtcact ggaaacagtc cccggctcga   4380
tgtggcgcta gatgagagtg gtgatttctc cctggtggag gatgacggtc cccccatgag   4440
agagatcata ctcaaggtgg tcctgatgac catctgtggc atgaacccaa tagccatacc   4500
ctttgcagct ggagcgtggt acgtatacgt gaagactgga aaaaggagtg gtgctctatg   4560
ggatgtgcct gctcccaagg aagtaaaaaa gggggagacc acagatggag tgtacagagt   4620
aatgactcgt agactgctag gttcaacaca agttggagtg ggagttatgc aagagggggt   4680
ctttcacact atgtggcacg tcacaaaagg atccgcgctg agaagcggtg aagggagact   4740
tgatccatac tggggagatg tcaagcagga tctggtgtca tactgtggtc catggaagct   4800
agatgccgcc tgggacgggc acagcgaggt gcagctcttg gccgtgcccc ccggagagag   4860
agcgaggaac atccagactc tgcccggaat atttaagaca aaggatgggg acattggagc   4920
ggttgcgctg gattacccag caggaacttc aggatctcct atcctagaca agtgtgggag   4980
agtgatagga ctttatggca atggggtcgt gatcaaaaat gggagttatg ttagtgccat   5040
cacccaaggg aggagggagg aagagactcc tgttgagtgc ttcgagcctt cgatgctgaa   5100
```

gaagaagcag ctaactgtct tagacttgca tcctggagct gggaaaacca ggagagttct 5160
tcctgaaata gtccgtgaag ccataaaaac aagactccgt actgtgatct tagctccaac 5220
cagggttgtc gctgctgaaa tggaggaggc ccttagaggg cttccagtgc gttatatgac 5280
aacagcagtc aatgtcaccc actctggaac agaaatcgtc gacttaatgt gccatgccac 5340
cttcacttcg cgtctactac agccaatcag agtccccaac tataatctgt atattatgga 5400
tgaggcccac ttcacagatc cctcaagtat agcagcaaga ggatacattt caacaagggt 5460
tgagatgggc gaggcggccg ccatcttcat gaccgccacg ccaccaggaa cccgtgacgc 5520
atttccggac tccaactcac caattatgga caccgaagtg gaagtcccag agagagcctg 5580
gagctcaggc tttgattggg tgacggatca ttctggaaaa acagtttggt ttgttccaag 5640
cgtgaggaac ggcaatgaga tcgcagcttg tctgacaaag gctggaaaac gggtcataca 5700
gctcagcaga aagacttttg agacagagtt ccagaaaaca aaacatcaag agtgggactt 5760
tgtcgtgaca actgacattt cagagatggg cgccaacttt aaagctgacc gtgtcataga 5820
ttccaggaga tgcctaaagc cggtcatact tgatggcgag agagtcattc tggctggacc 5880
catgcctgtc acacatgcca gcgctgccca gaggaggggg cgcataggca ggaatcccaa 5940
caaacctgga gatgagtatc tgtatggagg tgggtgcgca gagactgacg aagaccatgc 6000
acactggctt gaagcaagaa tgctccttga caatatttac ctccaagatg gcctcatagc 6060
ctcgctctat cgacctgagg ccgacaaagt agcagccatt gagggagagt tcaagcttag 6120
gacggagcaa aggaagacct ttgtggaact catgaaaaga ggagatcttc ctgtttggct 6180
ggcctatcag gttgcatctg ccggaataac ctacacagat agaagatggt gctttgatgg 6240
cacgaccaac aacaccataa tggaagacag tgtgccggca gaagtgtgga ccagacacgg 6300
agagaaaaga gtgctcaaac cgaggtggat ggacgccaga gtttgttcag atcatgcggc 6360
cctgaagtca ttcaaggagt ttgccgctgg gaaaagagga gcggcttttg gagtgatgga 6420
agccctggga acactgccag gacacatgac agagagattc caggaagcca ttgacaacct 6480
cgctgtgctc atgcgggcag agactggaag caggccttac aaagccgcgg cggcccaatt 6540
gccggagacc ctagagacca ttatgctttt ggggttgctg ggaacagtct cgctgggaat 6600
cttcttcgtc ttgatgagga acaagggcat agggaagatg ggctttggaa tggtgactct 6660
tggggccagc gcatggctca tgtggctctc ggaaattgag ccagccagaa ttgcatgtgt 6720
cctcattgtt gtgttcctat tgctggtggt gctcatacct gagccagaaa agcaaagatc 6780
tccccaggac aaccaaatgg caatcatcat catggtagca gtaggtcttc tgggcttgat 6840
taccgccaat gaactcggat ggttggagag aacaaagagt gacctaagcc atctaatggg 6900
aaggagagag gagggggcaa ccataggatt ctcaatggac attgacctgc ggccagcctc 6960
agcttgggcc atctatgctg ccttgacaac tttcattacc ccagccgtcc aacatgcagt 7020
gaccacctca tacaacaact actccttaat ggcgatggcc acgcaagctg gagtgttgtt 7080
tggtatgggc aaagggatgc cattctacgc atgggacttt ggagtcccgc tgctaatgat 7140
aggttgctac tcacaattaa cacccctgac cctaatagtg gccatcattt tgctcgtggc 7200
gcactacatg tacttgatcc cagggctgca ggcagcagct gcgcgtgctg cccagaagag 7260
aacggcagct ggcatcatga agaaccctgt tgtggatgga atagtggtga ctgacattga 7320
cacaatgaca attgaccccc aagtggagaa aaagatggga caggtgctac tcatagcagt 7380
agccgtctcc agcgccatac tgtcgcggac cgcctggggg tggggggagg ctggggccct 7440
gatcacagcc gcaacttcca ctttgtggga aggctctccg aacaagtact ggaactcctc 7500

```
tacagccact tcactgtgta acatttttag gggaagttac ttggctggag cttctctaat   7560
ctacacagta acaagaaacg ctggcttggt caagagacgt gggggtggaa caggagagac   7620
cctgggagag aaatggaagg cccgcttgaa ccagatgtcg gccctggagt tctactccta   7680
caaaaagtca ggcatcaccg aggtgtgcag agaagaggcc cgccgcgccc tcaaggacgg   7740
tgtggcaacg ggaggccatg ctgtgtcccg aggaagtgca aagctgagat ggttggtgga   7800
gcggggatac ctgcagccct atggaaaggt cattgatctt ggatgtggca gagggggctg   7860
gagttactac gccgccacca tccgcaaagt tcaagaagtg aaaggataca caaaaggagg   7920
ccctggtcat gaagaacccg tgttggtgca aagctatggg tggaacatag tccgtcttaa   7980
gagtggggtg gacgtctttc atatggcggc tgagccgtgt gacacgttgc tgtgtgacat   8040
aggtgagtca tcatctagtc ctgaagtgga agaagcacgg acgctcagag tcctctccat   8100
ggtgggggat tggcttgaaa aaagaccagg agccttttgt ataaaagtgt tgtgcccata   8160
caccagcact atgatggaaa ccctggagcg actgcagcgt aggtatgggg gaggactggt   8220
cagagtgcca ctctcccgca actctacaca tgagatgtac tgggtctctg gagcgaaaag   8280
caacaccata aaaagtgtgt ccaccacgag ccagctcctc ttggggcgca tggacgggcc   8340
taggaggcca gtgaaatatg aggaggatgt gaatctcggc tctggcacgc gggctgtggt   8400
aagctgcgct gaagctccca acatgaagat cattggtaac cgcattgaaa ggatccgcag   8460
tgagcacgcg gaaacgtggt tctttgacga gaaccaccca tataggacat gggcttacca   8520
tggaagctat gaggccccca cacaagggtc agcgtcctct ctaataaacg gggttgtcag   8580
gctcctgtca aaaccctggg atgtggtgac tggagtcaca ggaatagcca tgaccgacac   8640
cacaccgtat ggtcagcaaa gagttttcaa ggaaaaagtg gacactaggg tgccagaccc   8700
ccaagaaggc actcgtcagg ttatgagcat ggtctcttcc tggttgtgga aagagctagg   8760
caaacacaaa cggccacgag tctgtaccaa agaagagttc atcaacaagg ttcgtagcaa   8820
tgcagcatta ggggcaatat ttgaagagga aaaagagtgg aagactgcag tggaagctgt   8880
gaacgatcca aggttctggg ctctagtgga caaggaaaga gagcaccacc tgagaggaga   8940
gtgccagagt tgtgtgtaca acatgatggg aaaaagagaa aagaaacaag gggaatttgg   9000
aaaggccaag ggcagccgcg ccatctggta tatgtggcta ggggctagat ttctagagtt   9060
cgaagccctt ggattcttga acgaggatca ctggatgggg agagagaact caggaggtgg   9120
tgttgaaggg ctgggattac aaagactcgg atatgtccta gaagagatga gtcgtatacc   9180
aggaggaagg atgtatgcag atgacactgc tggctgggac acccgcatta gcaggtttga   9240
tctggagaat gaagctctaa tcaccaacca aatggagaaa gggcacaggg ccttggcatt   9300
ggccataatc aagtacacat accaaaacaa agtggtaaag gtccttagac cagctgaaaa   9360
agggaaaaca gttatggaca ttatttcgag acaagaccaa agggggagcg gacaagttgt   9420
cacttacgct cttaacacat ttaccaacct agtggtgcaa ctcattcgga atatggaggc   9480
tgaggaagtt ctagagatgc aagacttgtg gctgctgcgg aggtcagaga aagtgactaa   9540
ctggttgcag agcaacggat gggataggct caaacgaatg gcagtcagtg gagatgattg   9600
cgttgtgaag ccaattgatg ataggtttgc acatgccctc aggttcttga atgatatggg   9660
aaaagttagg aaggacacac aagagtggaa accctcaact ggatgggaca actgggaaga   9720
agttccgttt tgctcccacc acttcaacaa gctccatctc aaggacggga ggtccattgt   9780
ggttccctgc cgccaccaag atgaactgat tggccgggcc cgcgtctctc caggggcggg   9840
```

-continued atggagcatc cgggagactg cttgcctagc aaaatcatat gcgcaaatgt ggcagctcct 9900
ttatttccac agaagggacc tccgactgat ggccaatgcc atttgttcat ctgtgccagt 9960
tgactgggtt ccaactggga gaactacctg gtcaatccat ggaaagggag aatggatgac 10020
cactgaagac atgcttgtgg tgtggaacag agtgtggatt gaggagaacg accacatgga 10080
agacaagacc ccagttacga aatggacaga cattccctat ttgggaaaaa gggaagactt 10140
gtggtgtgga tctctcatag ggcacagacc gcgcaccacc tgggctgaga acattaaaaa 10200
cacagtcaac atggtgcgca ggatcatagg tgatgaagaa aagtacatgg actacctatc 10260
cacccaagtt cgctacttgg gtgaagaagg gtctacacct ggagtgctgt aagcaccaat 10320
cttaatgttg tcaggcctgc tagtcagcca cagcttgggg aaagctgtgc agcc 10374

<210> SEQ ID NO 30
<211> LENGTH: 57
<212> TYPE: DNA
<213> ORGANISM: Artificial sequence
<220> FEATURE:
<223> OTHER INFORMATION: transfer initiation peptide

<400> SEQUENCE: 30
acaagtgtcg gaattgttgg cctcctgctg accacagcta tggcagcgga ggtcact 57

<210> SEQ ID NO 31
<211> LENGTH: 45
<212> TYPE: DNA
<213> ORGANISM: Artificial sequence
<220> FEATURE:
<223> OTHER INFORMATION: transfer initiation peptide

<400> SEQUENCE: 31
gtcatatact tggtcatgat actgctgatt gccccggcat acagc 45

<210> SEQ ID NO 32
<211> LENGTH: 51
<212> TYPE: DNA
<213> ORGANISM: Artificial sequence
<220> FEATURE:
<223> OTHER INFORMATION: initiation sequence

<400> SEQUENCE: 32
atgctgagaa taatcaatgc taggaaggag aagaagagac gaggcgcaga t 51

<210> SEQ ID NO 33
<211> LENGTH: 27
<212> TYPE: DNA
<213> ORGANISM: Artificial sequence
<220> FEATURE:
<223> OTHER INFORMATION: initiation sequence

<400> SEQUENCE: 33
atgttgggaa gctcaacgag ccaaaaa 27

<210> SEQ ID NO 34
<211> LENGTH: 2061
<212> TYPE: DNA
<213> ORGANISM: Artificial sequence
<220> FEATURE:
<223> OTHER INFORMATION: E deleted + S deleted

<400> SEQUENCE: 34
atcaggtgca taggagtcag caatagggac tttgtggaag gtatgtcagg tgggacttgg 60
gttgatgttg tcttggaaca tggaggttgt gtcactgtaa tggcacagga caaaccgact 120

```
gtcgacatag agctggttac aacaacagtc agcaacatgg cggaggtaag atcctactgc    180
tatgaggcat caatatcaga catggcttcg gacagccgct gcccaacaca aggtgaagcc    240
taccttgaca agcaatcaga cactcaatat gtctgcaaaa gaacgttagt ggacagaggc    300
tggggaaatg gatgtggact tttggcaaa gggagcctgg tgacatgcgc taagtttgca    360
tgctccaaga aaatgaccgg gaagagcatc cagccagaga atctggagta ccggataatg    420
ctgtcagttc atggctccca gcacagtggg atgatcgtta atgacacagg acatgaaact    480
gatgagaata gagcgaaagt tgagataacg cccaattcac caagagccga agccaccctg    540
ggggggtttg gaagcctagg acttgattgt gaaccgagga caggccttga cttttcagat    600
ttgtattact tgactatgaa taacaagcac tggctggttc acaaggagtg gttccacgac    660
attccattac cttggcacgc tggggcagac accggaactc cacactggaa caacaaagaa    720
gcactggtag agttcaagga cgcacatgcc aaaaggcaaa ctgtcgtggt tctagggagt    780
caagaaggag cagttcacac ggcccttgct ggagctctgg aggctgagat ggatggtgca    840
aagggaaggc tgtcctctgg ccacttgaaa tgtcgcctga aaatggataa acttagattg    900
aagggcgtgt catactcctt gtgtactgca gcgttcacat tcaccaagat cccggctgaa    960
acactgcacg ggacagtcac agtggaggta cagtacgcag ggacagatgg accttgcaag   1020
gttccagctc agatggcggt ggacatgcaa actctgaccc cagttgggag gttgataacc   1080
gctaaccccg taatcactga aagcactgag aactctaaga tgatgctgga acttgatcca   1140
ccatttgggg actcttacat tgtcatagga gtcggggaga agaagatcac ccaccactgg   1200
cacaggagtg gcagcaccat tggaaaagca tttgaagcca ctgtgagagg tgccaagaga   1260
atggcagtct tgggagacac agcctgggac tttggatcag ttggaggcgc tctcaactca   1320
ttgggcaagg gcatccatca aatctttgga gcagctttca aatcattgtt tggaggaatg   1380
tcctggttct cacaaattct cattggaacg ttgctgatgt ggttgggtct gaacgcaaag   1440
aatggatcta gaatcctcac aataccgcag agtctagact cgtggtggac ttctctcaat   1500
tttctagggg gatctcccgt gtgtcttggc caaaattcgc agtccccaac ctccaatcac   1560
tcaccaacct cctgtcctcc aatttgtcct ggttatcgct ggatgtgtct gcggcgtttt   1620
atcatattcc tcttcatcct gctgctatgc ctcatcttct tattggttct tctggattat   1680
caaggtatgt tgcccgtttg tcctctaatt ccaggatcaa caacaaccag tacgggacca   1740
tgcaaaacct gcacgactcc tgctcaaggc aactctatgt ttccctcatg ttgctgtaca   1800
aaacctacgg atggaaattg cacctgtatt cccatcccat cgtcctgggc tttcgcaaaa   1860
tacctatggg agtgggcctc agtccgtttc tcttggctca gtttactagt gccatttgtt   1920
cagtggttcg tagggctttc cccactgtt tggctttcag ctatatggat gatgtggtat   1980
tgggggccaa gtctgtacag catcgtgagt ccctttatac cgctgttacc aattttcttt   2040
tgtctctggg tatacattta a                                            2061
```

<210> SEQ ID NO 35
<211> LENGTH: 2553
<212> TYPE: DNA
<213> ORGANISM: Artificial sequence
<220> FEATURE:
<223> OTHER INFORMATION: prM + E deleted + S deleted

<400> SEQUENCE: 35

```
agacgtggga gtgcatacta tatgtacttg gacagaaacg atgctgggga ggccatatct     60
```

-continued

```
tttccaacca cattggggat gaataagtgt tatatacaga tcatggatct tggacacacg    120
tgtgatgcca ccatgagcta tgaatgccct atgctggatg agggggtgga accagatgac    180
gtcgattgtt ggtgcaacac gacgtcaact tgggttgtgt acggaacctg ccatcacaaa    240
aaaggtgaag cacggagatc tagaagagct gtgacgctcc cctcccattc cactaggaag    300
ctgcaaacgc ggtcgcaaac ctggttggaa tcaagagaat acacaaagca cttgattaga    360
gtcgaaaatt ggatattcag gaaccctggc ttcgcgttag cagcagctgc catcgcttgg    420
cttttgggaa gctcaacgag ccaaaaagtc atatacttgg tcatgatact gctgattgcc    480
ccggcataca gcatcaggtg cataggagtc agcaataggg actttgtgga aggtatgtca    540
ggtgggactt gggttgatgt tgtcttggaa catggaggtt gtgtcactgt aatggcacag    600
gacaaaccga ctgtcgacat agagctggtt acaacaacag tcagcaacat ggcggaggta    660
agatcctact gctatgaggc atcaatatca gacatggctt cggacagccg ctgcccaaca    720
caaggtgaag cctaccttga caagcaatca gacactcaat atgtctgcaa aagaacgtta    780
gtggacagag gctggggaaa tggatgtgga ctttttggca aagggagcct ggtgacatgc    840
gctaagtttg catgctccaa gaaaatgacc gggaagagca tccagccaga gaatctggag    900
taccggataa tgctgtcagt tcatggctcc cagcacagtg ggatgatcgt taatgacaca    960
ggacatgaaa ctgatgagaa tagagcgaaa gttgagataa cgcccaattc accaagagcc   1020
gaagccaccc tgggggggtt tggaagccta ggacttgatt gtgaaccgag gacaggcctt   1080
gacttttcag atttgtatta cttgactatg aataacaagc actggctggt tcacaaggag   1140
tggttccacg acattccatt accttggcac gctggggcag acaccggaac tccacactgg   1200
aacaacaaag aagcactggt agagttcaag gacgcacatg ccaaaaggca aactgtcgtg   1260
gttctaggga gtcaagaagg agcagttcac acggcccttg ctggagctct ggaggctgag   1320
atggatggtg caaagggaag gctgtcctct ggccacttga aatgtcgcct gaaaatggat   1380
aaacttagat tgaagggcgt gtcatactcc ttgtgtactg cagcgttcac attcaccaag   1440
atcccggctg aaacactgca cgggacagtc acagtggagg tacagtacgc agggacagat   1500
ggaccttgca aggttccagc tcagatggcg gtggacatgc aaactctgac cccagttggg   1560
aggttgataa ccgctaaccc cgtaatcact gaaagcactg agaactctaa gatgatgctg   1620
gaacttgatc caccatttgg ggactcttac attgtcatag gagtcgggga gaagaagatc   1680
acccaccact ggcacaggag tggcagcacc attggaaaag catttgaagc cactgtgaga   1740
ggtgccaaga gaatggcagt cttgggagac acagcctggg actttggatc agttggaggc   1800
gctctcaact cattgggcaa gggcatccat caaatctttg gagcagcttt caaatcattg   1860
tttggaggaa tgtcctggtt ctcacaaatt ctcattggaa cgttgctgat gtggttgggt   1920
ctgaacgcaa agaatggatc tagaatcctc acaataccgc agagtctaga ctcgtggtgg   1980
acttctctca attttctagg gggatctccc gtgtgtcttg gccaaaattc gcagtcccca   2040
acctccaatc actcaccaac ctcctgtcct ccaatttgtc ctggttatcg ctggatgtgt   2100
ctgcggcgtt ttatcatatt cctcttcatc ctgctgctat gcctcatctt cttattggtt   2160
cttctggatt atcaaggtat gttgcccgtt tgtcctctaa ttccaggatc aacaacaacc   2220
agtacgggac catgcaaaac ctgcacgact cctgctcaag gcaactctat gtttccctca   2280
tgttgctgta caaaacctac ggatggaaat tgcacctgta ttcccatccc atcgtcctgg   2340
gctttcgcaa aatacctatg ggagtgggcc tcagtccgtt tctcttggct cagtttacta   2400
gtgccatttg ttcagtggtt cgtagggctt tcccccactg tttggctttc agctatatgg   2460
```

atgatgtggt attgggggcc aagtctgtac agcatcgtga gtccctttat accgctgtta 2520
ccaattttct tttgtctctg ggtatacatt taa 2553

<210> SEQ ID NO 36
<211> LENGTH: 2190
<212> TYPE: DNA
<213> ORGANISM: Artificial sequence
<220> FEATURE:
<223> OTHER INFORMATION: E + S

<400> SEQUENCE: 36
atcaggtgca taggagtcag caatagggac tttgtggaag gtatgtcagg tgggacttgg 60
gttgatgttg tcttggaaca tggaggttgt gtcactgtaa tggcacagga caaaccgact 120
gtcgacatag agctggttac aacaacagtc agcaacatgg cggaggtaag atcctactgc 180
tatgaggcat caatatcaga catggcttcg gacagccgct gcccaacaca aggtgaagcc 240
taccttgaca agcaatcaga cactcaatat gtctgcaaaa gaacgttagt ggacagaggc 300
tggggaaatg gatgtggact tttggcaaa gggagcctgg tgacatgcgc taagtttgca 360
tgctccaaga aaatgaccgg gaagagcatc cagccagaga atctggagta ccggataatg 420
ctgtcagttc atggctccca gcacagtggg atgatcgtta atgacacagg acatgaaact 480
gatgagaata gagcgaaagt tgagataacg cccaattcac caagagccga agccaccctg 540
ggggggtttg gaagcctagg acttgattgt gaaccgagga caggccttga cttttcagat 600
ttgtattact tgactatgaa taacaagcac tggctggttc acaaggagtg gttccacgac 660
attccattac cttggcacgc tggggcagac accggaactc cacactggaa caacaaagaa 720
gcactggtag agttcaagga cgcacatgcc aaaaggcaaa ctgtcgtggt tctagggagt 780
caagaaggag cagttcacac ggcccttgct ggagctctgg aggctgagat ggatggtgca 840
aagggaaggc tgtcctctgg ccacttgaaa tgtcgcctga aaatggataa acttagattg 900
aagggcgtgt catactcctt gtgtactgca gcgttcacat tcaccaagat cccggctgaa 960
acactgcacg ggacagtcac agtggaggta cagtacgcag ggacagatgg accttgcaag 1020
gttccagctc agatggcggt ggacatgcaa actctgaccc cagttgggag gttgataacc 1080
gctaaccccg taatcactga aagcactgag aactctaaga tgatgctgga acttgatcca 1140
ccatttgggg actcttacat tgtcatagga gtcggggaga agaagatcac ccaccactgg 1200
cacaggagtg gcagcaccat tggaaaagca tttgaagcca ctgtgagagg tgccaagaga 1260
atggcagtct tgggagacac agcctgggac tttggatcag ttggaggcgc tctcaactca 1320
ttgggcaagg gcatccatca aatctttgga gcagctttca aatcattgtt tggaggaatg 1380
tcctggttct cacaaattct cattggaacg ttgctgatgt ggttgggtct gaacgcaaag 1440
aatggatcta tttcccttat gtgcttggcc ttagggggag tgttgatctt cttatccaca 1500
gccgtctctg ctgagaacat cacatcagga ttcctaggac ccctgctcgt gttacaggcg 1560
gggtttttct tgttgacaag aatcctcaca ataccgcaga gtctagactc gtggtggact 1620
tctctcaatt ttctaggggg atctcccgtg tgtcttggcc aaaattcgca gtccccaacc 1680
tccaatcact caccaacctc ctgtcctcca atttgtcctg gttatcgctg gatgtgtctg 1740
cggcgtttta tcatattcct cttcatcctg ctgctatgcc tcatcttctt attggttctt 1800
ctggattatc aaggtatgtt gcccgtttgt cctctaattc caggatcaac aacaaccagt 1860
acgggaccat gcaaaacctg cacgactcct gctcaaggca actctatgtt tccctcatgt 1920

```
tgctgtacaa aacctacgga tggaaattgc acctgtattc ccatcccatc gtcctgggct   1980

ttcgcaaaat acctatggga gtgggcctca gtccgtttct cttggctcag tttactagtg   2040

ccatttgttc agtggttcgt agggctttcc cccactgttt ggctttcagc tatatggatg   2100

atgtggtatt gggggccaag tctgtacagc atcgtgagtc cctttatacc gctgttacca   2160

attttctttt gtctctgggt atacatttaa                                     2190


<210> SEQ ID NO 37
<211> LENGTH: 2682
<212> TYPE: DNA
<213> ORGANISM: Artificial sequence
<220> FEATURE:
<223> OTHER INFORMATION: prM + E + S

<400> SEQUENCE: 37

agacgtggga gtgcatacta tatgtacttg gacagaaacg atgctgggga ggccatatct     60

tttccaacca cattggggat gaataagtgt tatatacaga tcatggatct tggacacacg    120

tgtgatgcca ccatgagcta tgaatgccct atgctggatg agggggtgga accagatgac    180

gtcgattgtt ggtgcaacac gacgtcaact tgggttgtgt acggaacctg ccatcacaaa    240

aaaggtgaag cacggagatc tagaagagct gtgacgctcc cctcccattc cactaggaag    300

ctgcaaacgc ggtcgcaaac ctggttggaa tcaagagaat acacaaagca cttgattaga    360

gtcgaaaatt ggatattcag gaaccctggc ttcgcgttag cagcagctgc catcgcttgg    420

cttttgggaa gctcaacgag ccaaaaagtc atatacttgg tcatgatact gctgattgcc    480

ccggcataca gcatcaggtg cataggagtc agcaataggg actttgtgga aggtatgtca    540

ggtgggactt gggttgatgt tgtcttggaa catggaggtt gtgtcactgt aatggcacag    600

gacaaaccga ctgtcgacat agagctggtt acaacaacag tcagcaacat ggcggaggta    660

agatcctact gctatgaggc atcaatatca gacatggctt cggacagccg ctgcccaaca    720

caaggtgaag cctaccttga caagcaatca gacactcaat atgtctgcaa aagaacgtta    780

gtggacagag gctggggaaa tggatgtgga ctttttggca aagggagcct ggtgacatgc    840

gctaagtttg catgctccaa gaaaatgacc gggaagagca tccagccaga gaatctggag    900

taccggataa tgctgtcagt tcatggctcc cagcacagtg ggatgatcgt taatgacaca    960

ggacatgaaa ctgatgagaa tagagcgaaa gttgagataa cgcccaattc accaagagcc   1020

gaagccaccc tgggggggtt tggaagccta ggacttgatt gtgaaccgag gacaggcctt   1080

gacttttcag atttgtatta cttgactatg aataacaagc actggctggt tcacaaggag   1140

tggttccacg acattccatt accttggcac gctggggcag acaccggaac tccacactgg   1200

aacaacaaag aagcactggt agagttcaag gacgcacatg ccaaaaggca aactgtcgtg   1260

gttctaggga gtcaagaagg agcagttcac acggcccttg ctggagctct ggaggctgag   1320

atggatggtg caaagggaag gctgtcctct ggccacttga aatgtcgcct gaaaatggat   1380

aaacttagat tgaagggcgt gtcatactcc ttgtgtactg cagcgttcac attcaccaag   1440

atcccggctg aaacactgca cgggacagtc acagtggagg tacagtacgc agggacagat   1500

ggaccttgca aggttccagc tcagatggcg gtggacatgc aaactctgac cccagttggg   1560

aggttgataa ccgctaaccc cgtaatcact gaaagcactg agaactctaa gatgatgctg   1620

gaacttgatc caccatttgg ggactcttac attgtcatag gagtcgggga gaagaagatc   1680

acccaccact ggcacaggag tggcagcacc attggaaaag catttgaagc cactgtgaga   1740

ggtgccaaga gaatggcagt cttgggagac acagcctggg actttggatc agttggaggc   1800
```

-continued

```
gctctcaact cattgggcaa gggcatccat caaatctttg gagcagcttt caaatcattg   1860
tttggaggaa tgtcctggtt ctcacaaatt ctcattggaa cgttgctgat gtggttgggt   1920
ctgaacgcaa agaatggatc tatttccctt atgtgcttgg ccttaggggg agtgttgatc   1980
ttcttatcca cagccgtctc tgctgagaac atcacatcag gattcctagg acccctgctc   2040
gtgttacagg cggggttttt cttgttgaca agaatcctca caataccgca gagtctagac   2100
tcgtggtgga cttctctcaa ttttctaggg ggatctcccg tgtgtcttgg ccaaaattcg   2160
cagtccccaa cctccaatca ctcaccaacc tcctgtcctc caatttgtcc tggttatcgc   2220
tggatgtgtc tgcggcgttt tatcatattc ctcttcatcc tgctgctatg cctcatcttc   2280
ttattggttc ttctggatta tcaaggtatg ttgcccgttt gtcctctaat tccaggatca   2340
acaacaacca gtacgggacc atgcaaaacc tgcacgactc ctgctcaagg caactctatg   2400
tttccctcat gttgctgtac aaaacctacg gatggaaatt gcacctgtat tcccatccca   2460
tcgtcctggg ctttcgcaaa atacctatgg gagtgggcct cagtccgttt ctcttggctc   2520
agtttactag tgccatttgt tcagtggttc gtagggcttt cccccactgt ttggctttca   2580
gctatatgga tgatgtggta ttgggggcca agtctgtaca gcatcgtgag tccctttata   2640
ccgctgttac caattttctt ttgtctctgg gtatacattt aa                       2682
```

<210> SEQ ID NO 38
<211> LENGTH: 2292
<212> TYPE: DNA
<213> ORGANISM: Artificial sequence
<220> FEATURE:
<223> OTHER INFORMATION: E deleted + M

<400> SEQUENCE: 38

```
atcaggtgca taggagtcag caatagggac tttgtggaag gtatgtcagg tgggacttgg     60
gttgatgttg tcttggaaca tggaggttgt gtcactgtaa tggcacagga caaaccgact    120
gtcgacatag agctggttac aacaacagtc agcaacatgg cggaggtaag atcctactgc    180
tatgaggcat caatatcaga catggcttcg gacagccgct gcccaacaca aggtgaagcc    240
taccttgaca agcaatcaga cactcaatat gtctgcaaaa gaacgttagt ggacagaggc    300
tggggaaatg gatgtggact tttggcaaa gggagcctgg tgacatgcgc taagtttgca    360
tgctccaaga aaatgaccgg gaagagcatc cagccagaga atctggagta ccggataatg    420
ctgtcagttc atggctccca gcacagtggg atgatcgtta atgacacagg acatgaaact    480
gatgagaata gagcgaaagt tgagataacg cccaattcac caagagccga agccaccctg    540
ggggggtttg gaagcctagg acttgattgt gaaccgagga caggccttga cttttcagat    600
ttgtattact tgactatgaa taacaagcac tggctggttc acaaggagtg gttccacgac    660
attccattac cttggcacgc tggggcagac accggaactc cacactggaa caacaaagaa    720
gcactggtag agttcaagga cgcacatgcc aaaaggcaaa ctgtcgtggt tctagggagt    780
caagaaggag cagttcacac ggcccttgct ggagctctgg aggctgagat ggatggtgca    840
aagggaaggc tgtcctctgg ccacttgaaa tgtcgcctga aaatggataa acttagattg    900
aagggcgtgt catactcctt gtgtactgca gcgttcacat tcaccaagat cccggctgaa    960
acactgcacg ggacagtcac agtggaggta cagtacgcag ggacagatgg accttgcaag   1020
gttccagctc agatggcggt ggacatgcaa actctgaccc cagttgggag gttgataacc   1080
gctaaccccg taatcactga aagcactgag aactctaaga tgatgctgga acttgatcca   1140
```

```
ccatttgggg actcttacat tgtcatagga gtcggggaga agaagatcac ccaccactgg   1200

cacaggagtg gcagcaccat tggaaaagca tttgaagcca ctgtgagagg tgccaagaga   1260

atggcagtct tgggagacac agcctgggac tttggatcag ttggaggcgc tctcaactca   1320

ttgggcaagg gcatccatca aatctttgga gcagctttca aatcattgtt tggaggaatg   1380

tcctggttct cacaaattct cattggaacg ttgctgatgt ggttgggtct gaacgcaaag   1440

aatggatctc agtggaattc cactgccttc caccaaactc tgcaggatcc cagagtcagg   1500

ggtctgtatc ttcctgctgg tggctccagt tcaggaacag taaaccctgc tccgaatatt   1560

gcctctcaca tctcgtcaat ctccgcgagg actggggacc ctgtgacgaa catggagaac   1620

atcacatcag gattcctagg acccctgctc gtgttacagg cggggttttt cttgttgaca   1680

agaatcctca caataccgca gagtctagac tcgtggtgga cttctctcaa ttttctaggg   1740

ggatctcccg tgtgtcttgg ccaaaattcg cagtccccaa cctccaatca ctcaccaacc   1800

tcctgtcctc caatttgtcc tggttatcgc tggatgtgtc tgcggcgttt tatcatattc   1860

ctcttcatcc tgctgctatg cctcatcttc ttattggttc ttctggatta tcaaggtatg   1920

ttgcccgttt gtcctctaat tccaggatca acaacaacca gtacgggacc atgcaaaacc   1980

tgcacgactc ctgctcaagg caactctatg tttccctcat gttgctgtac aaaacctacg   2040

gatggaaatt gcacctgtat tcccatccca tcgtcctggg ctttcgcaaa atacctatgg   2100

gagtgggcct cagtccgttt ctcttggctc agtttactag tgccatttgt tcagtggttc   2160

gtagggcttt cccccactgt ttggctttca gctatatgga tgatgtggta ttgggggcca   2220

agtctgtaca gcatcgtgag tccctttata ccgctgttac caattttctt ttgtctctgg   2280

gtatacattt aa                                                       2292
```

<210> SEQ ID NO 39
<211> LENGTH: 2784
<212> TYPE: DNA
<213> ORGANISM: Artificial sequence
<220> FEATURE:
<223> OTHER INFORMATION: prM + E deleted + M

<400> SEQUENCE: 39

```
agacgtggga gtgcatacta tatgtacttg gacagaaacg atgctgggga ggccatatct     60

tttccaacca cattggggat gaataagtgt tatatacaga tcatggatct tggacacacg    120

tgtgatgcca ccatgagcta tgaatgccct atgctggatg agggggtgga accagatgac    180

gtcgattgtt ggtgcaacac gacgtcaact tgggttgtgt acggaacctg ccatcacaaa    240

aaaggtgaag cacggagatc tagaagagct gtgacgctcc cctcccattc cactaggaag    300

ctgcaaacgc ggtcgcaaac ctggttggaa tcaagagaat acacaaagca cttgattaga    360

gtcgaaaatt ggatattcag gaaccctggc ttcgcgttag cagcagctgc catcgcttgg    420

cttttgggaa gctcaacgag ccaaaaagtc atatacttgg tcatgatact gctgattgcc    480

ccggcataca gcatcaggtg cataggagtc agcaataggg actttgtgga aggtatgtca    540

ggtgggactt gggttgatgt tgtcttggaa catggaggtt gtgtcactgt aatggcacag    600

gacaaaccga ctgtcgacat agagctggtt acaacaacag tcagcaacat ggcggaggta    660

agatcctact gctatgaggc atcaatatca gacatggctt cggacagccg ctgcccaaca    720

caaggtgaag cctaccttga caagcaatca gacactcaat atgtctgcaa aagaacgtta    780

gtggacagag gctggggaaa tggatgtgga ctttttggca aagggagcct ggtgacatgc    840

gctaagtttg catgctccaa gaaaatgacc gggaagagca tccagccaga gaatctggag    900
```

taccggataa tgctgtcagt tcatggctcc cagcacagtg ggatgatcgt taatgacaca 960
ggacatgaaa ctgatgagaa tagagcgaaa gttgagataa cgcccaattc accaagagcc 1020
gaagccaccc tggggggtt tggaagccta ggacttgatt gtgaaccgag gacaggcctt 1080
gacttttcag atttgtatta cttgactatg aataacaagc actggctggt tcacaaggag 1140
tggttccacg acattccatt accttggcac gctggggcag acaccggaac tccacactgg 1200
aacaacaaag aagcactggt agagttcaag gacgcacatg ccaaaaggca aactgtcgtg 1260
gttctaggga gtcaagaagg agcagttcac acggcccttg ctggagctct ggaggctgag 1320
atggatggtg caaagggaag gctgtcctct ggccacttga aatgtcgcct gaaaatggat 1380
aaacttagat tgaagggcgt gtcatactcc ttgtgtactg cagcgttcac attcaccaag 1440
atcccggctg aaacactgca cgggacagtc acagtggagg tacagtacgc agggacagat 1500
ggaccttgca aggttccagc tcagatggcg gtggacatgc aaactctgac cccagttggg 1560
aggttgataa ccgctaaccc cgtaatcact gaaagcactg agaactctaa gatgatgctg 1620
gaacttgatc caccatttgg ggactcttac attgtcatag gagtcgggga gaagaagatc 1680
acccaccact ggcacaggag tggcagcacc attggaaaag catttgaagc cactgtgaga 1740
ggtgccaaga gaatggcagt cttgggagac acagcctggg actttggatc agttggaggc 1800
gctctcaact cattgggcaa gggcatccat caaatctttg gagcagcttt caaatcattg 1860
tttggaggaa tgtcctggtt ctcacaaatt ctcattggaa cgttgctgat gtggttgggt 1920
ctgaacgcaa agaatggatc tcagtggaat tccactgcct tccaccaaac tctgcaggat 1980
cccagagtca ggggtctgta tcttcctgct ggtggctcca gttcaggaac agtaaaccct 2040
gctccgaata ttgcctctca catctcgtca atctccgcga ggactgggga ccctgtgacg 2100
aacatggaga acatcacatc aggattccta ggacccctgc tcgtgttaca ggcggggttt 2160
ttcttgttga caagaatcct cacaataccg cagagtctag actcgtggtg gacttctctc 2220
aattttctag gggatctcc cgtgtgtctt ggccaaaatt cgcagtcccc aacctccaat 2280
cactcaccaa cctcctgtcc tccaatttgt cctggttatc gctggatgtg tctgcggcgt 2340
tttatcatat tcctcttcat cctgctgcta tgcctcatct tcttattggt tcttctggat 2400
tatcaaggta tgttgcccgt ttgtcctcta attccaggat caacaacaac cagtacggga 2460
ccatgcaaaa cctgcacgac tcctgctcaa ggcaactcta tgtttccctc atgttgctgt 2520
acaaaaccta cggatggaaa ttgcacctgt attcccatcc catcgtcctg ggctttcgca 2580
aaatacctat gggagtgggc ctcagtccgt ttctcttggc tcagtttact agtgccattt 2640
gttcagtggt tcgtagggct ttcccccact gtttggcttt cagctatatg gatgatgtgg 2700
tattgggggc caagtctgta cagcatcgtg agtcccttta taccgctgtt accaattttc 2760
ttttgtctct gggtatacat ttaa 2784

<210> SEQ ID NO 40
<211> LENGTH: 2355
<212> TYPE: DNA
<213> ORGANISM: Artificial sequence
<220> FEATURE:
<223> OTHER INFORMATION: E + M

<400> SEQUENCE: 40
atcaggtgca taggagtcag caatagggac tttgtggaag gtatgtcagg tgggacttgg 60
gttgatgttg tcttggaaca tggaggttgt gtcactgtaa tggcacagga caaaccgact 120

-continued

```
gtcgacatag agctggttac aacaacagtc agcaacatgg cggaggtaag atcctactgc    180
tatgaggcat caatatcaga catggcttcg gacagccgct gcccaacaca aggtgaagcc    240
taccttgaca agcaatcaga cactcaatat gtctgcaaaa gaacgttagt ggacagaggc    300
tggggaaatg gatgtggact tttggcaaa gggagcctgg tgacatgcgc taagtttgca    360
tgctccaaga aaatgaccgg gaagagcatc cagccagaga atctggagta ccggataatg    420
ctgtcagttc atggctccca gcacagtggg atgatcgtta atgacacagg acatgaaact    480
gatgagaata gagcgaaagt tgagataacg cccaattcac caagagccga agccaccctg    540
ggggggtttg gaagcctagg acttgattgt gaaccgagga caggccttga cttttcagat    600
ttgtattact tgactatgaa taacaagcac tggctggttc acaaggagtg gttccacgac    660
attccattac cttggcacgc tggggcagac accggaactc cacactggaa caacaaagaa    720
gcactggtag agttcaagga cgcacatgcc aaaaggcaaa ctgtcgtggt tctagggagt    780
caagaaggag cagttcacac ggcccttgct ggagctctgg aggctgagat ggatggtgca    840
aagggaaggc tgtcctctgg ccacttgaaa tgtcgcctga aaatggataa acttagattg    900
aagggcgtgt catactcctt gtgtactgca gcgttcacat tcaccaagat cccggctgaa    960
acactgcacg ggacagtcac agtggaggta cagtacgcag ggacagatgg accttgcaag   1020
gttccagctc agatggcggt ggacatgcaa actctgaccc cagttgggag gttgataacc   1080
gctaaccccg taatcactga aagcactgag aactctaaga tgatgctgga acttgatcca   1140
ccatttgggg actcttacat tgtcatagga gtcggggaga agaagatcac ccaccactgg   1200
cacaggagtg gcagcaccat tggaaaagca tttgaagcca ctgtgagagg tgccaagaga   1260
atggcagtct tgggagacac agcctgggac tttggatcag ttggaggcgc tctcaactca   1320
ttgggcaagg gcatccatca aatctttgga gcagctttca aatcattgtt tggaggaatg   1380
tcctggttct cacaaattct cattggaacg ttgctgatgt ggttgggtct gaacgcaaag   1440
aatggatcta tttcccttat gtgcttggcc ttagggggag tgttgatctt cttatccaca   1500
gccgtctctg ctcagtggaa ttccactgcc ttccaccaaa ctctgcagga tcccagagtc   1560
aggggtctgt atcttcctgc tggtggctcc agttcaggaa cagtaaaccc tgctccgaat   1620
attgcctctc acatctcgtc aatctccgcg aggactgggg accctgtgac gaacatggag   1680
aacatcacat caggattcct aggacccctg ctcgtgttac aggcggggtt tttcttgttg   1740
acaagaatcc tcacaatacc gcagagtcta gactcgtggt ggacttctct caattttcta   1800
gggggatctc ccgtgtgtct tggccaaaat tcgcagtccc caacctccaa tcactcacca   1860
acctcctgtc ctccaatttg tcctggttat cgctggatgt gtctgcggcg ttttatcata   1920
ttcctcttca tcctgctgct atgcctcatc ttcttattgg ttcttctgga ttatcaaggt   1980
atgttgcccg tttgtcctct aattccagga tcaacaacaa ccagtacggg accatgcaaa   2040
acctgcacga ctcctgctca aggcaactct atgtttccct catgttgctg tacaaaacct   2100
acggatggaa attgcacctg tattcccatc ccatcgtcct gggctttcgc aaaataccta   2160
tgggagtggg cctcagtccg tttctcttgg ctcagtttac tagtgccatt tgttcagtgg   2220
ttcgtagggc tttcccccac tgtttggctt tcagctatat ggatgatgtg gtattggggg   2280
ccaagtctgt acagcatcgt gagtcccttt ataccgctgt taccaatttt cttttgtctc   2340
tgggtataca tttaa                                                    2355
```

<210> SEQ ID NO 41
<211> LENGTH: 2847

<212> TYPE: DNA
<213> ORGANISM: Artificial sequence
<220> FEATURE:
<223> OTHER INFORMATION: prM + E + M

<400> SEQUENCE: 41
agacgtggga gtgcatacta tatgtacttg gacagaaacg atgctgggga ggccatatct 60
tttccaacca cattggggat gaataagtgt tatatacaga tcatggatct tggacacacg 120
tgtgatgcca ccatgagcta tgaatgccct atgctggatg agggggtgga accagatgac 180
gtcgattgtt ggtgcaacac gacgtcaact tgggttgtgt acggaacctg ccatcacaaa 240
aaaggtgaag cacggagatc tagaagagct gtgacgctcc cctcccattc cactaggaag 300
ctgcaaacgc ggtcgcaaac ctggttggaa tcaagagaat acacaaagca cttgattaga 360
gtcgaaaatt ggatattcag gaaccctggc ttcgcgttag cagcagctgc catcgcttgg 420
cttttgggaa gctcaacgag ccaaaaagtc atatacttgg tcatgatact gctgattgcc 480
ccggcataca gcatcaggtg cataggagtc agcaataggg actttgtgga aggtatgtca 540
ggtgggactt gggttgatgt tgtcttggaa catggaggtt gtgtcactgt aatggcacag 600
gacaaaccga ctgtcgacat agagctggtt acaacaacag tcagcaacat ggcggaggta 660
agatcctact gctatgaggc atcaatatca gacatggctt cggacagccg ctgcccaaca 720
caaggtgaag cctaccttga caagcaatca gacactcaat atgtctgcaa aagaacgtta 780
gtggacagag gctggggaaa tggatgtgga ctttttggca aagggagcct ggtgacatgc 840
gctaagtttg catgctccaa gaaaatgacc gggaagagca tccagccaga gaatctggag 900
taccggataa tgctgtcagt tcatggctcc cagcacagtg ggatgatcgt taatgacaca 960
ggacatgaaa ctgatgagaa tagagcgaaa gttgagataa cgcccaattc accaagagcc 1020
gaagccaccc tgggggggtt tggaagccta ggacttgatt gtgaaccgag gacaggcctt 1080
gacttttcag atttgtatta cttgactatg aataacaagc actggctggt tcacaaggag 1140
tggttccacg acattccatt accttggcac gctggggcag acaccggaac tccacactgg 1200
aacaacaaag aagcactggt agagttcaag gacgcacatg ccaaaaggca aactgtcgtg 1260
gttctaggga gtcaagaagg agcagttcac acggcccttg ctggagctct ggaggctgag 1320
atggatggtg caaagggaag gctgtcctct ggccacttga aatgtcgcct gaaaatggat 1380
aaacttagat tgaagggcgt gtcatactcc ttgtgtactg cagcgttcac attcaccaag 1440
atcccggctg aaacactgca cgggacagtc acagtggagg tacagtacgc agggacagat 1500
ggaccttgca aggttccagc tcagatggcg gtggacatgc aaactctgac cccagttggg 1560
aggttgataa ccgctaaccc cgtaatcact gaaagcactg agaactctaa gatgatgctg 1620
gaacttgatc caccatttgg ggactcttac attgtcatag gagtcgggga gaagaagatc 1680
acccaccact ggcacaggag tggcagcacc attggaaaag catttgaagc cactgtgaga 1740
ggtgccaaga gaatggcagt cttgggagac acagcctggg actttggatc agttggaggc 1800
gctctcaact cattgggcaa gggcatccat caaatctttg gagcagcttt caaatcattg 1860
tttggaggaa tgtcctggtt ctcacaaatt ctcattggaa cgttgctgat gtggttgggt 1920
ctgaacgcaa agaatggatc tatttccctt atgtgcttgg ccttaggggg agtgttgatc 1980
ttcttatcca cagccgtctc tgctcagtgg aattccactg ccttccacca aactctgcag 2040
gatcccagag tcaggggtct gtatcttcct gctggtggct ccagttcagg aacagtaaac 2100
cctgctccga atattgcctc tcacatctcg tcaatctccg cgaggactgg ggaccctgtg 2160

-continued

```
acgaacatgg agaacatcac atcaggattc ctaggacccc tgctcgtgtt acaggcgggg   2220

tttttcttgt tgacaagaat cctcacaata ccgcagagtc tagactcgtg gtggacttct   2280

ctcaattttc taggggggatc tcccgtgtgt cttggccaaa attcgcagtc cccaacctcc   2340

aatcactcac caacctcctg tcctccaatt tgtcctggtt atcgctggat gtgtctgcgg   2400

cgttttatca tattcctctt catcctgctg ctatgcctca tcttcttatt ggttcttctg   2460

gattatcaag gtatgttgcc cgtttgtcct ctaattccag gatcaacaac aaccagtacg   2520

ggaccatgca aaacctgcac gactcctgct caaggcaact ctatgtttcc ctcatgttgc   2580

tgtacaaaac ctacggatgg aaattgcacc tgtattccca tcccatcgtc ctgggctttc   2640

gcaaaatacc tatgggagtg ggcctcagtc cgtttctctt ggctcagttt actagtgcca   2700

tttgttcagt ggttcgtagg gctttccccc actgtttggc tttcagctat atggatgatg   2760

tggtattggg ggccaagtct gtacagcatc gtgagtccct ttataccgct gttaccaatt   2820

ttcttttgtc tctgggtata catttaa                                        2847
```

<210> SEQ ID NO 42
<211> LENGTH: 2133
<212> TYPE: DNA
<213> ORGANISM: Artificial sequence
<220> FEATURE:
<223> OTHER INFORMATION: TIP + E deleted + S deleted

<400> SEQUENCE: 42

```
atgttgggaa gctcaacgag ccaaaaagtc atatacttgg tcatgatact gctgattgcc     60

ccggcataca gcatcaggtg cataggagtc agcaataggg actttgtgga aggtatgtca    120

ggtgggactt gggttgatgt tgtcttggaa catggaggtt gtgtcactgt aatggcacag    180

gacaaaccga ctgtcgacat agagctggtt acaacaacag tcagcaacat ggcggaggta    240

agatcctact gctatgaggc atcaatatca gacatggctt cggacagccg ctgcccaaca    300

caaggtgaag cctaccttga caagcaatca gacactcaat atgtctgcaa aagaacgtta    360

gtggacagag gctggggaaa tggatgtgga ctttttggca aagggagcct ggtgacatgc    420

gctaagtttg catgctccaa gaaaatgacc gggaagagca tccagccaga gaatctggag    480

taccggataa tgctgtcagt tcatggctcc cagcacagtg ggatgatcgt taatgacaca    540

ggacatgaaa ctgatgagaa tagagcgaaa gttgagataa cgcccaattc accaagagcc    600

gaagccaccc tgggggggtt tggaagccta ggacttgatt gtgaaccgag gacaggcctt    660

gacttttcag atttgtatta cttgactatg aataacaagc actggctggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtactg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140

aggttgataa ccgctaaccc cgtaatcact gaaagcactg agaactctaa gatgatgctg   1200

gaacttgatc caccatttgg ggactcttac attgtcatag gagtcgggga gaagaagatc   1260

acccaccact ggcacaggag tggcagcacc attggaaaag catttgaagc cactgtgaga   1320

ggtgccaaga gaatggcagt cttgggagac acagcctggg actttggatc agttggaggc   1380
```

-continued gctctcaact cattgggcaa gggcatccat caaatctttg gagcagcttt caaatcattg 1440
tttggaggaa tgtcctggtt ctcacaaatt ctcattggaa cgttgctgat gtggttgggt 1500
ctgaacgcaa agaatggatc tagaatcctc acaataccgc agagtctaga ctcgtggtgg 1560
acttctctca attttctagg gggatctccc gtgtgtcttg gccaaaattc gcagtcccca 1620
acctccaatc actcaccaac ctcctgtcct ccaatttgtc ctggttatcg ctggatgtgt 1680
ctgcggcgtt ttatcatatt cctcttcatc ctgctgctat gcctcatctt cttattggtt 1740
cttctggatt atcaaggtat gttgcccgtt tgtcctctaa ttccaggatc aacaacaacc 1800
agtacgggac catgcaaaac ctgcacgact cctgctcaag gcaactctat gtttccctca 1860
tgttgctgta caaaacctac ggatggaaat tgcacctgta ttcccatccc atcgtcctgg 1920
gctttcgcaa aatacctatg ggagtgggcc tcagtccgtt tctcttggct cagtttacta 1980
gtgccatttg ttcagtggtt cgtagggctt tcccccactg tttggctttc agctatatgg 2040
atgatgtggt attgggggcc aagtctgtac agcatcgtga gtccctttat accgctgtta 2100
ccaattttct tttgtctctg ggtatacatt taa 2133

<210> SEQ ID NO 43
<211> LENGTH: 2661
<212> TYPE: DNA
<213> ORGANISM: Artificial sequence
<220> FEATURE:
<223> OTHER INFORMATION: TIP + prM + E deleted + S deleted

<400> SEQUENCE: 43
atgctgagaa taatcaatgc taggaaggag aagaagagac gaggcgcaga tacaagtgtc 60
ggaattgttg gcctcctgct gaccacagct atggcagcgg aggtcactag acgtgggagt 120
gcatactata tgtacttgga cagaaacgat gctggggagg ccatatcttt tccaaccaca 180
ttggggatga ataagtgtta tatacagatc atggatcttg gacacacgtg tgatgccacc 240
atgagctatg aatgccctat gctggatgag ggggtggaac cagatgacgt cgattgttgg 300
tgcaacacga cgtcaacttg ggttgtgtac ggaacctgcc atcacaaaaa aggtgaagca 360
cggagatcta gaagagctgt gacgctcccc tcccattcca ctaggaagct gcaaacgcgg 420
tcgcaaacct ggttggaatc aagagaatac acaaagcact tgattagagt cgaaaattgg 480
atattcagga accctggctt cgcgttagca gcagctgcca tcgcttggct tttgggaagc 540
tcaacgagcc aaaaagtcat atacttggtc atgatactgc tgattgcccc ggcatacagc 600
atcaggtgca taggagtcag caatagggac tttgtggaag gtatgtcagg tgggacttgg 660
gttgatgttg tcttggaaca tggaggttgt gtcactgtaa tggcacagga caaaccgact 720
gtcgacatag agctggttac aacaacagtc agcaacatgg cggaggtaag atcctactgc 780
tatgaggcat caatatcaga catggcttcg gacagccgct gcccaacaca aggtgaagcc 840
taccttgaca agcaatcaga cactcaatat gtctgcaaaa gaacgttagt ggacagaggc 900
tggggaaatg gatgtggact ttttggcaaa gggagcctgg tgacatgcgc taagtttgca 960
tgctccaaga aaatgaccgg gaagagcatc cagccagaga atctggagta ccggataatg 1020
ctgtcagttc atggctccca gcacagtggg atgatcgtta atgacacagg acatgaaact 1080
gatgagaata gagcgaaagt tgagataacg cccaattcac caagagccga agccaccctg 1140
ggggggtttg gaagcctagg acttgattgt gaaccgagga caggccttga cttttcagat 1200
ttgtattact tgactatgaa taacaagcac tggctggttc acaaggagtg gttccacgac 1260

-continued

```
attccattac cttggcacgc tggggcagac accggaactc cacactggaa caacaaagaa   1320
gcactggtag agttcaagga cgcacatgcc aaaaggcaaa ctgtcgtggt tctagggagt   1380
caagaaggag cagttcacac ggcccttgct ggagctctgg aggctgagat ggatggtgca   1440
aagggaaggc tgtcctctgg ccacttgaaa tgtcgcctga aaatggataa acttagattg   1500
aagggcgtgt catactcctt gtgtactgca gcgttcacat tcaccaagat cccggctgaa   1560
acactgcacg ggacagtcac agtggaggta cagtacgcag ggacagatgg accttgcaag   1620
gttccagctc agatggcggt ggacatgcaa actctgaccc cagttgggag gttgataacc   1680
gctaaccccg taatcactga aagcactgag aactctaaga tgatgctgga acttgatcca   1740
ccatttgggg actcttacat tgtcatagga gtcggggaga agaagatcac ccaccactgg   1800
cacaggagtg gcagcaccat tggaaaagca tttgaagcca ctgtgagagg tgccaagaga   1860
atggcagtct tgggagacac agcctgggac tttggatcag ttggaggcgc tctcaactca   1920
ttgggcaagg gcatccatca aatctttgga gcagctttca aatcattgtt tggaggaatg   1980
tcctggttct cacaaattct cattggaacg ttgctgatgt ggttgggtct gaacgcaaag   2040
aatggatcta gaatcctcac aataccgcag agtctagact cgtggtggac ttctctcaat   2100
tttctagggg gatctcccgt gtgtcttggc caaaattcgc agtccccaac ctccaatcac   2160
tcaccaacct cctgtcctcc aatttgtcct ggttatcgct ggatgtgtct gcggcgtttt   2220
atcatattcc tcttcatcct gctgctatgc ctcatcttct tattggttct tctggattat   2280
caaggtatgt tgcccgtttg tcctctaatt ccaggatcaa caacaaccag tacgggacca   2340
tgcaaaacct gcacgactcc tgctcaaggc aactctatgt ttccctcatg ttgctgtaca   2400
aaacctacgg atggaaattg cacctgtatt cccatcccat cgtcctgggc tttcgcaaaa   2460
tacctatggg agtgggcctc agtccgtttc tcttggctca gtttactagt gccatttgtt   2520
cagtggttcg tagggctttc cccactgtt tggctttcag ctatatggat gatgtggtat   2580
tgggggccaa gtctgtacag catcgtgagt ccctttatac cgctgttacc aattttcttt   2640
tgtctctggg tatacattta a                                              2661
```

<210> SEQ ID NO 44
<211> LENGTH: 2262
<212> TYPE: DNA
<213> ORGANISM: Artificial sequence
<220> FEATURE:
<223> OTHER INFORMATION: TIP + E + S

<400> SEQUENCE: 44

```
atgttgggaa gctcaacgag ccaaaaagtc atatacttgg tcatgatact gctgattgcc     60
ccggcataca gcatcaggtg cataggagtc agcaataggg actttgtgga aggtatgtca    120
ggtgggactt gggttgatgt tgtcttggaa catggaggtt gtgtcactgt aatggcacag    180
gacaaaccga ctgtcgacat agagctggtt acaacaacag tcagcaacat ggcggaggta    240
agatcctact gctatgaggc atcaatatca gacatggctt cggacagccg ctgcccaaca    300
caaggtgaag cctaccttga caagcaatca gacactcaat atgtctgcaa aagaacgtta    360
gtggacagag gctggggaaa tggatgtgga ctttttggca aagggagcct ggtgacatgc    420
gctaagtttg catgctccaa gaaaaatgacc gggaagagca tccagccaga gaatctggag    480
taccggataa tgctgtcagt tcatggctcc cagcacagtg ggatgatcgt taatgacaca    540
ggacatgaaa ctgatgagaa tagagcgaaa gttgagataa cgcccaattc accaagagcc    600
gaagccaccc tgggggggtt tggaagccta ggacttgatt gtgaaccgag gacaggcctt    660
```

```
gacttttcag atttgtatta cttgactatg aataacaagc actggctggt tcacaaggag    720
tggttccacg acattccatt accttggcac gctggggcag acaccggaac tccacactgg    780
aacaacaaag aagcactggt agagttcaag gacgcacatg ccaaaaggca aactgtcgtg    840
gttctaggga gtcaagaagg agcagttcac acggcccttg ctggagctct ggaggctgag    900
atggatggtg caaagggaag gctgtcctct ggccacttga aatgtcgcct gaaaatggat    960
aaacttagat tgaagggcgt gtcatactcc ttgtgtactg cagcgttcac attcaccaag   1020
atcccggctg aaacactgca cgggacagtc acagtggagg tacagtacgc agggacagat   1080
ggaccttgca aggttccagc tcagatggcg gtggacatgc aaactctgac cccagttggg   1140
aggttgataa ccgctaaccc cgtaatcact gaaagcactg agaactctaa gatgatgctg   1200
gaacttgatc caccatttgg ggactcttac attgtcatag gagtcgggga gaagaagatc   1260
acccaccact ggcacaggag tggcagcacc attggaaaag catttgaagc cactgtgaga   1320
ggtgccaaga gaatggcagt cttgggagac acagcctggg actttggatc agttggaggc   1380
gctctcaact cattgggcaa gggcatccat caaatctttg gagcagcttt caaatcattg   1440
tttggaggaa tgtcctggtt ctcacaaatt ctcattggaa cgttgctgat gtggttgggt   1500
ctgaacgcaa agaatggatc tatttccctt atgtgcttgg ccttaggggg agtgttgatc   1560
ttcttatcca cagccgtctc tgctgagaac atcacatcag gattcctagg accccctgctc  1620
gtgttacagg cggggttttt cttgttgaca agaatcctca caataccgca gagtctagac   1680
tcgtggtgga cttctctcaa ttttctaggg ggatctcccg tgtgtcttgg ccaaaattcg   1740
cagtccccaa cctccaatca ctcaccaacc tcctgtcctc caatttgtcc tggttatcgc   1800
tggatgtgtc tgcggcgttt tatcatattc ctcttcatcc tgctgctatg cctcatcttc   1860
ttattggttc ttctggatta tcaaggtatg ttgcccgttt gtcctctaat tccaggatca   1920
acaacaacca gtacgggacc atgcaaaacc tgcacgactc ctgctcaagg caactctatg   1980
tttccctcat gttgctgtac aaaacctacg gatggaaatt gcacctgtat tcccatccca   2040
tcgtcctggg ctttcgcaaa atacctatgg gagtgggcct cagtccgttt ctcttggctc   2100
agtttactag tgccatttgt tcagtggttc gtagggcttt cccccactgt ttggctttca   2160
gctatatgga tgatgtggta ttgggggcca agtctgtaca gcatcgtgag tccctttata   2220
ccgctgttac caattttctt ttgtctctgg gtatacattt aa                      2262
```

<210> SEQ ID NO 45
<211> LENGTH: 2790
<212> TYPE: DNA
<213> ORGANISM: Artificial sequence
<220> FEATURE:
<223> OTHER INFORMATION: TIP + prM + E + S

<400> SEQUENCE: 45

```
atgctgagaa taatcaatgc taggaaggag aagaagagac gaggcgcaga tacaagtgtc     60
ggaattgttg gcctcctgct gaccacagct atggcagcgg aggtcactag acgtgggagt    120
gcatactata tgtacttgga cagaaacgat gctggggagg ccatatcttt tccaaccaca    180
ttggggatga ataagtgtta tatacagatc atggatcttg gacacacgtg tgatgccacc    240
atgagctatg aatgccctat gctggatgag ggggtggaac cagatgacgt cgattgttgg    300
tgcaacacga cgtcaacttg ggttgtgtac ggaacctgcc atcacaaaaa aggtgaagca    360
cggagatcta gaagagctgt gacgctcccc tcccattcca ctaggaagct gcaaacgcgg    420
```

-continued

```
tcgcaaacct ggttggaatc aagagaatac acaaagcact tgattagagt cgaaaattgg    480
atattcagga accctggctt cgcgttagca gcagctgcca tcgcttggct tttgggaagc    540
tcaacgagcc aaaaagtcat atacttggtc atgatactgc tgattgcccc ggcatacagc    600
atcaggtgca taggagtcag caatagggac tttgtggaag gtatgtcagg tgggacttgg    660
gttgatgttg tcttggaaca tggaggttgt gtcactgtaa tggcacagga caaaccgact    720
gtcgacatag agctggttac aacaacagtc agcaacatgg cggaggtaag atcctactgc    780
tatgaggcat caatatcaga catggcttcg gacagccgct gcccaacaca aggtgaagcc    840
taccttgaca agcaatcaga cactcaatat gtctgcaaaa gaacgttagt ggacagaggc    900
tggggaaatg gatgtggact tttggcaaa gggagcctgg tgacatgcgc taagtttgca    960
tgctccaaga aaatgaccgg gaagagcatc cagccagaga atctggagta ccggataatg   1020
ctgtcagttc atggctccca gcacagtggg atgatcgtta atgacacagg acatgaaact   1080
gatgagaata gagcgaaagt tgagataacg cccaattcac caagagccga agccaccctg   1140
ggggggtttg gaagcctagg acttgattgt gaaccgagga caggccttga cttttcagat   1200
ttgtattact tgactatgaa taacaagcac tggctggttc acaaggagtg gttccacgac   1260
attccattac cttggcacgc tggggcagac accggaactc cacactggaa caacaaagaa   1320
gcactggtag agttcaagga cgcacatgcc aaaaggcaaa ctgtcgtggt tctagggagt   1380
caagaaggag cagttcacac ggcccttgct ggagctctgg aggctgagat ggatggtgca   1440
aagggaaggc tgtcctctgg ccacttgaaa tgtcgcctga aaatggataa acttagattg   1500
aagggcgtgt catactcctt gtgtactgca gcgttcacat tcaccaagat cccggctgaa   1560
acactgcacg ggacagtcac agtggaggta cagtacgcag ggacagatgg accttgcaag   1620
gttccagctc agatggcggt ggacatgcaa actctgaccc cagttgggag gttgataacc   1680
gctaaccccg taatcactga aagcactgag aactctaaga tgatgctgga acttgatcca   1740
ccatttgggg actcttacat tgtcatagga gtcggggaga agaagatcac ccaccactgg   1800
cacaggagtg gcagcaccat tggaaaagca tttgaagcca ctgtgagagg tgccaagaga   1860
atggcagtct tgggagacac agcctgggac tttggatcag ttggaggcgc tctcaactca   1920
ttgggcaagg gcatccatca aatctttgga gcagctttca aatcattgtt tggaggaatg   1980
tcctggttct cacaaattct cattggaacg ttgctgatgt ggttgggtct gaacgcaaag   2040
aatggatcta tttcccttat gtgcttggcc ttagggggag tgttgatctt cttatccaca   2100
gccgtctctg ctgagaacat cacatcagga ttcctaggac ccctgctcgt gttacaggcg   2160
gggtttttct tgttgacaag aatcctcaca ataccgcaga gtctagactc gtggtggact   2220
tctctcaatt ttctaggggg atctcccgtg tgtcttggcc aaaattcgca gtccccaacc   2280
tccaatcact caccaacctc ctgtcctcca atttgtcctg gttatcgctg gatgtgtctg   2340
cggcgtttta tcatattcct cttcatcctg ctgctatgcc tcatcttctt attggttctt   2400
ctggattatc aaggtatgtt gcccgtttgt cctctaattc caggatcaac aacaaccagt   2460
acgggaccat gcaaaacctg cacgactcct gctcaaggca actctatgtt tccctcatgt   2520
tgctgtacaa aacctacgga tggaaattgc acctgtattc ccatcccatc gtcctgggct   2580
ttcgcaaaat acctatggga gtgggcctca gtccgtttct cttggctcag tttactagtg   2640
ccatttgttc agtggttcgt agggctttcc cccactgttt ggctttcagc tatatggatg   2700
atgtggtatt gggggccaag tctgtacagc atcgtgagtc cctttatacc gctgttacca   2760
attttctttt gtctctgggt atacatttaa                                    2790
```

<210> SEQ ID NO 46
<211> LENGTH: 2364
<212> TYPE: DNA
<213> ORGANISM: Artificial sequence
<220> FEATURE:
<223> OTHER INFORMATION: TIP + E deleted + M

<400> SEQUENCE: 46
atgttgggaa gctcaacgag ccaaaaagtc atatacttgg tcatgatact gctgattgcc 60
ccggcataca gcatcaggtg cataggagtc agcaataggg actttgtgga aggtatgtca 120
ggtgggactt gggttgatgt tgtcttggaa catggaggtt gtgtcactgt aatggcacag 180
gacaaaccga ctgtcgacat agagctggtt acaacaacag tcagcaacat ggcggaggta 240
agatcctact gctatgaggc atcaatatca gacatggctt cggacagccg ctgcccaaca 300
caaggtgaag cctaccttga caagcaatca gacactcaat atgtctgcaa aagaacgtta 360
gtggacagag gctggggaaa tggatgtgga ctttttggca aagggagcct ggtgacatgc 420
gctaagtttg catgctccaa gaaaatgacc gggaagagca tccagccaga gaatctggag 480
taccggataa tgctgtcagt tcatggctcc cagcacagtg ggatgatcgt taatgacaca 540
ggacatgaaa ctgatgagaa tagagcgaaa gttgagataa cgcccaattc accaagagcc 600
gaagccaccc tgggggggtt tggaagccta ggacttgatt gtgaaccgag gacaggcctt 660
gacttttcag atttgtatta cttgactatg aataacaagc actggctggt tcacaaggag 720
tggttccacg acattccatt accttggcac gctggggcag acaccggaac tccacactgg 780
aacaacaaag aagcactggt agagttcaag gacgcacatg ccaaaaggca aactgtcgtg 840
gttctaggga gtcaagaagg agcagttcac acggcccttg ctggagctct ggaggctgag 900
atggatggtg caaagggaag gctgtcctct ggccacttga aatgtcgcct gaaaatggat 960
aaacttagat tgaagggcgt gtcatactcc ttgtgtactg cagcgttcac attcaccaag 1020
atcccggctg aaacactgca cgggacagtc acagtggagg tacagtacgc agggacagat 1080
ggaccttgca aggttccagc tcagatggcg gtggacatgc aaactctgac cccagttggg 1140
aggttgataa ccgctaaccc cgtaatcact gaaagcactg agaactctaa gatgatgctg 1200
gaacttgatc caccatttgg ggactcttac attgtcatag gagtcgggga gaagaagatc 1260
acccaccact ggcacaggag tggcagcacc attggaaaag catttgaagc cactgtgaga 1320
ggtgccaaga gaatggcagt cttgggagac acagcctggg actttggatc agttggaggc 1380
gctctcaact cattgggcaa gggcatccat caaatctttg gagcagcttt caaatcattg 1440
tttggaggaa tgtcctggtt ctcacaaatt ctcattggaa cgttgctgat gtggttgggt 1500
ctgaacgcaa agaatggatc tcagtggaat tccactgcct tccaccaaac tctgcaggat 1560
cccagagtca ggggtctgta tcttcctgct ggtggctcca gttcaggaac agtaaaccct 1620
gctccgaata ttgcctctca catctcgtca atctccgcga ggactgggga ccctgtgacg 1680
aacatggaga acatcacatc aggattccta ggacccctgc tcgtgttaca ggcggggttt 1740
ttcttgttga caagaatcct cacaataccg cagagtctag actcgtggtg gacttctctc 1800
aattttctag ggggatctcc cgtgtgtctt ggccaaaatt cgcagtcccc aacctccaat 1860
cactcaccaa cctcctgtcc tccaatttgt cctggttatc gctggatgtg tctgcggcgt 1920
tttatcatat tcctcttcat cctgctgcta tgcctcatct tcttattggt tcttctggat 1980
tatcaaggta tgttgcccgt ttgtcctcta attccaggat caacaacaac cagtacggga 2040

```
ccatgcaaaa cctgcacgac tcctgctcaa ggcaactcta tgtttccctc atgttgctgt   2100

acaaaaccta cggatggaaa ttgcacctgt attcccatcc catcgtcctg ggctttcgca   2160

aaatacctat gggagtgggc ctcagtccgt ttctcttggc tcagtttact agtgccattt   2220

gttcagtggt tcgtagggct ttcccccact gtttggcttt cagctatatg gatgatgtgg   2280

tattgggggc caagtctgta cagcatcgtg agtcccttta taccgctgtt accaattttc   2340

ttttgtctct gggtatacat ttaa                                          2364


<210> SEQ ID NO 47
<211> LENGTH: 2892
<212> TYPE: DNA
<213> ORGANISM: Artificial sequence
<220> FEATURE:
<223> OTHER INFORMATION: TIP + prM + E deleted + M

<400> SEQUENCE: 47

atgctgagaa taatcaatgc taggaaggag aagaagagac gaggcgcaga tacaagtgtc     60

ggaattgttg gcctcctgct gaccacagct atggcagcgg aggtcactag acgtgggagt    120

gcatactata tgtacttgga cagaaacgat gctggggagg ccatatcttt tccaaccaca    180

ttggggatga ataagtgtta tatacagatc atggatcttg gacacacgtg tgatgccacc    240

atgagctatg aatgccctat gctggatgag ggggtggaac cagatgacgt cgattgttgg    300

tgcaacacga cgtcaacttg ggttgtgtac ggaacctgcc atcacaaaaa aggtgaagca    360

cggagatcta gaagagctgt gacgctcccc tcccattcca ctaggaagct gcaaacgcgg    420

tcgcaaacct ggttggaatc aagagaatac acaaagcact tgattagagt cgaaaattgg    480

atattcagga accctggctt cgcgttagca gcagctgcca tcgcttggct tttgggaagc    540

tcaacgagcc aaaaagtcat atacttggtc atgatactgc tgattgcccc ggcatacagc    600

atcaggtgca taggagtcag caatagggac tttgtggaag gtatgtcagg tgggacttgg    660

gttgatgttg tcttggaaca tggaggttgt gtcactgtaa tggcacagga caaaccgact    720

gtcgacatag agctggttac aacaacagtc agcaacatgg cggaggtaag atcctactgc    780

tatgaggcat caatatcaga catggcttcg gacagccgct gcccaacaca aggtgaagcc    840

taccttgaca agcaatcaga cactcaatat gtctgcaaaa gaacgttagt ggacagaggc    900

tggggaaatg gatgtggact tttggcaaa gggagcctgg tgacatgcgc taagtttgca     960

tgctccaaga aaatgaccgg gaagagcatc cagccagaga atctggagta ccggataatg   1020

ctgtcagttc atggctccca gcacagtggg atgatcgtta atgacacagg acatgaaact   1080

gatgagaata gagcgaaagt tgagataacg cccaattcac caagagccga agccaccctg   1140

ggggggtttg gaagcctagg acttgattgt gaaccgagga caggccttga cttttcagat   1200

ttgtattact tgactatgaa taacaagcac tggctggttc acaaggagtg gttccacgac   1260

attccattac cttggcacgc tggggcagac accggaactc cacactggaa caacaaagaa   1320

gcactggtag agttcaagga cgcacatgcc aaaaggcaaa ctgtcgtggt tctagggagt   1380

caagaaggag cagttcacac ggcccttgct ggagctctgg aggctgagat ggatggtgca   1440

aagggaaggc tgtcctctgg ccacttgaaa tgtcgcctga aaatggataa acttagattg   1500

aagggcgtgt catactcctt gtgtactgca gcgttcacat tcaccaagat cccggctgaa   1560

acactgcacg ggacagtcac agtggaggta cagtacgcag ggacagatgg accttgcaag   1620

gttccagctc agatggcggt ggacatgcaa actctgaccc cagttgggag gttgataacc   1680

gctaaccccg taatcactga aagcactgag aactctaaga tgatgctgga acttgatcca   1740
```

ccatttgggg actcttacat tgtcatagga gtcggggaga agaagatcac ccaccactgg 1800
cacaggagtg gcagcaccat tggaaaagca tttgaagcca ctgtgagagg tgccaagaga 1860
atggcagtct tgggagacac agcctgggac tttggatcag ttggaggcgc tctcaactca 1920
ttgggcaagg gcatccatca aatctttgga gcagctttca aatcattgtt tggaggaatg 1980
tcctggttct cacaaattct cattggaacg ttgctgatgt ggttgggtct gaacgcaaag 2040
aatggatctc agtggaattc cactgccttc caccaaactc tgcaggatcc cagagtcagg 2100
ggtctgtatc ttcctgctgg tggctccagt tcaggaacag taaaccctgc tccgaatatt 2160
gcctctcaca tctcgtcaat ctccgcgagg actggggacc ctgtgacgaa catggagaac 2220
atcacatcag gattcctagg acccctgctc gtgttacagg cggggttttt cttgttgaca 2280
agaatcctca caataccgca gagtctagac tcgtggtgga cttctctcaa ttttctaggg 2340
ggatctcccg tgtgtcttgg ccaaaattcg cagtccccaa cctccaatca ctcaccaacc 2400
tcctgtcctc caatttgtcc tggttatcgc tggatgtgtc tgcggcgttt tatcatattc 2460
ctcttcatcc tgctgctatg cctcatcttc ttattggttc ttctggatta tcaaggtatg 2520
ttgcccgttt gtcctctaat tccaggatca acaacaacca gtacgggacc atgcaaaacc 2580
tgcacgactc ctgctcaagg caactctatg tttccctcat gttgctgtac aaaacctacg 2640
gatggaaatt gcacctgtat tcccatccca tcgtcctggg ctttcgcaaa atacctatgg 2700
gagtgggcct cagtccgttt ctcttggctc agtttactag tgccatttgt tcagtggttc 2760
gtagggcttt cccccactgt ttggctttca gctatatgga tgatgtggta ttgggggcca 2820
agtctgtaca gcatcgtgag tccctttata ccgctgttac caattttctt ttgtctctgg 2880
gtatacattt aa 2892

<210> SEQ ID NO 48
<211> LENGTH: 2427
<212> TYPE: DNA
<213> ORGANISM: Artificial sequence
<220> FEATURE:
<223> OTHER INFORMATION: TIP + E + M

<400> SEQUENCE: 48
atgttgggaa gctcaacgag ccaaaaagtc atatacttgg tcatgatact gctgattgcc 60
ccggcataca gcatcaggtg cataggagtc agcaataggg actttgtgga aggtatgtca 120
ggtgggactt gggttgatgt tgtcttggaa catggaggtt gtgtcactgt aatggcacag 180
gacaaaccga ctgtcgacat agagctggtt acaacaacag tcagcaacat ggcggaggta 240
agatcctact gctatgaggc atcaatatca gacatggctt cggacagccg ctgcccaaca 300
caaggtgaag cctaccttga caagcaatca gacactcaat atgtctgcaa aagaacgtta 360
gtggacagag gctggggaaa tggatgtgga ctttttggca aagggagcct ggtgacatgc 420
gctaagtttg catgctccaa gaaaatgacc gggaagagca tccagccaga gaatctggag 480
taccggataa tgctgtcagt tcatggctcc cagcacagtg ggatgatcgt taatgacaca 540
ggacatgaaa ctgatgagaa tagagcgaaa gttgagataa cgcccaattc accaagagcc 600
gaagccaccc tggggggggtt tggaagccta ggacttgatt gtgaaccgag gacaggcctt 660
gacttttcag atttgtatta cttgactatg aataacaagc actggctggt tcacaaggag 720
tggttccacg acattccatt accttggcac gctggggcag acaccggaac tccacactgg 780
aacaacaaag aagcactggt agagttcaag gacgcacatg ccaaaaggca aactgtcgtg 840

```
gttctaggga gtcaagaagg agcagttcac acggcccttg ctggagctct ggaggctgag    900
atggatggtg caaagggaag gctgtcctct ggccacttga aatgtcgcct gaaaatggat    960
aaacttagat tgaagggcgt gtcatactcc ttgtgtactg cagcgttcac attcaccaag   1020
atcccggctg aaacactgca cgggacagtc acagtggagg tacagtacgc agggacagat   1080
ggaccttgca aggttccagc tcagatggcg gtggacatgc aaactctgac cccagttggg   1140
aggttgataa ccgctaaccc cgtaatcact gaaagcactg agaactctaa gatgatgctg   1200
gaacttgatc caccatttgg ggactcttac attgtcatag gagtcgggga gaagaagatc   1260
acccaccact ggcacaggag tggcagcacc attggaaaag catttgaagc cactgtgaga   1320
ggtgccaaga gaatggcagt cttgggagac acagcctggg actttggatc agttggaggc   1380
gctctcaact cattgggcaa gggcatccat caaatctttg gagcagcttt caaatcattg   1440
tttggaggaa tgtcctggtt ctcacaaatt ctcattggaa cgttgctgat gtggttgggt   1500
ctgaacgcaa agaatggatc tatttccctt atgtgcttgg ccttaggggg agtgttgatc   1560
ttcttatcca cagccgtctc tgctcagtgg aattccactg ccttccacca aactctgcag   1620
gatcccagag tcaggggtct gtatcttcct gctggtggct ccagttcagg aacagtaaac   1680
cctgctccga atattgcctc tcacatctcg tcaatctccg cgaggactgg ggaccctgtg   1740
acgaacatgg agaacatcac atcaggattc ctaggacccc tgctcgtgtt acaggcgggg   1800
tttttcttgt tgacaagaat cctcacaata ccgcagagtc tagactcgtg gtggacttct   1860
ctcaattttc taggggggatc tcccgtgtgt cttggccaaa attcgcagtc cccaacctcc   1920
aatcactcac caacctcctg tcctccaatt tgtcctggtt atcgctggat gtgtctgcgg   1980
cgttttatca tattcctctt catcctgctg ctatgcctca tcttcttatt ggttcttctg   2040
gattatcaag gtatgttgcc cgtttgtcct ctaattccag gatcaacaac aaccagtacg   2100
ggaccatgca aaacctgcac gactcctgct caaggcaact ctatgtttcc ctcatgttgc   2160
tgtacaaaac ctacggatgg aaattgcacc tgtattccca tcccatcgtc ctgggctttc   2220
gcaaaatacc tatgggagtg ggcctcagtc cgtttctctt ggctcagttt actagtgcca   2280
tttgttcagt ggttcgtagg gctttccccc actgtttggc tttcagctat atggatgatg   2340
tggtattggg ggccaagtct gtacagcatc gtgagtccct ttataccgct gttaccaatt   2400
ttcttttgtc tctgggtata catttaa                                        2427
```

<210> SEQ ID NO 49
<211> LENGTH: 2955
<212> TYPE: DNA
<213> ORGANISM: Artificial sequence
<220> FEATURE:
<223> OTHER INFORMATION: TIP + prM + E + M

<400> SEQUENCE: 49

```
atgctgagaa taatcaatgc taggaaggag aagaagagac gaggcgcaga tacaagtgtc     60
ggaattgttg gcctcctgct gaccacagct atggcagcgg aggtcactag acgtgggagt    120
gcatactata tgtacttgga cagaaacgat gctggggagg ccatatcttt tccaaccaca    180
ttggggatga ataagtgtta tatacagatc atggatcttg gacacacgtg tgatgccacc    240
atgagctatg aatgccctat gctggatgag ggggtggaac cagatgacgt cgattgttgg    300
tgcaacacga cgtcaacttg ggttgtgtac ggaacctgcc atcacaaaaa aggtgaagca    360
cggagatcta gaagagctgt gacgctcccc tcccattcca ctaggaagct gcaaacgcgg    420
tcgcaaacct ggttggaatc aagagaatac acaaagcact tgattagagt cgaaaattgg    480
```

atattcagga accctggctt cgcgttagca gcagctgcca tcgcttggct tttgggaagc 540
tcaacgagcc aaaaagtcat atacttggtc atgatactgc tgattgcccc ggcatacagc 600
atcaggtgca taggagtcag caatagggac tttgtggaag gtatgtcagg tgggacttgg 660
gttgatgttg tcttggaaca tggaggttgt gtcactgtaa tggcacagga caaaccgact 720
gtcgacatag agctggttac aacaacagtc agcaacatgg cggaggtaag atcctactgc 780
tatgaggcat caatatcaga catggcttcg gacagccgct gcccaacaca aggtgaagcc 840
taccttgaca agcaatcaga cactcaatat gtctgcaaaa gaacgttagt ggacagaggc 900
tggggaaatg gatgtggact tttggcaaa gggagcctgg tgacatgcgc taagtttgca 960
tgctccaaga aaatgaccgg gaagagcatc cagccagaga atctggagta ccggataatg 1020
ctgtcagttc atggctccca gcacagtggg atgatcgtta atgacacagg acatgaaact 1080
gatgagaata gagcgaaagt tgagataacg cccaattcac caagagccga agccaccctg 1140
ggggggtttg gaagcctagg acttgattgt gaaccgagga caggccttga cttttcagat 1200
ttgtattact tgactatgaa taacaagcac tggctggttc acaaggagtg gttccacgac 1260
attccattac cttggcacgc tggggcagac accggaactc cacactggaa caacaaagaa 1320
gcactggtag agttcaagga cgcacatgcc aaaaggcaaa ctgtcgtggt tctagggagt 1380
caagaaggag cagttcacac ggcccttgct ggagctctgg aggctgagat ggatggtgca 1440
aagggaaggc tgtcctctgg ccacttgaaa tgtcgcctga aaatggataa acttagattg 1500
aagggcgtgt catactcctt gtgtactgca gcgttcacat tcaccaagat cccggctgaa 1560
acactgcacg ggacagtcac agtggaggta cagtacgcag ggacagatgg accttgcaag 1620
gttccagctc agatggcggt ggacatgcaa actctgaccc cagttgggag gttgataacc 1680
gctaaccccg taatcactga aagcactgag aactctaaga tgatgctgga acttgatcca 1740
ccatttgggg actcttacat tgtcatagga gtcggggaga agaagatcac ccaccactgg 1800
cacaggagtg gcagcaccat tggaaaagca tttgaagcca ctgtgagagg tgccaagaga 1860
atggcagtct tgggagacac agcctgggac tttggatcag ttggaggcgc tctcaactca 1920
ttgggcaagg gcatccatca aatctttgga gcagctttca aatcattgtt tggaggaatg 1980
tcctggttct cacaaattct cattggaacg ttgctgatgt ggttgggtct gaacgcaaag 2040
aatggatcta tttcccttat gtgcttggcc ttagggggag tgttgatctt cttatccaca 2100
gccgtctctg ctcagtggaa ttccactgcc ttccaccaaa ctctgcagga tcccagagtc 2160
aggggtctgt atcttcctgc tggtggctcc agttcaggaa cagtaaaccc tgctccgaat 2220
attgcctctc acatctcgtc aatctccgcg aggactgggg accctgtgac gaacatggag 2280
aacatcacat caggattcct aggacccctg ctcgtgttac aggcggggtt tttcttgttg 2340
acaagaatcc tcacaatacc gcagagtcta gactcgtggt ggacttctct caattttcta 2400
gggggatctc ccgtgtgtct tggccaaaat tcgcagtccc caacctccaa tcactcacca 2460
acctcctgtc ctccaatttg tcctggttat cgctggatgt gtctgcggcg ttttatcata 2520
ttcctcttca tcctgctgct atgcctcatc ttcttattgg ttcttctgga ttatcaaggt 2580
atgttgcccg tttgtcctct aattccagga tcaacaacaa ccagtacggg accatgcaaa 2640
acctgcacga ctcctgctca aggcaactct atgtttccct catgttgctg tacaaaacct 2700
acggatggaa attgcacctg tattcccatc ccatcgtcct gggctttcgc aaaataccta 2760
tgggagtggg cctcagtccg tttctcttgg ctcagtttac tagtgccatt tgttcagtgg 2820
ttcgtagggc tttcccccac tgtttggctt tcagctatat ggatgatgtg gtattggggg 2880
ccaagtctgt acagcatcgt gagtcccttt ataccgctgt taccaatttt cttttgtctc 2940
tgggtataca tttaa 2955

<210> SEQ ID NO 50
<211> LENGTH: 164
<212> TYPE: PRT
<213> ORGANISM: Zika virus

<400> SEQUENCE: 50

Arg Arg Gly Ser Ala Tyr Tyr Met Tyr Leu Asp Arg Asn Asp Ala Gly
1 5 10 15

Glu Ala Ile Ser Phe Pro Thr Thr Leu Gly Met Asn Lys Cys Tyr Ile
20 25 30

Gln Ile Met Asp Leu Gly His Thr Cys Asp Ala Thr Met Ser Tyr Glu
35 40 45

Cys Pro Met Leu Asp Glu Gly Val Glu Pro Asp Asp Val Asp Cys Trp
50 55 60

Cys Asn Thr Thr Ser Thr Trp Val Val Tyr Gly Thr Cys His His Lys
65 70 75 80

Lys Gly Glu Ala Arg Arg Ser Arg Arg Ala Val Thr Leu Pro Ser His
85 90 95

Ser Thr Arg Lys Leu Gln Thr Arg Ser Gln Thr Trp Leu Glu Ser Arg
100 105 110

Glu Tyr Thr Lys His Leu Ile Arg Val Glu Asn Trp Ile Phe Arg Asn
115 120 125

Pro Gly Phe Ala Leu Ala Ala Ala Ala Ile Ala Trp Leu Leu Gly Ser
130 135 140

Ser Thr Ser Gln Lys Val Ile Tyr Leu Val Met Ile Leu Leu Ile Ala
145 150 155 160

Pro Ala Tyr Ser

<210> SEQ ID NO 51
<211> LENGTH: 2419
<212> TYPE: DNA
<213> ORGANISM: Artificial sequence
<220> FEATURE:
<223> OTHER INFORMATION: Synthesis gene C + prM + E

<400> SEQUENCE: 51
cccgggatcc atgaaaaacc caaaaaagaa atccggagga ttccggattg tcaatatgct 60
aaaacgcgga gtagcccgtg tgagcccctt tgggggcttg aagaggctgc cagccggact 120
tctgctgggt catgggccca tcaggatggt cttggcgatt ctagcctttt tgagattcac 180
ggcaatcaag ccatcactgg gtctcatcaa tagatggggt tcagtgggga aaaaagaggc 240
tatggaaata ataaagaagt tcaagaaaga tctggctgcc atgctgagaa taatcaatgc 300
taggaaggag aagaagagac gaggcgcaga tacaagtgtc ggaattgttg gcctcctgct 360
gaccacagct atggcagcgg aggtcactag acgtgggagt gcatactata tgtacttgga 420
cagaaacgat gctggggagg ccatatcttt tccaaccaca ttggggatga ataagtgtta 480
tatacagatc atggatcttg gacacacgtg tgatgccacc atgagctatg aatgccctat 540
gctggatgag ggggtggaac cagatgacgt cgattgttgg tgcaacacga cgtcaacttg 600
ggttgtgtac ggaacctgcc atcacaaaaa aggtgaagca cggagatcta gaagagctgt 660
gacgctcccc tcccattcca ctaggaagct gcaaacgcgg tcgcaaacct ggttggaatc 720

-continued aagagaatac acaaagcact tgattagagt cgaaaattgg atattcagga accctggctt 780
cgcgttagca gcagctgcca tcgcttggct tttgggaagc tcaacgagcc aaaaagtcat 840
atacttggtc atgatactgc tgattgcccc ggcatacagc atcaggtgca taggagtcag 900
caatagggac tttgtggaag gtatgtcagg tgggacttgg gttgatgttg tcttggaaca 960
tggaggttgt gtcactgtaa tggcacagga caaaccgact gtcgacatag agctggttac 1020
aacaacagtc agcaacatgg cggaggtaag atcctactgc tatgaggcat caatatcaga 1080
catggcttcg gacagccgct gcccaacaca aggtgaagcc taccttgaca agcaatcaga 1140
cactcaatat gtctgcaaaa gaacgttagt ggacagaggc tggggaaatg gatgtggact 1200
ttttggcaaa gggagcctgg tgacatgcgc taagtttgca tgctccaaga aaatgaccgg 1260
gaagagcatc cagccagaga atctggagta ccggataatg ctgtcagttc atggctccca 1320
gcacagtggg atgatcgtta atgacacagg acatgaaact gatgagaata gagcgaaagt 1380
tgagataacg cccaattcac caagagccga agccaccctg gggggggtttg gaagcctagg 1440 acttgattgt gaaccgagga caggccttga cttttcagat ttgtattact tgactatgaa 1500
taacaagcac tggctggttc acaaggagtg gttccacgac attccattac cttggcacgc 1560
tggggcagac accggaactc cacactggaa caacaaagaa gcactggtag agttcaagga 1620
cgcacatgcc aaaaggcaaa ctgtcgtggt tctagggagt caagaaggag cagttcacac 1680
ggcccttgct ggagctctgg aggctgagat ggatggtgca aagggaaggc tgtcctctgg 1740
ccacttgaaa tgtcgcctga aaatggataa acttagattg aagggcgtgt catactcctt 1800
gtgtactgca gcgttcacat tcaccaagat cccggctgaa acactgcacg ggacagtcac 1860
agtggaggta cagtacgcag ggacagatgg accttgcaag gttccagctc agatggcggt 1920
ggacatgcaa actctgaccc cagttgggag gttgataacc gctaaccccg taatcactga 1980
aagcactgag aactctaaga tgatgctgga acttgatcca ccatttgggg actcttacat 2040
tgtcatagga gtcggggaga agaagatcac ccaccactgg cacaggagtg gcagcaccat 2100
tggaaaagca tttgaagcca ctgtgagagg tgccaagaga atggcagtct tgggagacac 2160
agcctgggac tttggatcag ttggaggcgc tctcaactca ttgggcaagg gcatccatca 2220
aatctttgga gcagctttca aatcattgtt tggaggaatg tcctggttct cacaaattct 2280
cattggaacg ttgctgatgt ggttgggtct gaacgcaaag aatggatcta tttcccttat 2340
gtgcttggcc ttagggggag tgttgatctt cttatccaca gccgtctctg ctgatgtggg 2400
gtagctcgag gatcccggg 2419

<210> SEQ ID NO 52
<211> LENGTH: 10676
<212> TYPE: DNA
<213> ORGANISM: Zika virus

<400> SEQUENCE: 52
gttgttactg ttgctgactc agactgcgac agttcgagtt tgaagcgaaa gctagcaaca 60
gtatcaacag gttttatttg gatttggaaa cgagagtttc tggtcatgaa aaacccaaaa 120
aagaaatccg gaggattccg gattgtcaat atgctaaaac gcggagtagc ccgtgtgagc 180
ccctttgggg gcttgaagag gctgccagcc ggacttctgc tgggtcatgg gcccatcagg 240
atggtcttgg caattctagc ctttttgaga ttcacggcaa tcaagccatc actgggtctc 300
atcaatagat ggggttcagt ggggaaaaaa gaggctatgg aaataataaa gaagttcaag 360

-continued

```
aaagatctgg ctgccatgct gagaataatc aatgctagga aggagaagaa gagacggggc    420
gcagatacta gtgtcggaat tgttggcctc ctgctgacca cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgagggggt ggaaccagat    660
gacgtcgatt gttggtgcaa cacgacgtca acttgggttg tgtacggaac ctgccatcac    720
aaaaaaggtg aagcacggag atctagaaga gctgtgacgc tccccctccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tattgtcttg gaacatggag gttgtgtcac cgtaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtctg caaaagaacg   1260
ttagtggaca gaggctgggg aaatggatgt ggactttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgat cgttaatgac   1440
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
```

```
tctgtaaaaa accccatgtg gagaggtcca cagagattgc ccgtgcctgt gaacgagctg   2820
ccccacggct ggaaggcttg gggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gcccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
ataccctttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gcccccccgga   4920
gagagagcga ggaacatcca gactctgccc ggaatattta agacaaagga tggggacatt   4980
ggagcggttg cgctggatta cccagcagga acttcaggat ctccaatcct agacaagtgt   5040
gggagagtga taggacttta tggcaatggg gtcgtgatca aaaatgggag ttatgttagt   5100
```

-continued

```
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttagct   5280
ccaaccaggg ttgtcgctgc tgaaatggag gaagccctta gagggcttcc agtgcgttat   5340
atgacaacag cagtcaatgt cacccactct ggaacagaaa tcgtcgactt aatgtgccat   5400
gccaccttca cttcacgtct actacagcca atcagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagaga   5640
gcctggagct caggctttga ttgggtgacg gattattctg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
atagattcca ggagatgcct aaagccggtc atacttgatg gcgagagagt cattctggct   5940
ggacccatgc ctgtcacaca tgccagcgct gcccagagga gggggcgcat aggcaggaat   6000
cccaacaaac ctggagatga gtatctgtat ggaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcacga ccaacaacac cataatggaa gacagtgtgc cggcagaggt gtggaccaga   6360
cacggagaga aaagagtgct caaaccgagg tggatggacg ccagagtttg ttcagatcat   6420
gcggccctga agtcattcaa ggagtttgcc gctgggaaaa gaggagcggc ttttggagtg   6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggcaatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
```

-continued gccctgatca cagccgcaac ttccactttg tgggaaggct ctccgaacaa gtactggaac 7560
tcctctacag ccacttcact gtgtaacatt tttaggggaa gttacttggc tggagcttct 7620
ctaatctaca cagtaacaag aaacgctggc ttggtcaaga gacgtggggg tggaacagga 7680
gagaccctgg gagagaaatg gaaggcccgc ttgaaccaga tgtcggccct ggagttctac 7740
tcctacaaaa agtcaggcat caccgaggtg tgcagagaag aggcccgccg cgccctcaag 7800
gacggtgtgg caacgggagg ccatgctgtg tcccgaggaa gtgcaaagct gagatggttg 7860
gtggagcggg gatacctgca gccctatgga aaggtcattg atcttggatg tggcagaggg 7920
ggctggagtt actacgccgc caccatccgc aaagttcaag aagtgaaagg atacacaaaa 7980
ggaggccctg gtcatgaaga acccgtgttg gtgcaaagct atgggtggaa catagtccgt 8040
cttaagagtg gggtggacgt ctttcatatg gcggctgagc cgtgtgacac gttgctgtgt 8100
gacataggtg agtcatcatc tagtcctgaa gtggaagaag cacggacgct cagagtcctc 8160
tccatggtgg gggattggct tgaaaaaaga ccaggagcct tttgtataaa agtgttgtgc 8220
ccatacacca gcactatgat ggaaaccctg gagcgactgc agcgtaggta tgggggagga 8280
ctggtcagag tgccactctc ccgcaactct acacatgaga tgtactgggt ctctggagcg 8340
aaaagcaaca ccataaaaag tgtgtccacc acgagccagc tcctcttggg gcgcatggac 8400
gggcctagga ggccagtgaa atatgaggag gatgtgaatc tcggctctgg cacgcgggct 8460
gtggtaagct gcgctgaagc tcccaacatg aagatcattg gtaaccgcat tgaaaggatc 8520
cgcagtgagc acgcggaaac gtggttcttt gacgagaacc acccatatag gacatgggct 8580
taccatggaa gctatgaggc ccccacacaa gggtcagcgt cctctctaat aaacggggtt 8640
gtcaggctcc tgtcaaaacc ctgggatgtg gtgactggag tcacaggaat agccatgacc 8700
gacaccacac cgtatggtca gcaaagagtt ttcaaggaaa aagtggacac tagggtgcca 8760
gacccccaag aaggtactcg tcaggttatg agcatggtct cttcctggtt gtggaaagag 8820
ctaggcaaac acaaacggcc acgagtctgt accaaagaag agttcatcaa caaggttcgt 8880
agcaatgcag cattaggggc aatatttgaa gaggaaaaag agtggaagac tgcagtggaa 8940
gctgtgaacg atccaaggtt ctgggctcta gtggacaagg aaagagagca ccacctgaga 9000
ggagagtgcc agagttgtgt gtacaacatg atgggaaaaa gagaaaagaa acaaggggaa 9060
tttggaaagg ccaagggcag ccgcgccatc tggtatatgt ggctaggggc tagatttcta 9120
gagttcgaag cccttggatt cttgaacgag gatcactgga tggggagaga gaactcagga 9180
ggtggtgttg aagggctggg attacaaaga ctcggatatg tcctagaaga gatgagtcgc 9240
ataccaggag gaaggatgta tgcagatgac actgctggct gggacacccg catcagcagg 9300
tttgatctgg agaatgaagc tctaatcacc aaccaaatgg agaaagggca cagggccttg 9360
gcattggcca taatcaagta cacataccaa aacaaagtgg taaaggtcct tagaccagct 9420
gaaaaaggga aaacagttat ggacattatt tcgagacaag accaaagggg gagcggacaa 9480
gttgtcactt acgctcttaa cacatttacc aacctagtgg tgcaactcat tcggaatatg 9540
gaggctgagg aagtcctaga gatgcaagac ttgtggctgc tgcggaggtc agagaaagtg 9600
accaactggt tgcagagcaa cggatgggat aggctcaaac gaatggcagt cagtggagat 9660
gattgcgttg tgaagccaat tgatgatagg tttgcacatg ccctcaggtt cttgaatgat 9720
atgggaaaag ttaggaagga cacacaagag tggaaaccct caactggatg ggacaactgg 9780
gaagaagttc cgttttgctc ccaccacttc aacaagctcc atctcaagga cgggaggtcc 9840

-continued

```
attgtggttc cctgccgcca ccaagatgaa ctgattggcc gggcccgcgt ctctccaggg   9900

gcgggatgga gcatccggga gactgcttgc ctagcaaaat catatgcgca aatgtggcag   9960

ctcctttatt tccacagaag ggacctccga ctgatggcca atgccatttg ttcatctgtg  10020

ccagttgact gggttccaac tgggagaact acctggtcaa tccatggaaa gggagaatgg  10080

atgaccactg aagacatgct tgtggtgtgg aacagagtgt ggattgagga gaacgaccac  10140

atggaagaca agaccccagt tacgaaatgg acagacattc cctatttggg aaaaagggaa  10200

gacttgtggt gtggatctct catagggcac agaccgcgca ccacctgggc tgagaacatt  10260

aaaaacacag tcaacatggt gcgcaggatc ataggtgatg aagaaaagta catggactac  10320

ctatccaccc aagttcgcta cttgggtgaa gaagggtcta cacctggagt gctgtaagca  10380

ccaatcttaa tgttgtcagg cctgctagtc agccacagct tggggaaagc tgtgcagcct  10440

gtgacccccc caggagaagc tgggaaacca agcctatagt caggccgaga acgccatggc  10500

acggaagaag ccatgctgcc tgtgagcccc tcagaggaca ctgagtcaaa aaaccccacg  10560

cgcttggagg cgcaggatgg gaaaagaagg tggcgacctt ccccaccctt caatctgggg  10620

cctgaactgg agatcagctg tggatctcca gaagagggac tagtggttag aggaga      10676
```

<210> SEQ ID NO 53
<211> LENGTH: 13855
<212> TYPE: DNA
<213> ORGANISM: Artificial sequence
<220> FEATURE:
<223> OTHER INFORMATION: pSFV1 - “prM + E + S”

<400> SEQUENCE: 53

```
gatggcggat gtgtgacata cacgacgcca aaagattttg ttccagctcc tgccacctcc     60

gctacgcgag agattaacca cccacgatgg ccgccaaagt gcatgttgat attgaggctg    120

acagcccatt catcaagtct ttgcagaagg catttccgtc gttcgaggtg gagtcattgc    180

aggtcacacc aaatgaccat gcaaatgcca gagcattttc gcacctggct accaaattga    240

tcgagcagga gactgacaaa gacacactca tcttggatat cggcagtgcg ccttccagga    300

gaatgatgtc tacgcacaaa taccactgcg tatgccctat gcgcagcgca gaagaccccg    360

aaaggctcga tagctacgca aagaaactgg cagcggcctc cgggaaggtg ctggatagag    420

agatcgcagg aaaaatcacc gacctgcaga ccgtcatggc tacgccagac gctgaatctc    480

ctaccttttg cctgcataca gacgtcacgt gtcgtacggc agccgaagtg gccgtatacc    540

aggacgtgta tgctgtacat gcaccaacat cgctgtacca tcaggcgatg aaaggtgtca    600

gaacggcgta ttggattggg tttgacacca ccccgtttat gtttgacgcg ctagcaggcg    660

cgtatccaac ctacgccaca aactgggccg acgagcaggt gttacaggcc aggaacatag    720

gactgtgtgc agcatccttg actgagggaa gactcggcaa actgtccatt ctccgcaaga    780

agcaattgaa accttgcgac acagtcatgt tctcggtagg atctacattg tacactgaga    840

gcagaaagct actgaggagc tggcacttac cctccgtatt ccacctgaaa ggtaaacaat    900

cctttacctg taggtgcgat accatcgtat catgtgaagg gtacgtagtt aagaaaatca    960

ctatgtgccc cggcctgtac ggtaaaacgg tagggtacgc cgtgacgtat cacgcggagg   1020

gattcctagt gtgcaagacc acagacactg tcaaaggaga aagagtctca ttccctgtat   1080

gcacctacgt cccctcaacc atctgtgatc aaatgactgg catactagcg accgacgtca   1140

caccggagga cgcacagaag ttgttagtgg gattgaatca gaggatagtt gtgaacggaa   1200

gaacacagcg aaacactaac acgatgaaga actatctgct tccgattgtg gccgtcgcat   1260
```

-continued ttagcaagtg ggcgagggaa tacaaggcag accttgatga tgaaaaacct ctgggtgtcc 1320
gagagaggtc acttacttgc tgctgcttgt gggcatttaa aacgaggaag atgcacacca 1380
tgtacaagaa accagacacc cagacaatag tgaaggtgcc ttcagagttt aactcgttcg 1440
tcatcccgag cctatggtct acaggcctcg caatcccagt cagatcacgc attaagatgc 1500
ttttggccaa gaagaccaag cgagagttaa tacctgttct cgacgcgtcg tcagccaggg 1560
atgctgaaca agaggagaag gagaggttgg aggccgagct gactagagaa gccttaccac 1620
ccctcgtccc catcgcgccg gcggagacgg gagtcgtcga cgtcgacgtt gaagaactag 1680
agtatcacgc aggtgcaggg gtcgtggaaa cacctcgcag cgcgttgaaa gtcaccgcac 1740
agccgaacga cgtactacta ggaaattacg tagttctgtc cccgcagacc gtgctcaaga 1800
gctccaagtt ggcccccgtg caccctctag cagagcaggt gaaaataata acacataacg 1860
ggagggccgg cggttaccag gtcgacggat atgacggcag ggtcctacta ccatgtggat 1920
cggccattcc ggtccctgag tttcaagctt tgagcgagag cgccactatg gtgtacaacg 1980
aaagggagtt cgtcaacagg aaactatacc atattgccgt tcacggaccg tcgctgaaca 2040
ccgacgagga gaactacgag aaagtcagag ctgaaagaac tgacgccgag tacgtgttcg 2100
acgtagataa aaaatgctgc gtcaagagag aggaagcgtc gggtttggtg ttggtgggag 2160
agctaaccaa cccccgttc catgaattcg cctacgaagg gctgaagatc aggccgtcgg 2220
caccatataa gactacagta gtaggagtct ttggggttcc gggatcaggc aagtctgcta 2280
ttattaagag cctcgtgacc aaacacgatc tggtcaccag cggcaagaag gagaactgcc 2340
aggaaatagt taacgacgtg aagaagcacc gcgggaaggg gacaagtagg gaaaacagtg 2400
actccatcct gctaaacggg tgtcgtcgtg ccgtggacat cctatatgtg gacgaggctt 2460
tcgcttgcca ttccggtact ctgctggccc taattgctct tgttaaacct cggagcaaag 2520
tggtgttatg cggagacccc aagcaatgcg gattcttcaa tatgatgcag cttaaggtga 2580
acttcaacca caacatctgc actgaagtat gtcataaaag tatatccaga cgttgcacgc 2640
gtccagtcac ggccatcgtg tctacgttgc actacggagg caagatgcgc acgaccaacc 2700
cgtgcaacaa acccataatc atagacacca caggacagac caagcccaag ccaggagaca 2760
tcgtgttaac atgcttccga ggctgggcaa agcagctgca gttggactac cgtggacacg 2820
aagtcatgac agcagcagca tctcagggcc tcacccgcaa aggggtatac gccgtaaggc 2880
agaaggtgaa tgaaaatccc ttgtatgccc ctgcgtcgga gcacgtgaat gtactgctga 2940
cgcgcactga ggataggctg gtgtggaaaa cgctggccgg cgatccctgg attaaggtcc 3000
tatcaaacat tccacagggt aactttacgg ccacattgga agaatggcaa gaagaacacg 3060
acaaaataat gaaggtgatt gaaggaccgg ctgcgcctgt ggacgcgttc cagaacaaag 3120
cgaacgtgtg ttgggcgaaa agcctggtgc ctgtcctgga cactgccgga atcagattga 3180
cagcagagga gtggagcacc ataattacag catttaagga ggacagagct tactctccag 3240
tggtggcctt gaatgaaatt tgcaccaagt actatggagt tgacctggac agtggcctgt 3300
tttctgcccc gaaggtgtcc ctgtattacg agaacaacca ctgggataac agacctggtg 3360
gaaggatgta tggattcaat gccgcaacag ctgccaggct ggaagctaga catacccttcc 3420
tgaaggggca gtggcatacg ggcaagcagg cagttatcgc agaaagaaaa atccaaccgc 3480
tttctgtgct ggacaatgta attcctatca accgcaggct gccgcacgcc ctggtggctg 3540
agtacaagac ggttaaaggc agtagggttg agtggctggt caataaagta agagggtacc 3600

-continued

```
acgtcctgct ggtgagtgag tacaacctgg ctttgcctcg acgcagggtc acttggttgt   3660
caccgctgaa tgtcacaggc gccgataggt gctacgacct aagtttagga ctgccggctg   3720
acgccggcag gttcgacttg gtctttgtga acattcacac ggaattcaga atccaccact   3780
accagcagtg tgtcgaccac gccatgaagc tgcagatgct tgggggagat gcgctacgac   3840
tgctaaaacc cggcggcatc ttgatgagag cttacggata cgccgataaa atcagcgaag   3900
ccgttgtttc ctccttaagc agaaagttct cgtctgcaag agtgttgcgc ccggattgtg   3960
tcaccagcaa tacagaagtg ttcttgctgt tctccaactt tgacaacgga aagagaccct   4020
ctacgctaca ccagatgaat accaagctga gtgccgtgta tgccggagaa gccatgcaca   4080
cggccgggtg tgcaccatcc tacagagtta agagagcaga catagccacg tgcacagaag   4140
cggctgtggt taacgcagct aacgcccgtg gaactgtagg ggatggcgta tgcagggccg   4200
tggcgaagaa atggccgtca gcctttaagg gagcagcaac accagtgggc acaattaaaa   4260
cagtcatgtg cggctcgtac cccgtcatcc acgctgtagc gcctaatttc tctgccacga   4320
ctgaagcgga aggggaccgc gaattggccg ctgtctaccg ggcagtggcc gccgaagtaa   4380
acagactgtc actgagcagc gtagccatcc cgctgctgtc cacaggagtg ttcagcggcg   4440
gaagagatag gctgcagcaa tccctcaacc atctattcac agcaatggac gccacggacg   4500
ctgacgtgac catctactgc agagacaaaa gttgggagaa gaaaatccag gaagccattg   4560
acatgaggac ggctgtggag ttgctcaatg atgacgtgga gctgaccaca gacttggtga   4620
gagtgcaccc ggacagcagc ctggtgggtc gtaagggcta cagtaccact gacgggtcgc   4680
tgtactcgta ctttgaaggt acgaaattca accaggctgc tattgatatg gcagagatac   4740
tgacgttgtg gcccagactg caagaggcaa acgaacagat atgcctatac gcgctgggcg   4800
aaacaatgga caacatcaga tccaaatgtc cggtgaacga ttccgattca tcaacacctc   4860
ccaggacagt gccctgcctg tgccgctacg caatgacagc agaacggatc gcccgcctta   4920
ggtcacacca agttaaaagc atggtggttt gctcatcttt tcccctcccg aaataccatg   4980
tagatggggt gcagaaggta aagtgcgaga aggttctcct gttcgacccg acggtacctt   5040
cagtggttag tccgcggaag tatgccgcat ctacgacgga ccactcagat cggtcgttac   5100
gagggtttga cttggactgg accaccgact cgtcttccac tgccagcgat accatgtcgc   5160
tacccagttt gcagtcgtgt gacatcgact cgatctacga gccaatggct cccatagtag   5220
tgacggctga cgtacaccct gaacccgcag gcatcgcgga cctggcggca gatgtgcacc   5280
ctgaacccgc agaccatgtg gacctcgaga acccgattcc tccaccgcgc ccgaagagag   5340
ctgcatacct tgcctcccgc gcggcggagc gaccggtgcc ggcgccgaga aagccgacgc   5400
ctgccccaag gactgcgttt aggaacaagc tgcctttgac gttcggcgac tttgacgagc   5460
acgaggtcga tgcgttggcc tccgggatta ctttcggaga cttcgacgac gtcctgcgac   5520
taggccgcgc gggtgcatat attttctcct cggacactgg cagcggacat ttacaacaaa   5580
aatccgttag gcagcacaat ctccagtgcg cacaactgga tgcggtccag gaggagaaaa   5640
tgtacccgcc aaaattggat actgagaggg agaagctgtt gctgctgaaa atgcagatgc   5700
acccatcgga ggctaataag agtcgatacc agtctcgcaa agtggagaac atgaaagcca   5760
cggtggtgga caggctcaca tcgggggcca gattgtacac gggagcggac gtaggccgca   5820
taccaacata cgcggttcgg taccccgcc ccgtgtactc ccctaccgtg atcgaaagat    5880
tctcaagccc cgatgtagca atcgcagcgt gcaacgaata cctatccaga aattacccaa   5940
cagtggcgtc gtaccagata acagatgaat acgacgcata cttggacatg gttgacgggt   6000
```

```
cggatagttg cttggacaga gcgacattct gcccggcgaa gctccggtgc tacccgaaac   6060
atcatgcgta ccaccagccg actgtacgca gtgccgtccc gtcacccttt cagaacacac   6120
tacagaacgt gctagcggcc gccaccaaga gaaactgcaa cgtcacgcaa atgcgagaac   6180
tacccaccat ggactcggca gtgttcaacg tggagtgctt caagcgctat gcctgctccg   6240
gagaatattg ggaagaatat gctaaacaac ctatccggat aaccactgag aacatcacta   6300
cctatgtgac caaattgaaa ggcccgaaag ctgctgcctt gttcgctaag acccacaact   6360
tggttccgct gcaggaggtt cccatggaca gattcacggt cgacatgaaa cgagatgtca   6420
aagtcactcc agggacgaaa cacacagagg aaagacccaa agtccaggta attcaagcag   6480
cggagccatt ggcgaccgct tacctgtgcg gcatccacag ggaattagta aggagactaa   6540
atgctgtgtt acgccctaac gtgcacacat tgtttgatat gtcggccgaa gactttgacg   6600
cgatcatcgc ctctcacttc cacccaggag acccggttct agagacggac attgcatcat   6660
tcgacaaaag ccaggacgac tccttggctc ttacaggttt aatgatcctc gaagatctag   6720
gggtggatca gtacctgctg gacttgatcg aggcagcctt tggggaaata tccagctgtc   6780
acctaccaac tggcacgcgc ttcaagttcg gagctatgat gaaatcgggc atgtttctga   6840
ctttgtttat taacactgtt ttgaacatca ccatagcaag cagggtactg gagcagagac   6900
tcactgactc cgcctgtgcg gccttcatcg gcgacgacaa catcgttcac ggagtgatct   6960
ccgacaagct gatggcggag aggtgcgcgt cgtgggtcaa catggaggtg aagatcattg   7020
acgctgtcat gggcgaaaaa cccccatatt tttgtggggg attcatagtt tttgacagcg   7080
tcacacagac cgcctgccgt gtttcagacc cacttaagcg cctgttcaag ttgggtaagc   7140
cgctaacagc tgaagacaag caggacgaag acaggcgacg agcactgagt gacgaggtta   7200
gcaagtggtt ccggacaggc ttgggggccg aactggaggt ggcactaaca tctaggtatg   7260
aggtagaggg ctgcaaaagt atcctcatag ccatggccac cttggcgagg gacattaagg   7320
cgtttaagaa attgagagga cctgttatac acctctacgg cggtcctaga ttggtgcgtt   7380
aatacacaga attctgattg gatcccgggc tcgagatgct gagaataatc aatgctagga   7440
aggagaagaa gagacgaggc gcagatacaa gtgtcggaat tgttggcctc ctgctgacca   7500
cagctatggc agcggaggtc actagacgtg ggagtgcata ctatatgtac ttggacagaa   7560
acgatgctgg ggaggccata tcttttccaa ccacattggg gatgaataag tgttatatac   7620
agatcatgga tcttggacac acgtgtgatg ccaccatgag ctatgaatgc cctatgctgg   7680
atgagggggt ggaaccagat gacgtcgatt gttggtgcaa cacgacgtca acttgggttg   7740
tgtacggaac ctgccatcac aaaaaaggtg aagcacggag atctagaaga gctgtgacgc   7800
tcccctccca ttccactagg aagctgcaaa cgcggtcgca aacctggttg gaatcaagag   7860
aatacacaaa gcacttgatt agagtcgaaa attggatatt caggaaccct ggcttcgcgt   7920
tagcagcagc tgccatcgct tggcttttgg gaagctcaac gagccaaaaa gtcatatact   7980
tggtcatgat actgctgatt gccccggcat acagcatcag gtgcatagga gtcagcaata   8040
gggactttgt ggaaggtatg tcaggtggga cttgggttga tgttgtcttg gaacatggag   8100
gttgtgtcac tgtaatggca caggacaaac cgactgtcga catagagctg gttacaacaa   8160
cagtcagcaa catggcggag gtaagatcct actgctatga ggcatcaata tcagacatgg   8220
cttcggacag ccgctgccca acacaaggtg aagcctacct tgacaagcaa tcagacactc   8280
aatatgtctg caaaagaacg ttagtggaca gaggctgggg aaatggatgt ggactttttg   8340
```

-continued

```
gcaaagggag cctggtgaca tgcgctaagt ttgcatgctc caagaaaatg accgggaaga   8400
gcatccagcc agagaatctg gagtaccgga taatgctgtc agttcatggc tcccagcaca   8460
gtgggatgat cgttaatgac acaggacatg aaactgatga gaatagagcg aaagttgaga   8520
taacgcccaa ttcaccaaga gccgaagcca ccctgggggg gtttggaagc ctaggacttg   8580
attgtgaacc gaggacaggc cttgactttt cagatttgta ttacttgact atgaataaca   8640
agcactggct ggttcacaag gagtggttcc acgacattcc attaccttgg cacgctgggg   8700
cagacaccgg aactccacac tggaacaaca aagaagcact ggtagagttc aaggacgcac   8760
atgccaaaag gcaaactgtc gtggttctag ggagtcaaga aggagcagtt cacacggccc   8820
ttgctggagc tctggaggct gagatggatg gtgcaaaggg aaggctgtcc tctggccact   8880
tgaaatgtcg cctgaaaatg gataaactta gattgaaggg cgtgtcatac tccttgtgta   8940
ctgcagcgtt cacattcacc aagatcccgg ctgaaacact gcacgggaca gtcacagtgg   9000
aggtacagta cgcagggaca gatggacctt gcaaggttcc agctcagatg gcggtggaca   9060
tgcaaactct gaccccagtt gggaggttga taaccgctaa ccccgtaatc actgaaagca   9120
ctgagaactc taagatgatg ctggaacttg atccaccatt tggggactct tacattgtca   9180
taggagtcgg ggagaagaag atcacccacc actggcacag gagtggcagc accattggaa   9240
aagcatttga agccactgtg agaggtgcca agagaatggc agtcttggga gacacagcct   9300
gggactttgg atcagttgga ggcgctctca actcattggg caagggcatc catcaaatct   9360
ttggagcagc tttcaaatca ttgtttggag gaatgtcctg gttctcacaa attctcattg   9420
gaacgttgct gatgtggttg ggtctgaacg caaagaatgg atctatttcc cttatgtgct   9480
tggccttagg gggagtgttg atcttcttat ccacagccgt ctctgctgag aacatcacat   9540
caggattcct aggacccctg ctcgtgttac aggcggggtt tttcttgttg acaagaatcc   9600
tcacaatacc gcagagtcta gactcgtggt ggacttctct caattttcta gggggatctc   9660
ccgtgtgtct tggccaaaat tcgcagtccc caacctccaa tcactcacca acctcctgtc   9720
ctccaatttg tcctggttat cgctggatgt gtctgcggcg ttttatcata ttcctcttca   9780
tcctgctgct atgcctcatc ttcttattgg ttcttctgga ttatcaaggt atgttgcccg   9840
tttgtcctct aattccagga tcaacaacaa ccagtacggg accatgcaaa acctgcacga   9900
ctcctgctca aggcaactct atgtttccct catgttgctg tacaaaacct acggatggaa   9960
attgcacctg tattcccatc ccatcgtcct gggctttcgc aaaataccta tgggagtggg  10020
cctcagtccg tttctcttgg ctcagtttac tagtgccatt tgttcagtgg ttcgtagggc  10080
tttcccccac tgtttggctt tcagctatat ggatgatgtg gtattggggg ccaagtctgt  10140
acagcatcgt gagtcccttt ataccgctgt taccaatttt cttttgtctc tgggtataca  10200
tttaactcga gcccgggatc ccgggtaatt aattgaatta catccctacg caaacgtttt  10260
acggccgccg gtggcgcccg cgcccggcgg cccgtccttg gccgttgcag gccactccgg  10320
tggctcccgt cgtccccgac ttccaggccc agcagatgca gcaactcatc agcgccgtaa  10380
atgcgctgac aatgagacag aacgcaattg ctcctgctag gcctcccaaa ccaaagaaga  10440
agaagacaac caaaccaaag ccgaaaacgc agcccaagaa gatcaacgga aaaacgcagc  10500
agcaaaagaa gaaagacaag caagccgaca agaagaagaa gaaacccgga aaaagagaaa  10560
gaatgtgcat gaagattgaa aatgactgta tcttcgtatg cggctagcca cagtaacgta  10620
gtgtttccag acatgtcggg caccgcacta tcatgggtgc agaaaatctc gggtggtctg  10680
ggggccttcg caatcggcgc tatcctggtg ctggttgtgg tcacttgcat tgggctccgc  10740
```

agataagtta gggtaggcaa tggcattgat atagcaagaa aattgaaaac agaaaaagtt 10800
agggtaagca atggcatata accataactg tataacttgt aacaaagcgc aacaagacct 10860
gcgcaattgg ccccgtggtc cgcctcacgg aaactcgggg caactcatat tgacacatta 10920
attggcaata attggaagct tacataagct taattcgacg aataattgga tttttatttt 10980
attttgcaat tggtttttaa tatttccaaa aaaaaaaaaa aaaaaaaaaa aaaaaaaaaa 11040
aaaaaaaaaa aaaaaaaaaa aaaaaaaaaa aaaaaattcg aaactagtct gcattaatga 11100
atcggccaac gcgcggggag aggcggtttg cgtattgggc gctcttccgc ttcctcgctc 11160
actgactcgc tgcgctcggt cgttcggctg cggcgagcgg tatcagctca ctcaaaggcg 11220
gtaatacggt tatccacaga atcaggggat aacgcaggaa agaacatgtg agcaaaaggc 11280
cagcaaaagg ccaggaaccg taaaaaggcc gcgttgctgg cgtttttcca taggctccgc 11340
ccccctgacg agcatcacaa aaatcgacgc tcaagtcaga ggtggcgaaa cccgacagga 11400
ctataaagat accaggcgtt tccccctgga agctccctcg tgcgctctcc tgttccgacc 11460
ctgccgctta ccggatacct gtccgccttt ctcccttcgg gaagcgtggc gctttctcaa 11520
tgctcgcgct gtaggtatct cagttcggtg taggtcgttc gctccaagct gggctgtgtg 11580
cacgaacccc ccgttcagcc cgaccgctgc gccttatccg gtaactatcg tcttgagtcc 11640
aacccggtaa gacacgactt atcgccactg gcagcagcca ctggtaacag gattagcaga 11700
gcgaggtatg taggcggtgc tacagagttc ttgaagtggt ggcctaacta cggctacact 11760
agaaggacag tatttggtat ctgcgctctg ctgaagccag ttaccttcgg aaaaagagtt 11820
ggtagctctt gatccggcaa acaaaccacc gctggtagcg gtggtttttt tgtttgcaag 11880
cagcagatta cgcgcagaaa aaaaggatct caagaagatc ctttgatctt ttctacgggg 11940
tctgacgctc agtggaacga aaactcacgt taagggattt tggtcatgag attatcaaaa 12000
aggatcttca cctagatcct tttaaattaa aaatgaagtt ttaaatcaat ctaaagtata 12060
tatgagtaaa cttggtctga cagttaccaa tgcttaatca gtgaggcacc tatctcagcg 12120
atctgtctat ttcgttcatc catagttgcc tgactccccg tcgtgtagat aactacgata 12180
cgggagggct taccatctgg ccccagtgct gcaatgatac cgcgagaccc acgctcaccg 12240
gctccagatt tatcagcaat aaaccagcca gccggaaggg ccgagcgcag aagtggtcct 12300
gcaactttat ccgcctccat ccagtctatt aattgttgcc gggaagctag agtaagtagt 12360
tcgccagtta atagtttgcg caacgttgtt gccattgcta caggcatcgt ggtgtcacgc 12420
tcgtcgtttg gtatggcttc attcagctcc ggttcccaac gatcaaggcg agttacatga 12480
tcccccatgt tgtgcaaaaa agcggttagc tccttcggtc ctccgatcgt tgtcagaagt 12540
aagttggccg cagtgttatc actcatggtt atggcagcac tgcataattc tcttactgtc 12600
atgccatccg taagatgctt ttctgtgact ggtgagtact caaccaagtc attctgagaa 12660
tagtgtatgc ggcgaccgag ttgctcttgc ccggcgtcaa tacgggataa taccgcgcca 12720
catagcagaa ctttaaaagt gctcatcatt ggaaaacgtt cttcggggcg aaaactctca 12780
aggatcttac cgctgttgag atccagttcg atgtaaccca ctcgtgcacc caactgatct 12840
tcagcatctt ttactttcac cagcgtttct gggtgagcaa aaacaggaag gcaaaatgcc 12900
gcaaaaaagg gaataagggc gacacggaaa tgttgaatac tcatactctt cctttttcaa 12960
tattattgaa gcatttatca gggttattgt ctcatgagcg gatacatatt tgaatgtatt 13020
tagaaaaata aacaaatagg ggttccgcgc acatttcccc gaaaagtgcc acctgacgtc 13080

-continued taagaaacca ttattatcat gacattaacc tataaaaata ggcgtatcac gaggcccttt 13140
cgtctcgcgc gtttcggtga tgacggtgaa aacctctgac acatgcagct cccggagacg 13200
gtcacagctt ctgtctaagc ggatgccggg agcagacaag cccgtcaggg cgcgtcagcg 13260
ggtgttggcg ggtgtcgggg ctggcttaac tatgcggcat cagagcagat tgtactgaga 13320
gtgcaccata tcgacgctct cccttatgcg actcctgcat taggaagcag cccagtacta 13380
ggttgaggcc gttgagcacc gccgccgcaa ggaatggtgc atgcaaggag atggcgccca 13440
acagtccccc ggccacgggg cctgccacca tacccacgcc gaaacaagcg ctcatgagcc 13500
cgaagtggcg agcccgatct tccccatcgg tgatgtcggc gatataggcg ccagcaaccg 13560
cacctgtggc gccggtgatg ccggccacga tgcgtccggc gtagaggatc tggctagcga 13620
tgaccctgct gattggttcg ctgaccattt ccggggtgcg gaacggcgtt accagaaact 13680
cagaaggttc gtccaaccaa accgactctg acggcagttt acgagagaga tgatagggtc 13740
tgcttcagta agccagatgc tacacaatta ggcttgtaca tattgtcgtt agaacgcggc 13800
tacaattaat acataacctt atgtatcata cacatacgat ttaggtgaca ctata 13855

<210> SEQ ID NO 54
<211> LENGTH: 13726
<212> TYPE: DNA
<213> ORGANISM: Artificial sequence
<220> FEATURE:
<223> OTHER INFORMATION: pSFV1 - “prM + E deleted + S deleted”

<400> SEQUENCE: 54
gatggcggat gtgtgacata cacgacgcca aaagattttg ttccagctcc tgccacctcc 60
gctacgcgag agattaacca cccacgatgg ccgccaaagt gcatgttgat attgaggctg 120
acagcccatt catcaagtct ttgcagaagg catttccgtc gttcgaggtg gagtcattgc 180
aggtcacacc aaatgaccat gcaaatgcca gagcattttc gcacctggct accaaattga 240
tcgagcagga gactgacaaa gacacactca tcttggatat cggcagtgcg ccttccagga 300
gaatgatgtc tacgcacaaa taccactgcg tatgccctat gcgcagcgca gaagaccccg 360
aaaggctcga tagctacgca aagaaactgg cagcggcctc cgggaaggtg ctggatagag 420
agatcgcagg aaaaatcacc gacctgcaga ccgtcatggc tacgccagac gctgaatctc 480
ctaccttttg cctgcataca gacgtcacgt gtcgtacggc agccgaagtg gccgtatacc 540
aggacgtgta tgctgtacat gcaccaacat cgctgtacca tcaggcgatg aaaggtgtca 600
gaacggcgta ttggattggg tttgacacca ccccgtttat gtttgacgcg ctagcaggcg 660
cgtatccaac ctacgccaca aactgggccg acgagcaggt gttacaggcc aggaacatag 720
gactgtgtgc agcatccttg actgagggaa gactcggcaa actgtccatt ctccgcaaga 780
agcaattgaa accttgcgac acagtcatgt tctcggtagg atctacattg tacactgaga 840
gcagaaagct actgaggagc tggcacttac cctccgtatt ccacctgaaa ggtaaacaat 900
cctttacctg taggtgcgat accatcgtat catgtgaagg gtacgtagtt aagaaaatca 960
ctatgtgccc cggcctgtac ggtaaaacgg tagggtacgc cgtgacgtat cacgcggagg 1020
gattcctagt gtgcaagacc acagacactg tcaaaggaga aagagtctca ttccctgtat 1080
gcacctacgt cccctcaacc atctgtgatc aaatgactgg catactagcg accgacgtca 1140
caccggagga cgcacagaag ttgttagtgg gattgaatca gaggatagtt gtgaacggaa 1200
gaacacagcg aaacactaac acgatgaaga actatctgct tccgattgtg gccgtcgcat 1260
ttagcaagtg ggcgagggaa tacaaggcag accttgatga tgaaaaacct ctgggtgtcc 1320

```
gagagaggtc acttacttgc tgctgcttgt gggcatttaa aacgaggaag atgcacacca   1380
tgtacaagaa accagacacc cagacaatag tgaaggtgcc ttcagagttt aactcgttcg   1440
tcatcccgag cctatggtct acaggcctcg caatcccagt cagatcacgc attaagatgc   1500
ttttggccaa gaagaccaag cgagagttaa tacctgttct cgacgcgtcg tcagccaggg   1560
atgctgaaca agaggagaag gagaggttgg aggccgagct gactagagaa gccttaccac   1620
ccctcgtccc catcgcgccg gcggagacgg gagtcgtcga cgtcgacgtt gaagaactag   1680
agtatcacgc aggtgcaggg gtcgtggaaa cacctcgcag cgcgttgaaa gtcaccgcac   1740
agccgaacga cgtactacta ggaaattacg tagttctgtc ccgcagaccc gtgctcaaga   1800
gctccaagtt ggcccccgtg caccctctag cagagcaggt gaaaataata acacataacg   1860
ggagggccgg cggttaccag gtcgacggat atgacggcag ggtcctacta ccatgtggat   1920
cggccattcc ggtccctgag tttcaagctt tgagcgagag cgccactatg gtgtacaacg   1980
aaagggagtt cgtcaacagg aaactatacc atattgccgt tcacggaccg tcgctgaaca   2040
ccgacgagga gaactacgag aaagtcagag ctgaaagaac tgacgccgag tacgtgttcg   2100
acgtagataa aaaatgctgc gtcaagagag aggaagcgtc gggtttggtg ttggtgggag   2160
agctaaccaa cccccccgttc catgaattcg cctacgaagg gctgaagatc aggccgtcgg   2220
caccatataa gactacagta gtaggagtct ttggggttcc gggatcaggc aagtctgcta   2280
ttattaagag cctcgtgacc aaacacgatc tggtcaccag cggcaagaag gagaactgcc   2340
aggaaatagt taacgacgtg aagaagcacc gcgggaaggg gacaagtagg gaaaacagtg   2400
actccatcct gctaaacggg tgtcgtcgtg ccgtggacat cctatatgtg gacgaggctt   2460
tcgcttgcca ttccggtact ctgctggccc taattgctct tgttaaacct cggagcaaag   2520
tggtgttatg cggagacccc aagcaatgcg gattcttcaa tatgatgcag cttaaggtga   2580
acttcaacca caacatctgc actgaagtat gtcataaaag tatatccaga cgttgcacgc   2640
gtccagtcac ggccatcgtg tctacgttgc actacggagg caagatgcgc acgaccaacc   2700
cgtgcaacaa acccataatc atagacacca caggacagac caagcccaag ccaggagaca   2760
tcgtgttaac atgcttccga ggctgggcaa agcagctgca gttggactac cgtggacacg   2820
aagtcatgac agcagcagca tctcagggcc tcacccgcaa aggggtatac gccgtaaggc   2880
agaaggtgaa tgaaaatccc ttgtatgccc ctgcgtcgga gcacgtgaat gtactgctga   2940
cgcgcactga ggataggctg gtgtggaaaa cgctggccgg cgatccctgg attaaggtcc   3000
tatcaaacat tccacagggt aactttacgg ccacattgga agaatggcaa gaagaacacg   3060
acaaaataat gaaggtgatt gaaggaccgg ctgcgcctgt ggacgcgttc cagaacaaag   3120
cgaacgtgtg ttgggcgaaa agcctggtgc ctgtcctgga cactgccgga atcagattga   3180
cagcagagga gtggagcacc ataattacag catttaagga ggacagagct tactctccag   3240
tggtggcctt gaatgaaatt tgcaccaagt actatggagt tgacctggac agtggcctgt   3300
tttctgcccc gaaggtgtcc ctgtattacg agaacaacca ctgggataac agacctggtg   3360
gaaggatgta tggattcaat gccgcaacag ctgccaggct ggaagctaga cataccttcc   3420
tgaaggggca gtggcatacg ggcaagcagg cagttatcgc agaaagaaaa atccaaccgc   3480
tttctgtgct ggacaatgta attcctatca accgcaggct gccgcacgcc ctggtggctg   3540
agtacaagac ggttaaaggc agtagggttg agtggctggt caataaagta agagggtacc   3600
acgtcctgct ggtgagtgag tacaacctgg ctttgcctcg acgcagggtc acttggttgt   3660
```

-continued caccgctgaa tgtcacaggc gccgataggt gctacgacct aagtttagga ctgccggctg 3720
acgccggcag gttcgacttg gtctttgtga acattcacac ggaattcaga atccaccact 3780
accagcagtg tgtcgaccac gccatgaagc tgcagatgct tggggagat gcgctacgac 3840
tgctaaaacc cggcggcatc ttgatgagag cttacggata cgccgataaa atcagcgaag 3900
ccgttgtttc ctccttaagc agaaagttct cgtctgcaag agtgttgcgc ccggattgtg 3960
tcaccagcaa tacagaagtg ttcttgctgt tctccaactt tgacaacgga aagagaccct 4020
ctacgctaca ccagatgaat accaagctga gtgccgtgta tgccggagaa gccatgcaca 4080
cggccgggtg tgcaccatcc tacagagtta agagagcaga catagccacg tgcacagaag 4140
cggctgtggt taacgcagct aacgcccgtg gaactgtagg ggatggcgta tgcagggccg 4200
tggcgaagaa atggccgtca gcctttaagg gagcagcaac accagtgggc acaattaaaa 4260
cagtcatgtg cggctcgtac cccgtcatcc acgctgtagc gcctaatttc tctgccacga 4320
ctgaagcgga aggggaccgc gaattggccg ctgtctaccg ggcagtggcc gccgaagtaa 4380
acagactgtc actgagcagc gtagccatcc cgctgctgtc cacaggagtg ttcagcggcg 4440
gaagagatag gctgcagcaa tccctcaacc atctattcac agcaatggac gccacggacg 4500
ctgacgtgac catctactgc agagacaaaa gttgggagaa gaaaatccag gaagccattg 4560
acatgaggac ggctgtggag ttgctcaatg atgacgtgga gctgaccaca gacttggtga 4620
gagtgcaccc ggacagcagc ctggtgggtc gtaagggcta cagtaccact gacgggtcgc 4680
tgtactcgta ctttgaaggt acgaaattca accaggctgc tattgatatg gcagagatac 4740
tgacgttgtg gcccagactg caagaggcaa acgaacagat atgcctatac gcgctgggcg 4800
aaacaatgga caacatcaga tccaaatgtc cggtgaacga ttccgattca tcaacacctc 4860
ccaggacagt gccctgcctg tgccgctacg caatgacagc agaacggatc gcccgcctta 4920
ggtcacacca agttaaaagc atggtggttt gctcatcttt tcccctcccg aaataccatg 4980
tagatggggt gcagaaggta aagtgcgaga aggttctcct gttcgacccg acggtacctt 5040
cagtggttag tccgcggaag tatgccgcat ctacgacgga ccactcagat cggtcgttac 5100
gagggtttga cttggactgg accaccgact cgtcttccac tgccagcgat accatgtcgc 5160
tacccagttt gcagtcgtgt gacatcgact cgatctacga gccaatggct cccatagtag 5220
tgacggctga cgtacaccct gaacccgcag gcatcgcgga cctggcggca gatgtgcacc 5280
ctgaacccgc agaccatgtg gacctcgaga acccgattcc tccaccgcgc ccgaagagag 5340
ctgcatacct tgcctcccgc gcggcggagc gaccggtgcc ggcgccgaga aagccgacgc 5400
ctgccccaag gactgcgttt aggaacaagc tgcctttgac gttcggcgac tttgacgagc 5460
acgaggtcga tgcgttggcc tccgggatta ctttcggaga cttcgacgac gtcctgcgac 5520
taggccgcgc gggtgcatat attttctcct cggacactgg cagcggacat ttacaacaaa 5580
aatccgttag gcagcacaat ctccagtgcg cacaactgga tgcggtccag gaggagaaaa 5640
tgtacccgcc aaaattggat actgagaggg agaagctgtt gctgctgaaa atgcagatgc 5700
acccatcgga ggctaataag agtcgatacc agtctcgcaa agtggagaac atgaaagcca 5760
cggtggtgga caggctcaca tcgggggcca gattgtacac gggagcggac gtaggccgca 5820
taccaacata cgcggttcgg tacccccgcc ccgtgtactc ccctaccgtg atcgaaagat 5880
tctcaagccc cgatgtagca atcgcagcgt gcaacgaata cctatccaga aattacccaa 5940
cagtggcgtc gtaccagata acagatgaat acgacgcata cttggacatg gttgacgggt 6000
cggatagttg cttggacaga gcgacattct gcccggcgaa gctccggtgc tacccgaaac 6060
atcatgcgta ccaccagccg actgtacgca gtgccgtccc gtcacccttt cagaacacac 6120
tacagaacgt gctagcggcc gccaccaaga gaaactgcaa cgtcacgcaa atgcgagaac 6180
tacccaccat ggactcggca gtgttcaacg tggagtgctt caagcgctat gcctgctccg 6240
gagaatattg ggaagaatat gctaaacaac ctatccggat aaccactgag aacatcacta 6300
cctatgtgac caaattgaaa ggcccgaaag ctgctgcctt gttcgctaag acccacaact 6360
tggttccgct gcaggaggtt cccatggaca gattcacggt cgacatgaaa cgagatgtca 6420
aagtcactcc agggacgaaa cacacagagg aaagacccaa agtccaggta attcaagcag 6480
cggagccatt ggcgaccgct tacctgtgcg gcatccacag ggaattagta aggagactaa 6540
atgctgtgtt acgccctaac gtgcacacat tgtttgatat gtcggccgaa gactttgacg 6600
cgatcatcgc ctctcacttc cacccaggag acccggttct agagacggac attgcatcat 6660
tcgacaaaag ccaggacgac tccttggctc ttacaggttt aatgatcctc gaagatctag 6720
gggtggatca gtacctgctg gacttgatcg aggcagcctt tggggaaata tccagctgtc 6780
acctaccaac tggcacgcgc ttcaagttcg gagctatgat gaaatcgggc atgtttctga 6840
ctttgtttat taacactgtt ttgaacatca ccatagcaag cagggtactg gagcagagac 6900
tcactgactc cgcctgtgcg gccttcatcg gcgacgacaa catcgttcac ggagtgatct 6960
ccgacaagct gatggcggag aggtgcgcgt cgtgggtcaa catggaggtg aagatcattg 7020
acgctgtcat gggcgaaaaa cccccatatt tttgtggggg attcatagtt tttgacagcg 7080
tcacacagac cgcctgccgt gtttcagacc cacttaagcg cctgttcaag ttgggtaagc 7140
cgctaacagc tgaagacaag caggacgaag acaggcgacg agcactgagt gacgaggtta 7200
gcaagtggtt ccggacaggc ttgggggccg aactggaggt ggcactaaca tctaggtatg 7260
aggtagaggg ctgcaaaagt atcctcatag ccatggccac cttggcgagg gacattaagg 7320
cgtttaagaa attgagagga cctgttatac acctctacgg cggtcctaga ttggtgcgtt 7380
aatacacaga attctgattg gatcccgggc tcgagatgct gagaataatc aatgctagga 7440
aggagaagaa gagacgaggc gcagatacaa gtgtcggaat tgttggcctc ctgctgacca 7500
cagctatggc agcggaggtc actagacgtg ggagtgcata ctatatgtac ttggacagaa 7560
acgatgctgg ggaggccata tcttttccaa ccacattggg gatgaataag tgttatatac 7620
agatcatgga tcttggacac acgtgtgatg ccaccatgag ctatgaatgc cctatgctgg 7680
atgagggggt ggaaccagat gacgtcgatt gttggtgcaa cacgacgtca acttgggttg 7740
tgtacggaac ctgccatcac aaaaaaggtg aagcacggag atctagaaga gctgtgacgc 7800
tcccctccca ttccactagg aagctgcaaa cgcggtcgca aacctggttg gaatcaagag 7860
aatacacaaa gcacttgatt agagtcgaaa attggatatt caggaaccct ggcttcgcgt 7920
tagcagcagc tgccatcgct tggcttttgg gaagctcaac gagccaaaaa gtcatatact 7980
tggtcatgat actgctgatt gccccggcat acagcatcag gtgcatagga gtcagcaata 8040
gggactttgt ggaaggtatg tcaggtggga cttgggttga tgttgtcttg gaacatggag 8100
gttgtgtcac tgtaatggca caggacaaac cgactgtcga catagagctg gttacaacaa 8160
cagtcagcaa catggcggag gtaagatcct actgctatga ggcatcaata tcagacatgg 8220
cttcggacag ccgctgccca acacaaggtg aagcctacct tgacaagcaa tcagacactc 8280
aatatgtctg caaaagaacg ttagtggaca gaggctgggg aaatggatgt ggactttttg 8340
gcaaagggag cctggtgaca tgcgctaagt ttgcatgctc caagaaaatg accgggaaga 8400

-continued

```
gcatccagcc agagaatctg gagtaccgga taatgctgtc agttcatggc tcccagcaca   8460
gtgggatgat cgttaatgac acaggacatg aaactgatga gaatagagcg aaagttgaga   8520
taacgcccaa ttcaccaaga gccgaagcca ccctgggggg gtttggaagc ctaggacttg   8580
attgtgaacc gaggacaggc cttgactttt cagatttgta ttacttgact atgaataaca   8640
agcactggct ggttcacaag gagtggttcc acgacattcc attaccttgg cacgctgggg   8700
cagacaccgg aactccacac tggaacaaca aagaagcact ggtagagttc aaggacgcac   8760
atgccaaaag gcaaactgtc gtggttctag ggagtcaaga aggagcagtt cacacggccc   8820
ttgctggagc tctggaggct gagatggatg gtgcaaaggg aaggctgtcc tctggccact   8880
tgaaatgtcg cctgaaaatg gataaactta gattgaaggg cgtgtcatac tccttgtgta   8940
ctgcagcgtt cacattcacc aagatcccgg ctgaaacact gcacgggaca gtcacagtgg   9000
aggtacagta cgcagggaca gatggacctt gcaaggttcc agctcagatg gcggtggaca   9060
tgcaaactct gaccccagtt gggaggttga taaccgctaa ccccgtaatc actgaaagca   9120
ctgagaactc taagatgatg ctggaacttg atccaccatt tggggactct tacattgtca   9180
taggagtcgg ggagaagaag atcacccacc actggcacag gagtggcagc accattggaa   9240
aagcatttga agccactgtg agaggtgcca agagaatggc agtcttggga gacacagcct   9300
gggactttgg atcagttgga ggcgctctca actcattggg caagggcatc catcaaatct   9360
ttggagcagc tttcaaatca ttgtttggag gaatgtcctg gttctcacaa attctcattg   9420
gaacgttgct gatgtggttg ggtctgaacg caaagaatgg atctagaatc ctcacaatac   9480
cgcagagtct agactcgtgg tggacttctc tcaattttct aggggggatct cccgtgtgtc   9540
ttggccaaaa ttcgcagtcc ccaacctcca atcactcacc aacctcctgt cctccaattt   9600
gtcctggtta tcgctggatg tgtctgcggc gttttatcat attcctcttc atcctgctgc   9660
tatgcctcat cttcttattg gttcttctgg attatcaagg tatgttgccc gtttgtcctc   9720
taattccagg atcaacaaca accagtacgg gaccatgcaa aacctgcacg actcctgctc   9780
aaggcaactc tatgtttccc tcatgttgct gtacaaaacc tacggatgga aattgcacct   9840
gtattcccat cccatcgtcc tgggctttcg caaaatacct atgggagtgg gcctcagtcc   9900
gtttctcttg gctcagttta ctagtgccat ttgttcagtg gttcgtaggg ctttccccca   9960
ctgtttggct ttcagctata tggatgatgt ggtattgggg gccaagtctg tacagcatcg  10020
tgagtccctt tataccgctg ttaccaattt tcttttgtct ctgggtatac atttaactcg  10080
agcccgggat cccgggtaat taattgaatt acatccctac gcaaacgttt tacggccgcc  10140
ggtggcgccc gcgcccggcg gcccgtcctt ggccgttgca ggccactccg gtggctcccg  10200
tcgtccccga cttccaggcc cagcagatgc agcaactcat cagcgccgta aatgcgctga  10260
caatgagaca gaacgcaatt gctcctgcta ggcctcccaa accaaagaag aagaagacaa  10320
ccaaaccaaa gccgaaaacg cagcccaaga agatcaacgg aaaaacgcag cagcaaaaga  10380
agaaagacaa gcaagccgac aagaagaaga agaaacccgg aaaaagagaa agaatgtgca  10440
tgaagattga aaatgactgt atcttcgtat gcggctagcc acagtaacgt agtgtttcca  10500
gacatgtcgg gcaccgcact atcatgggtg cagaaaatct cgggtggtct gggggccttc  10560
gcaatcggcg ctatcctggt gctggttgtg gtcacttgca ttgggctccg cagataagtt  10620
agggtaggca atggcattga tatagcaaga aaattgaaaa cagaaaaagt tagggtaagc  10680
aatggcatat aaccataact gtataacttg taacaaagcg caacaagacc tgcgcaattg  10740
gccccgtggt ccgcctcacg gaaactcggg gcaactcata ttgacacatt aattggcaat  10800
```

```
aattggaagc ttacataagc ttaattcgac gaataattgg atttttattt tattttgcaa  10860

ttggttttta atatttccaa aaaaaaaaaa aaaaaaaaaa aaaaaaaaaa aaaaaaaaaa  10920

aaaaaaaaaa aaaaaaaaaa aaaaaaattc gaaactagtc tgcattaatg aatcggccaa  10980

cgcgcgggga gaggcggttt gcgtattggg cgctcttccg cttcctcgct cactgactcg  11040

ctgcgctcgg tcgttcggct gcggcgagcg gtatcagctc actcaaaggc ggtaatacgg  11100

ttatccacag aatcagggga taacgcagga aagaacatgt gagcaaaagg ccagcaaaag  11160

gccaggaacc gtaaaaaggc cgcgttgctg gcgtttttcc ataggctccg cccccctgac  11220

gagcatcaca aaaatcgacg ctcaagtcag aggtggcgaa acccgacagg actataaaga  11280

taccaggcgt ttccccctgg aagctccctc gtgcgctctc ctgttccgac cctgccgctt  11340

accggatacc tgtccgcctt tctcccttcg ggaagcgtgg cgctttctca atgctcgcgc  11400

tgtaggtatc tcagttcggt gtaggtcgtt cgctccaagc tgggctgtgt gcacgaaccc  11460

cccgttcagc ccgaccgctg cgccttatcc ggtaactatc gtcttgagtc caacccggta  11520

agacacgact tatcgccact ggcagcagcc actggtaaca ggattagcag agcgaggtat  11580

gtaggcggtg ctacagagtt cttgaagtgg tggcctaact acggctacac tagaaggaca  11640

gtatttggta tctgcgctct gctgaagcca gttaccttcg gaaaaagagt tggtagctct  11700

tgatccggca aacaaaccac cgctggtagc ggtggttttt ttgtttgcaa gcagcagatt  11760

acgcgcagaa aaaaaggatc tcaagaagat cctttgatct tttctacggg gtctgacgct  11820

cagtggaacg aaaactcacg ttaagggatt ttggtcatga gattatcaaa aaggatcttc  11880

acctagatcc ttttaaatta aaaatgaagt tttaaatcaa tctaaagtat atatgagtaa  11940

acttggtctg acagttacca atgcttaatc agtgaggcac ctatctcagc gatctgtcta  12000

tttcgttcat ccatagttgc ctgactcccc gtcgtgtaga taactacgat acgggagggc  12060

ttaccatctg gccccagtgc tgcaatgata ccgcgagacc cacgctcacc ggctccagat  12120

ttatcagcaa taaaccagcc agccggaagg gccgagcgca gaagtggtcc tgcaacttta  12180

tccgcctcca tccagtctat taattgttgc cgggaagcta gagtaagtag ttcgccagtt  12240

aatagtttgc gcaacgttgt tgccattgct acaggcatcg tggtgtcacg ctcgtcgttt  12300

ggtatggctt cattcagctc cggttcccaa cgatcaaggc gagttacatg atcccccatg  12360

ttgtgcaaaa aagcggttag ctccttcggt cctccgatcg ttgtcagaag taagttggcc  12420

gcagtgttat cactcatggt tatggcagca ctgcataatt ctcttactgt catgccatcc  12480

gtaagatgct tttctgtgac tggtgagtac tcaaccaagt cattctgaga atagtgtatg  12540

cggcgaccga gttgctcttg cccggcgtca atacgggata ataccgcgcc acatagcaga  12600

actttaaaag tgctcatcat tggaaaacgt tcttcggggc gaaaactctc aaggatctta  12660

ccgctgttga gatccagttc gatgtaaccc actcgtgcac ccaactgatc ttcagcatct  12720

tttactttca ccagcgtttc tgggtgagca aaaacaggaa ggcaaaatgc cgcaaaaaag  12780

ggaataaggg cgacacggaa atgttgaata ctcatactct tcctttttca atattattga  12840

agcatttatc agggttattg tctcatgagc ggatacatat ttgaatgtat ttagaaaaat  12900

aaacaaatag gggttccgcg cacatttccc cgaaaagtgc cacctgacgt ctaagaaacc  12960

attattatca tgacattaac ctataaaaat aggcgtatca cgaggccctt tcgtctcgcg  13020

cgtttcggtg atgacggtga aaacctctga cacatgcagc tcccggagac ggtcacagct  13080

tctgtctaag cggatgccgg gagcagacaa gcccgtcagg gcgcgtcagc gggtgttggc  13140
```

```
gggtgtcggg gctggcttaa ctatgcggca tcagagcaga ttgtactgag agtgcaccat  13200

atcgacgctc tcccttatgc gactcctgca ttaggaagca gcccagtact aggttgaggc  13260

cgttgagcac cgccgccgca aggaatggtg catgcaagga gatggcgccc aacagtcccc  13320

cggccacggg gcctgccacc atacccacgc cgaaacaagc gctcatgagc ccgaagtggc  13380

gagcccgatc ttccccatcg gtgatgtcgg cgatataggc gccagcaacc gcacctgtgg  13440

cgccggtgat gccggccacg atgcgtccgg cgtagaggat ctggctagcg atgaccctgc  13500

tgattggttc gctgaccatt tccggggtgc ggaacggcgt taccagaaac tcagaaggtt  13560

cgtccaacca aaccgactct gacggcagtt tacgagagag atgatagggt ctgcttcagt  13620

aagccagatg ctacacaatt aggcttgtac atattgtcgt tagaacgcgg ctacaattaa  13680

tacataacct tatgtatcat acacatacga tttaggtgac actata                13726
```

```
<210> SEQ ID NO 55
<211> LENGTH: 14020
<212> TYPE: DNA
<213> ORGANISM: Artificial sequence
<220> FEATURE:
<223> OTHER INFORMATION: pSFV1- " prM + E + M"

<400> SEQUENCE: 55

gatggcggat gtgtgacata cacgacgcca aaagattttg ttccagctcc tgccacctcc     60

gctacgcgag agattaacca cccacgatgg ccgccaaagt gcatgttgat attgaggctg    120

acagcccatt catcaagtct ttgcagaagg catttccgtc gttcgaggtg gagtcattgc    180

aggtcacacc aaatgaccat gcaaatgcca gagcattttc gcacctggct accaaattga    240

tcgagcagga gactgacaaa gacacactca tcttggatat cggcagtgcg ccttccagga    300

gaatgatgtc tacgcacaaa taccactgcg tatgccctat gcgcagcgca gaagaccccg    360

aaaggctcga tagctacgca aagaaactgg cagcggcctc cgggaaggtg ctggatagag    420

agatcgcagg aaaaatcacc gacctgcaga ccgtcatggc tacgccagac gctgaatctc    480

ctaccttttg cctgcataca gacgtcacgt gtcgtacggc agccgaagtg gccgtatacc    540

aggacgtgta tgctgtacat gcaccaacat cgctgtacca tcaggcgatg aaaggtgtca    600

gaacggcgta ttggattggg tttgacacca ccccgtttat gtttgacgcg ctagcaggcg    660

cgtatccaac ctacgccaca aactgggccg acgagcaggt gttacaggcc aggaacatag    720

gactgtgtgc agcatccttg actgagggaa gactcggcaa actgtccatt ctccgcaaga    780

agcaattgaa accttgcgac acagtcatgt tctcggtagg atctacattg tacactgaga    840

gcagaaagct actgaggagc tggcacttac cctccgtatt ccacctgaaa ggtaaacaat    900

cctttacctg taggtgcgat accatcgtat catgtgaagg gtacgtagtt aagaaaatca    960

ctatgtgccc cggcctgtac ggtaaaacgg tagggtacgc cgtgacgtat cacgcggagg   1020

gattcctagt gtgcaagacc acagacactg tcaaaggaga aagagtctca ttccctgtat   1080

gcacctacgt cccctcaacc atctgtgatc aaatgactgg catactagcg accgacgtca   1140

caccggagga cgcacagaag ttgttagtgg gattgaatca gaggatagtt gtgaacggaa   1200

gaacacagcg aaacactaac acgatgaaga actatctgct tccgattgtg gccgtcgcat   1260

ttagcaagtg ggcgagggaa tacaaggcag accttgatga tgaaaaacct ctgggtgtcc   1320

gagagaggtc acttacttgc tgctgcttgt gggcatttaa aacgaggaag atgcacacca   1380

tgtacaagaa accagacacc cagacaatag tgaaggtgcc ttcagagttt aactcgttcg   1440

tcatcccgag cctatggtct acaggcctcg caatcccagt cagatcacgc attaagatgc   1500
```

-continued

```
ttttggccaa gaagaccaag cgagagttaa tacctgttct cgacgcgtcg tcagccaggg   1560
atgctgaaca agaggagaag gagaggttgg aggccgagct gactagagaa gccttaccac   1620
ccctcgtccc catcgcgccg gcggagacgg gagtcgtcga cgtcgacgtt gaagaactag   1680
agtatcacgc aggtgcaggg gtcgtggaaa cacctcgcag cgcgttgaaa gtcaccgcac   1740
agccgaacga cgtactacta ggaaattacg tagttctgtc cccgcagacc gtgctcaaga   1800
gctccaagtt ggcccccgtg caccctctag cagagcaggt gaaaataata acacataacg   1860
ggagggccgg cggttaccag gtcgacggat atgacggcag ggtcctacta ccatgtggat   1920
cggccattcc ggtccctgag tttcaagctt tgagcgagag cgccactatg gtgtacaacg   1980
aaagggagtt cgtcaacagg aaactatacc atattgccgt tcacggaccg tcgctgaaca   2040
ccgacgagga gaactacgag aaagtcagag ctgaaagaac tgacgccgag tacgtgttcg   2100
acgtagataa aaaatgctgc gtcaagagag aggaagcgtc gggtttggtg ttggtgggag   2160
agctaaccaa cccccgttc catgaattcg cctacgaagg gctgaagatc aggccgtcgg   2220
caccatataa gactacagta gtaggagtct ttggggttcc gggatcaggc aagtctgcta   2280
ttattaagag cctcgtgacc aaacacgatc tggtcaccag cggcaagaag gagaactgcc   2340
aggaaatagt taacgacgtg aagaagcacc gcgggaaggg gacaagtagg gaaaacagtg   2400
actccatcct gctaaacggg tgtcgtcgtg ccgtggacat cctatatgtg gacgaggctt   2460
tcgcttgcca ttccggtact ctgctggccc taattgctct tgttaaacct cggagcaaag   2520
tggtgttatg cggagacccc aagcaatgcg gattcttcaa tatgatgcag cttaaggtga   2580
acttcaacca caacatctgc actgaagtat gtcataaaag tatatccaga cgttgcacgc   2640
gtccagtcac ggccatcgtg tctacgttgc actacggagg caagatgcgc acgaccaacc   2700
cgtgcaacaa acccataatc atagacacca caggacagac caagcccaag ccaggagaca   2760
tcgtgttaac atgcttccga ggctgggcaa agcagctgca gttggactac cgtggacacg   2820
aagtcatgac agcagcagca tctcagggcc tcacccgcaa aggggtatac gccgtaaggc   2880
agaaggtgaa tgaaaatccc ttgtatgccc ctgcgtcgga gcacgtgaat gtactgctga   2940
cgcgcactga ggataggctg gtgtggaaaa cgctggccgg cgatccctgg attaaggtcc   3000
tatcaaacat tccacagggt aactttacgg ccacattgga agaatggcaa gaagaacacg   3060
acaaaataat gaaggtgatt gaaggaccgg ctgcgcctgt ggacgcgttc cagaacaaag   3120
cgaacgtgtg ttgggcgaaa agcctggtgc ctgtcctgga cactgccgga atcagattga   3180
cagcagagga gtggagcacc ataattacag catttaagga ggacagagct tactctccag   3240
tggtggcctt gaatgaaatt tgcaccaagt actatggagt tgacctggac agtggcctgt   3300
tttctgcccc gaaggtgtcc ctgtattacg agaacaacca ctgggataac agacctggtg   3360
gaaggatgta tggattcaat gccgcaacag ctgccaggct ggaagctaga cataccttcc   3420
tgaaggggca gtggcatacg ggcaagcagg cagttatcgc agaaagaaaa atccaaccgc   3480
tttctgtgct ggacaatgta attcctatca accgcaggct gccgcacgcc ctggtggctg   3540
agtacaagac ggttaaaggc agtagggttg agtggctggt caataaagta agagggtacc   3600
acgtcctgct ggtgagtgag tacaacctgg ctttgcctcg acgcagggtc acttggttgt   3660
caccgctgaa tgtcacaggc gccgataggt gctacgacct aagtttagga ctgccggctg   3720
acgccggcag gttcgacttg gtctttgtga acattcacac ggaattcaga atccaccact   3780
accagcagtg tgtcgaccac gccatgaagc tgcagatgct tgggggagat gcgctacgac   3840
```

-continued

```
tgctaaaacc cggcggcatc ttgatgagag cttacggata cgccgataaa atcagcgaag   3900
ccgttgtttc ctccttaagc agaaagttct cgtctgcaag agtgttgcgc ccggattgtg   3960
tcaccagcaa tacagaagtg ttcttgctgt tctccaactt tgacaacgga aagagaccct   4020
ctacgctaca ccagatgaat accaagctga gtgccgtgta tgccggagaa gccatgcaca   4080
cggccgggtg tgcaccatcc tacagagtta agagagcaga catagccacg tgcacagaag   4140
cggctgtggt taacgcagct aacgcccgtg gaactgtagg ggatggcgta tgcagggccg   4200
tggcgaagaa atggccgtca gcctttaagg gagcagcaac accagtgggc acaattaaaa   4260
cagtcatgtg cggctcgtac cccgtcatcc acgctgtagc gcctaatttc tctgccacga   4320
ctgaagcgga aggggaccgc gaattggccg ctgtctaccg ggcagtggcc gccgaagtaa   4380
acagactgtc actgagcagc gtagccatcc cgctgctgtc cacaggagtg ttcagcggcg   4440
gaagagatag gctgcagcaa tccctcaacc atctattcac agcaatggac gccacggacg   4500
ctgacgtgac catctactgc agagacaaaa gttgggagaa gaaaatccag gaagccattg   4560
acatgaggac ggctgtggag ttgctcaatg atgacgtgga gctgaccaca gacttggtga   4620
gagtgcaccc ggacagcagc ctggtgggtc gtaagggcta cagtaccact gacgggtcgc   4680
tgtactcgta ctttgaaggt acgaaattca accaggctgc tattgatatg gcagagatac   4740
tgacgttgtg gcccagactg caagaggcaa acgaacagat atgcctatac gcgctgggcg   4800
aaacaatgga caacatcaga tccaaatgtc cggtgaacga ttccgattca tcaacacctc   4860
ccaggacagt gccctgcctg tgccgctacg caatgacagc agaacggatc gcccgcctta   4920
ggtcacacca agttaaaagc atggtggttt gctcatcttt tccccctcccg aaataccatg   4980
tagatggggt gcagaaggta aagtgcgaga aggttctcct gttcgacccg acggtacctt   5040
cagtggttag tccgcggaag tatgccgcat ctacgacgga ccactcagat cggtcgttac   5100
gagggtttga cttggactgg accaccgact cgtcttccac tgccagcgat accatgtcgc   5160
tacccagttt gcagtcgtgt gacatcgact cgatctacga gccaatggct cccatagtag   5220
tgacggctga cgtacaccct gaacccgcag gcatcgcgga cctggcggca gatgtgcacc   5280
ctgaacccgc agaccatgtg gacctcgaga acccgattcc tccaccgcgc ccgaagagag   5340
ctgcatacct tgcctcccgc gcggcggagc gaccggtgcc ggcgccgaga aagccgacgc   5400
ctgccccaag gactgcgttt aggaacaagc tgcctttgac gttcggcgac tttgacgagc   5460
acgaggtcga tgcgttggcc tccgggatta ctttcggaga cttcgacgac gtcctgcgac   5520
taggccgcgc gggtgcatat attttctcct cggacactgg cagcggacat ttacaacaaa   5580
aatccgttag gcagcacaat ctccagtgcg cacaactgga tgcggtccag gaggagaaaa   5640
tgtacccgcc aaaattggat actgagaggg agaagctgtt gctgctgaaa atgcagatgc   5700
acccatcgga ggctaataag agtcgatacc agtctcgcaa agtggagaac atgaaagcca   5760
cggtggtgga caggctcaca tcgggggcca gattgtacac gggagcggac gtaggccgca   5820
taccaacata cgcggttcgg taccccccgcc ccgtgtactc ccctaccgtg atcgaaagat   5880
tctcaagccc cgatgtagca atcgcagcgt gcaacgaata cctatccaga aattacccaa   5940
cagtggcgtc gtaccagata acagatgaat acgacgcata cttggacatg gttgacgggt   6000
cggatagttg cttggacaga gcgacattct gcccggcgaa gctccggtgc tacccgaaac   6060
atcatgcgta ccaccagccg actgtacgca gtgccgtccc gtcacccttt cagaacacac   6120
tacagaacgt gctagcggcc gccaccaaga gaaactgcaa cgtcacgcaa atgcgagaac   6180
tacccaccat ggactcggca gtgttcaacg tggagtgctt caagcgctat gcctgctccg   6240
```

-continued

```
gagaatattg ggaagaatat gctaaacaac ctatccggat aaccactgag aacatcacta   6300
cctatgtgac caaattgaaa ggcccgaaag ctgctgcctt gttcgctaag acccacaact   6360
tggttccgct gcaggaggtt cccatggaca gattcacggt cgacatgaaa cgagatgtca   6420
aagtcactcc agggacgaaa cacacagagg aaagacccaa agtccaggta attcaagcag   6480
cggagccatt ggcgaccgct tacctgtgcg gcatccacag ggaattagta aggagactaa   6540
atgctgtgtt acgccctaac gtgcacacat tgtttgatat gtcggccgaa gactttgacg   6600
cgatcatcgc ctctcacttc cacccaggag acccggttct agagacggac attgcatcat   6660
tcgacaaaag ccaggacgac tccttggctc ttacaggttt aatgatcctc gaagatctag   6720
gggtggatca gtacctgctg gacttgatcg aggcagcctt tggggaaata tccagctgtc   6780
acctaccaac tggcacgcgc ttcaagttcg gagctatgat gaaatcgggc atgtttctga   6840
ctttgtttat taacactgtt ttgaacatca ccatagcaag cagggtactg gagcagagac   6900
tcactgactc cgcctgtgcg gccttcatcg gcgacgacaa catcgttcac ggagtgatct   6960
ccgacaagct gatggcggag aggtgcgcgt cgtgggtcaa catggaggtg aagatcattg   7020
acgctgtcat gggcgaaaaa cccccatatt tttgtggggg attcatagtt tttgacagcg   7080
tcacacagac cgcctgccgt gtttcagacc cacttaagcg cctgttcaag ttgggtaagc   7140
cgctaacagc tgaagacaag caggacgaag acaggcgacg agcactgagt gacgaggtta   7200
gcaagtggtt ccggacaggc ttgggggccg aactggaggt ggcactaaca tctaggtatg   7260
aggtagaggg ctgcaaaagt atcctcatag ccatggccac cttggcgagg gacattaagg   7320
cgtttaagaa attgagagga cctgttatac acctctacgg cggtcctaga ttggtgcgtt   7380
aatacacaga attctgattg gatcccgggc tcgagatgct gagaataatc aatgctagga   7440
aggagaagaa gagacgaggc gcagatacaa gtgtcggaat tgttggcctc ctgctgacca   7500
cagctatggc agcggaggtc actagacgtg ggagtgcata ctatatgtac ttggacagaa   7560
acgatgctgg ggaggccata tcttttccaa ccacattggg gatgaataag tgttatatac   7620
agatcatgga tcttggacac acgtgtgatg ccaccatgag ctatgaatgc cctatgctgg   7680
atgagggggt ggaaccagat gacgtcgatt gttggtgcaa cacgacgtca acttgggttg   7740
tgtacggaac ctgccatcac aaaaaaggtg aagcacggag atctagaaga gctgtgacgc   7800
tccccctccca ttccactagg aagctgcaaa cgcggtcgca aacctggttg gaatcaagag   7860
aatacacaaa gcacttgatt agagtcgaaa attggatatt caggaaccct ggcttcgcgt   7920
tagcagcagc tgccatcgct tggcttttgg gaagctcaac gagccaaaaa gtcatatact   7980
tggtcatgat actgctgatt gccccggcat acagcatcag gtgcatagga gtcagcaata   8040
gggactttgt ggaaggtatg tcaggtggga cttgggttga tgttgtcttg gaacatggag   8100
gttgtgtcac tgtaatggca caggacaaac cgactgtcga catagagctg gttacaacaa   8160
cagtcagcaa catggcggag gtaagatcct actgctatga ggcatcaata tcagacatgg   8220
cttcggacag ccgctgccca acacaaggtg aagcctacct tgacaagcaa tcagacactc   8280
aatatgtctg caaaagaacg ttagtggaca gaggctgggg aaatggatgt ggactttttg   8340
gcaaagggag cctggtgaca tgcgctaagt ttgcatgctc caagaaaatg accgggaaga   8400
gcatccagcc agagaatctg gagtaccgga taatgctgtc agttcatggc tcccagcaca   8460
gtgggatgat cgttaatgac acaggacatg aaactgatga gaatagagcg aaagttgaga   8520
taacgcccaa ttcaccaaga gccgaagcca ccctgggggg gtttggaagc ctaggacttg   8580
```

-continued

```
attgtgaacc gaggacaggc cttgactttt cagatttgta ttacttgact atgaataaca   8640
agcactggct ggttcacaag gagtggttcc acgacattcc attaccttgg cacgctgggg   8700
cagacaccgg aactccacac tggaacaaca aagaagcact ggtagagttc aaggacgcac   8760
atgccaaaag gcaaactgtc gtggttctag ggagtcaaga aggagcagtt cacacggccc   8820
ttgctggagc tctggaggct gagatggatg gtgcaaaggg aaggctgtcc tctggccact   8880
tgaaatgtcg cctgaaaatg gataaactta gattgaaggg cgtgtcatac tccttgtgta   8940
ctgcagcgtt cacattcacc aagatcccgg ctgaaacact gcacgggaca gtcacagtgg   9000
aggtacagta cgcagggaca gatggacctt gcaaggttcc agctcagatg gcggtggaca   9060
tgcaaactct gaccccagtt gggaggttga taaccgctaa ccccgtaatc actgaaagca   9120
ctgagaactc taagatgatg ctggaacttg atccaccatt tggggactct tacattgtca   9180
taggagtcgg ggagaagaag atcacccacc actggcacag gagtggcagc accattggaa   9240
aagcatttga agccactgtg agaggtgcca agagaatggc agtcttggga gacacagcct   9300
gggactttgg atcagttgga ggcgctctca actcattggg caagggcatc catcaaatct   9360
ttggagcagc tttcaaatca ttgtttggag gaatgtcctg gttctcacaa attctcattg   9420
gaacgttgct gatgtggttg ggtctgaacg caaagaatgg atctatttcc cttatgtgct   9480
tggccttagg gggagtgttg atcttcttat ccacagccgt ctctgctcag tggaattcca   9540
ctgccttcca ccaaactctg caggatccca gagtcagggg tctgtatctt cctgctggtg   9600
gctccagttc aggaacagta aaccctgctc cgaatattgc ctctcacatc tcgtcaatct   9660
ccgcgaggac tggggaccct gtgacgaaca tggagaacat cacatcagga ttcctaggac   9720
ccctgctcgt gttacaggcg gggtttttct tgttgacaag aatcctcaca ataccgcaga   9780
gtctagactc gtggtggact tctctcaatt ttctaggggg atctcccgtg tgtcttggcc   9840
aaaattcgca gtccccaacc tccaatcact caccaacctc ctgtcctcca atttgtcctg   9900
gttatcgctg gatgtgtctg cggcgtttta tcatattcct cttcatcctg ctgctatgcc   9960
tcatcttctt attggttctt ctggattatc aaggtatgtt gcccgtttgt cctctaattc  10020
caggatcaac aacaaccagt acgggaccat gcaaaacctg cacgactcct gctcaaggca  10080
actctatgtt tccctcatgt tgctgtacaa aacctacgga tggaaattgc acctgtattc  10140
ccatcccatc gtcctgggct ttcgcaaaat acctatggga gtgggcctca gtccgtttct  10200
cttggctcag tttactagtg ccatttgttc agtggttcgt agggctttcc cccactgttt  10260
ggctttcagc tatatggatg atgtggtatt gggggccaag tctgtacagc atcgtgagtc  10320
cctttatacc gctgttacca attttctttt gtctctgggt atacatttaa ctcgagcccg  10380
ggatcccggg taattaattg aattacatcc ctacgcaaac gttttacggc cgccggtggc  10440
gcccgcgccc ggcggcccgt ccttggccgt tgcaggccac tccggtggct cccgtcgtcc  10500
ccgacttcca ggcccagcag atgcagcaac tcatcagcgc cgtaaatgcg ctgacaatga  10560
gacagaacgc aattgctcct gctaggcctc ccaaaccaaa gaagaagaag acaaccaaac  10620
caaagccgaa aacgcagccc aagaagatca acggaaaaac gcagcagcaa aagaagaaag  10680
acaagcaagc cgacaagaag aagaagaaac ccggaaaaag agaaagaatg tgcatgaaga  10740
ttgaaaatga ctgtatcttc gtatgcggct agccacagta acgtagtgtt tccagacatg  10800
tcgggcaccg cactatcatg ggtgcagaaa atctcgggtg gtctgggggc cttcgcaatc  10860
ggcgctatcc tggtgctggt tgtggtcact tgcattgggc tccgcagata agttagggta  10920
ggcaatggca ttgatatagc aagaaaattg aaaacagaaa aagttagggt aagcaatggc  10980
```

atataaccat aactgtataa cttgtaacaa agcgcaacaa gacctgcgca attggccccg 11040
tggtccgcct cacggaaact cggggcaact catattgaca cattaattgg caataattgg 11100
aagcttacat aagcttaatt cgacgaataa ttggattttt attttatttt gcaattggtt 11160
tttaatattt ccaaaaaaaa aaaaaaaaaa aaaaaaaaaa aaaaaaaaaa aaaaaaaaaa 11220
aaaaaaaaaa aaaaaaaaaa attcgaaact agtctgcatt aatgaatcgg ccaacgcgcg 11280
gggagaggcg gtttgcgtat tgggcgctct tccgcttcct cgctcactga ctcgctgcgc 11340
tcggtcgttc ggctgcggcg agcggtatca gctcactcaa aggcggtaat acggttatcc 11400
acagaatcag gggataacgc aggaaagaac atgtgagcaa aaggccagca aaaggccagg 11460
aaccgtaaaa aggccgcgtt gctggcgttt ttccataggc tccgcccccc tgacgagcat 11520
cacaaaaatc gacgctcaag tcagaggtgg cgaaacccga caggactata aagataccag 11580
gcgtttcccc ctggaagctc cctcgtgcgc tctcctgttc cgaccctgcc gcttaccgga 11640
tacctgtccg cctttctccc ttcgggaagc gtggcgcttt ctcaatgctc gcgctgtagg 11700
tatctcagtt cggtgtaggt cgttcgctcc aagctgggct gtgtgcacga accccccgtt 11760
cagcccgacc gctgcgcctt atccggtaac tatcgtcttg agtccaaccc ggtaagacac 11820
gacttatcgc cactggcagc agccactggt aacaggatta gcagagcgag gtatgtaggc 11880
ggtgctacag agttcttgaa gtggtggcct aactacggct acactagaag gacagtattt 11940
ggtatctgcg ctctgctgaa gccagttacc ttcggaaaaa gagttggtag ctcttgatcc 12000
ggcaaacaaa ccaccgctgg tagcggtggt ttttttgttt gcaagcagca gattacgcgc 12060
agaaaaaaag gatctcaaga agatcctttg atcttttcta cggggtctga cgctcagtgg 12120
aacgaaaact cacgttaagg gattttggtc atgagattat caaaaaggat cttcacctag 12180
atccttttaa attaaaaatg aagttttaaa tcaatctaaa gtatatatga gtaaacttgg 12240
tctgacagtt accaatgctt aatcagtgag gcacctatct cagcgatctg tctatttcgt 12300
tcatccatag ttgcctgact ccccgtcgtg tagataacta cgatacggga gggcttacca 12360
tctggcccca gtgctgcaat gataccgcga gacccacgct caccggctcc agatttatca 12420
gcaataaacc agccagccgg aagggccgag cgcagaagtg gtcctgcaac tttatccgcc 12480
tccatccagt ctattaattg ttgccgggaa gctagagtaa gtagttcgcc agttaatagt 12540
ttgcgcaacg ttgttgccat tgctacaggc atcgtggtgt cacgctcgtc gtttggtatg 12600
gcttcattca gctccggttc ccaacgatca aggcgagtta catgatcccc catgttgtgc 12660
aaaaaagcgg ttagctcctt cggtcctccg atcgttgtca gaagtaagtt ggccgcagtg 12720
ttatcactca tggttatggc agcactgcat aattctctta ctgtcatgcc atccgtaaga 12780
tgcttttctg tgactggtga gtactcaacc aagtcattct gagaatagtg tatgcggcga 12840
ccgagttgct cttgcccggc gtcaatacgg gataataccg cgccacatag cagaacttta 12900
aaagtgctca tcattggaaa acgttcttcg gggcgaaaac tctcaaggat cttaccgctg 12960
ttgagatcca gttcgatgta acccactcgt gcacccaact gatcttcagc atcttttact 13020
ttcaccagcg tttctgggtg agcaaaaaca ggaaggcaaa atgccgcaaa aaagggaata 13080
agggcgacac ggaaatgttg aatactcata ctcttccttt ttcaatatta ttgaagcatt 13140
tatcagggtt attgtctcat gagcggatac atatttgaat gtatttagaa aaataaacaa 13200
ataggggttc cgcgcacatt tccccgaaaa gtgccacctg acgtctaaga aaccattatt 13260
atcatgacat taacctataa aaataggcgt atcacgaggc cctttcgtct cgcgcgtttc 13320

-continued ggtgatgacg gtgaaaacct ctgacacatg cagctcccgg agacggtcac agcttctgtc 13380
taagcggatg ccgggagcag acaagcccgt cagggcgcgt cagcgggtgt tggcgggtgt 13440
cggggctggc ttaactatgc ggcatcagag cagattgtac tgagagtgca ccatatcgac 13500
gctctccctt atgcgactcc tgcattagga agcagcccag tactaggttg aggccgttga 13560
gcaccgccgc cgcaaggaat ggtgcatgca aggagatggc gcccaacagt cccccggcca 13620
cggggcctgc caccataccc acgccgaaac aagcgctcat gagcccgaag tggcgagccc 13680
gatcttcccc atcggtgatg tcggcgatat aggcgccagc aaccgcacct gtggcgccgg 13740
tgatgccggc cacgatgcgt ccggcgtaga ggatctggct agcgatgacc ctgctgattg 13800
gttcgctgac catttccggg gtgcggaacg gcgttaccag aaactcagaa ggttcgtcca 13860
accaaaccga ctctgacggc agtttacgag agagatgata gggtctgctt cagtaagcca 13920
gatgctacac aattaggctt gtacatattg tcgttagaac gcggctacaa ttaatacata 13980
accttatgta tcatacacat acgatttagg tgacactata 14020

<210> SEQ ID NO 56
<211> LENGTH: 12345
<212> TYPE: DNA
<213> ORGANISM: Artificial sequence
<220> FEATURE:
<223> OTHER INFORMATION: pHR'puro - HBV - “prM + E + S”

<400> SEQUENCE: 56
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540
atggtgcact ctcagtacaa tctgctctga tgccgcatag ttaagccagc cccgacaccc 600
gccaacaccc gctgacgcgc cctgacgggc ttgtctgctc ccggcatccg cttacagaca 660
agctgtgacc gtctccggga gctgcatgtg tcagaggttt tcaccgtcat caccgaaacg 720
cgcgagacga aagggcctcg tgatacgcct atttttatag gttaatgtca tgataataat 780
ggtttcttag acgtcaggtg gcacttttcg gggaaatgtg cgcggaaccc ctatttgttt 840
atttttctaa atacattcaa atatgtatcc gctcatgaga caataaccct gataaatgct 900
tcaataatat tgaaaaagga agagtatgag tattcaacat ttccgtgtcg cccttattcc 960
cttttttgcg gcattttgcc ttcctgtttt tgctcaccca gaaacgctgg tgaaagtaaa 1020
agatgctgaa gatcagttgg gtgcacgagt gggttacatc gaactggatc tcaacagcgg 1080
taagatcctt gagagttttc gccccgaaga acgttttcca atgatgagca cttttaaagt 1140
tctgctatgt ggcgcggtat tatcccgtat tgacgccggg caagagcaac tcggtcgccg 1200
catacactat tctcagaatg acttggttga gtactcacca gtcacagaaa agcatcttac 1260
ggatggcatg acagtaagag aattatgcag tgctgccata accatgagtg ataacactgc 1320
ggccaactta cttctgacaa cgatcggagg accgaaggag ctaaccgctt ttttgcacaa 1380

-continued

```
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
```

-continued

```
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
cataccacat ttgtagaggt ttacttgct ttaaaaaacc tcccacacct cccctgaac   4860
ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aaacatatag tatgggcaag cagggagcta gaacgattcg   6120
```

cagttaatcc tggcctgtta gaaacatcag aaggctgtag acaaatactg ggacagctac 6180
aaccatccct tcagacagga tcagaagaac ttagatcatt atataataca gtagcaaccc 6240
tctattgtgt gcatcaaagg atagagataa aagacaccaa ggaagcttta gacaagatag 6300
aggaagagca aaacaaaagt aagaccaccg cacagcaagc ggccgctgat cttcagacct 6360
ggaggaggag atatgaggga caattggaga agtgaattat ataaatataa agtagtaaaa 6420
attgaaccat taggagtagc acccaccaag gcaaagagaa gagtggtgca gagagaaaaa 6480
agagcagtgg gaataggagc tttgttcctt gggttcttgg gagcagcagg aagcactatg 6540
ggcgcagcgt caatgacgct gacggtacag gccagacaat tattgtctgg tatagtgcag 6600
cagcagaaca atttgctgag ggctattgag gcgcaacagc atctgttgca actcacagtc 6660
tggggcatca agcagctcca ggcaagaatc ctggctgtgg aaagatacct aaaggatcaa 6720
cagctcctgg ggatttgggg ttgctctgga aaactcattt gcaccactgc tgtgccttgg 6780
aatgctagtt ggagtaataa atctctggaa cagatttgga atcacacgac ctggatggag 6840
tgggacagag aaattaacaa ttacacaagc ttaatacact ccttaattga agaatcgcaa 6900
aaccagcaag aaaagaatga acaagaatta ttggaattag ataaatgggc aagtttgtgg 6960
aattggttta acataacaaa ttggctgtgg tatataaaat tattcataat gatagtagga 7020
ggcttggtag gtttaagaat agtttttgct gtactttcta tagtgaatag agttaggcag 7080
ggatattcac cattatcgtt tcagacccac ctcccaaccc cgaggggacc cgacaggccc 7140
gaaggaatag aagaagaagg tggagagaga gacagagaca gatccattcg attagtgaac 7200
ggatctcgac ggtatcgccg aattcacaaa tggcagtatt catccacaat tttaaaagaa 7260
aaggggggat tggggggtac agtgcagggg aaagaatagt agacataata gcaacagaca 7320
tacaaactaa agaattacaa aaacaaatta caaaaattca aaattttcgg gtttattaca 7380
gggacagcag agatccactt tatcgataag cttgggagtt ccgcgttaca taacttacgg 7440
taaatggccc gcctggctga ccgcccaacg acccccgccc attgacgtca ataatgacgt 7500
atgttcccat agtaacgcca atagggactt tccattgacg tcaatgggtg gagtatttac 7560
ggtaaactgc ccacttggca gtacatcaag tgtatcatat gccaagtacg ccccctattg 7620
acgtcaatga cggtaaatgg cccgcctggc attatgccca gtacatgacc ttacgggact 7680
ttcctacttg gcagtacatc tacgtattag tcatcgctat taccatggtg atgcggtttt 7740
ggcagtacac caatgggcgt ggatagcggt ttgactcacg gggatttcca agtctccacc 7800
ccattgacgt caatgggagt ttgttttggc accaaaatca acgggacttt ccaaaatgtc 7860
gtaacaactc cgccccattg acgcaaatgg gcggtaggcg tgtacggtgg gaggtctata 7920
taagcagagc tcgtttagtg aaccgtcaga tcgcctggag acgccatcca cgctgttttg 7980
acctccatag aagacaccga ctctagctag aggatcccgg gctcgagatg ctgagaataa 8040
tcaatgctag gaaggagaag aagagacgag gcgcagatac aagtgtcgga attgttggcc 8100
tcctgctgac cacagctatg gcagcggagg tcactagacg tgggagtgca tactatatgt 8160
acttggacag aaacgatgct ggggaggcca tatcttttcc aaccacattg gggatgaata 8220
agtgttatat acagatcatg gatcttggac acacgtgtga tgccaccatg agctatgaat 8280
gccctatgct ggatgagggg gtggaaccag atgacgtcga ttgttggtgc aacacgacgt 8340
caacttgggt tgtgtacgga acctgccatc acaaaaaagg tgaagcacgg agatctagaa 8400
gagctgtgac gctcccctcc cattccacta ggaagctgca aacgcggtcg caaacctggt 8460

```
tggaatcaag agaatacaca aagcacttga ttagagtcga aaattggata ttcaggaacc   8520
ctggcttcgc gttagcagca gctgccatcg cttggctttt gggaagctca acgagccaaa   8580
aagtcatata cttggtcatg atactgctga ttgccccggc atacagcatc aggtgcatag   8640
gagtcagcaa tagggacttt gtggaaggta tgtcaggtgg gacttgggtt gatgttgtct   8700
tggaacatgg aggttgtgtc actgtaatgg cacaggacaa accgactgtc gacatagagc   8760
tggttacaac aacagtcagc aacatggcgg aggtaagatc ctactgctat gaggcatcaa   8820
tatcagacat ggcttcggac agccgctgcc caacacaagg tgaagcctac cttgacaagc   8880
aatcagacac tcaatatgtc tgcaaaagaa cgttagtgga cagaggctgg ggaaatggat   8940
gtggactttt tggcaaaggg agcctggtga catgcgctaa gtttgcatgc tccaagaaaa   9000
tgaccgggaa gagcatccag ccagagaatc tggagtaccg gataatgctg tcagttcatg   9060
gctcccagca cagtgggatg atcgttaatg acacaggaca tgaaactgat gagaatagag   9120
cgaaagttga gataacgccc aattcaccaa gagccgaagc caccctgggg gggtttggaa   9180
gcctaggact tgattgtgaa ccgaggacag gccttgactt ttcagatttg tattacttga   9240
ctatgaataa caagcactgg ctggttcaca aggagtggtt ccacgacatt ccattacctt   9300
ggcacgctgg ggcagacacc ggaactccac actggaacaa caaagaagca ctggtagagt   9360
tcaaggacgc acatgccaaa aggcaaactg tcgtggttct agggagtcaa gaaggagcag   9420
ttcacacggc ccttgctgga gctctggagg ctgagatgga tggtgcaaag ggaaggctgt   9480
cctctggcca cttgaaatgt cgcctgaaaa tggataaact tagattgaag ggcgtgtcat   9540
actccttgtg tactgcagcg ttcacattca ccaagatccc ggctgaaaca ctgcacggga   9600
cagtcacagt ggaggtacag tacgcaggga cagatggacc ttgcaaggtt ccagctcaga   9660
tggcggtgga catgcaaact ctgaccccag ttgggaggtt gataaccgct aaccccgtaa   9720
tcactgaaag cactgagaac tctaagatga tgctggaact tgatccacca tttggggact   9780
cttacattgt cataggagtc ggggagaaga agatcaccca ccactggcac aggagtggca   9840
gcaccattgg aaaagcattt gaagccactg tgagaggtgc caagagaatg gcagtcttgg   9900
gagacacagc ctgggacttt ggatcagttg gaggcgctct caactcattg ggcaagggca   9960
tccatcaaat ctttggagca gctttcaaat cattgtttgg aggaatgtcc tggttctcac  10020
aaattctcat tggaacgttg ctgatgtggt tgggtctgaa cgcaaagaat ggatctattt  10080
cccttatgtg cttggcctta gggggagtgt tgatcttctt atccacagcc gtctctgctg  10140
agaacatcac atcaggattc ctaggacccc tgctcgtgtt acaggcgggg tttttcttgt  10200
tgacaagaat cctcacaata ccgcagagtc tagactcgtg gtggacttct ctcaattttc  10260
taggggggatc tcccgtgtgt cttggccaaa attcgcagtc cccaacctcc aatcactcac  10320
caacctcctg tcctccaatt tgtcctggtt atcgctggat gtgtctgcgg cgttttatca  10380
tattcctctt catcctgctg ctatgcctca tcttcttatt ggttcttctg gattatcaag  10440
gtatgttgcc cgtttgtcct ctaattccag gatcaacaac aaccagtacg ggaccatgca  10500
aaacctgcac gactcctgct caaggcaact ctatgtttcc ctcatgttgc tgtacaaaac  10560
ctacggatgg aaattgcacc tgtattccca tcccatcgtc ctgggctttc gcaaaatacc  10620
tatgggagtg ggcctcagtc cgtttctctt ggctcagttt actagtgcca tttgttcagt  10680
ggttcgtagg gctttccccc actgtttggc tttcagctat atggatgatg tggtattggg  10740
ggccaagtct gtacagcatc gtgagtccct ttataccgct gttaccaatt ttcttttgtc  10800
tctgggtata catttaactc gagcccggga tccggactag taactcgagg cccctctccc  10860
```

tcccccccc ctaacgttac tggccgaagc cgcttggaat aaggccggtg tgcgtttgtc 10920
tatatgttat tttccaccat attgccgtct tttggcaatg tgagggcccg gaaacctggc 10980
cctgtcttct tgacgagcat tcctaggggt ctttcccctc tcgccaaagg aatgcaaggt 11040
ctgttgaatg tcgtgaagga agcagttcct ctggaagctt cttgaagaca aacaacgtct 11100
gtagcgaccc tttgcaggca gcggaacccc ccacctggcg acaggtgcct ctgcggccaa 11160
aagccacgtg tataagatac acctgcaaag gcggcacaac cccagtgcca cgttgtgagt 11220
tggatagttg tggaaagagt caaatggctc tcctcaagcg tattcaacaa ggggctgaag 11280
gatgcccaga aggtacccca ttgtatggga tctgatctgg ggcctcggta cacatgcttt 11340
acatgtgttt agtcgaggtt aaaaaaacgt ctaggccccc cgaaccacgg ggacgtggtt 11400
ttcctttgaa aaacacgatg ataatatggc cacaaccttg gatgaccgag tacaagccca 11460
cggtgcgcct cgccacccgc gacgacgtcc cccgggccgt acgcaccctc gccgccgcgt 11520
tcgccgacta ccccgccacg cgccacaccg tcgacccgga ccgccacatc gagcgggtca 11580
ccgagctgca agaactcttc ctcacgcgcg tcgggctcga catcggcaag gtgtgggtcg 11640
cggacgacgg cgccgcggtg gcggtctgga ccacgccgga gagcgtcgaa gcgggggcgg 11700
tgttcgccga gatcggcccg cgcatggccg agttgagcgg ttcccggctg gccgcgcagc 11760
aacagatgga aggcctcctg gcgccgcacc ggcccaagga gcccgcgtgg ttcctggcca 11820
ccgtcggcgt ctcgcccgac caccagggca agggtctggg cagcgccgtc gtgctccccg 11880
gagtggaggc ggccgagcgc gccggggtgc ccgccttcct ggagacctcc gcgccccgca 11940
acctcccctt ctacgagcgg ctcggcttca ccgtcaccgc cgacgtcgag gtgcccgaag 12000
gaccgcgcac ctggtgcatg acccgcaagc ccggtgcctg ataaggtacc tttaagacca 12060
atgacttaca aggcagctgt agatcttagc cactttttaa aagaaaaggg gggactggaa 12120
gggctaattc actcccaacg aagacaagat ctttttgctt gtactgggtc tctctggtta 12180
gaccagatct gagcctggga gctctctggc taactaggga acccactgct taagcctcaa 12240
taaagcttgc cttgagtgct tcaagtagtg tgtgcccgtc tgttgtgtga ctctggtaac 12300
tagagatccc tcagaccctt ttagtcagtg tggaaaatct ctaga 12345

<210> SEQ ID NO 57
<211> LENGTH: 12216
<212> TYPE: DNA
<213> ORGANISM: Artificial sequence
<220> FEATURE:
<223> OTHER INFORMATION: pHR'puro - HBV - “prM + E deleted + S deleted”

<400> SEQUENCE: 57
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540

-continued

```
atggtgcact ctcagtacaa tctgctctga tgccgcatag ttaagccagc cccgacaccc    600
gccaacaccc gctgacgcgc cctgacgggc ttgtctgctc ccggcatccg cttacagaca    660
agctgtgacc gtctccggga gctgcatgtg tcagaggttt tcaccgtcat caccgaaacg    720
cgcgagacga aagggcctcg tgatacgcct atttttatag gttaatgtca tgataataat    780
ggtttcttag acgtcaggtg gcacttttcg gggaaatgtg cgcggaaccc ctatttgttt    840
atttttctaa atacattcaa atatgtatcc gctcatgaga caataaccct gataaatgct    900
tcaataatat tgaaaaagga agagtatgag tattcaacat ttccgtgtcg cccttattcc    960
cttttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
```

-continued

```
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
cataccacat ttgtagaggt tttacttgct ttaaaaaacc tcccacacct ccccctgaac   4860
ctgaaacata aaatgaatgc aattgttgtt gttaacttgt ttattgcagc ttataatggt   4920
tacaaataaa gcaatagcat cacaaatttc acaaataaag cattttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
```

-continued

```
agaactacac accagggcca ggggtcagat atccactgac ctttggatgg tgctacaagc   5340

tagtaccagt tgagccagat aaggtagaag aggccaataa aggagagaac accagcttgt   5400

tacaccctgt gagcctgcat gggatggatg acccggagag agaagtgtta gagtggaggt   5460

ttgacagccg cctagcattt catcacgtgg cccgagagct gcatccggag tacttcaaga   5520

actgctgata tcgagcttgc tacaagggac tttccgctgg ggactttcca gggaggcgtg   5580

gcctgggcgg gactggggag tggcgagccc tcagatcctg catataagca gctgcttttt   5640

gcctgtactg ggtctctctg gttagaccag atctgagcct gggagctctc tggctaacta   5700

gggaacccac tgcttaagcc tcaataaagc ttgccttgag tgcttcaagt agtgtgtgcc   5760

cgtctgttgt gtgactctgg taactagaga tccctcagac ccttttagtc agtgtggaaa   5820

atctctagca gtggcgcccg aacagggact tgaaagcgaa agggaaacca gaggagctct   5880

ctcgacgcag gactcggctt gctgaagcgc gcacggcaag aggcgagggg cggcgactgg   5940

tgagtacgcc aaaaattttg actagcggag gctagaagga gagagatggg tgcgagagcg   6000

tcagtattaa gcgggggaga attagatcgc gatgggaaaa aattcggtta aggccagggg   6060

gaaagaaaaa atataaatta aaacatatag tatgggcaag cagggagcta gaacgattcg   6120

cagttaatcc tggcctgtta gaaacatcag aaggctgtag acaaatactg ggacagctac   6180

aaccatccct tcagacagga tcagaagaac ttagatcatt atataataca gtagcaaccc   6240

tctattgtgt gcatcaaagg atagagataa aagacaccaa ggaagcttta gacaagatag   6300

aggaagagca aaacaaaagt aagaccaccg cacagcaagc ggccgctgat cttcagacct   6360

ggaggaggag atatgaggga caattggaga agtgaattat ataaatataa agtagtaaaa   6420

attgaaccat taggagtagc acccaccaag gcaaagagaa gagtggtgca gagagaaaaa   6480

agagcagtgg gaataggagc tttgttcctt gggttcttgg gagcagcagg aagcactatg   6540

ggcgcagcgt caatgacgct gacggtacag gccagacaat tattgtctgg tatagtgcag   6600

cagcagaaca atttgctgag ggctattgag gcgcaacagc atctgttgca actcacagtc   6660

tggggcatca agcagctcca ggcaagaatc ctggctgtgg aaagatacct aaaggatcaa   6720

cagctcctgg ggatttgggg ttgctctgga aaactcattt gcaccactgc tgtgccttgg   6780

aatgctagtt ggagtaataa atctctggaa cagatttgga atcacacgac ctggatggag   6840

tgggacagag aaattaacaa ttacacaagc ttaatacact ccttaattga agaatcgcaa   6900

aaccagcaag aaaagaatga acaagaatta ttggaattag ataaatgggc aagtttgtgg   6960

aattggttta acataacaaa ttggctgtgg tatataaaat tattcataat gatagtagga   7020

ggcttggtag gtttaagaat agtttttgct gtactttcta tagtgaatag agttaggcag   7080

ggatattcac cattatcgtt tcagacccac ctcccaaccc cgaggggacc cgacaggccc   7140

gaaggaatag aagaagaagg tggagagaga gacagagaca gatccattcg attagtgaac   7200

ggatctcgac ggtatcgccg aattcacaaa tggcagtatt catccacaat tttaaaagaa   7260

aaggggggat tggggggtac agtgcagggg aaagaatagt agacataata gcaacagaca   7320

tacaaactaa agaattacaa aaacaaatta caaaaattca aaattttcgg gtttattaca   7380

gggacagcag agatccactt tatcgataag cttgggagtt ccgcgttaca taacttacgg   7440

taaatggccc gcctggctga ccgcccaacg acccccgccc attgacgtca ataatgacgt   7500

atgttcccat agtaacgcca atagggactt tccattgacg tcaatgggtg gagtatttac   7560

ggtaaactgc ccacttggca gtacatcaag tgtatcatat gccaagtacg ccccctattg   7620

acgtcaatga cggtaaatgg cccgcctggc attatgccca gtacatgacc ttacgggact   7680
```

```
ttcctacttg gcagtacatc tacgtattag tcatcgctat taccatggtg atgcggtttt   7740
ggcagtacac caatgggcgt ggatagcggt ttgactcacg gggatttcca agtctccacc   7800
ccattgacgt caatgggagt ttgttttggc accaaaatca acgggacttt ccaaaatgtc   7860
gtaacaactc cgccccattg acgcaaatgg gcggtaggcg tgtacggtgg gaggtctata   7920
taagcagagc tcgtttagtg aaccgtcaga tcgcctggag acgccatcca cgctgttttg   7980
acctccatag aagacaccga ctctagctag aggatcccgg gctcgagatg ctgagaataa   8040
tcaatgctag gaaggagaag aagagacgag gcgcagatac aagtgtcgga attgttggcc   8100
tcctgctgac cacagctatg gcagcggagg tcactagacg tgggagtgca tactatatgt   8160
acttggacag aaacgatgct ggggaggcca tatcttttcc aaccacattg gggatgaata   8220
agtgttatat acagatcatg gatcttggac acacgtgtga tgccaccatg agctatgaat   8280
gccctatgct ggatgagggg gtggaaccag atgacgtcga ttgttggtgc aacacgacgt   8340
caacttgggt tgtgtacgga acctgccatc acaaaaaagg tgaagcacgg agatctagaa   8400
gagctgtgac gctcccctcc cattccacta ggaagctgca aacgcggtcg caaacctggt   8460
tggaatcaag agaatacaca aagcacttga ttagagtcga aaattggata ttcaggaacc   8520
ctggcttcgc gttagcagca gctgccatcg cttggctttt gggaagctca acgagccaaa   8580
aagtcatata cttggtcatg atactgctga ttgccccggc atacagcatc aggtgcatag   8640
gagtcagcaa tagggacttt gtggaaggta tgtcaggtgg gacttgggtt gatgttgtct   8700
tggaacatgg aggttgtgtc actgtaatgg cacaggacaa accgactgtc gacatagagc   8760
tggttacaac aacagtcagc aacatggcgg aggtaagatc ctactgctat gaggcatcaa   8820
tatcagacat ggcttcggac agccgctgcc caacacaagg tgaagcctac cttgacaagc   8880
aatcagacac tcaatatgtc tgcaaaagaa cgttagtgga cagaggctgg ggaaatggat   8940
gtggactttt tggcaaaggg agcctggtga catgcgctaa gtttgcatgc tccaagaaaa   9000
tgaccgggaa gagcatccag ccagagaatc tggagtaccg gataatgctg tcagttcatg   9060
gctcccagca cagtgggatg atcgttaatg acacaggaca tgaaactgat gagaatagag   9120
cgaaagttga gataacgccc aattcaccaa gagccgaagc caccctgggg gggtttggaa   9180
gcctaggact tgattgtgaa ccgaggacag gccttgactt ttcagatttg tattacttga   9240
ctatgaataa caagcactgg ctggttcaca aggagtggtt ccacgacatt ccattacctt   9300
ggcacgctgg ggcagacacc ggaactccac actggaacaa caaagaagca ctggtagagt   9360
tcaaggacgc acatgccaaa aggcaaactg tcgtggttct agggagtcaa gaaggagcag   9420
ttcacacggc ccttgctgga gctctggagg ctgagatgga tggtgcaaag ggaaggctgt   9480
cctctggcca cttgaaatgt cgcctgaaaa tggataaact tagattgaag ggcgtgtcat   9540
actccttgtg tactgcagcg ttcacattca ccaagatccc ggctgaaaca ctgcacggga   9600
cagtcacagt ggaggtacag tacgcaggga cagatggacc ttgcaaggtt ccagctcaga   9660
tggcggtgga catgcaaact ctgaccccag ttgggaggtt gataaccgct aaccccgtaa   9720
tcactgaaag cactgagaac tctaagatga tgctggaact tgatccacca tttggggact   9780
cttacattgt cataggagtc ggggagaaga agatcaccca ccactggcac aggagtggca   9840
gcaccattgg aaaagcattt gaagccactg tgagaggtgc caagagaatg gcagtcttgg   9900
gagacacagc ctgggacttt ggatcagttg gaggcgctct caactcattg ggcaagggca   9960
tccatcaaat ctttggagca gctttcaaat cattgtttgg aggaatgtcc tggttctcac  10020
```

-continued

```
aaattctcat tggaacgttg ctgatgtggt tgggtctgaa cgcaaagaat ggatctagaa  10080
tcctcacaat accgcagagt ctagactcgt ggtggacttc tctcaatttt ctagggggat  10140
ctcccgtgtg tcttggccaa aattcgcagt ccccaacctc caatcactca ccaacctcct  10200
gtcctccaat ttgtcctggt tatcgctgga tgtgtctgcg gcgttttatc atattcctct  10260
tcatcctgct gctatgcctc atcttcttat tggttcttct ggattatcaa ggtatgttgc  10320
ccgtttgtcc tctaattcca ggatcaacaa caaccagtac gggaccatgc aaaacctgca  10380
cgactcctgc tcaaggcaac tctatgtttc cctcatgttg ctgtacaaaa cctacggatg  10440
gaaattgcac ctgtattccc atcccatcgt cctgggcttt cgcaaaatac ctatgggagt  10500
gggcctcagt ccgtttctct tggctcagtt tactagtgcc atttgttcag tggttcgtag  10560
ggctttcccc cactgtttgg ctttcagcta tatggatgat gtggtattgg gggccaagtc  10620
tgtacagcat cgtgagtccc tttataccgc tgttaccaat tttcttttgt ctctgggtat  10680
acatttaact cgagcccggg atccggacta gtaactcgag gcccctctcc ctcccccccc  10740
cctaacgtta ctggccgaag ccgcttggaa taaggccggt gtgcgtttgt ctatatgtta  10800
ttttccacca tattgccgtc ttttggcaat gtgagggccc ggaaacctgg ccctgtcttc  10860
ttgacgagca ttcctagggg tctttcccct ctcgccaaag gaatgcaagg tctgttgaat  10920
gtcgtgaagg aagcagttcc tctggaagct tcttgaagac aaacaacgtc tgtagcgacc  10980
ctttgcaggc agcggaaccc cccacctggc gacaggtgcc tctgcggcca aaagccacgt  11040
gtataagata cacctgcaaa ggcggcacaa ccccagtgcc acgttgtgag ttggatagtt  11100
gtggaaagag tcaaatggct ctcctcaagc gtattcaaca aggggctgaa ggatgcccag  11160
aaggtacccc attgtatggg atctgatctg gggcctcggt acacatgctt tacatgtgtt  11220
tagtcgaggt taaaaaaacg tctaggcccc ccgaaccacg gggacgtggt tttcctttga  11280
aaaacacgat gataatatgg ccacaacctt ggatgaccga gtacaagccc acggtgcgcc  11340
tcgccacccg cgacgacgtc ccccgggccg tacgcaccct cgccgccgcg ttcgccgact  11400
accccgccac gcgccacacc gtcgacccgg accgccacat cgagcgggtc accgagctgc  11460
aagaactctt cctcacgcgc gtcgggctcg acatcggcaa ggtgtgggtc gcggacgacg  11520
gcgccgcggt ggcggtctgg accacgccgg agagcgtcga agcgggggcg gtgttcgccg  11580
agatcggccc gcgcatggcc gagttgagcg gttcccggct ggccgcgcag caacagatgg  11640
aaggcctcct ggcgccgcac cggcccaagg agcccgcgtg gttcctggcc accgtcggcg  11700
tctcgcccga ccaccagggc aagggtctgg gcagcgccgt cgtgctcccc ggagtggagg  11760
cggccgagcg cgccggggtg cccgccttcc tggagacctc cgcgccccgc aacctcccct  11820
tctacgagcg gctcggcttc accgtcaccg ccgacgtcga ggtgcccgaa ggaccgcgca  11880
cctggtgcat gacccgcaag cccggtgcct gataaggtac ctttaagacc aatgacttac  11940
aaggcagctg tagatcttag ccactttta aaagaaaagg ggggactgga agggctaatt  12000
cactcccaac gaagacaaga tctttttgct tgtactgggt ctctctggtt agaccagatc  12060
tgagcctggg agctctctgg ctaactaggg aacccactgc ttaagcctca ataaagcttg  12120
ccttgagtgc ttcaagtagt gtgtgcccgt ctgttgtgtg actctggtaa ctagagatcc  12180
ctcagaccct tttagtcagt gtggaaaatc tctaga                            12216
```

<210> SEQ ID NO 58
<211> LENGTH: 12510
<212> TYPE: DNA
<213> ORGANISM: Artificial sequence
<220> FEATURE:
<223> OTHER INFORMATION: pHR'puro - HBV - "prM + E + M"

<400> SEQUENCE: 58
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540
atggtgcact ctcagtacaa tctgctctga tgccgcatag ttaagccagc cccgacaccc 600
gccaacaccc gctgacgcgc cctgacgggc ttgtctgctc ccggcatccg cttacagaca 660
agctgtgacc gtctccggga gctgcatgtg tcagaggttt tcaccgtcat caccgaaacg 720
cgcgagacga aagggcctcg tgatacgcct atttttatag gttaatgtca tgataataat 780
ggtttcttag acgtcaggtg gcacttttcg gggaaatgtg cgcggaaccc ctatttgttt 840
atttttctaa atacattcaa atatgtatcc gctcatgaga caataaccct gataaatgct 900
tcaataatat tgaaaaagga agagtatgag tattcaacat ttccgtgtcg cccttattcc 960
cttttttgcg gcattttgcc ttcctgtttt tgctcaccca gaaacgctgg tgaaagtaaa 1020
agatgctgaa gatcagttgg gtgcacgagt gggttacatc gaactggatc tcaacagcgg 1080
taagatcctt gagagttttc gccccgaaga acgttttcca atgatgagca cttttaaagt 1140
tctgctatgt ggcgcggtat tatcccgtat tgacgccggg caagagcaac tcggtcgccg 1200
catacactat tctcagaatg acttggttga gtactcacca gtcacagaaa agcatcttac 1260
ggatggcatg acagtaagag aattatgcag tgctgccata accatgagtg ataacactgc 1320
ggccaactta cttctgacaa cgatcggagg accgaaggag ctaaccgctt ttttgcacaa 1380
catgggggat catgtaactc gccttgatcg ttgggaaccg gagctgaatg aagccatacc 1440
aaacgacgag cgtgacacca cgatgcctgt agcaatggca acaacgttgc gcaaactatt 1500
aactggcgaa ctacttactc tagcttcccg gcaacaatta atagactgga tggaggcgga 1560
taaagttgca ggaccacttc tgcgctcggc ccttccggct ggctggttta ttgctgataa 1620
atctggagcc ggtgagcgtg ggtctcgcgg tatcattgca gcactggggc cagatggtaa 1680
gccctcccgt atcgtagtta tctacacgac ggggagtcag gcaactatgg atgaacgaaa 1740
tagacagatc gctgagatag gtgcctcact gattaagcat tggtaactgt cagaccaagt 1800
ttactcatat atactttaga ttgatttaaa acttcatttt taatttaaaa ggatctaggt 1860
gaagatcctt tttgataatc tcatgaccaa aatcccttaa cgtgagtttt cgttccactg 1920
agcgtcagac cccgtagaaa agatcaaagg atcttcttga gatccttttt ttctgcgcgt 1980
aatctgctgc ttgcaaacaa aaaaaccacc gctaccagcg gtggtttgtt tgccggatca 2040
agagctacca actctttttc cgaaggtaac tggcttcagc agagcgcaga taccaaatac 2100
tgtccttcta gtgtagccgt agttaggcca ccacttcaag aactctgtag caccgcctac 2160
atacctcgct ctgctaatcc tgttaccagt ggctgctgcc agtggcgata agtcgtgtct 2220

-continued

```
taccgggttg gactcaagac gatagttacc ggataaggcg cagcggtcgg gctgaacggg   2280

gggttcgtgc acacagccca gcttggagcg aacgacctac accgaactga gatacctaca   2340

gcgtgagcat tgagaaagcg ccacgcttcc cgaagggaga aaggcggaca ggtatccggt   2400

aagcggcagg gtcggaacag gagagcgcac gagggagctt ccagggggaa acgcctggta   2460

tctttatagt cctgtcgggt ttcgccacct ctgacttgag cgtcgatttt tgtgatgctc   2520

gtcagggggg cggagcctat ggaaaaacgc cagcaacgcg gcctttttac ggttcctggc   2580

cttttgctgg ccttttgctc acatgttctt tcctgcgtta tcccctgatt ctgtggataa   2640

ccgtattacc gcctttgagt gagctgatac cgctcgccgc agccgaacga ccgagcgcag   2700

cgagtcagtg agcgaggaag cggaagagcg cccaatacgc aaaccgcctc tccccgcgcg   2760

ttggccgatt cattaatgca gctgtggaat gtgtgtcagt tagggtgtgg aaagtcccca   2820

ggctccccag caggcagaag tatgcaaagc atgcatctca attagtcagc aaccaggtgt   2880

ggaaagtccc caggctcccc agcaggcaga agtatgcaaa gcatgcatct caattagtca   2940

gcaaccatag tcccgcccct aactccgccc atcccgcccc taactccgcc cagttccgcc   3000

cattctccgc cccatggctg actaattttt tttatttatg cagaggccga ggccgcctcg   3060

gcctctgagc tattccagaa gtagtgagga ggcttttttg gaggcctagg cttttgcaaa   3120

aagcttggac acaagacagg cttgcgagat atgtttgaga ataccacttt atcccgcgtc   3180

agggagaggc agtgcgtaaa aagacgcgga ctcatgtgaa atactggttt ttagtgcgcc   3240

agatctctat aatctcgcgc aacctatttt cccctcgaac actttttaag ccgtagataa   3300

acaggctggg acacttcaca tgagcgaaaa atacatcgtc acctgggaca tgttgcagat   3360

ccatgcacgt aaactcgcaa gccgactgat gccttctgaa caatggaaag gcattattgc   3420

cgtaagccgt ggcggtctgt accgggtgcg ttactggcgc gtgaactggg tattcgtcat   3480

gtcgataccg tttgtatttc cagctacgat cacgacaacc agcgcgagct taaagtgctg   3540

aaacgcgcag aaggcgatgg cgaaggcttc atcgttattg atgacctggt ggataccggt   3600

ggtactgcgg ttgcgattcg tgaaatgtat ccaaaagcgc actttgtcac catcttcgca   3660

aaaccggctg gtcgtccgct ggttgatgac tatgttgttg atatcccgca agatacctgg   3720

attgaacagc cgtgggatat gggcgtcgta ttcgtcccgc caatctccgg tcgctaatct   3780

tttcaacgcc tggcactgcc gggcgttgtt ctttttaact tcaggcgggt tacaatagtt   3840

tccagtaagt attctggagg ctgcatccat gacacaggca aacctgagcg aaaccctgtt   3900

caaaccccgc tttaaacatc ctgaaacctc gacgctagtc cgccgcttta atcacggcgc   3960

acaaccgcct gtgcagtcgg cccttgatgg taaaaccatc cctcactggt atcgcatgat   4020

taaccgtctg atgtggatct ggcgcggcat tgacccacgc gaaatcctcg acgtccaggc   4080

acgtattgtg atgagcgatg ccgaacgtac cgacgatgat ttatacgata cggtgattgg   4140

ctaccgtggc ggcaactgga tttatgagtg ggccccggat ctttgtgaag gaaccttact   4200

tctgtggtgt gacataattg gacaaactac ctacagagat ttaaagctct aaggtaaata   4260

taaaattttt aagtgtataa tgtgttaaac tactgattct aattgtttgt gtattttaga   4320

ttccaaccta tggaactgat gaatgggagc agtggtggaa tgcctttaat gaggaaaacc   4380

tgttttgctc agaagaaatg ccatctagtg atgatgaggc tactgctgac tctcaacatt   4440

ctactcctcc aaaaaagaag agaaaggtag aagaccccaa ggactttcct tcagaattgc   4500

taagtttttt gagtcatgct gtgtttagta atagaactct tgcttgcttt gctatttaca   4560

ccacaaagga aaaagctgca ctgctataca agaaaattat ggaaaaatat tctgtaacct   4620
```

ttataagtag gcataacagt tataatcata acatactgtt ttttcttact ccacacaggc 4680
atagagtgtc tgctattaat aactatgctc aaaaattgtg tacctttagc tttttaattt 4740
gtaaaggggt taataaggaa tatttgatgt atagtgcctt gactagagat cataatcagc 4800
cataccacat ttgtagaggt tttacttgct ttaaaaaacc tcccacacct ccccctgaac 4860
ctgaaacata aaatgaatgc aattgttgtt gttaacttgt ttattgcagc ttataatggt 4920
tacaaataaa gcaatagcat cacaaatttc acaaataaag catttttttc actgcattct 4980
agttgtggtt tgtccaaact catcaatgta tcttatcatg tctggatcaa ctggataact 5040
caagctaacc aaaatcatcc caaacttccc accccatacc ctattaccac tgccaattac 5100
ctagtggttt catttactct aaacctgtga ttcctctgaa ttattttcat tttaaagaaa 5160
ttgtatttgt taaatatgta ctacaaactt agtagttgga agggctaatt cactcccaaa 5220
gaagacaaga tatccttgat ctgtggatct accacacaca aggctacttc cctgattagc 5280
agaactacac accagggcca ggggtcagat atccactgac ctttggatgg tgctacaagc 5340
tagtaccagt tgagccagat aaggtagaag aggccaataa aggagagaac accagcttgt 5400
tacaccctgt gagcctgcat gggatggatg acccggagag agaagtgtta gagtggaggt 5460
ttgacagccg cctagcattt catcacgtgg cccgagagct gcatccggag tacttcaaga 5520
actgctgata tcgagcttgc tacaagggac tttccgctgg ggactttcca gggaggcgtg 5580
gcctgggcgg gactggggag tggcgagccc tcagatcctg catataagca gctgcttttt 5640
gcctgtactg ggtctctctg gttagaccag atctgagcct gggagctctc tggctaacta 5700
gggaacccac tgcttaagcc tcaataaagc ttgccttgag tgcttcaagt agtgtgtgcc 5760
cgtctgttgt gtgactctgg taactagaga tccctcagac ccttttagtc agtgtggaaa 5820
atctctagca gtggcgcccg aacagggact tgaaagcgaa agggaaacca gaggagctct 5880
ctcgacgcag gactcggctt gctgaagcgc gcacggcaag aggcgagggg cggcgactgg 5940
tgagtacgcc aaaaattttg actagcggag gctagaagga gagagatggg tgcgagagcg 6000
tcagtattaa gcgggggaga attagatcgc gatgggaaaa aattcggtta aggccagggg 6060
gaaagaaaaa atataaatta aaacatatag tatgggcaag cagggagcta gaacgattcg 6120
cagttaatcc tggcctgtta gaaacatcag aaggctgtag acaaatactg ggacagctac 6180
aaccatccct tcagacagga tcagaagaac ttagatcatt atataataca gtagcaaccc 6240
tctattgtgt gcatcaaagg atagagataa aagacaccaa ggaagcttta gacaagatag 6300
aggaagagca aaacaaaagt aagaccaccg cacagcaagc ggccgctgat cttcagacct 6360
ggaggaggag atatgaggga caattggaga agtgaattat ataaatataa agtagtaaaa 6420
attgaaccat taggagtagc acccaccaag gcaaagagaa gagtggtgca gagagaaaaa 6480
agagcagtgg gaataggagc tttgttcctt gggttcttgg gagcagcagg aagcactatg 6540
ggcgcagcgt caatgacgct gacggtacag gccagacaat tattgtctgg tatagtgcag 6600
cagcagaaca atttgctgag ggctattgag gcgcaacagc atctgttgca actcacagtc 6660
tggggcatca agcagctcca ggcaagaatc ctggctgtgg aaagatacct aaaggatcaa 6720
cagctcctgg ggatttgggg ttgctctgga aaactcattt gcaccactgc tgtgccttgg 6780
aatgctagtt ggagtaataa atctctggaa cagatttgga atcacacgac ctggatggag 6840
tgggacagag aaattaacaa ttacacaagc ttaatacact ccttaattga agaatcgcaa 6900
aaccagcaag aaaagaatga acaagaatta ttggaattag ataaatgggc aagtttgtgg 6960

-continued

```
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgataag cttgggagtt ccgcgttaca taacttacgg   7440
taaatggccc gcctggctga ccgcccaacg acccccgccc attgacgtca ataatgacgt   7500
atgttcccat agtaacgcca atagggactt tccattgacg tcaatgggtg gagtatttac   7560
ggtaaactgc ccacttggca gtacatcaag tgtatcatat gccaagtacg ccccctattg   7620
acgtcaatga cggtaaatgg cccgcctggc attatgccca gtacatgacc ttacgggact   7680
ttcctacttg gcagtacatc tacgtattag tcatcgctat taccatggtg atgcggtttt   7740
ggcagtacac caatgggcgt ggatagcggt ttgactcacg gggatttcca agtctccacc   7800
ccattgacgt caatgggagt ttgttttggc accaaaatca acgggacttt ccaaaatgtc   7860
gtaacaactc cgccccattg acgcaaatgg gcggtaggcg tgtacggtgg gaggtctata   7920
taagcagagc tcgtttagtg aaccgtcaga tcgcctggag acgccatcca cgctgttttg   7980
acctccatag aagacaccga ctctagctag aggatcccgg gctcgagatg ctgagaataa   8040
tcaatgctag gaaggagaag aagagacgag gcgcagatac aagtgtcgga attgttggcc   8100
tcctgctgac cacagctatg gcagcggagg tcactagacg tgggagtgca tactatatgt   8160
acttggacag aaacgatgct ggggaggcca tatcttttcc aaccacattg gggatgaata   8220
agtgttatat acagatcatg gatcttggac acacgtgtga tgccaccatg agctatgaat   8280
gccctatgct ggatgagggg gtggaaccag atgacgtcga ttgttggtgc aacacgacgt   8340
caacttgggt tgtgtacgga acctgccatc acaaaaaagg tgaagcacgg agatctagaa   8400
gagctgtgac gctcccctcc cattccacta ggaagctgca aacgcggtcg caaacctggt   8460
tggaatcaag agaatacaca aagcacttga ttagagtcga aaattggata ttcaggaacc   8520
ctggcttcgc gttagcagca gctgccatcg cttggctttt gggaagctca acgagccaaa   8580
aagtcatata cttggtcatg atactgctga ttgccccggc atacagcatc aggtgcatag   8640
gagtcagcaa tagggacttt gtggaaggta tgtcaggtgg gacttgggtt gatgttgtct   8700
tggaacatgg aggttgtgtc actgtaatgg cacaggacaa accgactgtc gacatagagc   8760
tggttacaac aacagtcagc aacatggcgg aggtaagatc ctactgctat gaggcatcaa   8820
tatcagacat ggcttcggac agccgctgcc caacacaagg tgaagcctac cttgacaagc   8880
aatcagacac tcaatatgtc tgcaaaagaa cgttagtgga cagaggctgg ggaaatggat   8940
gtggactttt tggcaaaggg agcctggtga catgcgctaa gtttgcatgc tccaagaaaa   9000
tgaccgggaa gagcatccag ccagagaatc tggagtaccg gataatgctg tcagttcatg   9060
gctcccagca cagtgggatg atcgttaatg acacaggaca tgaaactgat gagaatagag   9120
cgaaagttga gataacgccc aattcaccaa gagccgaagc caccctgggg gggtttggaa   9180
gcctaggact tgattgtgaa ccgaggacag gccttgactt ttcagatttg tattacttga   9240
ctatgaataa caagcactgg ctggttcaca aggagtggtt ccacgacatt ccattacctt   9300
ggcacgctgg ggcagacacc ggaactccac actggaacaa caaagaagca ctggtagagt   9360
```

-continued

```
tcaaggacgc acatgccaaa aggcaaactg tcgtggttct agggagtcaa gaaggagcag   9420
ttcacacggc ccttgctgga gctctggagg ctgagatgga tggtgcaaag ggaaggctgt   9480
cctctggcca cttgaaatgt cgcctgaaaa tggataaact tagattgaag ggcgtgtcat   9540
actccttgtg tactgcagcg ttcacattca ccaagatccc ggctgaaaca ctgcacggga   9600
cagtcacagt ggaggtacag tacgcaggga cagatggacc ttgcaaggtt ccagctcaga   9660
tggcggtgga catgcaaact ctgaccccag ttgggaggtt gataaccgct aaccccgtaa   9720
tcactgaaag cactgagaac tctaagatga tgctggaact tgatccacca tttggggact   9780
cttacattgt cataggagtc ggggagaaga agatcaccca ccactggcac aggagtggca   9840
gcaccattgg aaaagcattt gaagccactg tgagaggtgc caagagaatg gcagtcttgg   9900
gagacacagc ctgggacttt ggatcagttg gaggcgctct caactcattg ggcaagggca   9960
tccatcaaat ctttggagca gctttcaaat cattgtttgg aggaatgtcc tggttctcac  10020
aaattctcat tggaacgttg ctgatgtggt tgggtctgaa cgcaaagaat ggatctattt  10080
cccttatgtg cttggcctta gggggagtgt tgatcttctt atccacagcc gtctctgctc  10140
agtggaattc cactgccttc caccaaactc tgcaggatcc cagagtcagg ggtctgtatc  10200
ttcctgctgg tggctccagt tcaggaacag taaaccctgc tccgaatatt gcctctcaca  10260
tctcgtcaat ctccgcgagg actggggacc ctgtgacgaa catggagaac atcacatcag  10320
gattcctagg acccctgctc gtgttacagg cggggttttt cttgttgaca agaatcctca  10380
caataccgca gagtctagac tcgtggtgga cttctctcaa ttttctaggg ggatctcccg  10440
tgtgtcttgg ccaaaattcg cagtccccaa cctccaatca ctcaccaacc tcctgtcctc  10500
caatttgtcc tggttatcgc tggatgtgtc tgcggcgttt tatcatattc ctcttcatcc  10560
tgctgctatg cctcatcttc ttattggttc ttctggatta tcaaggtatg ttgcccgttt  10620
gtcctctaat tccaggatca acaacaacca gtacgggacc atgcaaaacc tgcacgactc  10680
ctgctcaagg caactctatg tttccctcat gttgctgtac aaaacctacg gatggaaatt  10740
gcacctgtat tcccatccca tcgtcctggg ctttcgcaaa atacctatgg gagtgggcct  10800
cagtccgttt ctcttggctc agtttactag tgccatttgt tcagtggttc gtagggcttt  10860
cccccactgt ttggctttca gctatatgga tgatgtggta ttgggggcca agtctgtaca  10920
gcatcgtgag tccctttata ccgctgttac caattttctt ttgtctctgg gtatacattt  10980
aactcgagcc cgggatccgg actagtaact cgaggcccct ctccctcccc ccccccctaac  11040
gttactggcc gaagccgctt ggaataaggc cggtgtgcgt ttgtctatat gttattttcc  11100
accatattgc cgtcttttgg caatgtgagg gcccggaaac ctggccctgt cttcttgacg  11160
agcattccta ggggtctttc ccctctcgcc aaaggaatgc aaggtctgtt gaatgtcgtg  11220
aaggaagcag ttcctctgga agcttcttga agacaaacaa cgtctgtagc gaccctttgc  11280
aggcagcgga acccccccacc tggcgacagg tgcctctgcg gccaaaagcc acgtgtataa  11340
gatacacctg caaaggcggc acaaccccag tgccacgttg tgagttggat agttgtggaa  11400
agagtcaaat ggctctcctc aagcgtattc aacaaggggc tgaaggatgc ccagaaggta  11460
ccccattgta tgggatctga tctggggcct cggtacacat gctttacatg tgtttagtcg  11520
aggttaaaaa aacgtctagg ccccccgaac cacggggacg tggttttcct ttgaaaaaca  11580
cgatgataat atggccacaa ccttggatga ccgagtacaa gcccacggtg cgcctcgcca  11640
cccgcgacga cgtccccgg gccgtacgca ccctcgccgc cgcgttcgcc gactaccccg   11700
```

ccacgcgcca caccgtcgac ccggaccgcc acatcgagcg ggtcaccgag ctgcaagaac 11760
tcttcctcac gcgcgtcggg ctcgacatcg gcaaggtgtg ggtcgcggac gacggcgccg 11820
cggtggcggt ctggaccacg ccggagagcg tcgaagcggg ggcggtgttc gccgagatcg 11880
gcccgcgcat ggccgagttg agcggttccc ggctggccgc gcagcaacag atggaaggcc 11940
tcctggcgcc gcaccggccc aaggagcccg cgtggttcct ggccaccgtc ggcgtctcgc 12000
ccgaccacca gggcaagggt ctgggcagcg ccgtcgtgct ccccggagtg gaggcggccg 12060
agcgcgccgg ggtgcccgcc ttcctggaga cctccgcgcc ccgcaacctc cccttctacg 12120
agcggctcgg cttcaccgtc accgccgacg tcgaggtgcc cgaaggaccg cgcacctggt 12180
gcatgacccg caagcccggt gcctgataag gtacctttaa gaccaatgac ttacaaggca 12240
gctgtagatc ttagccactt tttaaaagaa aaggggggac tggaagggct aattcactcc 12300
caacgaagac aagatctttt tgcttgtact gggtctctct ggttagacca gatctgagcc 12360
tgggagctct ctggctaact agggaaccca ctgcttaagc ctcaataaag cttgccttga 12420
gtgcttcaag tagtgtgtgc ccgtctgttg tgtgactctg gtaactagag atccctcaga 12480
cccttttagt cagtgtggaa aatctctaga 12510

<210> SEQ ID NO 59
<211> LENGTH: 10807
<212> TYPE: DNA
<213> ORGANISM: Zika virus polynesian strain

<400> SEQUENCE: 59
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480
tcactagacg tgggagtgca tactatatgt acttggacag aaacgacgct ggggaggcca 540
tatcttttcc aaccacattg ggatgaata agtgttatat acagatcatg gatcttggac 600
acatgtgtga tgccaccatg agctatgaat gccctatgct ggatgagggg gtggaaccag 660
atgacgtcga ttgttggtgc aacacgacgt caacttgggt tgtgtacgga acctgccatc 720
acaaaaaagg tgaagcacgg agatctagaa gagctgtgac gctcccctcc cattccacta 780
ggaagctgca aacgcggtcg caaacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagcaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcggacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggactttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaataa caagcactgg ttggttcaca 1620
aggagtggtt ccacgacatt ccattacctt ggcacgctgg ggcagacacc ggaactccac 1680
actggaacaa caaagaagca ctggtagagt tcaaggacgc acatgccaaa aggcaaactg 1740
tcgtggttct agggagtcaa gaaggagcag ttcacacggc ccttgctgga gctctggagg 1800
ctgagatgga tggtgcaaag ggaaggctgt cctctggcca cttgaaatgt cgcctgaaaa 1860
tggataaact tagattgaag ggcgtgtcat actccttgtg taccgcagcg ttcacattca 1920
ccaagatccc ggctgaaaca ctgcacggga cagtcacagt ggaggtacag tacgcaggga 1980
cagatggacc ttgcaaggtt ccagctcaga tggcggtgga catgcaaact ctgaccccag 2040
ttgggaggtt gataaccgct aaccccgtaa tcactgaaag cactgagaac tctaagatga 2100
tgctggaact tgatccacca tttggggact cttacattgt cataggagtc ggggagaaga 2160
agatcaccca ccactggcac aggagtggca gcaccattgg aaaagcattt gaagccactg 2220
tgagaggtgc caagagaatg gcagtcttgg gagacacagc ctgggacttt ggatcagttg 2280
gaggcgctct caactcattg ggcaagggca tccatcaaat ttttggagca gctttcaaat 2340
cattgtttgg aggaatgtcc tggttctcac aaattctcat tggaacgttg ctgatgtggt 2400
tgggtctgaa cacaaagaat ggatctattt cccttatgtg cttggcctta gggggagtgt 2460
tgatcttctt atccacagct gtctctgctg atgtggggtg ctcggtggac ttctcaaaga 2520
aggagacgag atgcggtaca ggggtgttcg tctataacga cgttgaagcc tggagggaca 2580
ggtacaagta ccatcctgac tcccccgta gattggcagc agcagtcaag caagcctggg 2640
aagatggtat ctgtgggatc tcctctgttt caagaatgga aaacatcatg tggagatcag 2700
tagaagggga gctcaacgca atcctggaag agaatggagt tcaactgacg gtcgttgtgg 2760
gatctgtaaa aaaccccatg tggagaggtc cacagagatt gcccgtgcct gtgaacgagc 2820
tgccccacgg ctggaaggct tgggggaaat cgtacttcgt cagagcagca aagacaaata 2880
acagctttgt cgtggatggt gacacactga aggaatgccc actcaaacat agagcatgga 2940
acagctttct tgtggaggat catgggttcg ggtatttca cactagtgtc tggctcaagg 3000
ttagagaaga ttattcatta gagtgtgatc cagccgttat tggaacagct gttaagggaa 3060
aggaggctgt acacagtgat ctaggctact ggattgagag tgagaagaat gacacatgga 3120
ggctgaagag ggcccatctg atcgagatga aaacatgtga atggccaaag tcccacacat 3180
tgtggacaga tggaatagaa gagagtgatc tgatcatacc caagtcttta gctgggccac 3240
tcagccatca caataccaga gagggctaca ggacccaaat gaaagggcca tggcacagtg 3300
aagagcttga aattcggttt gaggaatgcc caggcactaa ggtccacgtg gaggaaacat 3360
gtggaacaag aggaccatct ctgagatcaa ccactgcaag cggaagggtg atcgaggaat 3420
ggtgctgcag ggagtgcaca atgcccccac tgtcgttccg ggctaaagat ggctgttggt 3480
atggaatgga gataaggccc aggaaagaac cagaaagtaa cttagtaagg tcaatggtga 3540
ctgcaggatc aactgatcac atggatcact tctcccttgg agtgcttgtg attctgctca 3600
tggtgcagga agggctgaag aagagaatga ccacaaagat catcataagc acatcgatgg 3660

-continued

```
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
```

accatgcaca ctggcttgaa gcaagaatgc tccttgacaa tatttacctc caagatggcc 6120
tcatagcctc gctctatcga cctgaggccg acaaagtagc agccattgag ggagagttca 6180
agcttaggac ggagcaaagg aagacctttg tggaactcat gaaaagagga gatcttcctg 6240
tttggctggc ctatcaggtt gcatctgccg gaataaccta cacagataga agatggtgct 6300
ttgatggcac gaccaacaac accataatgg aagacagtgt gccggcagag gtgtggacca 6360
gacacggaga gaaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagacccta gagaccatta tgcttttggg gttgctggga acagtctcgc 6660
tgggaatctt tttcgtcttg atgaggaaca agggcatagg gaagatgggc tttggaatgg 6720
tgactcttgg ggccagcgca tggctcatgt ggctctcgga aattgagcca gccagaattg 6780
catgtgtcct cattgttgtg ttcctattgc tggtggtgct catacctgag ccagaaaagc 6840
aaagatctcc ccaggacaac caaatggcaa tcatcatcat ggtagcagta ggtcttctgg 6900
gcttgattac cgccaatgaa ctcggatggt tggagagaac aaagagtgac ctaagccatc 6960
taatgggaag gagagaggag gggcaacca taggattctc aatggacatt gacctgcggc 7020
cagcctcagc ttgggccatc tatgctgcct tgacaacttt cattacccca gccgtccaac 7080
atgcagtgac cacttcatac aacaactact ccttaatggc gatggccacg caagctggag 7140
tgttgtttgg tatgggcaaa gggatgccat tctacgcatg ggactttgga gtcccgctgc 7200
taatgatagg ttgctactca caattaacac ccctgaccct aatagtggcc atcattttgc 7260
tcgtggcgca ctacatgtac ttgatcccag ggctgcaggc agcagctgcg cgtgctgccc 7320
agaagagaac ggcagctggc atcatgaaga accctgttgt ggatggaata gtggtgactg 7380
acattgacac aatgacaatt gacccccaag tggagaaaaa gatgggacag gtgctactca 7440
tagcagtagc cgtctccagc gccatactgt cgcggaccgc ctgggggtgg ggggaggctg 7500
gggccctgat cacagcggca acttccactt tgtgggaagg ctctccgaac aagtactgga 7560
actcctctac agccacttca ctgtgtaaca tttttagggg aagttacttg gctggagctt 7620
ctctaatcta cacagtaaca agaaacgctg gcttggtcaa gagacgtggg ggtggaacag 7680
gagagaccct gggagagaaa tggaaggccc gcttgaacca gatgtcggcc ctggagttct 7740
actcctacaa aaagtcaggc atcaccgagg tgtgcagaga agaggcccgc cgcgccctca 7800
aggacggtgt ggcaacggga ggccatgctg tgtcccgagg aagtgcaaag ctgagatggt 7860
tggtggagcg gggatacctg cagccctatg gaaaggtcat tgatcttgga tgtggcagag 7920
ggggctggag ttactacgcc gccaccatcc gcaaagttca agaagtgaaa ggatacacaa 7980
aaggaggccc tggtcatgaa gaacccatgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160
tctccatggt gggggattgg cttgaaaaaa gaccaggagc cttttgtata aaagtgttgt 8220
gcccatacac cagcactatg atggaaaccc tggagcgact gcagcgtagg tatgggggag 8280
gactggtcag agtgccactc tcccgcaact ctacacatga gatgtactgg gtctctggag 8340
cgaaaagcaa caccataaaa agtgtgtcca ccacgagcca gctcctcttg ggcgcatgg 8400

-continued

```
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagacccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt agtgttgtca ggcctgctag tcagccacag cttggggaaa gctgtgcagc  10440
ctgtgacccc cccaggagaa gctgggaaac caagcctata gtcaggccga gaacgccatg  10500
gcacggaaga agccatgctg cctgtgagcc cctcagagga cactgagtca aaaaaacccca  10560
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
```

-continued

```
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtct                                                            10807
```